United States Patent
Burny et al.

(10) Patent No.: US 11,266,733 B2
(45) Date of Patent: Mar. 8, 2022

(54) VIRAL ANTIGENS

(71) Applicant: GLAXOSMITHKLINE BIOLOGICALS SA, Rixensart (BE)

(72) Inventors: Wivine Burny, Rixensart (BE); Cindy Castado, Rixensart (BE); Sandra Giannini, Rixensart (BE); Julien Thierry Massaux, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/650,790

(22) PCT Filed: Sep. 25, 2018

(86) PCT No.: PCT/EP2018/076009
§ 371 (c)(1),
(2) Date: Mar. 25, 2020

(87) PCT Pub. No.: WO2019/063565
PCT Pub. Date: Apr. 4, 2019

(65) Prior Publication Data
US 2020/0230226 A1    Jul. 23, 2020

(30) Foreign Application Priority Data

Sep. 27, 2017 (EP) .................................. 17193469

(51) Int. Cl.
| | | |
|---|---|---|
| *C12N 15/86* | (2006.01) | |
| *A61K 39/00* | (2006.01) | |
| *A61K 39/12* | (2006.01) | |
| *A61K 39/155* | (2006.01) | |
| *A61K 39/385* | (2006.01) | |

(52) U.S. Cl.
CPC .............. *A61K 39/12* (2013.01); *C12N 15/86* (2013.01); *C12N 2710/20034* (2013.01)

(58) Field of Classification Search
CPC ................... C12N 15/86; A61K 39/12; A61K 2039/5256; A61P 35/00; A61P 43/00
See application file for complete search history.

(56) References Cited

U.S. PATENT DOCUMENTS

2020/0123571 A1    4/2020   Burny et al.

FOREIGN PATENT DOCUMENTS

| EP | 1195438 | * | 4/2002 |
|---|---|---|---|
| EP | 1195438 A1 | | 4/2002 |
| WO | 03031583 A2 | | 4/2003 |
| WO | 2004030636 A2 | | 4/2004 |
| WO | 2005089164 A2 | | 9/2005 |
| WO | 2008092854 A2 | | 8/2008 |
| WO | 2008138648 A1 | | 11/2008 |
| WO | 2008145745 A1 | | 12/2008 |
| WO | 2011106705 A2 | | 9/2011 |
| WO | 2016198531 A2 | | 12/2016 |
| WO | 2017029360 A1 | | 2/2017 |
| WO | 2018060288 A1 | | 4/2018 |
| WO | WO2018060288 | * | 4/2018 |

OTHER PUBLICATIONS

International Search Report and Written Opinion for corresponding International Application No. PCT/EP2018/076009, dated Dec. 19, 2018 (5 pages).
Kaufmann A. et al., "Safety and Immunogenicity of TA-HPV, a Recombinant Vaccinia Virus Expressing Modified Human Papillomavirus (HPV)-16 and HPV-18 E6 and E7 Genes, in Women with Progressive Cervical Cancer", Clinical Cancer Research, Dec. 1, 2002, p. 3676-3685.
Trimble C. et al., "Safety, efficacy, and immunogenicity of VGX-3100, a therapeutic synthetic DNA vaccine targeting Human papillomavirus 16 and 18 E6 and E7 proteins for cervical intraepithelial neoplasia 2/3: a randomised, double-blind, placebo-controlled phase 2b trial", The Lancet, Sep. 17, 2015, vol. 386, No. 10008, p. 2078-2088.
Hung C-F. et al., "Therapeutic human papillomavirus vaccines: current clinical trials and future directions", Expert Opinion on Biological Therapy, vol. 8, No. 4, p. 421-439.
Anonymous, "High- and Low-Risk HPV Types—theHPVtest.com", (Nov. 16, 2017), URL: http://www.thehpvtest.com/about-hpv/high-and-low-risk-hpv-types/, (Nov. 16, 2017), XP055425654 [AP] 1-23 * section headed "Low risk types of HPV" *; p. 1.
Khallouf H. et al., "Therapeutic Vaccine Strategies against Human Papillomavirus", Vaccines, 2014, vol. 2, No. 2, p. 422-462.

* cited by examiner

*Primary Examiner* — Barry A Chestnut

(57) ABSTRACT

Nucleotide constructs encoding antigenic peptides or polypeptides derived from multiple Human Papilloma Virus (HPV) early proteins, immunogenic compositions comprising such constructs and a pharmaceutically acceptable carrier, and uses thereof.

19 Claims, 15 Drawing Sheets

Specification includes a Sequence Listing.

A) insert n°1 - Gly_E2$^4$

B) insert n°2 - Gly_E2$^3$E7$^2$

C) insert n°3 - Gly_E1$^2$E6$^7$

Evaluation of the polyfunctionality profile of systemic HPV16E1-specific CD8+T cell response induced at 15 day post primo-immunization with SAM-HPV construct formulated in LNP Evaluation of the polyfunctionality profile of systemic HPV35E1 cross-reactive CD8+T cell response induced at 15 day post primo-immunization with SAM-HPV construct formulated in LNP

SEQUENCE LISTING

<160> NUMBER OF SEQ ID NOS: 38

<210> SEQ ID NO 1
<211> LENGTH: 9993
<212> TYPE: DNA
<213> ORGANISM: Artificial
<220> FEATURE:
<223> OTHER INFORMATION: synthetic polynucleotide

<400> SEQUENCE: 1

| | | | | | |
|---|---|---|---|---|---|
| ataggcggcg | catgagagaa | gcccagacca | attacctacc | caaaatggag | aaagttcacg |      60 |
| ttgacatcga | ggaagacagc | ccattcctca | gagctttgca | gcggagcttc | ccgcagtttg |     120 |
| aggtagaagc | caagcaggtc | actgataatg | accatgctaa | tgccagagcg | ttttcgcatc |     180 |
| tggcttcaaa | actgatcgaa | acggaggtgg | acccatccga | cacgatcctt | gacattggaa |     240 |
| gtgcgcccgc | ccgcagaatg | tattctaagc | acaagtatca | ttgtatctgt | ccgatgagat |     300 |
| gtgcggaaga | tccggacaga | ttgtataagt | atgcaactaa | gctgaagaaa | aactgtaagg |     360 |
| aaataactga | taaggaattg | gacaagaaaa | tgaaggagct | cgccgccgtc | atgagcgacc |     420 |
| ctgacctgga | aactgagact | atgtgcctcc | acgacgacga | gtcgtgtcgc | tacgaagggc |     480 |
| aagtcgctgt | ttaccaggat | gtatacgcgg | ttgacggacc | gacaagtctc | tatcaccaag |     540 |
| ccaataaggg | agttagagtc | gcctactgga | taggctttga | caccacccct | tttatgttta |     600 |
| agaacttggc | tggagcatat | ccatcatact | ctaccaactg | ggccgacgaa | accgtgttaa |     660 |
| cggctcgtaa | cataggccta | tgcagctctg | acgttatgga | gcggtcacgt | agagggatgt |     720 |
| ccattcttag | aaagaagtat | ttgaaaccat | ccaacaatgt | tctattctct | gttggctcga |     780 |
| ccatctacca | cgagaagagg | gacttactga | ggagctggca | cctgccgtct | gtatttcact |     840 |
| tacgtggcaa | gcaaaattac | acatgtcggt | gtgagactat | agttagttgc | gacgggtacg |     900 |
| tcgttaaaag | aatagctatc | agtccaggcc | tgtatgggaa | gccttcaggc | tatgctgcta |     960 |
| cgatgcaccg | cgagggattc | ttgtgctgca | aagtgacaga | cacattgaac | ggggagaggg |    1020 |
| tctcttttcc | cgtgtgcacg | tatgtgccag | ctacattgtg | tgaccaaatg | actggcatac |    1080 |
| tggcaacaga | tgtcagtgcg | gacgacgcgc | aaaaactgct | ggttgggctc | aaccagcgta |    1140 |
| tagtcgtcaa | cggtcgcacc | cagagaaaca | ccaataccat | gaaaaattac | cttttgcccg |    1200 |
| tagtggccca | ggcatttgct | aggtgggcaa | aggaatataa | ggaagatcaa | gaagatgaaa |    1260 |
| ggccactagg | actacgagat | agacagttag | tcatggggtg | ttgttgggct | tttagaaggc |    1320 |
| acaagataac | atctatttat | aagcgcccgg | atacccaaac | catcatcaaa | gtgaacagcg |    1380 |
| atttccactc | attcgtgctg | cccaggatag | gcagtaacac | attggagatc | gggctgagaa |    1440 |
| caagaatcag | gaaaatgtta | gaggagcaca | aggagccgtc | acctctcatt | accgccgagg |    1500 |
| acgtacaaga | agctaagtgc | gcagccgatg | aggctaagga | ggtgcgtgaa | gccgaggagt |    1560 |
| tgcgcgcagc | tctaccacct | ttggcagctg | atgttgagga | gcccactctg | gaagccgatg |    1620 |
| tcgacttgat | gttacaagag | gctgggccgc | gctcagtgga | gacacctcgt | ggcttgataa |    1680 |
| aggttaccag | ctacgatggc | gaggacaaga | tcggctctta | cgctgtgctt | tctcccgcagg |    1740 |
| ctgtactcaa | gagtgaaaaa | ttatcttgca | tccaccctct | cgctgaacaa | gtcatagtga |    1800 |
| taacacactc | tggccgaaaa | gggcgttatg | ccgtggaacc | ataccatggt | aaagtagtgg |    1860 |
| tgccagaggg | acatgcaata | cccgtccagg | actttcaagc | tctgagtgaa | agtgccacca |    1920 |
| ttgtgtacaa | cgaacgtgag | ttcgtaaaca | ggtacctgca | ccatattgcc | acacatggaa |    1980 |
| gagcgctgaa | cactgatgaa | gaatattaca | aaactgtcaa | gcccagcgag | cacgacggcg |    2040 |

```
aatacctgta cgacatcgac aggaaacagt gcgtcaagaa agaactagtc actgggctag      2100
ggctcacagg cgagctggtg gatcctccct tccatgaatt cgcctacgag agtctgagaa      2160
cacgaccagc cgctccttac caagtaccaa ccataggggt gtatggcgtg ccaggatcag      2220
gcaagtctgg catcattaaa agcgcagtca ccaaaaaaga tctagtggtg agcgccaaga      2280
aagaaaactg tgcagaaatt ataagggacg tcaagaaaat gaagggctg acgtcaatg       2340 ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatccca acagtgcgg ttttttttaac atgatgtgcc     2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt ggggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgcttag    3480 tcctccacca taatgaacac ccacagagtg acttttcttc attcgtcagc aaattgaagg   3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggaccc atataaatac catcactatc     3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag acaacctgg cggagggtg tgcggagcgc     4140 tgtataagaa attcccggaa agcttcgatt tacagccgat cgaagtagga aaagcgcgac    4200
tggtcaaagg tgcagctaaa catatcattc atgccgtagg accaaacttc aacaaagttt   4260
cggaggttga aggtgacaaa cagttggcag aggcttatga gtccatcgct aagattgtca    4320
acgataacaa ttacaagtca gtagcgattc cactgttgtc caccggcatc ttttccggga    4380
```

```
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcg agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
```

```
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggttttattt tgtgtgactc cgtgaccggc acagcgtgcc    7260
gtgtggcaga cccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
ggcccctat aactctctac ggctaacctg aatggactac gacatagtct agtccgccaa    7560
gggcgcgccc acccagcggc cgcatacagc agcaattggc aagctgctta catagaactc    7620
gcggcgattg gcatgccgcc ttaaaatttt tattttattt ttcttttctt ttccgaatcg    7680
gattttgttt ttaatatttc aaaaaaaaaa aaaaaaaaa aaaaaaaaa aaaaaaaaa      7740
gaagagcgtt taaacacgtg atatctggcc tcatgggcct tcctttcact gcccgctttc    7800
cagtcgggaa acctgtcgtg ccagctgcat taacatggtc atagctgttt ccttgcgtat    7860
tgggcgctct ccgcttcctc gctcactgac tcgctgcgct cggtcgttcg ggtaaagcct    7920
ggggtgccta atgagcaaaa ggccagcaaa aggccaggaa ccgtaaaaag gccgcgttgc    7980
tggcgttttt ccataggctc cgcccccctg acgagcatca caaaaatcga cgctcaagtc    8040
agaggtggcg aaacccgaca ggactataaa gataccaggc gtttccccct ggaagctccc    8100
tcgtgcgctc tcctgttccg accctgccgc ttaccggata cctgtccgcc tttctccctt    8160
cgggaagcgt ggcgctttct catagctcac gctgtaggta tctcagttcg gtgtaggtcg    8220
ttcgctccaa gctgggctgt gtgcacgaac cccccgttca gcccgaccgc tgcgccttat    8280
ccggtaacta tcgtcttgag tccaacccgg taagacacga cttatcgcca ctggcagcag    8340
ccactggtaa caggattagc agagcgaggt atgtaggcgg tgctacagag ttcttgaagt    8400
ggtggcctaa ctacggctac actagaagaa cagtatttgg tatctgcgct ctgctgaagc    8460
cagttacctt cggaaaaaga gttggtagct cttgatccgg caaacaaacc accgctggta    8520
gcggtggttt ttttgtttgc aagcagcaga ttacgcgcag aaaaaaagga tctcaagaag    8580
atcctttgat cttttctacg gggtctgacg ctcagtggaa cgaaaactca cgttaaggga    8640
ttttggtcat gaatacacgg tgcctgactg cgttagcaat ttaactgtga taaactaccg    8700
cattaaagct tatcgatgat aagctgtcaa acatgagaat tcttagaaaa actcatcgag    8760
catcaaatga aactgcaatt tattcatatc aggattatca ataccatatt tttgaaaaag    8820
ccgtttctgt aatgaaggag aaaactcacc gaggcagttc cataggatgg caagatcctg    8880
gtatcggtct gcgattccga ctcgtccaac atcaatacaa cctattaatt tcccctcgtc    8940
aaaaataagg ttatcaagtg agaaatcacc atgagtgacg actgaatccg gtgagaatgg    9000
caaaagctta tgcatttctt tccagacttg ttcaacaggc cagccattac gctcgtcatc    9060
aaaatcactc gcatcaacca aaccgttatt cattcgtgat tgcgcctgag cgagacgaaa    9120
```

```
tacgcgatcg ctgttaaaag gacaattaca aacaggaatc gaatgcaacc ggcgcaggaa      9180
cactgccagc gcatcaacaa tatttcacc tgaatcagga tattcttcta atacctggaa       9240
tgctgttttc ccggggatcg cagtggtgag taaccatgca tcatcaggag tacggataaa      9300
atgcttgatg gtcggaagag gcataaaattc cgtcagccag tttagtctga ccatctcatc    9360
tgtaacatca ttggcaacgc taccttgcc atgtttcaga aacaactctg gcgcatcggg      9420
cttcccatac aatcgataga ttgtcgcacc tgattgcccg acattatcgc gagcccattt     9480
atacccatat aaatcagcat ccatgttgga atttaatcgc ggcctcgagc aagacgtttc     9540
ccgttgaata tggctcataa cacccctttgt attactgttt atgtaagcag acagtttat    9600 tgttcatgag cggatacata tttgaatgta tttagaaaaa taaacaaata ggggttccgc     9660
gcacatttcc ccgaaaagtg ccacctaaat tgtaagcgtt aatattttgt taaaattcgc    9720
gttaaatttt tgttaaatca gctcatttt taaccaatag gccgaaatcg gcaaaatccc     9780
ttataaatca aaagaataga ccgagatagg gttgagtggc cgctacaggg cgctcccatt    9840
cgccattcag gctgcgcaac tgttgggaag ggcgtttcgg tgcgggcctc ttcgctatta    9900
cgccagctgg cgaaagggg atgtgctgca aggcgattaa gttgggtaac gccagggttt    9960
tcccagtcac acgcgtaata cgactcacta tag                                   9993
```

<210> SEQ ID NO 2
<211> LENGTH: 1171
<212> TYPE: PRT
<213> ORGANISM: Artificial
<220> FEATURE:
<223> OTHER INFORMATION: synthetic polypeptide

<400> SEQUENCE: 2

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Ala Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Gly Gly Thr Gly Gly Ser Thr
        195                 200                 205

-continued

```
Thr Pro Ile Val His Leu Lys Gly Asp Ala Asn Thr Leu Lys Cys Leu
210             215                 220
Arg Tyr Arg Phe Lys Lys His Cys Thr Leu Tyr Thr Ala Val Ser Ser
225                 230                 235                 240
Thr Trp His Trp Thr Gly His Asn Val Lys His Lys Ser Ala Ile Val
                245                 250                 255
Thr Leu Thr Tyr Asp Ser Glu Trp Gln Arg Asp Gln Phe Leu Ser Gln
                260                 265                 270
Val Lys Ile Pro Lys Thr Ile Thr Val Ser Thr Gly Phe Met Ser Ile
                275                 280                 285
Gly Gly Gly Gly Met Gln Thr Pro Lys Glu Thr Leu Ser Glu Arg
290                 295                 300
Leu Ser Cys Val Gln Asp Lys Ile Ile Asp His Tyr Glu Asn Asp Ser
305                 310                 315                 320
Lys Asp Ile Asp Ser Gln Ile Gln Tyr Trp Gln Leu Ile Arg Trp Glu
                325                 330                 335
Asn Ala Ile Phe Phe Ala Ala Arg Glu His Gly Ile Gln Thr Leu Asn
                340                 345                 350
His Gln Val Val Pro Ala Tyr Asn Ile Ser Lys Ser Lys Ala His Lys
                355                 360                 365
Ala Ile Glu Leu Gln Met Ala Leu Gln Gly Leu Ala Gln Ser Ala Tyr
370                 375                 380
Lys Thr Glu Asp Trp Thr Leu Gln Asp Thr Cys Glu Glu Leu Trp Asn
385                 390                 395                 400
Thr Glu Pro Thr His Cys Phe Ala Lys Gly Gly Gln Thr Val Gln Val
                405                 410                 415
Tyr Phe Asp Gly Asn Lys Asp Asn Cys Met Thr Tyr Val Ala Trp Asp
                420                 425                 430
Ser Val Tyr Tyr Met Thr Asp Ala Gly Thr Trp Asp Lys Thr Ala Thr
                435                 440                 445
Cys Val Ser His Arg Gly Leu Tyr Tyr Val Lys Glu Gly Tyr Asn Thr
450                 455                 460
Phe Tyr Ile Glu Phe Lys Ser Glu Cys Glu Lys Tyr Gly Asn Thr Gly
465                 470                 475                 480
Thr Trp Glu Val His Phe Gly Asn Asn Val Ile Asp Cys Asn Asp Ser
                485                 490                 495
Met Cys Ser Gly Gly Thr Gly Gly Ser Thr Thr Pro Ile Ile His Leu
                500                 505                 510
Lys Gly Asp Arg Asn Ser Leu Lys Cys Leu Arg Tyr Arg Leu Arg Lys
                515                 520                 525
His Ser Asp His Tyr Arg Asp Ile Ser Ser Thr Trp His Trp Thr Gly
530                 535                 540
Ala Gly Asn Glu Lys Thr Gly Ile Leu Thr Val Thr Tyr His Ser Glu
545                 550                 555                 560
Thr Gln Arg Thr Lys Phe Leu Asn Thr Val Ala Ile Pro Asp Ser Val
                565                 570                 575
Gln Ile Leu Val Gly Tyr Met Thr Met Gly Gly Gly Gly Met Glu
                580                 585                 590
Thr Leu Ser Gln Arg Leu Asn Val Cys Gln Asp Lys Ile Leu Glu His
                595                 600                 605
Tyr Glu Asn Asp Ser Lys Arg Leu Cys Asp His Ile Asp Tyr Trp Lys
610                 615                 620
His Ile Arg Leu Glu Cys Val Leu Met Tyr Lys Ala Arg Glu Met Gly
```

-continued

```
625                 630                 635                 640
Ile His Ser Ile Asn His Gln Val Val Pro Ala Leu Ser Val Ser Lys
                645                 650                 655

Ala Lys Ala Leu Gln Ala Ile Glu Leu Gln Met Met Leu Glu Thr Leu
                660                 665                 670

Asn Asn Thr Glu Tyr Lys Asn Glu Asp Trp Thr Met Gln Gln Thr Ser
                675                 680                 685

Leu Glu Leu Tyr Leu Thr Ala Pro Thr Gly Cys Leu Ala Lys His Gly
                690                 695                 700

Tyr Thr Val Glu Val Gln Phe Asp Gly Asp Val His Asn Thr Met His
705                 710                 715                 720

Tyr Thr Asn Trp Lys Phe Ile Tyr Leu Cys Ile Asp Gly Gln Cys Thr
                725                 730                 735

Val Val Glu Gly Gln Val Asn Cys Lys Gly Ile Tyr Tyr Val His Glu
                740                 745                 750

Gly His Ile Thr Tyr Phe Val Asn Phe Thr Glu Glu Ala Lys Lys Tyr
                755                 760                 765

Gly Thr Gly Lys Lys Trp Glu Val His Ala Gly Gly Gln Val Ile Val
                770                 775                 780

Phe Pro Glu Ser Val Phe Ser Gly Gly Thr Gly Gly Ser Thr Thr Pro
785                 790                 795                 800

Ile Ile His Leu Lys Gly Asp Ala Asn Ile Leu Lys Cys Leu Arg Tyr
                805                 810                 815

Arg Leu Ser Lys Tyr Lys Gln Leu Tyr Glu Gln Val Ser Ser Thr Trp
                820                 825                 830

His Trp Thr Cys Thr Asp Gly Lys His Lys Asn Ala Ile Val Thr Leu
                835                 840                 845

Thr Tyr Ile Ser Thr Ser Gln Arg Asp Asp Phe Leu Asn Thr Val Lys
                850                 855                 860

Ile Pro Asn Thr Val Ser Val Ser Thr Gly Tyr Met Thr Ile Gly Gly
865                 870                 875                 880

Gly Gly Gly Met Glu Glu Ile Ser Ala Arg Leu Asn Ala Val Gln Glu
                885                 890                 895

Lys Ile Leu Asp Leu Tyr Glu Ala Asp Lys Thr Asp Leu Pro Ser Gln
                900                 905                 910

Ile Glu His Trp Lys Leu Ile Arg Met Glu Cys Ala Leu Leu Tyr Thr
                915                 920                 925

Ala Lys Gln Met Gly Phe Ser His Leu Cys His Gln Val Val Pro Ser
930                 935                 940

Leu Leu Ala Ser Lys Thr Lys Ala Phe Gln Val Ile Glu Leu Gln Met
945                 950                 955                 960

Ala Leu Glu Thr Leu Ser Lys Ser Gln Tyr Ser Thr Ser Gln Trp Thr
                965                 970                 975

Leu Gln Gln Thr Ser Leu Glu Val Trp Leu Cys Glu Pro Pro Lys Cys
                980                 985                 990

Phe Ala Lys Gln Gly Glu Thr Val Thr Val Gln Tyr Asp Asn Asp Lys
                995                1000                1005

Lys Asn Thr Met Asp Tyr Thr Asn Trp Gly Glu Ile Tyr Ile Ile
1010                1015                1020

Glu Glu Asp Thr Cys Thr Met Val Thr Gly Lys Val Asp Tyr Ile
1025                1030                1035

Gly Met Tyr Tyr Ile His Asn Cys Glu Lys Val Tyr Phe Lys Tyr
1040                1045                1050
```

```
Phe Lys Glu Asp Ala Ala Lys Tyr Ser Lys Thr Gln Met Trp Glu
    1055                1060                1065

Val His Val Gly Gly Gln Val Ile Val Cys Pro Thr Ser Ile Ser
    1070                1075                1080

Ser Gly Gly Thr Gly Gly Ser Val Ala Pro Ile Val His Leu Lys
    1085                1090                1095

Gly Glu Ser Asn Ser Leu Lys Cys Leu Arg Tyr Arg Leu Lys Pro
    1100                1105                1110

Tyr Lys Glu Leu Tyr Ser Ser Met Ser Ser Thr Trp His Trp Thr
    1115                1120                1125

Ser Asp Asn Lys Asn Ser Lys Asn Gly Ile Val Thr Val Thr Phe
    1130                1135                1140

Val Thr Glu Gln Gln Gln Gln Met Phe Leu Gly Thr Val Lys Ile
    1145                1150                1155

Pro Pro Thr Val Gln Ile Ser Thr Gly Phe Met Thr Leu
    1160                1165                1170

<210> SEQ ID NO 3
<211> LENGTH: 3519
<212> TYPE: DNA
<213> ORGANISM: Artificial
<220> FEATURE:
<223> OTHER INFORMATION: synthetic polynucleotide

<400> SEQUENCE: 3
atggaaaccc tgtgtcagag gctgaatgtg tgtcaagaca aaatcctgac ccactacgag      60
aatgactcca cagacctgag ggaccacatc gattactgga agcacatgag gctcgagtgc     120
gccatctact ataaggccag agagatgggc tttaagcata tcaatcatca agtcgtgccc     180
acactggccg tgagcaagaa caaggccctg caagctattg agctccaact gaccctcgag     240
accatctaca cagccagta cagcaacgag aaatggacac tgcaggatgt gtccctcgaa     300
gtgtacctca cagcccctac cggatgtatc gccaagcacg gctacacagt ggaagtgcag     360
tttgacggcg atatctgcaa tacaatgcat tacaccaact ggacccacat ctatatctgc     420
gaggaagcta gcgtcacagt ggtggagggc caggtcgact attacggcct ctattacgtg     480
catgagggca tcaggaccta ctttgtgcag tttaaggacg atgccgaaaa atacagcaaa     540
aataaagtgt gggaagtcca tgccggaggc caggtgatcc tgtgtcccac ctccgtcttt     600
agcggaggca ccggcggcag cacaaccct atcgtccacc tgaaaggaga tgccaacaca     660
ctgaaatgtc tcaggtacag gttcaagaag cactgtaccc tgtatacagc cgtcagcagc     720
acatggcatt ggaccggcca caacgtcaag cataagagcg ccatcgtgac cctcacatac     780
gatagcgaat ggcaaaggga ccagttcctg agccaggtca gatcccaa gacaatcaca     840 gtgtccaccg gctttatgtc catcggcgga ggaggcggaa tgcagacccc taaggagacc     900
ctcagcgaaa gactcagctg cgtgcaggat aaaatcattg accattatga gaatgattcc     960
aaggacatcg atagccagat tcaatactgg cagctgatca ggtgggagaa cgccatcttc    1020
ttcgccgcca gggagcacgg cattcaaacc ctcaaccatc aggtggtgcc cgcttacaac    1080
atcagcaaga gcaaagccca taggccatt gagctgcaga tggccctcca gggcctggct    1140
cagagcgctt ataaaaccga agactggacc ctgcaagaca catgcgagga gctgtggaac    1200
accgaaccca cacactgctt cgccaaaggc ggcaaacag tgcaggtgta cttcgatggc    1260
aacaaggaca attgcatgac ctacgtcgct tgggactccg tctattacat gacagatgcc    1320
```

|  |  |
|---|---|
| ggcacatggg acaagaccgc cacatgcgtc agccacaggg gactgtacta cgtgaaagag | 1380 |
| ggatacaata ccttctacat cgagttcaaa tccgagtgtg agaagtacgg caatacaggc | 1440 |
| acctgggagg tgcatttcgg caataatgtg attgactgca acgatagcat gtgtagcggc | 1500 |
| ggaaccggcg gttctacaac ccccatcatc cacctgaagg gcgaccgtaa ttctctgaag | 1560 |
| tgcctgaggt acagactcag gaagcacagc gaccattaca gggatatctc cagcacctgg | 1620 |
| cactggacag gcgctggcaa tgaaaagaca ggaatcctca cagtgaccta ccactccgag | 1680 |
| acccagagga caaaattcct gaacaccgtg gccatccccg acagcgtcca gattctggtg | 1740 |
| ggctatatga ccatgggagg aggcggaggc atggagacac tcagccaaag gctcaacgtg | 1800 |
| tgccaggata agatcctgga gcactacgag aacgacagca aaaggctgtg tgatcatatc | 1860 |
| gactactgga agcatatcag gctggagtgc gtcctgatgt acaaggccag agaaatggga | 1920 |
| atccattcca tcaaccacca agtggtccct gctctctccg tcagcaaagc caaggctctg | 1980 |
| caggctattg aactgcaaat gatgctggag accctcaaca acaccgagta caaaaacgag | 2040 |
| gattggacca tgcaacagac ctccctcgaa ctctatctga cagcccccac aggctgcctc | 2100 |
| gccaagcatg gctacaccgt ggaggtgcaa ttcgacggcg atgtccacaa cacaatgcac | 2160 |
| tacacaaact ggaagttcat ctacctctgc atcgacggac agtgtaccgt cgtggaagga | 2220 |
| caagtgaact gcaagggcat ctactacgtc cacgagggcc acattaccta cttcgtgaac | 2280 |
| ttcaccgagg aagccaagaa atacggcacc ggaaagaagt gggaggtcca cgccggcggc | 2340 |
| caagtcattg tgtttcctga aagcgtcttc agcggaggca caggcggctc caccacaccc | 2400 |
| atcatccatc tgaaaggcga tgccaacatc ctcaaatgcc tcaggtatag gctgagcaaa | 2460 |
| tacaaacaac tgtacgaaca agtgtcctcc acctggcatt ggacatgtac cgacggcaag | 2520 |
| cacaaaaacg ccatcgtcac cctgacctac attagcacca gccagagaga cgacttcctc | 2580 |
| aatacagtga agatccctaa caccgtgagc gtgagcaccg gctacatgac aattggaggc | 2640 |
| ggcggcggca tggaagagat ttccgccaga ctcaacgccg tgcaggagaa atcctggac | 2700 |
| ctctacgagg ccgataaaac cgatctcccc tcccagattg agcactggaa gctgatcaga | 2760 |
| atggaatgcg ccctgctcta caccgccaaa cagatgggct tctcccacct ctgccaccag | 2820 |
| gtcgtgccct ccctcctggc ttccaagacc aaggccttcc aggtgatcga gctgcaaatg | 2880 |
| gctctcgaaa ccctgtccaa gagccagtat agcacctccc aatggaccct gcagcaaacc | 2940 |
| tccctggaag tctggctgtg tgaaccccc aaatgcttcg ctaagcaagg cgagaccgtc | 3000 |
| acagtccagt acgacaatga taagaagaat accatggact ataccaactg gggcgagatc | 3060 |
| tacattatcg aggaggatac ctgcaccatg gtgaccggca aggtggacta tattggaatg | 3120 |
| tactatatcc ataactgcga gaaagtctat ttcaagtatt tcaaagagga cgccgccaaa | 3180 |
| tacagcaaga cccagatgtg ggaggtgcac gtcggaggac aggtgattgt ctgtcctacc | 3240 |
| tccatctcct ccggcggaac aggcggaagc gtggccccta ttgtccatct caagggcgag | 3300 |
| agcaactccc tgaagtgtct caggtataga ctgaagccct acaaggagct gtactccagc | 3360 |
| atgagctcca cctggcactg gaccagcgat aacaagaaca gcaagaacgg catcgtgaca | 3420 |
| gtgacattcg tgacagaaca gcagcagcag atgttcctcg gcacagtgaa aattcccccc | 3480 |
| accgtgcaaa ttagcaccgg cttcatgaca ctgtgatga | 3519 |

<210> SEQ ID NO 4
<211> LENGTH: 1046
<212> TYPE: PRT
<213> ORGANISM: Artificial

```
<220> FEATURE:
<223> OTHER INFORMATION: synthetic polypeptide

<400> SEQUENCE: 4

Met Lys Met Gln Thr Pro Lys Glu Ser Leu Ser Glu Arg Leu Ser Ala
1               5                   10                  15

Leu Gln Asp Lys Ile Leu Asp His Tyr Glu Asn Asp Ser Lys Asp Ile
                20                  25                  30

Asn Ser Gln Ile Ser Tyr Trp Gln Leu Ile Arg Leu Glu Asn Ala Ile
            35                  40                  45

Leu Phe Thr Ala Arg Glu His Gly Ile Thr Lys Leu Asn His Gln Val
    50                  55                  60

Val Pro Pro Ile Asn Ile Ser Lys Ser Lys Ala His Lys Ala Ile Glu
65                  70                  75                  80

Leu Gln Met Ala Leu Lys Gly Leu Ala Gln Ser Lys Tyr Asn Asn Glu
                85                  90                  95

Glu Trp Thr Leu Gln Asp Thr Cys Glu Glu Leu Trp Asn Thr Glu Pro
            100                 105                 110

Ser Gln Cys Phe Ala Lys Gly Gly Lys Thr Val His Val Tyr Phe Asp
        115                 120                 125

Gly Asn Lys Asp Asn Cys Met Asn Tyr Val Val Trp Asp Ser Ile Tyr
130                 135                 140

Tyr Ile Thr Glu Thr Gly Ile Trp Asp Lys Thr Ala Ala Cys Val Ser
145                 150                 155                 160

Tyr Trp Gly Val Tyr Tyr Ile Lys Asp Gly Asp Thr Thr Tyr Tyr Val
                165                 170                 175

Gln Phe Lys Ser Glu Cys Glu Lys Tyr Gly Asn Ser Asn Thr Trp Glu
            180                 185                 190

Val Gln Tyr Gly Gly Asn Val Ile Asp Cys Asn Asp Ser Met Cys Ser
        195                 200                 205

Gly Gly Thr Gly Gly Ser Thr Thr Pro Ile Ile His Leu Lys Gly Asp
210                 215                 220

Lys Asn Ser Leu Lys Cys Leu Arg Tyr Arg Leu Arg Lys Tyr Ala Asp
225                 230                 235                 240

His Tyr Ser Glu Ile Ser Ser Thr Trp His Trp Thr Gly Cys Asn Lys
                245                 250                 255

Asn Thr Gly Ile Leu Thr Val Thr Tyr Asn Ser Glu Val Gln Arg Asn
            260                 265                 270

Thr Phe Leu Asp Val Val Thr Ile Pro Asn Ser Val Gln Ile Ser Val
        275                 280                 285

Gly Tyr Met Thr Ile Gly Gly Gly Gly Met Glu Ser Ile Pro Ala
290                 295                 300

Arg Leu Asn Ala Val Gln Glu Lys Ile Leu Leu Tyr Glu Ala Asp
305                 310                 315                 320

Ser Asn Asp Leu Asn Ala Gln Ile Glu His Trp Lys Leu Thr Arg Met
                325                 330                 335

Glu Cys Val Leu Phe Tyr Lys Ala Lys Glu Leu Gly Ile Thr His Ile
            340                 345                 350

Gly His Gln Val Val Pro Pro Met Ala Val Ser Lys Ala Lys Ala Cys
        355                 360                 365

Gln Ala Ile Glu Leu Gln Leu Ala Leu Glu Ala Leu Asn Lys Thr Gln
370                 375                 380

Tyr Ser Thr Asp Gly Trp Thr Leu Gln Gln Thr Ser Leu Glu Met Trp
385                 390                 395                 400
```

```
Arg Ala Glu Pro Gln Lys Tyr Phe Ala Lys His Gly Tyr Thr Ile Thr
            405                 410                 415
Val Gln Tyr Asp Asn Asp Lys Asn Asn Thr Met Asp Tyr Thr Asn Trp
            420                 425                 430
Lys Glu Ile Tyr Leu Leu Gly Glu Cys Glu Cys Thr Ile Val Glu Gly
            435                 440                 445
Gln Val Asp Tyr Tyr Gly Leu Tyr Tyr Trp Cys Asp Gly Glu Lys Ile
            450                 455                 460
Tyr Phe Val Lys Phe Ser Asn Asp Ala Lys Gln Tyr Cys Val Thr Gly
465                 470                 475                 480
Val Trp Glu Val His Val Gly Gly Gln Val Ile Val Cys Pro Ala Ser
            485                 490                 495
Val Ser Ser Gly Gly Thr Gly Gly Ser Thr Ala Pro Ile Ile His Leu
            500                 505                 510
Lys Gly Asp Pro Asn Ser Leu Lys Cys Leu Arg Tyr Arg Val Lys Thr
            515                 520                 525
His Lys Ser Leu Tyr Val Gln Ile Ser Ser Thr Trp His Trp Thr Ser
            530                 535                 540
Asn Glu Cys Thr Asn Asn Lys Leu Gly Ile Val Thr Ile Thr Tyr Ser
545                 550                 555                 560
Asp Glu Thr Gln Arg Gln Gln Phe Leu Lys Thr Val Lys Ile Pro Asn
            565                 570                 575
Thr Val Gln Val Ile Gln Gly Val Met Ser Leu Gly Gly Gly Gly Gly
            580                 585                 590
Met Glu Glu Ile Ser Ala Arg Leu Ser Ala Val Gln Asp Lys Ile Leu
            595                 600                 605
Asp Ile Tyr Glu Ala Asp Lys Asn Asp Leu Thr Ser Gln Ile Glu His
            610                 615                 620
Trp Lys Leu Ile Arg Met Glu Cys Ala Ile Met Tyr Thr Ala Arg Gln
625                 630                 635                 640
Met Gly Ile Ser His Leu Cys His Gln Val Val Pro Ser Leu Val Ala
            645                 650                 655
Ser Lys Thr Lys Ala Phe Gln Val Ile Glu Leu Gln Met Ala Leu Glu
            660                 665                 670
Thr Leu Asn Ala Ser Pro Tyr Lys Thr Asp Glu Trp Thr Leu Gln Gln
            675                 680                 685
Thr Ser Leu Glu Val Trp Leu Ser Glu Pro Gln Lys Cys Phe Ala Lys
            690                 695                 700
Lys Gly Ile Thr Val Thr Val Gln Tyr Asp Asn Asp Lys Ala Asn Thr
705                 710                 715                 720
Met Asp Tyr Thr Asn Trp Ser Glu Ile Tyr Ile Ile Glu Glu Thr Thr
            725                 730                 735
Cys Thr Leu Val Ala Gly Glu Val Asp Tyr Val Gly Leu Tyr Tyr Ile
            740                 745                 750
His Gly Asn Glu Lys Thr Tyr Phe Lys Tyr Phe Lys Glu Asp Ala Lys
            755                 760                 765
Lys Tyr Ser Lys Thr Gln Leu Trp Glu Val His Val Gly Ser Arg Val
            770                 775                 780
Ile Val Cys Pro Thr Ser Ile Pro Ser Gly Gly Thr Gly Gly Ser Val
785                 790                 795                 800
Ser Pro Ile Val His Leu Lys Gly Asp Pro Asn Ser Leu Lys Cys Leu
            805                 810                 815
```

```
Arg Tyr Arg Leu Lys Pro Phe Lys Asp Leu Tyr Cys Asn Met Ser Ser
            820                 825                 830

Thr Trp His Trp Thr Ser Asp Asp Lys Gly Asp Lys Val Gly Ile Val
            835                 840                 845

Thr Val Thr Tyr Thr Thr Glu Thr Gln Arg Gln Leu Phe Leu Asn Thr
            850                 855                 860

Val Lys Ile Pro Pro Thr Val Gln Ile Ser Thr Gly Val Met Ser Leu
865                 870                 875                 880

Gly Gly Gly Gly Gly Arg Ala His Tyr Asn Ile Val Thr Phe Cys Cys
                885                 890                 895

Lys Cys Asp Ser Thr Leu Arg Leu Cys Val Gln Ser Thr His Val Asp
            900                 905                 910

Ile Arg Thr Leu Glu Asp Leu Leu Met Gly Thr Leu Gly Ile Val Cys
            915                 920                 925

Pro Ile Cys Ser Gln Lys Pro Thr Leu His Glu Tyr Met Leu Asp Leu
            930                 935                 940

Gln Pro Glu Thr Thr Asp Leu Tyr Gly Tyr Gln Leu Gly Gly Gly
945                 950                 955                 960

Gly Gly Arg His Thr Met Leu Cys Met Cys Cys Lys Cys Glu Ala Arg
                965                 970                 975

Ile Lys Leu Val Val Glu Ser Ser Ala Asp Asp Leu Arg Ala Phe Gln
            980                 985                 990

Gln Leu Phe Leu Asn Thr Leu Ser Phe Val Cys Pro Trp Cys Ala Ser
            995                 1000                1005

Gln Gln  Thr Leu Gln Asp Ile  Val Leu His Leu Glu  Pro Gln Asn
    1010                1015                 1020

Glu Ile  Pro Val Asp Leu Leu  Gly His Gln Gln Leu  Ser Asp Ser
    1025                1030                 1035

Glu Glu  Glu Asn Asp Glu Ile  Asp
    1040                1045

<210> SEQ ID NO 5
<211> LENGTH: 3144
<212> TYPE: DNA
<213> ORGANISM: Artificial
<220> FEATURE:
<223> OTHER INFORMATION: synthetic polynucleotide

<400> SEQUENCE: 5
atgaagatgc agacccccaa agaatccctg tccgagaggc tcagcgccct gcaggataag      60
atcctcgacc actacgaaaa cgactccaag gacatcaact cccagatctc ctattggcag     120
ctcatcaggc tggagaacgc tatcctgttc acagccagag agcacggcat taccaagctg     180
aaccatcaag tggtcccccc tattaacatc tccaaaagca aggcccacaa ggccatcgag     240
ctgcaaatgg ccctcaaagg cctggcccag tccaagtata caacgagga gtggaccctg     300 caggatacat gcgaggagct gtggaacacc gagccctccc aatgtttcgc caagggcggc     360
aagacagtgc atgtctattt cgatggcaat aaagataact gcatgaacta cgtggtgtgg     420
gacagcattt actacattac cgaaaccggc atttgggaca agaccgctgc ttgcgtcagc     480
tattggggcg tgtactacat taaggatggc gataccacct actacgtcca gttcaagtcc     540
gaatgcgaga aatatggcaa ttccaacacc tgggaagtgc agtatggagg caatgtgatc     600
gactgcaacg actccatgtg ttccggagga acaggaggaa gcacaacccc catcatccat     660
ctgaagggag ataagaacag cctcaagtgc ctgaggtaca ggctgaggaa atacgctgac     720
```

```
cactactccg aaatctcctc cacatggcac tggaccggct gcaataagaa caccggaatc    780
ctgaccgtga cctacaactc cgaggtgcag aggaacacct tcctggatgt cgtgacaatc    840
cccaattccg tccagattag cgtcggctac atgacaatcg gcggaggagg cggaatggaa    900
agcattcccg ccaggctgaa tgctgtgcag gaaaaaatcc tcgatctgta cgaagccgac    960
tccaacgacc tgaacgccca gatcgaacac tggaaactga ccaggatgga atgcgtcctg   1020
ttttataaag ccaaggagct cggcatcacc catatcggcc accaagtcgt ccctcccatg   1080
gccgtgtcca aggccaaggc ctgtcaggct attgagctcc agctggccct ggaggccctc   1140
aataaaaccc aatatagcac agacggctgg accctccagc aaaccagcct cgagatgtgg   1200
agggccgaac cccagaaata ctttgccaaa cacggctata caatcacagt gcagtacgat   1260
aatgacaaga ataataccat ggactacaca aattggaaag agatctacct gctcggcgag   1320
tgtgagtgca ccatcgtcga gggccaggtg gattactacg gcctgtacta ctggtgtgat   1380
ggcgaaaaga tctattttgt gaagttctcc aacgacgcta agcagtactg tgtcacaggc   1440
gtctgggagg tccacgtcgg aggccaggtg atcgtctgcc ctgctagcgt gagcagcggc   1500
ggaacaggag gctccaccgc tcccattatt catctgaaag gcgacccccaa ttccctgaag   1560
tgtctgaggt atagagtcaa gacccacaaa gcctctacg tgcagatcag cagcacatgg   1620
cactggacct ccaatgagtg tacaaataat aaactgggaa tcgtcacaat cacctacagc   1680
gatgagaccc aaaggcagca gttcctcaaa accgtcaaga tccccaatac cgtccaggtg   1740
atccaaggcg tcatgtcccct cggcggagga ggaggaatgg aagagatcag cgccaggctc   1800
agcgctgtgc aagacaaaat tctggacatc tacgaggctg acaagaacga tctcacatcc   1860
cagatcgagc actggaagct catcaggatg gagtgcgcca ttatgtacac cgccaggcaa   1920
atgggcatta gccacctgtg ccaccaagtg gtgccctccc tcgtcgcctc caagaccaaa   1980
gccttccagg tgatcgagct ccaaatggcc ctggagaccc tgaacgccag ccccctacaag   2040
acagacgagt ggacactgca gcagacctcc ctggaagtct ggctgtccga gccccagaag   2100
tgctttgcta agaagggcat caccgtgacc gtgcaatacg acaacgacaa ggccaacacc   2160
atggattata ccaactggag cgaaatctac atcatcgagg agaccacctg tacccctcgtg   2220
gccggcgagg tcgactacgt gggcctgtat tacatccacg gaaatgagaa aacatacttt   2280
aaatatttta aggaggacgc caaaaaatat agcaagacac aactgtggga ggtgcacgtc   2340
ggcagcaggg tgattgtgtg tcctaccagc atccctagcg gaggcacagg aggctccgtg   2400
tccccctattg tccacctgaa aggcgatcct aattccctga atgcctgag gtataggctc   2460
aaaccttca aggacctcta ctgcaacatg agctccacat ggcattggac aagcgacgat   2520
aagggcgata aggtgggcat tgtgaccgtg acctacacca ccgaaaccca gaggcaactg   2580
ttcctcaaca ccgtgaagat ccctcctaca gtccagatct ccaccggcgt gatgtccctg   2640
ggaggcggag gaggccgtgc tcattataac atcgtgacct ctgttgcaa atgtgactcc   2700
accctgagac tctgtgtcca gtccacccac gtggacatta gaaccctgga agacctgctc   2760
atgggcacac tgggcattgt gtgtcccatc tgctcccaga gcccaccct ccatgagtac   2820
atgctggacc tgcagcccga gaccacagac ctgtacggct accaacagct gggcggagga   2880
ggaggaagac acaccatgct gtgtatgtgc tgcaagtgtg aggctaggat caagctcgtg   2940
gtcgagagca gcgccgatga cctcagagcc tttcagcagc tgtttctgaa caccctgagc   3000
ttcgtgtgtc cttggtgtgc ctcccagcag acccctgcaag acatcgtcct gcatctggag   3060
ccccagaacg aaaattcccgt ggacctgctg ggccatcagc agctctccga ctccgaggag   3120
```
gaaaacgacg agatcgattg atga					3144

<210> SEQ ID NO 6
<211> LENGTH: 1861
<212> TYPE: PRT
<213> ORGANISM: Artificial
<220> FEATURE:
<223> OTHER INFORMATION: synthetic polypeptide

<400> SEQUENCE: 6

```
Met Ala Lys Ala Ala Met Leu Ala Lys Phe Lys Glu Leu Tyr Gly Val
1               5                   10                  15

Ser Phe Ser Glu Leu Val Arg Pro Phe Lys Ser Asn Lys Ser Thr Cys
            20                  25                  30

Cys Asp Trp Cys Ile Ala Ala Phe Gly Leu Thr Pro Ser Ile Ala Asp
        35                  40                  45

Ser Ile Lys Thr Leu Leu Gln Gln Tyr Cys Leu Tyr Leu His Ile Gln
    50                  55                  60

Ser Leu Ala Cys Ser Trp Gly Met Val Val Leu Leu Val Arg Tyr
65                  70                  75                  80

Lys Cys Gly Lys Asn Arg Glu Thr Ile Glu Lys Leu Leu Ser Lys Leu
                85                  90                  95

Leu Cys Val Ser Pro Met Cys Met Met Ile Glu Pro Pro Lys Leu Arg
            100                 105                 110

Ser Thr Ala Ala Ala Leu Tyr Trp Tyr Lys Thr Gly Ile Ser Asn Ile
        115                 120                 125

Ser Glu Val Tyr Gly Asp Thr Pro Glu Trp Ile Gln Arg Gln Thr Val
    130                 135                 140

Leu Gln His Ser Phe Asn Asp Cys Thr Phe Glu Leu Ser Gln Met Val
145                 150                 155                 160

Gln Trp Ala Tyr Asp Asn Asp Ile Val Asp Asp Ser Glu Ile Ala Tyr
                165                 170                 175

Lys Tyr Ala Gln Leu Ala Asp Thr Asn Ser Asn Ala Ser Ala Phe Leu
            180                 185                 190

Lys Ser Asn Ser Gln Ala Lys Ile Val Lys Asp Cys Ala Thr Met Cys
        195                 200                 205

Arg His Tyr Lys Arg Ala Glu Lys Lys Gln Met Ser Met Ser Gln Trp
    210                 215                 220

Ile Lys Tyr Arg Cys Asp Arg Val Asp Asp Gly Gly Asp Trp Lys Gln
225                 230                 235                 240

Ile Val Met Phe Leu Arg Tyr Gln Gly Val Glu Phe Met Ser Phe Leu
                245                 250                 255

Thr Ala Leu Lys Arg Phe Leu Gln Gly Ile Pro Lys Lys Asn Cys Ile
            260                 265                 270

Leu Leu Tyr Gly Ala Ala Asn Thr Asp Lys Ser Leu Phe Gly Met Ser
        275                 280                 285

Leu Met Lys Phe Leu Gln Gly Ser Val Ile Cys Phe Val Asn Ser Lys
    290                 295                 300

Ser His Phe Trp Leu Gln Pro Leu Ala Asp Ala Lys Ile Gly Met Leu
305                 310                 315                 320

Asp Asp Ala Thr Val Pro Cys Trp Asn Tyr Ile Asp Asp Asn Leu Arg
                325                 330                 335

Asn Ala Leu Asp Gly Asn Leu Val Ser Met Asp Val Lys His Arg Pro
            340                 345                 350
```

-continued

Leu Val Gln Leu Lys Cys Pro Pro Leu Leu Ile Thr Ser Asn Ile Asn
            355                 360                 365

Ala Gly Thr Asp Ser Arg Trp Pro Tyr Leu His Asn Arg Leu Val Val
    370                 375                 380

Phe Thr Phe Pro Asn Glu Phe Pro Phe Asp Glu Asn Gly Asn Pro Val
385                 390                 395                 400

Tyr Glu Leu Asn Asp Lys Asn Trp Lys Ser Phe Phe Ser Arg Thr Trp
                405                 410                 415

Ser Arg Leu Ser Leu Gly Gly Gly Gly Lys Gln Gly Ala Met Leu
            420                 425                 430

Ala Val Phe Lys Asp Thr Tyr Gly Leu Ser Phe Thr Asp Leu Val Arg
            435                 440                 445

Asn Phe Lys Ser Asp Lys Thr Thr Cys Thr Asp Trp Val Thr Ala Ile
    450                 455                 460

Phe Gly Val Asn Pro Thr Ile Ala Glu Gly Phe Lys Thr Leu Ile Gln
465                 470                 475                 480

Pro Phe Ile Leu Tyr Ala His Ile Gln Cys Leu Asp Cys Lys Trp Gly
                485                 490                 495

Val Leu Ile Leu Ala Leu Leu Arg Tyr Lys Cys Gly Lys Ser Arg Leu
            500                 505                 510

Thr Val Ala Lys Gly Leu Ser Thr Leu Leu His Val Pro Glu Thr Cys
    515                 520                 525

Met Leu Ile Gln Pro Pro Lys Leu Arg Ser Ser Val Ala Ala Leu Tyr
    530                 535                 540

Trp Tyr Arg Thr Gly Ile Ser Asn Ile Ser Glu Val Met Gly Asp Thr
545                 550                 555                 560

Pro Glu Trp Ile Gln Arg Leu Thr Ile Ile Gln His Gly Ile Asp Asp
                565                 570                 575

Ser Asn Phe Asp Leu Ser Glu Met Val Gln Trp Ala Phe Asp Asn Glu
            580                 585                 590

Leu Thr Asp Glu Ser Asp Met Ala Phe Glu Tyr Ala Leu Leu Ala Asp
            595                 600                 605

Ser Asn Ser Asn Ala Ala Ala Phe Leu Lys Ser Asn Cys Gln Ala Lys
    610                 615                 620

Tyr Leu Lys Asp Cys Ala Thr Met Cys Lys His Tyr Arg Arg Ala Gln
625                 630                 635                 640

Lys Arg Gln Met Asn Met Ser Gln Trp Ile Arg Phe Arg Cys Ser Lys
                645                 650                 655

Ile Asp Glu Gly Gly Asp Trp Arg Pro Ile Val Gln Phe Leu Arg Tyr
            660                 665                 670

Gln Gln Ile Glu Phe Ile Thr Phe Leu Gly Ala Leu Lys Ser Phe Leu
    675                 680                 685

Lys Gly Thr Pro Lys Lys Asn Cys Leu Val Phe Cys Gly Pro Ala Asn
    690                 695                 700

Thr Asp Lys Ser Tyr Phe Gly Met Ser Phe Ile His Phe Ile Gln Gly
705                 710                 715                 720

Ala Val Ile Ser Phe Val Asn Ser Thr Ser His Phe Trp Leu Glu Pro
                725                 730                 735

Leu Thr Asp Thr Lys Val Ala Met Leu Asp Asp Ala Thr Thr Thr Cys
            740                 745                 750

Trp Thr Tyr Phe Asp Thr Tyr Met Arg Asn Ala Leu Asp Gly Asn Pro
            755                 760                 765

Ile Ser Ile Asp Arg Lys His Lys Pro Leu Ile Gln Leu Lys Cys Pro

```
            770            775            780
Pro Ile Leu Leu Thr Thr Asn Ile His Pro Ala Lys Asp Asn Arg Trp
785                790                795                800

Pro Tyr Leu Glu Ser Arg Ile Thr Val Phe Glu Phe Pro Asn Ala Phe
                805                810                815

Pro Phe Asp Lys Asn Gly Asn Pro Val Tyr Glu Ile Asn Asp Lys Asn
                820                825                830

Trp Lys Cys Phe Phe Glu Arg Thr Trp Ser Arg Leu Asp Leu Gly Gly
                835                840                845

Gly Gly Gly Asp Pro Gln Glu Arg Pro Arg Lys Leu Pro Gln Leu Cys
                850                855                860

Thr Glu Leu Gln Thr Thr Ile His Asp Ile Ile Leu Glu Cys Val Tyr
865                870                875                880

Cys Lys Gln Gln Leu Leu Arg Arg Glu Val Tyr Asp Phe Ala Arg Arg
                885                890                895

Asp Leu Cys Ile Val Tyr Arg Asp Gly Asn Pro Tyr Ala Val Cys Asp
                900                905                910

Lys Cys Leu Lys Phe Tyr Ser Lys Ile Ser Glu Tyr Arg His Tyr Cys
                915                920                925

Tyr Ser Leu Tyr Gly Thr Thr Leu Glu Gln Gln Tyr Asn Lys Pro Leu
930                935                940

Cys Asp Leu Leu Ile Arg Arg Ile Asn Cys Gln Lys Pro Leu Cys Pro
945                950                955                960

Glu Glu Lys Gln Arg His Leu Asp Lys Lys Gln Arg Phe His Asn Ile
                965                970                975

Arg Gly Arg Trp Thr Gly Arg Cys Met Ser Cys Cys Arg Ser Ser Gly
                980                985                990

Gly Gly Gly Gly Asp Pro Thr Arg Pro Tyr Lys Leu Pro Asp Leu
                995                1000               1005

Cys Thr Glu Leu Asn Thr Ser Leu Gln Asp Ile Glu Ile Thr Cys
    1010               1015               1020

Val Tyr Cys Lys Thr Val Leu Glu Leu Thr Glu Val Phe Glu Phe
    1025               1030               1035

Ala Arg Lys Asp Leu Phe Val Val Tyr Arg Asp Ser Ile Pro His
    1040               1045               1050

Ala Ala Cys His Lys Cys Ile Asp Phe Tyr Ser Arg Ile Arg Glu
    1055               1060               1065

Leu Arg His Tyr Ser Asp Ser Val Tyr Gly Asp Thr Leu Glu Lys
    1070               1075               1080

Leu Thr Asn Thr Gly Leu Tyr Asn Leu Leu Ile Arg Arg Leu Arg
    1085               1090               1095

Cys Gln Lys Pro Leu Asn Pro Ala Glu Lys Leu Arg His Leu Asn
    1100               1105               1110

Glu Lys Arg Arg Phe His Asn Ile Ala Gly His Tyr Arg Gly Gln
    1115               1120               1125

Cys His Ser Cys Cys Asn Arg Ala Gly Gly Gly Gly Asp Thr
    1130               1135               1140

Glu Glu Lys Pro Arg Thr Leu His Asp Leu Cys Gln Ala Leu Glu
    1145               1150               1155

Thr Thr Ile His Asn Ile Glu Leu Gln Cys Val Glu Cys Lys Lys
    1160               1165               1170

Pro Leu Gln Arg Ser Glu Val Tyr Asp Phe Ala Arg Ala Asp Leu
    1175               1180               1185
```

```
Thr Val Val Tyr Arg Glu Gly Asn Pro Phe Gly Ile Cys Lys Leu
    1190            1195            1200

Cys Leu Arg Phe Leu Ser Lys Ile Ser Glu Tyr Arg His Tyr Asn
    1205            1210            1215

Tyr Ser Val Tyr Gly Asn Thr Leu Glu Gln Thr Val Lys Lys Pro
    1220            1225            1230

Leu Asn Glu Ile Leu Ile Arg Arg Ile Ile Cys Gln Arg Pro Leu
    1235            1240            1245

Cys Pro Gln Glu Lys Lys Arg His Val Asp Leu Asn Lys Arg Phe
    1250            1255            1260

His Asn Ile Ser Gly Arg Trp Ala Gly Arg Cys Ala Ala Cys Trp
    1265            1270            1275

Arg Ser Arg Gly Gly Gly Gly Asp Pro Lys Gln Arg Pro Tyr
    1280            1285            1290

Lys Leu Pro Asp Leu Cys Thr Glu Leu Asn Thr Ser Leu Gln Asp
    1295            1300            1305

Val Ser Ile Ala Cys Val Tyr Cys Lys Ala Thr Leu Glu Arg Thr
    1310            1315            1320

Glu Val Tyr Gln Phe Ala Arg Lys Asp Leu Cys Ile Val Tyr Arg
    1325            1330            1335

Asp Cys Ile Ala Tyr Ala Ala Cys His Lys Cys Ile Asp Phe Tyr
    1340            1345            1350

Ser Arg Ile Arg Glu Leu Arg Tyr Tyr Ser Asn Ser Val Tyr Gly
    1355            1360            1365

Glu Thr Leu Glu Lys Ile Thr Asn Thr Glu Leu Tyr Asn Leu Leu
    1370            1375            1380

Ile Arg Arg Leu Arg Cys Gln Lys Pro Leu Asn Pro Ala Glu Lys
    1385            1390            1395

Arg Arg His Leu Lys Asp Lys Arg Arg Phe His Ser Ile Ala Gly
    1400            1405            1410

Gln Tyr Arg Gly Gln Cys Asn Thr Cys Cys Asp Gln Ala Gly Gly
    1415            1420            1425

Gly Gly Gly Asp Pro Ala Thr Arg Pro Arg Thr Leu His Glu Leu
    1430            1435            1440

Cys Glu Val Leu Glu Glu Ser Val His Glu Ile Arg Leu Gln Cys
    1445            1450            1455

Val Gln Cys Lys Lys Glu Leu Gln Arg Arg Glu Val Tyr Lys Phe
    1460            1465            1470

Leu Arg Thr Asp Leu Arg Ile Val Tyr Arg Asp Asn Asn Pro Tyr
    1475            1480            1485

Gly Val Cys Ile Met Cys Leu Arg Phe Leu Ser Lys Ile Ser Glu
    1490            1495            1500

Tyr Arg His Tyr Gln Tyr Ser Leu Tyr Gly Lys Thr Leu Glu Glu
    1505            1510            1515

Arg Val Lys Lys Pro Leu Ser Glu Ile Thr Ile Arg Arg Ile Ile
    1520            1525            1530

Cys Gln Thr Pro Leu Cys Pro Glu Glu Lys Glu Arg His Val Asn
    1535            1540            1545

Ala Asn Lys Arg Phe His Asn Ile Met Gly Arg Trp Thr Gly Arg
    1550            1555            1560

Cys Ser Glu Cys Trp Arg Pro Arg Gly Gly Gly Gly Asp Ala
    1565            1570            1575
```

| | | | | | | | | | | |
|---|---|---|---|---|---|---|---|---|---|---|
| Glu | Glu | Lys | Pro | Arg | Thr | Leu | His | Asp | Leu | Cys | Gln | Ala | Leu | Glu |
| 1580 | | | | | 1585 | | | | | 1590 |

Thr Ser Val His Glu Ile Glu Leu Lys Cys Val Glu Cys Lys Lys
    1595                1600                1605

Thr Leu Gln Arg Ser Glu Val Tyr Asp Phe Val Arg Ala Asp Leu
    1610                1615                1620

Arg Ile Val Tyr Arg Asp Gly Asn Pro Phe Ala Val Cys Lys Val
    1625                1630                1635

Cys Leu Arg Leu Leu Ser Lys Ile Ser Glu Tyr Arg His Tyr Asn
    1640                1645                1650

Tyr Ser Leu Tyr Gly Asp Thr Leu Glu Gln Thr Leu Lys Lys Cys
    1655                1660                1665

Leu Asn Glu Ile Leu Ile Arg Arg Ile Ile Cys Gln Arg Pro Leu
    1670                1675                1680

Cys Pro Gln Glu Lys Lys Arg His Val Asp Leu Asn Lys Arg Phe
    1685                1690                1695

His Asn Ile Ser Gly Arg Trp Thr Gly Arg Cys Ala Val Cys Trp
    1700                1705                1710

Arg Pro Arg Gly Gly Gly Gly Asn Pro Ala Glu Arg Pro Arg
    1715                1720                1725

Lys Leu His Glu Leu Ser Ser Ala Leu Glu Ile Pro Tyr Asp Glu
    1730                1735                1740

Leu Arg Leu Asn Cys Val Tyr Cys Lys Gly Gln Leu Thr Glu Thr
    1745                1750                1755

Glu Val Leu Asp Phe Ala Arg Thr Asp Leu Thr Ile Val Tyr Arg
    1760                1765                1770

Asp Asp Thr Pro His Gly Val Cys Thr Lys Cys Leu Arg Phe Tyr
    1775                1780                1785

Ser Lys Val Ser Glu Phe Arg Trp Tyr Arg Tyr Ser Val Tyr Gly
    1790                1795                1800

Thr Thr Leu Glu Lys Leu Thr Asn Lys Gly Ile Cys Asp Leu Leu
    1805                1810                1815

Ile Arg Arg Ile Thr Cys Gln Arg Pro Leu Cys Pro Glu Glu Lys
    1820                1825                1830

Gln Arg His Leu Asp Lys Lys Arg Phe His Asn Ile Gly Gly
    1835                1840                1845

Arg Trp Thr Gly Arg Cys Ile Ala Cys Trp Arg Arg Pro
    1850                1855                1860

<210> SEQ ID NO 7
<211> LENGTH: 5589
<212> TYPE: DNA
<213> ORGANISM: Artificial
<220> FEATURE:
<223> OTHER INFORMATION: synthetic polynucleotide

<400> SEQUENCE: 7

```
atggctaagg ccgccatgct cgctaagttt aaggaactgt acggcgtctc cttttccgag      60
ctcgtgagac ctttcaagtc caacaagtcc acctgctgtg actggtgcat tgctgccttc     120
ggcctgcaca cctccatcgc cgactccatc aagacactgc tgcaacagta ctgcctgtat     180
ctgcacatcc agagcctggc ttgcagctgg ggaatggtgg tgctgctgct cgtcaggtac     240
aagtgcggca agaacaggga aaccattgag aagctgctga gcaagctgct gtgcgtcagc     300
cctatgtgca tgatgattga gccccctaag ctcaggagca cagctgccgc tctctattgg     360
```

```
tacaaaaccg gaatctccaa catcagcgag gtgtacggcg acacccctga gtggattcaa    420
aggcaaacag tgctccagca tagcttcaac gattgcacct tcgagctgag ccaaatggtg    480
caatgggcct acgataacga catcgtggat gatagcgaga ttgcttacaa atatgcccag    540
ctggccgaca caaacagcaa cgcctccgct ttcctgaagt ccaacagcca agccaaaatc    600
gtgaaggact gcgctaccat gtgtaggcac tacaaaagag ccgagaagaa gcaaatgagc    660
atgagccagt ggatcaaata tagatgcgac agggtcgacg atggaggaga ttggaagcag    720
atcgtcatgt ttctcagata ccagggcgtg gaatttatga gctttctgac cgccctgaag    780
agatttctcc agggcatccc taaaaagaac tgtattctgc tgtatggcgc tgccaacacc    840
gacaaaagcc tgttcggaat gagcctcatg aagtttctgc agggcagcgt gatctgtttc    900
gtgaacagca gagccatttc tggctccag cccctcgctg acgccaagat cggaatgctg    960
gacgacgcta ccgtcccttg ctggaactac atcgatgata atctcagaaa cgctctggat    1020
ggcaacctgg tgagcatgga cgtcaagcac agaccctgg tccaactgaa atgtccccct    1080
ctcctcatca aagcaacat taacgccggc accgatagca ggtggccta tctccataac    1140
agactggtgg tgtttacctt ccccaacgaa tttcccttcg acgaaaacgg caatcctgtg    1200
tacgagctca acgacaaaaa ctggaagtcc ttcttcagca gaacatggtc cagactgagc    1260
ctcggaggag gaggaggaaa acaaggagcc atgctcgccg tcttcaagga cacctacggc    1320
ctcagcttta ccgacctcgt cagaaacttt aaatccgata aaaccacctg cacagattgg    1380
gtgaccgcca ttttcggagt gaatcccacc attgccgaag gcttcaagac actgatccaa    1440
cctttcatcc tgtacgccca cattcagtgt ctcgactgta agtggggcgt gctgattctg    1500
gccctgctga gatacaaatg cggcaagtcc agactcacag tggccaaggg cctctccaca    1560
ctgctgcatg tccccgagac ctgcatgctg attcaacctc ccaaactcag gagcagcgtg    1620
gctgctctgt actggtatag gacaggcatt ccaacatttt ccgaggtcat gggagacaca    1680
cctgaatgga ttcaaagact gaccatcatc cagcacggca tcgatgactc caacttcgac    1740
ctgagcgaaa tggtccagtg gctttcgac aacgagctga ccgacgagtc cgacatggcc    1800
ttcgagtacg ctctcctcgc tgactccaac tccaatgctg ctgcttttct caagtccaac    1860
tgccaggcta agtacctgaa agactgcgcc accatgtgca agcattacag gcgtgctcaa    1920
aaaaggcaga tgaatatgtc ccaatggatt agatttaggt gctccaagat cgatgaggga    1980
ggcgactgga gacccattgt gcagttcctc aggtaccagc agatcgagtt tatcacattt    2040
ctgggagctc tgaagtcctt cctgaagggc accccaaga aaaactgtct ggtgttctgc    2100
ggccctgcta atacagataa aagctacttc ggcatgtcct tcatccactt tatccagggc    2160
gctgtgatca gcttcgtgaa tagcacatcc cacttttggc tggaacccct cacagacaca    2220
aaggtggcca tgctggatga cgctacaaca acctgttgga cctatttcga tacctacatg    2280
aggaacgctc tcgacggcaa ccctattagc attgataaa aacacaaacc tctgatccag    2340
ctgaagtgcc ctcccatcct cctcacaacc aacattcacc ccgccaagga caatagatgg    2400
ccttacctcg agagcaggat caccgtcttt gagtttccta cgccttccc ctttgacaag    2460
aacggcaacc ccgtgtatga atcaatgat aaaaattgga atgtttcctt cgagaggaca    2520
tggagcagac tcgatctcgg aggcggcggc ggagatcctc aggaaaggcc taggaaactc    2580
ccccagctgt gcaccgagct gcagaccacc attcacgaca ttatcctgga gtgcgtctac    2640
tgcaagcaac agctgctcag aagggaggtc tatgattttg ccagaaggga tctgtgcatt    2700
gtgtacagag acggcaatcc ttatgccgtc tgcgataagt gcctgaaatt ctatagcaaa    2760
```

```
atctccgaat acagacacta ctgctacagc ctgtatggaa ccaccctcga gcagcagtac    2820
aataaacccc tgtgcgatct gctcatcagg aggatcaact gtcaaaagcc cctgtgtccc    2880
gaggaaaagc agagacacct ggataagaaa cagaggttcc acaatatcag gggcagatgg    2940
accggcagat gcatgtcctg ttgtaggtcc agcggcggag gaggaggaga ccctaccaga    3000
aggccctata agctgcctga cctctgcaca gaactcaata ccagcctgca ggatatcgag    3060
atcacatgtg tctattgcaa gaccgtgctg gaactgaccg aagtgttcga gtttgctagg    3120
aaagacctct tcgtcgtgta cagggacagc atcccccatg ccgcctgcca caagtgtatt    3180
gacttctact ccaggattag ggagctcagg cactactccg actccgtcta tggcgacacc    3240
ctcgagaagc tcacaaacac cggcctctat aatctcctca tcaggaggct gagatgccaa    3300
aagcccctca accctgctga gaaactgagg cacctgaatg agaagagaag atttcataac    3360
attgccggac actacagagg acagtgtcac agctgttgca cagggctgg cggaggagga     3420 ggcgacaccg aagagaaacc cagaaccctc cacgacctgt gtcaggctct cgagacaacc    3480
atccataaca tcgagctcca gtgtgtggaa tgcaagaaac ccctgcagag gtccgaggtg    3540
tatgatttcg ccagagccga tctgacagtg gtctataggg agggaaaccc ttttggcatc    3600
tgcaaactgt gtctcaggtt tctctccaag atcagcgagt atagacatta taactacagc    3660
gtgtacggca cacccctgga gcaaaccgtg aaaaagcccc tgaacgagat cctcattagg    3720
aggatcattt gtcagaggcc cctctgtccc caggagaaga agagacatgt ggacctgaat    3780
aaaagattcc ataacatcag cggcagatgg gccggcagat gtgccgcttg ctggagatcc    3840
agaggaggag gaggcggcga tcccaagcaa agaccctaca agctgcctga tctgtgcaca    3900
gagctgaaca caagcctcca agatgtctcc atcgcctgtg tctactgtaa ggccacactg    3960
gaaaggacag aggtgtacca gttgccagg aaggatctct gcatcgtcta cagggattgc    4020
atcgcttacg ccgcttgtca caatgtatc gatttttatt ccagaatcag ggaactgaga    4080
tactatagca actccgtcta cggcgaaacc ctcgagaaaa ttacaaacac agaactctac    4140
aacctgctga ttaggaggct gagatgtcaa aagcctctca accccgccga gaaagaagg    4200 cacctcaaag acaagaggag attccactcc atcgctggcc agtacagagg ccagtgtaac    4260
acatgttgcg atcaggccgg aggaggaggc ggcgaccctg ccacaagacc caggaccctc    4320
cacgagctct gcgaggtgct ggaggagtcc gtgcacgaga ttaggctcca gtgcgtgcag    4380
tgcaagaagg aactccaaag gagagaagtg tataaattcc tgaggaccga cctcaggatt    4440
gtctataggg acaacaaccc ctacggagtg tgcattatgt gcctgaggtt cctcagcaag    4500
atttccgaat acaggcatta tcagtacagc ctctacggca aaaccctcga ggagagggtc    4560
aaaaaacccc tctccgaaat caccatcaga aggatcatct gtcagacacc tctctgccct    4620
gaggaaaagg aaaggcacgt gaacgctaac aagaggttcc ataatatcat gggcaggtgg    4680
accggaagat gcagcgagtg ctggagacct agaggcggcg gcgaggcga tgctgaagag    4740 aagcctagga ccctgcacga tctgtgtcaa gccctggaaa ccagcgtcca cgaaatcgaa    4800
ctgaaatgtg tcgagtgcaa aaagacccctg cagaggagcg aagtctacga ttttgtgaga    4860
gccgacctga gaattgtcta cagagacgga aaccccttcg ccgtctgcaa ggtctgcctc    4920
aggctgctct ccaaaatcag cgaatatagg cattacaatt actccctcta cggcgacaca    4980
ctggagcaaa cactcaagaa gtgcctcaac gagatcctga tcagaagaat catctgccag    5040
aggcctctct gccccaaga gaagaagagg cacgtggatc tgaacaaaag gtttcacaac    5100
```

```
atcagcggca ggtggaccgg cagatgcgcc gtgtgttgga gacctagagg cggaggcgga    5160
ggaaatcccg ctgagaggcc cagaaaactg cacgaactgt ccagcgccct ggagattcct    5220
tacgacgaac tgaggctcaa ctgcgtgtat tgcaagggac aactcaccga gaccgaagtg    5280
ctggacttcg ccaggaccga tctcaccatt gtctatagag acgacacccc tcacggcgtg    5340
tgcaccaaat gcctcaggtt ctactccaag gtcagcgagt ttaggtggta cagatactcc    5400
gtgtacggca ccaccctcga aaagctgacc aacaagggaa tttgcgacct cctgattaga    5460
aggattacat gccagagacc cctgtgccct gaggagaaac aaaggcacct ggacaagaag    5520
aagagattcc acaacatcgg cggcagatgg acaggcagat gcatcgcctg ctggaggagg    5580
ccttgatga                                                            5589

<210> SEQ ID NO 8
<211> LENGTH: 13512
<212> TYPE: DNA
<213> ORGANISM: Artificial
<220> FEATURE:
<223> OTHER INFORMATION: synthetic polynucleotide

<400> SEQUENCE: 8
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa actgtaaggg     360
aaataactga taaggaattg acaagaaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgc ttgacggacc gacaagtctc tatcaccaag     540
ccaataaggg agttagagtc gcctactgga taggctttga caccaccccct tttatgttta     600 agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc tgtgctgcaa aagtgacaga cattgaac ggggagaggg    1020 tctcttttcc cgtgtgcacg tatgtgccag ctacattgtg tgaccaaatg actggcatac    1080
tgcaacagat tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtt tgttgggct tttgaaaggc    1320 acaagataac atctatttat aagcgccggg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
```

```
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt ggactcgat ctggactccg    3240 gtctattttc tgcacccact gttccgtat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc gggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttccccg ggtatgcaaa ccgaaatcct    3900
```

```
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccaccccgc    5520 caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttgtat tcatctagtg tgaaccgtgc cttttcaagc ccaaggtcg    6060 cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gcttccaaa gaaacactcc tatttggaac    6240
ccacaatacg atcggcagtg ccttcagcga tccagaacac gctccagaac gtcctggcag    6300
```

```
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatggaaacc ctgtgtcaga ggctgaatgt gtgtcaagac aaaatcctga cccactacga   7620
gaatgactcc acagacctga ggaccacat cgattactgg aagcacatga ggctcgagtg   7680
cgccatctac tataaggcca gagagatggg ctttaagcat atcaatcatc aagtcgtgcc   7740
cacactggcc gtgagcaaga acaaggccct gcaagctatt gagctccaac tgaccctcga   7800
gaccatctac aacagccagt acagcaacga gaaatggaca ctgcaggatg tgtccctcga   7860
agtgtacctc acagccccta ccggatgtat cgccaagcac ggctacacag tggaagtgca   7920
gtttgacggc gatatctgca atacaatgca ttacaccaac tggacccaca tctatatctg   7980
cgaggaagct agcgtcacag tggtggaggg ccaggtcgac tattacgcc tctattacgt   8040 gcatgagggc atcaggacct actttgtgca gtttaaggac gatgccgaaa aatacagcaa   8100
aaataaagtg tgggaagtcc atgccggagg ccaggtgatc ctgtgtccca cctccgtctt   8160
tagcggaggc accggcggca gcacaacccc tatcgtccac ctgaaaggag atgccaacac   8220
actgaaatgt ctcaggtaca ggttcaagaa gcactgtacc ctgtatacag ccgtcagcag   8280
cacatggcat tggaccggcc acaacgtcaa gcataagagc gccatcgtga ccctcacata   8340
cgatagcgaa tggcaaaggg accagttcct gagccaggtc aagatcccca agacaatcac   8400
agtgtccacc ggctttatgt ccatcggcgg aggaggcgga atgcagaccc ctaaggagac   8460
cctcagcgaa agactcagct gcgtgcagga taaaatcatt gaccattatg agaatgattc   8520
caaggacatc gatagccaga ttcaatactg gcagctgatc aggtgggaga acgccatctt   8580
cttcgccgcc agggagcacg gcattcaaac cctcaaccat caggtggtgc ccgcttacaa   8640
```

```
catcagcaag agcaaagccc ataaggccat tgagctgcag atggccctcc agggcctggc    8700
tcagagcgct tataaaaccg aagactggac cctgcaagac acatgcgagg agctgtggaa    8760
caccgaaccc acacactgct tcgccaaagg cggccaaaca gtgcaggtgt acttcgatgg    8820
caacaaggac aattgcatga cctacgtcgc ttgggactcc gtctattaca tgacagatgc    8880
cggcacatgg gacaagaccg ccacatgcgt cagccacagg ggactgtact acgtgaaaga    8940
gggatacaat accttctaca tcgagttcaa atccgagtgt gagaagtacg caatacagg     9000 cacctgggag gtgcatttcg gcaataatgt gattgactgc aacgatagca tgtgtagcgg    9060
cggaaccggc ggttctacaa ccccccatcat ccacctgaag ggcgaccgta attctctgaa    9120
gtgcctgagg tacagactca ggaagcacag cgaccattac agggatatct ccagcacctg    9180
gcactggaca ggcgctggca atgaaaagac aggaatcctc acagtgacct accactccga    9240
gacccagagg acaaaattcc tgaacaccgt ggccatcccc gacagcgtcc agattctggt    9300
gggctatatg accatgggag gaggcggagg catggagaca ctcagccaaa ggctcaacgt    9360
gtgccaggat aagatcctgg agcactacga gaacgacagc aaaaggctgt gtgatcatat    9420
cgactactgg aagcatatca ggctggagtg cgtcctgatg tacaaggcca gagaaatggg    9480
aatccattcc atcaaccacc aagtggtccc tgctctctcc gtcagcaaag ccaaggctct    9540
gcaggctatt gaactgcaaa tgatgctgga cccctcaac aacaccgagt acaaaaacga    9600
ggattggacc atgcaacaga cctccctcga actctatctg acagccccca caggctgcct    9660
cgccaagcat ggctacaccg tggaggtgca attcgacggc gatgtccaca acacaatgca    9720
ctacacaaac tggaagttca tctacctctg catcgacgga cagtgtaccg tcgtggaagg    9780
acaagtgaac tgcaagggca tctactacgt ccacgagggc cacattacct acttcgtgaa    9840
cttcaccgag gaagccaaga aatacggcac cggaaagaag tgggaggtcc acgccggcgg    9900
ccaagtcatt gtgtttcctg aaagcgtctt cagcggaggc acaggcggct ccaccacacc    9960
catcatccat ctgaaaggcg atgccaacat cctcaaatgc ctcaggtata ggctgagcaa   10020
atacaaacaa ctgtacgaac aagtgtcctc cacctggcat tggacatgta ccgacggcaa   10080
gcacaaaaac gccatcgtca ccctgaccta cattagcacc agccagagag acgacttcct   10140
caatacagtg aagatcccta acaccgtgag cgtgagcacc ggctacatga caattggagg   10200
cggcggcggc atggaagaga ttttccgccag actcaacgcc gtgcaggaga aatcctgga    10260 cctctacgag gccgataaaa ccgatctccc ctcccagatt gagcactgga agctgatcag   10320
aatggaatgc gccctgctct acaccgccaa acagatgggc ttctcccacc tctgccacca   10380
ggtcgtgccc tccctcctgg cttccaagac caaggccttc caggtgatcg agctgcaaat   10440
ggctctcgaa accctgtcca agagccagta tagcacctcc caatggaccc tgcagcaaac   10500
ctccctggaa gtctggctgt gtgaaccccc caaatgcttc gctaagcaag gcgagaccgt   10560
cacagtccag tacgacaatg ataagaagaa taccatggac tataccaact ggggcgagat   10620
ctacattatc gaggaggata cctgcaccat ggtgaccggc aagtggact atattggaat    10680 gtactatatc cataactgcg agaaagtcta tttcaagtat ttcaaagagg acgccgccaa   10740
atacagcaag acccagatgt gggaggtgca cgtcggagga caggtgattg tctgtcctac   10800
ctccatctcc tccggcggaa caggcggaag cgtggcccct attgtccatc tcaagggcga   10860
gagcaactcc ctgaagtgtc tcaggtatag actgaagccc tacaaggagc tgtactccag   10920
catgagctcc acctggcact ggaccagcga taacaagaac agcaagaacg gcatcgtgac   10980
agtgacattc gtgacagaac agcagcagca gatgttcctc ggcacagtga aaattccccc   11040
```

```
caccgtgcaa attagcaccg gcttcatgac actgtgatga ggcgcgccca cccagcggcc    11100
gcatacagca gcaattggca agctgcttac atagaactcg cggcgattgg catgccgcct    11160
taaaattttt attttatttt tcttttcttt tccgaatcgg attttgtttt taatatttca    11220
aaaaaaaaaa aaaaaaaaaa aaaaaaaaaa aaaaaaaag aagagcgttt aaacacgtga     11280
tatctggcct catgggcctt cctttcactg cccgctttcc agtcgggaaa cctgtcgtgc    11340
cagctgcatt aacatggtca tagctgtttc cttgcgtatt gggcgctctc cgcttcctcg    11400
ctcactgact cgctgcgctc ggtcgttcgg gtaaagcctg gggtgcctaa tgagcaaaag    11460
gccagcaaaa ggccaggaac cgtaaaaagg ccgcgttgct ggcgtttttc cataggctcc    11520
gcccccctga cgagcatcac aaaaatcgac gctcaagtca gaggtggcga acccgacag     11580
gactataaag ataccaggcg tttccccctg gaagctccct cgtgcgctct cctgttccga    11640
ccctgccgct taccggatac ctgtccgcct ttctcccttc gggaagcgtg gcgctttctc    11700
atagctcacg ctgtaggtat ctcagttcgg tgtaggtcgt tcgctccaag ctgggctgtg    11760
tgcacgaacc ccccgttcag cccgaccgct gcgccttatc cggtaactat cgtcttgagt    11820
ccaacccggt aagacacgac ttatcgccac tggcagcagc cactggtaac aggattagca    11880
gagcgaggta tgtaggcggt gctacagagt tcttgaagtg gtggcctaac tacggctaca    11940
ctagaagaac agtatttggt atctgcgctc tgctgaagcc agttaccttc ggaaaaagag    12000
ttggtagctc ttgatccggc aaacaaacca ccgctggtag cggtggtttt tttgtttgca    12060
agcagcagat tacgcgcaga aaaaaaggat ctcaagaaga tcctttgatc ttttctacgg    12120
ggtctgacgc tcagtggaac gaaaactcac gttaagggat tttggtcatg aatacacggt    12180
gcctgactgc gttagcaatt taactgtgat aaactaccgc attaaagctt atcgatgata    12240
agctgtcaaa catgagaatt cttagaaaaa ctcatcgagc atcaaatgaa actgcaattt    12300
attcatatca ggattatcaa taccatattt tgaaaaagc cgtttctgta atgaaggaga    12360
aaactcaccg aggcagttcc ataggatggc aagatcctgg tatcggtctg cgattccgac    12420
tcgtccaaca tcaatacaac ctattaattt cccctcgtca aaataaggt tatcaagtga    12480
gaaatcacca tgagtgacga ctgaatccgg tgagaatggc aaaagcttat gcatttcttt    12540
ccagacttgt tcaacaggcc agccattacg ctcgtcatca aaatcactcg catcaaccaa    12600
accgttattc attcgtgatt gcgcctgagc gagacgaaat acgcgatcgc tgttaaaagg    12660
acaattacaa acaggaatcg aatgcaaccg gcgcaggaac actgccagcg catcaacaat    12720
attttcacct gaatcaggat attcttctaa tacctggaat gctgttttcc cggggatcgc    12780
agtggtgagt aaccatgcat catcaggagt acggataaaa tgcttgatgg tcggaagagg    12840
cataaattcc gtcagccagt ttagtctgac catctcatct gtaacatcat ggcaacgct    12900
acctttgcca tgtttcagaa acaactctgg cgcatcgggc ttcccataca atcgatagat    12960
tgtcgcacct gattgcccga cattatcgcg agcccattta tacccatata atcagcatc    13020
catgttggaa tttaatcgcg gcctcgagca agacgtttcc cgttgaatat ggctcataac    13080
accccttgta ttactgttta tgtaagcaga cagtttatt gttcatgagc ggatacatat    13140
ttgaatgtat ttagaaaaat aaacaaatag gggttccgcg cacatttccc cgaaaagtgc    13200
cacctaaatt gtaagcgtta atattttgtt aaaattcgcg ttaaattttt gttaaatcag    13260
ctcattttt aaccaataggccgaaatcgg caaaatccct tataaatcaa agaatagac     13320
cgagataggg ttgagtggcc gctacagggc gctcccattc gccattcagg ctgcgcaact    13380
```

-continued

| | |
|---|---|
| gttgggaagg gcgtttcggt gcgggcctct tcgctattac gccagctggc gaaaggggga | 13440 |
| tgtgctgcaa ggcgattaag ttgggtaacg ccagggtttt cccagtcaca cgcgtaatac | 13500 |
| gactcactat ag | 13512 |

<210> SEQ ID NO 9
<211> LENGTH: 13512
<212> TYPE: RNA
<213> ORGANISM: Artificial
<220> FEATURE:
<223> OTHER INFORMATION: synthetic polynucleotide

<400> SEQUENCE: 9

| | |
|---|---|
| auaggcggcg caugagagaa gcccagacca auuaccuacc caaaauggag aaaguucacg | 60 |
| uugacaucga ggaagacagc ccauuccuca gagcuuugca gcggagcuuc ccgcaguuug | 120 |
| agguagaagc caagcagguc acugauaaug accaugcuaa gccagagcg uuuucgcauc | 180 |
| uggcuucaaa acugaucgaa acggaggugg acccauccga cacgauccuu gacauuggaa | 240 |
| gugcgcccgc ccgcagaaug uauucuaagc acaaguauca uuguaucugu ccgaugagau | 300 |
| gugcggaaga uccggacaga uuguauaagu augcaacuaa gcugaagaaa aacuguaagg | 360 |
| aaauaacuga uaaggaauug acaagaaaaa ugaaggagcu cgccgccguc augagcgacc | 420 |
| cugaccugga aacugagacu augugccucc acgacgacga gucgugucgc uacgaagggc | 480 |
| aagucgcugu uuaccaggau guauacgcgg uugacggacc gacaagucuc uaucaccaag | 540 |
| ccaauaaggg aguuagaguc gccuacugga uaggcuuuga caccaccccu uuuaugunua | 600 |
| agaacuuggc uggagcauau ccaucauacu cuaccaacug ggccgacgaa accguguuaa | 660 |
| cggcucguaa cauaggccua ugcagcucug acguuaugga gcggucacgu agagggaugu | 720 |
| ccauucuuag aaagaaguau uugaaaccau ccaacaaugu ucuauucucu guuggcucga | 780 |
| ccaucuacca cgagaagagg gacuuacuga ggagcuggca ccugccgucu guauuucacu | 840 |
| uacguggcaa gcaaaauuac acaugucggu gugagacuau aguuaguugc gacgggacg | 900 |
| ucguuaaaag aauagcuauc aguccaggcc uguauggaa gccuucaggc uaugcugcua | 960 |
| cgaugcaccg cgagggauuc uugugcugca aagugacaga cacauugaac ggggagaggg | 1020 |
| ucucuuuucc cgugugcacg uaugugccag cuacauugug ugaccaaaug acuggcauac | 1080 |
| uggcaacaga ugucagugcg gacgacgcgc aaaaacugcu gguugggcuc aaccagcgua | 1140 |
| uagucgucaa cggucgcacc cagagaaaca ccaauaccau gaaaaauuac cuuuugcccg | 1200 |
| uaguggccca ggcauuugcu agguggggcaa aggaauauaa ggaagaucaa gaagaugaaa | 1260 |
| ggccacuagg acuacgagau agacaguuag ucaugggggu uguuggggcu uuuagaaggc | 1320 |
| acaagauaac aucuauuuau aagcgcccgg auacccaaac caucaucaaa gugaacagcg | 1380 |
| auuccacuc auucgugcug cccaggauag gcaguaacac auuggagauc gggcugagaa | 1440 |
| caagaaucag gaaauguua gaggagcaca aggagccguc accucucauu accgccgagg | 1500 |
| acguacaaga agcuaagugc gcagccgaug aggcuaagga ggugcgugaa gccgaggagu | 1560 |
| ugcgcgcagc ucuaccaccu uuggcagcug auguugagga gcccacucug gaagccgaug | 1620 |
| ucgacuugau guuacaagag gcuggggccg gucagugga gacacccgu ggcuugauaa | 1680 |
| agguuaccag cuacgauggc gaggacaaga ucggcucuua cgcugugcuu ucccgcaggu | 1740 |
| cuguacucaa gagugaaaaa uuaucuugca uccacccucu cgcugaacaa gucauaguga | 1800 |
| uaacacacuc uggccgaaaa gggcguuaug ccgggaacc auaccauggu aaaguagugg | 1860 |
| ugccagaggg acaugcaaua cccguccagg acuuucaagc ucugagugaa agugccacca | 1920 |

```
uuguguacaa cgaacgugag uucguaaaca gguaccugca ccauauugcc acacauggag    1980
gagcgcugaa cacugaugaa gaauauuaca aaacugucaa gcccagcgag cacgacggcg    2040
aauaccugua cgacaucgac aggaaacagu gcgucaagaa agaacuaguc acugggcuag    2100
ggcucacagg cgagcuggug gauccucccu uccaugaauu cgccuacgag agucugagaa    2160
cacgaccagc cgcuccuuac caaguaccaa ccauaggggu guaggcgug ccaggaucag     2220 gcaagucugg caucauuaaa agcgcaguca ccaaaaaaga ucuaguggug agcgccaaga    2280
aagaaaacug ugcagaaauu auaagggacg ucaagaaaau gaagggcug gacgucaaug     2340 ccagaacugu ggacucagug cucuugaaug gaugcaaaca ccccguagag acccuauaua    2400
uugacgaagc uuuugcuugu caugcaggua cucucagagc gcucauagcc auuauaagac    2460
cuaaaaaggc agugcucugc ggggaucccaaa acagugcgg uuuuuuuaac augaugugcc    2520
ugaaagugca uuuuaaccac gagauuugca cacaagucuu ccacaaaagc aucucucgcc    2580
guugcacuaa aucgugacu ucggucgucu caaccuuguu uuacgacaaa aaaugagaa      2640 cgacgaaucc gaaagagacu aagauuguga uugacacuac cggcaguacc aaaccuaagc    2700
aggacgaucu cauucucacu uguuucagag gguggugaa gcaguugcaa auagauuaca     2760
aaggcaacga aauaaugacg gcagcugccu cucaagggcu gacccguaaa ggugugaug     2820 ccguucggua caaggugaau gaaaauccuc uguacgcacc caccucagaa caugugaacg    2880
uccuacugac ccgcacggag gaccgcaucg uguggaaaac acuagccggc gacccaugga    2940
uaaaaacacu gacugccaag uacccuggga auuucacugc cacgauagag gaguggcaag    3000
cagagcauga ugccaucaug aggcacaucu uggagagacc ggacccuacc gacgucuucc    3060
agaauaaggc aaacgugugu ugggccaagg cuuuagugcc ggugcugaag accgcuggca    3120
uagacaugac cacugaacaa uggaacacug uggauuauuu ugaaacggac aaagcucacu    3180
cagcagagau aguauugaac caacuaugcg ugaggucuu uggacucgau cuggacuccg    3240
gucuauuuuc ugcacccacu guuccguuau ccauuaggaa uaaucacugg gauaacuccc    3300
cgucgccuaa cauguacggg cugaauaaag aagugguccg ucagcucucu cgcagguacc    3360
cacaacugcc ucgggcaguu gccacuggaa gagucuauga caugaacacu ggacacugc     3420 gcaauuauga uccgcgcaua aaccuaguac cuguaaacag aagacugcca caugcuuuag    3480
uccuccacca uaaugaacac ccacagagug acuuuucuuc auucgucagc aaauugaagg    3540
gcagaacugu ccugguggu ggggaaaagu uguccgucc aggcaaaaug uugacuggu      3600 ugucagaccg gccugaggcu accuucagag cucggcugga uuuaggcauc caggugaug    3660 ugcccaaaua ugacauaaua uuuguuaaug ugaggacccc auauaaauac caucacuauc    3720
agcaguguga agaccaugcc auuaagcuua gcauguugac caagaaagcu ugucugcauc    3780
ugaaucccgg cggaaccugu gucagcauag guuaugguua cgcugacagg gccagcgaaa    3840
gcaucauugg ugcuauagcg cggcaguuca guuuucccg gguaugcaaa ccgaaauccu    3900
cacuugaaga gacggaaguu cuguuuguau caugggua cgaucgcaag gcccguacgc     3960
acaauccuua caagcuuuca ucaaccuuga ccaacauuua uacagguucc agacuccacg    4020
aagccggaug ugcacccuca uaucaugugg ugcgagggga uauugccacg gccaccgaag    4080
gagugauuau aaaaugcugcu aacagcaaag acaaccuug cggaggggug ugcggagcgc    4140
uguauaagaa auucccggaa agcuucgauu uacagccgau cgaaguagga aaagcgcgac    4200
uggucaaagg ugcagcuaaa cauaucauuc augccguagg accaaacuuc aacaaaguuu    4260
```

-continued

```
cggagguuga aggugacaaa caguuggcag aggcuuauga guccaucgcu aagauuguca    4320
acgauaacaa uuacaaguca guagcgauuc cacuguuguc caccggcauc uuuuccggga    4380
acaaagaucg acuaacccaa ucauugaacc auuugcugac agcuuuagac accacugaug    4440
cagauguagc cauauacugc agggacaaga aaugggaaau gacucucaag gaagcagugg    4500
cuaggagaga agcaguggag gagauaugca uauccgacga cucuucagug acagaaccug    4560
augcagagcu ggugagggug cauccgaaga guucuuuggc uggaaggaag ggcuacagca    4620
caagcgaugg caaaacuuuc ucauauuugg aagggaccaa guucaccag gcggccaagg     4680 auauagcaga aauuaaugcc augugggccg ugcaacggaa ggccaaugag cagguaugca    4740
uguauauccu cggagaaagc augagcagua uuaggucgaa augccccguc gaagagucgg    4800
aagccuccac accaccuagc acgcugccuu gcugugcau ccaugccaug acuccagaaa     4860
gaguacagcg ccuaaaagcc ucacguccag aacaaauuac ugugugcuca uccuuuccau    4920
ugccgaagua uagaaucacu ggugugcaga agauccaaug cucccagccu auauuguucu    4980
caccgaaagu gccugcguau auucauccaa ggaaguaucu cguggaaaca ccaccgguag    5040
acgagacucc ggagccaucg gcagagaacc aauccacaga ggggacaccu gaacaaccac    5100
cacuuauaac cgaggaugag accaggacua gaacgccuga gccgaucauc aucgaagagg    5160
aagaagagga uagcauaagu uugcugucga auggcccgac ccaccaggug cugcaagucg    5220
aggcagacau ucacgggccg cccucuguau cuagcucauc cuggucccau ccucaugcau    5280
ccgacuuuga uguggacagu uuauccauac uugacacccu ggagggagcu agcgugacca    5340
gcggggcaac gucagccgag acuaacucuu acuucgcaaa gaguauggag uuucggcgc    5400 gaccggugcc ugcgccucga acaguauuca ggaaccccucc acaucccgcu ccgcgcacaa    5460
gaacaccguc acuugcaccc agcagggccu gcucgagaac cagccuaguu ccacccccgc    5520
caggcgugaa uagggugauc acuagagagg agcucgaggc gcuuacccg ucacgcacuc     5580 cuagcagguc ggucucgaga accagccugg ucuccaaccc gccaggcgua aauaggguga    5640
uuacaagaga ggaguuugag gcguucgauag cacaacaaca augacgguuu gaugcggug     5700 cauacaucuu uuccuccgac accgucaag ggcauuuaca caaaaauca guaaggcaaa      5760 cggugcuauc cgaaguggug uuggagagga ccgaauugga gauuucguau gccccgcgcc    5820
ucgaccaaga aaaagaagaa uuacuacgca agaaauuaca guuaaauccc acaccugcua    5880
acagaagcag auaccagucc aggaaggugg agaacaugaa agccauaaca gcuagacgua    5940
uucugcaagg ccuagggcau uauuugaagg cagaaggaaa aguggagugc uaccgaaccc    6000
ugcauccugu uccuuuguau ucaucuagug ugaaccgugc cuuuucaagc cccaaggucg    6060
caguggaagc cuguaacgcc augugaaag agaacuuucc gacugugggcu ucuuacugua    6120 uuauuccaga guacgaugcc uauuuggaca ugguugacgg agcuucaugc ugcuuagaca    6180
cugccaguuu uugcccugca aagcugcgca gcuuuccaaa gaaacacucc uauuuggaac    6240
ccacaauacg aucggcagug ccuucagcga uccagaacac gcuccagaac guccuggcag    6300
cugccacaaa aagaaauugc aaugucacgc aaaugagaga auugcccgua uuggauucgg    6360
cggccuuuaa uguggaauge uucaagaaau augcguguaa uaaugauau ugggaaacgu      6420 uuaaagaaaa ccccaucagg cuuacugaag aaaacguggu aaauucauu accaaauuaa      6480 aaggaccaaa agcugcugcu cuuuuugcga agacacauaa uuugaauaug uugcaggaca    6540
uaccaauggu ugguuugua auggacuuaa agagagacgu gaaagugacu ccaggaacaa    6600
aacauacuga agaacggccc aagguacagg ugauccaggc ugccgauccg cuagcaacag    6660
```

```
cguaucugug cggaauccac cgagagcugg uuaggagauu aaaugcgguc cugcuuccga      6720
acauucauac acuguuugau augucggcug aagacuuuga cgcuauuaua gccgagcacu      6780
uccagccugg ggaugugduu cuggaaacug acaucgcguc guuugauaaa agugaggacg      6840
acgccauggc ucugaccgcg uuaaugauuc uggaagacuu aggugdggac gcagagcugu      6900
ugacgcugau ugaggcggcu uucggcgaaa uucaucaau acauuugccc acuaaaacua       6960
aauuuaaauu cggagccaug augaaaucug gaaugduccu cacacuguuu gugaacacag      7020
ucauuaacau uguaaucgca agcagagugu ugagagaacg gcuaaccgga ucaccaugug      7080
cagcauucau uggagaugac aauaucguga aggagucaa aucggacaaa uuaauggcag       7140
acaggugcgc caccugguug aauauggaag ucaagauuau agaugcugug gugggcgaga      7200
aagcgccuua uuucgudgga ggguuuauuu ugugugacuc cgudaccggc acagcgugcc      7260
guguggcaga cccccuaaaa aggcuguuua agcuuggcaa accucuggca gcagacgaug      7320
aacaugauga ugacaggaga agggcauugc augaagaguc aacacgcugg aaccgagugg      7380
guauucuuuc agagcugugc aaggcaguag aaucaaggua ugaaaccgua ggaacuucca      7440
ucauaguuau ggccaugacu acucuagcua gcaguguuaa aucauucagc uaccugagag      7500 gggcccccuau aacucucuac ggcuaaccug aauggacuac gacauagucu aguccgccaa      7560
gauggaaacc cugucdaga ggcugaaugu gucdaagac aaaauccuga cccacuacga        7620
gaaugacucc acagaccuga ggaccacau cgauuacugg aagcacauga ggcucgagug       7680
cgccaucuac uauaaggcca gagaugaugg cuuuagcau aucaaucauc aagucgudcc       7740
cacacuggcc gugagcaaga acaaggcccu gcaagcuauu gagcuccaac ugacccucga     7800
gaccaucuac aacagccagu acagcaacga gaaauggaca cugcaggaug ugucccucga     7860
aguguaccuc acagcccca ccggaugau cgccaagcac ggcuacacag uggaagugca      7920
guuugacggc gauaucugca auacaaugca uuacaccaac uggacccaca ucuauaucug      7980
cgaggaagcu agcgucacag uggugdaggg ccaggucgac uauacggcc ucuauuacgu     8040 gcaugagggc aucaggaccu acudugugca guuuaaggac gaugccgaaa aauacagcaa     8100
aaauaaagug ugggaagucc augccggagg ccaggugauc cugugcccca ccuccgucuu    8160
uagcggaggc accggcggca gcacaacccc uaucgudcac cugaaaggag augccaacac    8220
acugaaaugu cucagguaca gguucaagaa gcacuguacc cuguauacag ccgucagcag    8280
cacauggcau uggaccggcc acaacgucaa gcauaagagc gccaucguga cccucacaua    8340
cgauagcgaa uggcaaaggg accagduuccu gagccaggduc aagauccca agacaaucac    8400 agugccacc ggcuuuaugu ccaucggcgg aggaggcgga augcagaccc cuaaggagac    8460
ccucagcgaa agacucagcu gcgugcagga uaaaaucauu gaccauuaug agaaugauuc     8520
caaggacauc gauagccaga uucaauacug gcagcugauc aggugggaga acgccaucuu     8580
cuucgccgcc agggagcacg gcauucaaac ccucaaccau caggdgggugc cgcuudacaa     8640 caucagcaag agcaaagccc auaaggcau ugagcugcag auggcccucc agggccuggc      8700
ucagagcgcu uauaaaaccg aagacuggac ccugcaagac acaugcgagg agcugdggaa     8760
caccgaaccc acacacugcu ucgccaaagg cggccaaaca gugcaggugu acuucgaugg    8820
caacaaggac aauugcauga ccuacgucgc uugggacucc gucuauaca ugacagaugc    8880 cggcacaugg acaagaccg ccacaugcgu cagccacagg ggacuguacu acgugaagag    8940
gggauacaau accuucuaca ucgaguucaa auccgagugu gagaaguacg gcauacagg     9000
```

| | |
|---|---|
| caccugggag gugcauuucg gcaauaaugu gauugacugc aacgauagca uguguagcgg | 9060 |
| cggaaccggc gguucuacaa cccccaucau ccaccugaag ggcgaccgua auucucugaa | 9120 |
| gugccugagg uacagacuca ggaagcacag cgaccauuac agggauaucu ccagcaccug | 9180 |
| gcacuggaca ggcgcuggca augaaaagac aggaauccuc acagugaccu accacuccga | 9240 |
| gacccagagg acaaaauucc ugaacaccgu ggccauccc gacagcgucc agauucuggu | 9300 |
| gggcuauaug accaugggag gaggcggagg cauggagaca cucagccaaa ggcucaacgu | 9360 |
| gugccaggau aagauccugg agcacuacga gaacgacagc aaaaggcugu gaucauau | 9420 |
| cgacuacugg aagcauauca ggcuggagug cguccgaug uacaaggcca gagaauggg | 9480 |
| aauccauucc aucaaccacc aagugguccc ugcucucucc gucagcaaag ccaaggcucu | 9540 |
| gcaggcuauu gaacugcaaa ugaugcugga ccccucaac aacaccgagu acaaaaacga | 9600 |
| ggauuggacc augcaacaga ccuccccucga acucuaucug acagccccca caggcugccu | 9660 |
| cgccaagcau ggcuacaccg uggaggugca auucgacggc gaugccaca acacaaugca | 9720 |
| cuacacaaac uggaaguuca cuaccucug caucgacgga cagguaccg ucuggaagg | 9780 |
| acaagugaac ugcaagggca ucuacuacgu ccacgagggc cacauuaccu acuucgugaa | 9840 |
| cuucaccgag gaagccaaga aauacggcac cggaaagaag ugggaggucc acgccggcgg | 9900 |
| ccaagucauu guguuccug aaagcgucuu cagcggaggc acaggcggcu ccaccacacc | 9960 |
| caucauccau cugaaaggcg augccaacau ccucaaaugc cucagguaua ggcugagcaa | 10020 |
| auacaaacaa cuguacgaac aaguguccuc caccggcau uggacaugua ccgacggcaa | 10080 |
| gcacaaaaac gccaucguca cccgaccua cauuagcacc agccagagag acgacuuccu | 10140 |
| caauacagug aagaucccua caccgugag cgugagcacc ggcuacauga caauuggagg | 10200 |
| cggcggcggc auggaagaga uuccgccag acucaacgcc gugcaggaga aaauccugga | 10260 |
| ccucuacgag gccgauaaaa ccgaucuccc cucccagauu gagcacugga agcugaucag | 10320 |
| aauggaaugc gcccugcucu acaccgccaa acagauggc uucucccacc ucugccacca | 10380 |
| ggucgugccc ucccuccugg cuuccaagac caaggccuuc caggugaucg agcugcaaau | 10440 |
| ggcucucgaa acccgucca agagccagua uagcaccucc caauggaccc ugcagcaaac | 10500 |
| cucccuggaa gucuggcugu gugaaccccc caaaugcuuc gcuaagcaag gcgagaccgu | 10560 |
| cacaguccag uacgacaaug auaagaagaa uaccauggac uauaccaacu ggggcgagau | 10620 |
| cuacauuauc gaggaggaua ccugcaccau ggugaccggc aagguggacu auauuggaau | 10680 |
| guacuauauc cauaacugcg agaaagucua uuucaaguau uucaagaggg acgccgccaa | 10740 |
| auacagcaag acccagaugu gggaggugca cgucggagga cagguagauu gucugccuac | 10800 |
| cuccaucucc uccggcggaa caggcggaag cguggcccu auugccauc uccaagggcga | 10860 |
| gagcaacucc cugaagaguc ucagguauag acugaagccc uacaaggagc uguacuccag | 10920 |
| caugagcucc accuggcacu ggaccagcga uaacaagaac agcaagaacg gcaucgugac | 10980 |
| agugacauuc gugacagaac agcagcagca gauguccuc ggcacaguga aaauuccccc | 11040 |
| caccgugcaa auuagcaccg gcuucaugac acugugauga ggcgcgccca cccagcggcc | 11100 |
| gcauacagca gcaauuggca agcugcuuac auagaacucg cggcgauugg caugccgccu | 11160 |
| uaaauuuuu auuuuauuuu ucuuucuuu uccgaaucgg auuuguuuu uaauauuuca | 11220 |
| aaaaaaaaaa aaaaaaaaa aaaaaaaaaa aaaaaaaaag aagagcguuu aaacacguga | 11280 |
| uaucuggccu caugggccuu ccuuucacug cccgcuuucc agucgggaaa ccugucgugc | 11340 |
| cagcugcauu aacaugguca uagcuguuuc cuugcguauu gggcgcucuc cgcuuccucg | 11400 |

```
cucacugacu cgcugcgcuc ggucguucgg guaaagccug ggugccuaa ugagcaaaag    11460 gccagcaaaa ggccaggaac cguaaaaagg ccgcguugcu ggcguuuuuc cauaggcucc    11520 gcccccuga cgagcaucac aaaaaucgac gcucaaguca gagguggcga aacccgacag    11580
gacuauaaag auaccaggcg uuccccccug gaagcuccu cgugcgcucu ccuguccga     11640 cccugccgcu uaccggauac cuguccgccu ucucccuuc gggaagcgug cgcuuucuc     11700 auagcucacg cuguagguau ucaguucgg guaggucgu ucgcuccaag cugggcgug      11760 ugcacgaacc ccccguucag cccgaccgcu gcgccuuauc cgguaacuau cgucuugagu    11820
ccaacccggu aagacacgac uuaucgccac uggcagcagc cacugguaac aggauuagca    11880
gagcgaggua uguaggcggu gcuacagagu cuugaagug guggccuaac uacggcuaca    11940
cuagaagaac aguauuuggu aucgcgcuc ugcugaagcc aguuaccuuc ggaaaaagag    12000
uugguagcuc uugauccggc aaacaaacca ccgcugguag cgguggguuu uuguuugca    12060 agcagcagau uacgcgcaga aaaaaaggau ucaagaaga uccuuugauc uuuucuacgg    12120
ggucugacgc ucaguggaac gaaaacucac guuaaggau uuuggucaug aauacacggu    12180
gccugacugc guuagcaauu uaacugugau aaacuaccgc auuaaagcuu aucgaugaua    12240
agcugucaaa caugagaauu cuuagaaaaa cucaucgagc aucaaaugaa acugcaauuu    12300
auucauauca ggauuaucaa uaccauauuu uugaaaagc cguuucugua augaaggaga    12360
aaacucaccg aggcaguucc auaggauggc aagauccugg uaucggucug cgauuccgac    12420
ucguccaaca ucaauacaac cuauuaauuu ccccucguca aaauaaggu uaucaaguga    12480 gaaaucacca ugagugacga cugaauccgg ugagaauggc aaaagcuuau gcauuucuuu    12540
ccagacuugu ucaacaggcc agccauuacg cucgucauca aaaucacucg caucaaccaa    12600
accguuauuc auucgugauu gcgccugagc gagacgaaau acgcgaucgc uguuaaaagg    12660
acaauuacaa acaggaaucg aaugcaaccg gcgcaggaac acugccagcg caucaacaau    12720
auuuucaccu gaaucaggau auucuucaa uaccuggaau gcuguuuucc cggggaucgc    12780
aguggugagu aaccaugcau caucaggagu acgauaaaa ugcuugaugg ucggaagagg    12840
cauaaauucc gucagccagu uuagucugac caucucaucu guaacaucau uggcaacgcu    12900
accuuugcca uguuucagaa acaacucugg cgcaucgggc uucccauaca aucgauagau    12960
ugucgcaccu gauugcccga cauuaucgcg agcccauuua uacccauaua aaucagcauc    13020
cauguuggaa uuuaaucgcg gccucgagca agacguuucc cguugaauau ggcucauaac    13080
accccuugua uuacuguuua guaagcaga caguuuauu guucaugagc ggauacauau    13140
uugaauguau uuagaaaaau aaacaaauag ggguuccgcg cacauuuccc gaaaagugc    13200 caccuaaauu guaagcguua auauuuuguu aaaauucgcg uuaaauuuuu guuaaaucag    13260
cucauuuuuu aaccaauagg ccgaaaucgg caaaauccu uauaaaucaa agaauagac    13320 cgagauaggg uugaguggcc gcuacagggc gcuccauuc gccaucagg cugcgcaacu    13380 guugggaagg gcguucggu gcgggccucu ucgcuauuac gccagcuggc aaaggggga    13440 ugucugcaa ggcgauuaag uugggguaacg ccaggguuuu cccagucaca cgcguaauac    13500
gacucacuau ag                                                      13512
```

<210> SEQ ID NO 10
<211> LENGTH: 13137
<212> TYPE: DNA
<213> ORGANISM: Artificial
<220> FEATURE:

<223> OTHER INFORMATION: synthetic polynucleotide

<400> SEQUENCE: 10

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctctttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gccagcgag cacgacggcg    2040
aatacctgta cgacatcgac aggaaacagt gcgtcaagaa agaactagtc actgggctag    2100
ggctcacagg cgagctggtg atcctcccct ccatgaatt cgcctacgag agtctgagaa    2160
cacgaccagc cgctccttac caagtaccaa ccataggggt gtatgcgtg ccaggatcag    2220
gcaagtctgg catcattaaa agcgcagtca ccaaaaaaga tctagtggtg agcgccaaga    2280
```

```
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc    2520 tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc    3060
agaataaggc aaacgtgtgt ggggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc    3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga atgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
```

```
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatgagg tttctggcgc    5400
gaccggtgcc tgcgcctcga acagtattca ggaaccctcc acatcccgct ccgcgcacaa    5460
gaacaccgtc acttgcaccc agcagggcct gctcagaaac cagcctagtt tccaccccgc    5520
caggcgtgaa tagggtgatc actagagagg agctcgaggc gcttacccccg tcacgcactc    5580 ctagcaggtc ggtctcgaga accagcctgg tctccaaccc gccaggcgta ataggtga    5640 ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
```

```
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgaagatg cagacccccca aagaatccct gtccgagagg ctcagcgccc tgcaggataa    7620
gatcctcgac cactacgaaa acgactccaa ggacatcaac tcccagatct cctattggca    7680
gctcatcagg ctggagaacg ctatcctgtt cacagccaga gagcacggca ttaccaagct    7740
gaaccatcaa gtggtccccc ctattaacat ctccaaaagc aaggcccaca aggccatcga    7800
gctgcaaatg gccctcaaag gcctggccca gtccaagtat aacaacgagg agtggaccct    7860
gcaggataca tgcgaggagc tgtggaacac cgagccctcc caatgtttcg ccaagggcgg    7920
caagacagtg catgtctatt tcgatggcaa taaagataac tgcatgaact acgtggtgtg    7980
ggacagcatt tactacatta ccgaaaccgg catttgggac aagaccgctg cttgcgtcag    8040 ctattgggc gtgtactaca ttaaggatgg cgataccacc tactacgtcc agttcaagtc    8100
cgaatgcgag aaatatggca attccaacac ctgggaagtg cagtatggag gcaatgtgat    8160
cgactgcaac gactccatgt gttccggagg aacaggagga agcacaaccc ccatcatcca    8220
tctgaaggga gataagaaca gcctcaagtg cctgaggtac aggctgagga aatacgctga    8280
ccactactcc gaaatctcct ccacatggca ctggaccggc tgcaataaga acaccggaat    8340
cctgaccgtg acctacaact ccgaggtgca gaggaacacc ttcctggatg tcgtgacaat    8400 cccccaattcc gtccagatta gcgtcggcta catgacaatc ggcggaggag gcggaatgga    8460
aagcattccc gccaggctga atgctgtgca ggaaaaaatc ctcgatctgt acgaagccga    8520
ctccaacgac ctgaacgccc agatcgaaca ctggaaactg accaggatgg aatgcgtcct    8580
gttttataaa gccaaggagc tcggcatcac ccatatcggc caccaagtcg tccctcccat    8640
ggccgtgtcc aaggccaagg cctgtcaggc tattgagctc cagctggccc tggaggccct    8700
caataaaacc caatatagca cagacggctg gacccctccag caaaccagcc tcgagatgtg    8760
gagggccgaa ccccagaaat actttgccaa acacggctat acaatcacag tgcagtacga    8820
taatgacaag aataatacca tggactacac aaattggaaa gagatctacc tgctcggcga    8880
gtgtgagtgc accatcgtcg agggccaggt ggattactac ggcctgtact actggtgtga    8940
tggcgaaaag atctattttg tgaagttctc caacgacgct aagcagtact gtgtcacagg    9000
cgtctgggag gtccacgtcg gaggccaggt gatcgtctgc cctgctagcg tgagcagcgg    9060
cggaacagga ggctccaccg ctcccattat tcatctgaaa ggcgaccca attccctgaa    9120 gtgtctgagg tatagagtca agaccacaa aagcctctac gtgcagatca gcagcacatg    9180
gcactggacc tccaatgagt gtacaaataa taaactggga atcgtcacaa tcacctacag    9240
cgatgagacc caaaggcagc agttcctcaa aaccgtcaag atccccaata ccgtccaggt    9300
gatccaaggc gtcatgtccc tcggcggagg aggaggaatg gaagagatca gcgccaggct    9360
```

```
cagcgctgtg caagacaaaa ttctggacat ctacgaggct gacaagaacg atctcacatc    9420
ccagatcgag cactggaagc tcatcaggat ggagtgcgcc attatgtaca ccgccaggca    9480
aatgggcatt agccacctgt gccaccaagt ggtgccctcc ctcgtcgcct ccaagaccaa    9540
agccttccag gtgatcgagc tccaaatggc cctggagacc ctgaacgcca gccctacaa     9600
gacagacgag tggacactgc agcagacctc cctggaagtc tggctgtccg agccccagaa    9660
gtgctttgct aagaagggca tcaccgtgac cgtgcaatac gacaacgaca aggccaacac    9720
catggattat accaactgga gcgaaatcta catcatcgag gagaccacct gtaccctcgt    9780
ggccggcgag gtcgactacg tgggcctgta ttacatccac ggaaatgaga aaacatactt    9840
taaatatttt aaggaggacg ccaaaaaata tagcaagaca caactgtggg aggtgcacgt    9900
cggcagcagg gtgattgtgt gtcctaccag catccctagc ggaggcacag gaggctccgt    9960
gtcccctatt gtccacctga aaggcgatcc taattccctg aaatgcctga ggtataggct   10020
caaacccttc aaggacctct actgcaacat gagctccaca tggcattgga caagcgacga   10080
taagggcgat aaggtgggca ttgtgaccgt gacctacacc accgaaaccc agaggcaact   10140
gttcctcaac accgtgaaga tccctcctac agtccagatc tccaccggcg tgatgtccct   10200
gggaggcgga ggaggccgtg ctcattataa catcgtgacc ttctgttgca aatgtgactc   10260
caccctgaga ctctgtgtcc agtccaccca cgtggacatt agaaccctgg aagacctgct   10320
catgggcaca ctgggcattg tgtgtcccat ctgctcccag aagcccaccc tccatgagta   10380
catgctggac ctgcagcccg agaccacaga cctgtacggc taccaacagc tgggcggagg   10440
aggaggaaga cacaccatgc tgtgtatgtg ctgcaagtgt gaggctagga tcaagctcgt   10500
ggtcgagagc agcgccgatg acctcagagc cttccagcag ctgtttctga cacccctgag   10560
cttcgtgtgt ccttggtgtg cctcccagca gaccctgcaa gacatcgtcc tgcatctgga   10620
gccccagaac gaaattcccg tggacctgct gggccatcag cagctctccg actccgagga   10680
ggaaaacgac gagatcgatt gatgaggcgc gcccacccag cggccgcata cagcagcaat   10740
tggcaagctg cttacataga actcgcggcg attggcatgc cgccttaaaa ttttttatttt   10800
attttctttt tcttttccga atcggatttt gtttttaata tttcaaaaaa aaaaaaaaaa   10860
aaaaaaaaaa aaaaaaaaaa aaaagaagag cgtttaaaca cgtgatatct ggcctcatgg   10920
gccttccttt cactgcccgc tttccagtcg ggaaacctgt cgtgccagct gcattaacat   10980
ggtcatagct gtttccttgc gtattgggcg ctctccgctt cctcgctcac tgactcgctg   11040
cgctcggtcg ttcgggtaaa gcctggggtg cctaatgagc aaaaggccag caaaaggcca   11100
ggaaccgtaa aaaggccgcg ttgctggcgt ttttccatag gctccgcccc cctgacgagc   11160
atcacaaaaa tcgacgctca agtcagaggt ggcgaaaccc gacaggacta taaagatacc   11220
aggcgtttcc ccctggaagc tccctcgtgc gctctcctgt tccgaccctg ccgcttaccg   11280
gatacctgtc cgcctttctc ccttcgggaa gcgtggcgct ttctcatagc tcacgctgta   11340
ggtatctcag ttcggtgtag gtcgttcgct ccaagctggg ctgtgtgcac gaaccccccg   11400
ttcagcccga ccgctgcgcc ttatccggta actatcgtct tgagtccaac ccggtaagac   11460
acgacttatc gccactggca gcagccactg gtaacaggat tagcagagcg aggtatgtag   11520
gcggtgctac agagttcttg aagtggtggc ctaactacgg ctacactaga agaacagtat   11580
ttggtatctg cgctctgctg aagccagtta ccttcggaaa aagagttggt agctcttgat   11640
ccggcaaaca aaccaccgct ggtagcggtg gttttttgt ttgcaagcag cagattacgc    11700
gcagaaaaaa aggatctcaa gaagatcctt tgatcttttc tacggggtct gacgctcagt   11760
```

```
ggaacgaaaa ctcacgttaa gggattttgg tcatgaatac acggtgcctg actgcgttag    11820
caatttaact gtgataaact accgcattaa agcttatcga tgataagctg tcaaacatga    11880
gaattcttag aaaaactcat cgagcatcaa atgaaactgc aatttattca tatcaggatt    11940
atcaatacca tattttgaa aaagccgttt ctgtaatgaa ggagaaaact caccgaggca     12000
gttccatagg atggcaagat cctggtatcg gtctgcgatt ccgactcgtc caacatcaat    12060
acaacctatt aatttcccct cgtcaaaaat aaggttatca agtgagaaat caccatgagt    12120
gacgactgaa tccggtgaga atggcaaaag cttatgcatt tctttccaga cttgttcaac    12180
aggccagcca ttacgctcgt catcaaaatc actcgcatca accaaaccgt tattcattcg    12240
tgattgcgcc tgagcgagac gaaatacgcg atcgctgtta aaaggacaat acaaacagg     12300 aatcgaatgc aaccgcgca ggaacactgc cagcgcatca acaatatttt cacctgaatc     12360
aggatattct tctaatacct ggaatgctgt tttcccgggg atcgcagtgg tgagtaacca    12420
tgcatcatca ggagtacgga taaaatgctt gatggtcgga agaggcataa attccgtcag    12480
ccagtttagt ctgaccatct catctgtaac atcattggca acgctacctt tgccatgttt    12540
cagaaacaac tctggcgcat cgggcttccc atacaatcga tagattgtcg cacctgattg    12600
cccgacatta tcgcgagccc atttataccc atataaatca gcatccatgt tggaatttaa    12660
tcgcggcctc gagcaagacg tttccgttg aatatggctc ataacacccc ttgtattact    12720
gtttatgtaa gcagacagtt ttattgttca tgagcggata catatttgaa tgtatttaga    12780 aaataaaca aataggggtt ccgcgcacat ttccccgaaa agtgccacct aaattgtaag    12840
cgttaatatt ttgttaaaat tcgcgttaaa tttttgttaa atcagctcat tttttaacca    12900
ataggccgaa atcggcaaaa tcccttataa atcaaaagaa tagaccgaga tagggttgag    12960
tggccgctac agggcgctcc cattcgccat tcaggctgcg caactgttgg gaagggcgtt    13020
tcggtgcggg cctcttcgct attacgccag ctggcgaaag gggatgtgc tgcaaggcga    13080 ttaagttggg taacgccagg gttttcccag tcacacgcgt aatacgactc actatag      13137
```

<210> SEQ ID NO 11
<211> LENGTH: 13137
<212> TYPE: RNA
<213> ORGANISM: Artificial
<220> FEATURE:
<223> OTHER INFORMATION: synthetic polynucleotide

<400> SEQUENCE: 11

```
auaggcggcg caugagagaa gcccagacca auuaccuacc caaaauggag aaaguucacg      60
uugacaucga ggaagacagc ccauuccuca gagcuuugca gcggagcuuc ccgcaguuug     120
agguagaagc caagcagguc acugauaaug accaugcuaa ugccagagcg uuuucgcauc     180
uggcuucaaa acugaucgaa acggaggugg acccauccga cacgauccuu gacauuggaa     240
gugcgcccgc ccgcagaaug uauucuaagc acaaguauca uuguaucugu ccgaugagau     300
gugcggaaga uccggacaga uuguauaagu augcaacuaa gcugaagaaa aacuguaagg     360
aaauaacuga uaaggaauug acaagaaaa ugaggagcu cgccgccguc augagcgacc      420
cugaccugga aacugagacu augugccucc acgacgacga gucgucgc uacgaagggc      480 aagucgcugu uuaccaggau guauacgcgg uugacggacc gacaagucuc uaucaccaag     540
ccaauaaggg aguuagaguc gccuacugga uaggcuuuga caccaccccu uuuauguuua     600
agaacuuggc uggagcauau ccaucauacu cuaccaacug ggccgacgaa accguguuaa     660
```

```
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga gucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucaugggug uuguugggcu uuuagaaggc   1320
acaagauaac aucuauuuau aagcgcccgg auacccaaac caucaucaaa gugaacagcg   1380
auuuccacuc auucgugcug cccaggauga gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcugguc gauccuccccu uccaugaauu cgccuacgag agucugagaa   2160
cacgaccagc cgcuccuuac caaguaccaa ccauaggggu guaggcgug ccaggaucag   2220 gcaagucugg caucauuaaa agcgcaguca ccaaaaaga ucuaguggug agcgccaaga   2280
aagaaaacug ugcagaaauu auaagggacg ucaagaaaau gaagggcug gacgucaaug   2340 ccagaacugu ggacucagug cucuugaaug gaugcaaaca ccccguagag acccuguaua   2400
uugacgaagc uuuugcuugu caugcaggua cucucagagc gcucauagcc auuauaagac   2460 cuaaaaggc agugcucugc ggggaucca aacagcgg uuuuuuaac augaugugcc   2520 ugaaagugca uuuuaaccac gagauuugca cacaagucuu ccacaaaagc aucucucgcc   2580
guugcacuaa aucgugacu ucggucgucu caaccuuguu uuacgacaaa aaaugagaa   2640 cgacgaaucc gaaagagacu aagauuguga uugacacuac cggcaguacc aaaccuaagc   2700
aggacgaucu cauucucacu guuucagag ggugggugaa gcaguugcaa auagauuaca   2760
aaggcaacga aauaaugacg gcagcugccu cucaagggcu gacccguaaa ggugugaug   2820 ccgucgguua caaggugaau gaaaauccuc ugacgcacc caccucagaa caugugaacg   2880
uccuacugac ccgcacggag gaccgcauc uguggaaaac acuagccggc gacccuggga   2940 uaaaacacu gacugccaag uacccuggga auucacugc cacgauagag gaguggcaag   3000
cagagcauga ugccaucaug aggcacaucu uggagagacc ggaccuuacc gacgucuucc   3060
```

```
agaauaaggc aaacgugugu ugggccaagg cuuuagugcc ggugcugaag accgcuggca    3120
uagacaugac cacugaacaa uggaacacug uggauuauuu ugaaacggac aaagcucacu    3180
cagcagagau aguauugaac caacuaugcg ugagguucuu uggacucgau cuggacuccg    3240
gucuauuuuc ugcacccacu guuccguuau ccauuaggaa uaaucacugg gauaaucccc    3300
cgucgccuaa cauguacggg cugaauaaag aaguggccg ucagcucucu cgcagguacc     3360
cacaacugcc ucgggcaguu gccacuggaa gagucuauga caugaacacu gguacacugc    3420
gcaauuauga uccgcgcaua aaccuaguac cuguaaacag aagacugccu caugcuuuag    3480
uccuccacca uaaugaacac ccacagagug acuuucuuc auucgucagc aaauugaagg     3540
gcagaacugu ccuggugguc ggggaaaagu uguccguccc aggcaaaaug guugacuggu    3600
ugucagaccg gccugaggcu accuucagag cucggcugga uuuaggcauc ccaggugaug    3660
ugcccaaaua ugacauaaua uuuguuaaug ugaggacccc auauaaauac caucacuauc    3720
agcaguguga agaccaugcc auuaagcuua gcauguugac caagaaagcu gucugcauc     3780 ugaaucccgg cggaaccugu gucagcauag guuaugguua cgcugacagg gccagcgaaa    3840
gcaucauugg ugcuauagcg cggcaguuca aguuucccg gguaugcaaa ccgaaauccu     3900
cacuugaaga gacggaaguu cuguuuguau cauggggua cgaucgcaag gcccguacgc     3960
acaauccuua caagcuuuca ucaaccuuga ccaacauuua uacagguucc agacuccacg    4020
aagccggaug ugcacccuca uaucauguqg ugcgagggga uauugccacg gccaccgaag    4080
gagugauuau aaaugcugcu aacagcaaag acaaccugg cggagggqug ugcggagcgc     4140 uguauaagaa auucccggaa agcuucgauu uacagccgau cgaaguagga aaagcgcgac    4200
uggucaaagg ugcagcuaaa cauaucauuc augccguagg accaaacuuc aacaaaguuu    4260 cggaagguuga aggugacaaa caguuggcag aggcuuauga guccaucgcu aagauuquca    4320 acgauaacaa uuacaaguca guagcgauuc cacuguuquc caccqqcauc uuuuccggga    4380 acaaagaucg acuaacccaa ucauuqaacc auuugcugac agcuuuagac accacugaug    4440
cagauguagc cauauacugc agggacaaga auqqqaaaau gacucucaag gaagcagugg    4500
cuaggagaga agcaquggag gagauaugca uaccgacga cucuucagug acagaaccug    4560
augcagagcu ggugagggug cauccqaaga guucuuuqgc uqgaaggaaq qgcuacagca    4620 caagcgaugg caaaacuuuc ucauauuuqq aaqggaccaa guuucaccag qcgqccaagg    4680 auauaqcaqa aauuaauqcc auquqqcccq uuqcaacqqa qqccaauqaq caqquauqca    4740 uguauauccu cggagaaagc augagcagua uuaggucgaa augccccguc gaaqaqucgq    4800 aagccuccac accaccuaqc acgcuqccuu qcuuqucau ccauqccauq acuccagaaa     4860 gaguacaqcg ccuaaaagcc ucacguccag aacaaauuac ugugqcuca uccuuuccau    4920 uqccqaaqua uaqaaucacu qqtqugcaqa aqauccaauq cucccaqccu auauugauucu   4980 caccgaaagu gccugcquau auucauccaa ggaaguaucu cgggaaaaca ccaccggtag    5040
acgagacucc ggagccaucg gcagagaacc aauccacaqa ggggacaccu qaacaaccac    5100 cacuuauaac cgaggaugag accaggacua qaacqccuqa gccqaucauc aucqaaqaqq    5160 aagaagagqa uaqcauaaqu uuqcuqcaq auqqcccqac ccaccaqquq cuqcaaqucq    5220 aggcaqacau ucacqqqccq ccucuquauu cuaqcucauc cugquccauu ccucaugcau    5280 ccgacuuuga uqugqacaqu uuauccqauc ugqacaccuu qqaqqqaquu aqcquqacca    5340 gcqqqqcaac qucaqccqaq acuaacucuu acuucqcaaa qaquauqqaq uuucuqqcqc    5400
```

```
gaccggugcc ugcgccucga acaguauuca ggaaccccucc acaucccgcu ccgcgcacaa   5460
gaacaccguc acuugcaccc agcagggccu gcucgagaac cagccuaguu uccacccgc    5520 caggcgugaa uagggugauc acuagagagg agcucgaggc gcuuacccg ucacgcacuc    5580 cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc augugaaaag agaacuuucc gacugugcu ucuuacugua    6120 uuauuccaga guacgaugcc uauuuggaca ugguugacgg agcuucaugc ugcuuagaca   6180
cugccaguuu uugccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420 uuaagaaaa cccccaucagg cuuacugaag aaaacguggu aaauuacauu accaaauuaa    6480
aaggaccaaa agcugcugcu cuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauugugu cuggaaacug acaucgcguc guuugauaaa agugaggacg    6840
acgccauggc ucugaccgcg uuaaugauuc uggaagacuu aggugggac gcagagcugu    6900 ugacgcugau ugaggcggcu uucggcgaaa uuucaucaau acauuugccc acuaaaacua   6960
aauuuaaauu cggagccaug augaaaucug gaaugucccu cacacuguuu gugaacacag   7020
ucauuaacau uguaaucgca agcagagugu ugagagaacg gcuaaccgga ucaccaugug   7080
cagcauucau uggagaugac aauaucguga aggagucaa aucggacaaa uuaauggcag    7140
acaggugcgc caccugguug aauauggaag ucaagauuau agaugcugug guggcgaga    7200 aagcgccuua uuucugugga gggguuauuu ugugugacuc cgugaccggc acagcgugcc   7260
guguggcaga ccccuaaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaccgua ggaacuucca    7440 ucauaguuau ggccaugacu acucuagcua gcaguguuaa aucauucagc uaccugagag   7500 gggcccuau aacucucuac ggcuaaccug aauggacuac gacauagucu aguccgccaa    7560
gaugaagaug cagacccca aagaaucccu guccgagagg cucagcgccc ugcaggauaa    7620
gauccucgac cacuacgaaa acgacuccaa ggacaucaac uccagaucu ccauuuggca   7680 gcucaucagg cuggagaacg cuauccguu cacagcagag agcacggca uuaccaagcu    7740 gaaccaucaa guggucccc cuauuaacau cuccaaaagc aaggcccaca aggccaucga    7800
```

```
gcugcaaaug gcccucaaag gccuggccca guccaaguau aacaacgagg aguggacccu   7860
gcaggauaca ugcgaggagc uguggaacac cgagcccucc caauguuucg ccaagggcgg   7920
caagacagug caugucuauu ucgauggcaa uaaagauaac ugcaugaacu acguggugug   7980
ggacagcauu uacuacauua ccgaaaccgg cauuugggca aagaccgcug cuugcgucag   8040
cuauuggggc uguacuaca uuaaggaugg cgauaccacc uacuacgucc aguucaaguc   8100
cgaaugcgag aaauauggca auuccaacac cugggaagug caguauggag gcaaugugau   8160
cgacugcaac gacuccaugu guuccggagg aacaggagga agcacaaccc ccaucaucca   8220
ucugaaggga gauaagaaca gccucaagug ccugagguac aggcugagga aauacgcuga   8280
ccacuacucc gaaaucuccu ccacauggca cuggaccggc ugcaauaaga acaccggaau   8340
ccugaccgug accuacaacu ccgaggugca gaggaacacc uuccuggaug ucugacaau   8400 ccccaauucc guccagauua gcgucggcua caugacaauc ggcggaggag gcggaaugga   8460
aagcauuccc gccaggcuga augcugugca ggaaaaaauc cucgaucugu acgaagccga   8520
cuccaacgac cugaacgccc agaucgaaca cuggaaacug accaggaugg aaugcgaccu   8580
guuuuauaaa gccaaggagc ucggcaucac ccauaucggc caccaagucg ucccucccau   8640
ggccgugucc aaggccaagg ccugucaggc uauugagcuc cagcuggccc uggaggcccu   8700
caauaaaacc caauauagca cagacggcug gacccuccag caaaccagcc ucgagaugug   8760
gagggccgaa ccccagaaau acuuugccaa acacggcuau acaaucacag ugcaguacga   8820
uaaugcaaag aauaauacca uggacuacac aaaauuggaaa gagaucuacc ugcucggcga   8880
gugugagugc accaucgucg agggccaggu ggauuacuac ggccuguacu acuggugug   8940 uggcgaaaag aucuauuuug ugaaguucuc caacgacgcu aagcaguacu gugucacagg   9000 cgucuggag guccacgucg gaggccaggu gaucgucugc ccugcuagcg ugagcagcgg   9060
cggaacagga ggcuccaccg cucccauuau ucaucugaaa ggcgacccca auucccugaa   9120
gugucugagg uauagaguca agaccacaa aagccucuac gugcagauca gcagcacaug   9180
gcacuggacc uccaaugagu guacaaauaa uaaacuggga aucgucacaa ucaccuacag   9240
cgaugagacc caaaggcagc aguuccucaa aaccgucaag auccccaaua ccguccaggu   9300
gauccaaggc gucaugucccu cggcggagg aggaggaaug gaagagauca cgccaggcu   9360 cagcgcugug caagacaaaa uucuggacau cuacgaggcu acaagaacg aucucacauc   9420 ccagaucgag cacugaagc ucaucaggau ggagugcgcc auuauguaca ccgccaggca   9480
aaugggcauu agccaccugu gccaccaagu ggugcccucc cucgucgccu ccaagaccaa   9540
agccuuccag gugaucgagc uccaaauggc ccuggagacc cugaacgcca gccccuacaa   9600
gacagacgag uggacacugc agcagaccuc ccuggaaguc uggcuguccg agccccagaa   9660
gugcuuugcu aagaagggca ucaccgugac cgugcaauac gacaacgaca aggccaacac   9720
caugauuaau accaacugga gcgaaaucua caucaucgag gagaccaccu guacccucgu   9780
ggccggcgag gucgacuacg uggcccugua uucauccac ggaaaugaga aaacauacuu   9840
uaaauauuuu aaggaggacg ccaaaaaaua uagcaagaca caacugggg aggugcacgu   9900 cggcagcagg gugauugugu guccuaccag cauccccagc ggaggcacag gaggcuccgu   9960 gucccccauuu guccaccuga aaggcgaucc uaauucccug aaaugccuga gguauaggcu  10020
caaacccuuc aaggacccucu acugcaacau gagcuccaca uggcauugga caagcgacga  10080
uaagggcgau aagguuggca uugugaccgu gaccuacacc accgaaaccc agaggcaacu  10140
```

-continued

```
guuccucaac accgugaaga ucccuccuac aguccagauc uccaccggcg ugaugucccu    10200
gggaggcgga ggaggccgug cucauuauaa caucgugacc uucuguugca aaugugacuc    10260 caccugaga cucugugucc aguccaccca cguggacauu agaacccugg aagaccugcu     10320
caugggcaca cugggcauug uguucccau cugcucccag aagcccaccc uccaugagua     10380
caugcuggac cugcagcccg agaccacaga ccuuacggc uaccaacagc ugggcggagg     10440
aggaggaaga cacaccaugc uguguaugug cugcaagugu gaggcuagga ucaagcucgu    10500
ggucgagagc agcgccgaug accucagagc cuuucagcag cuguuucuga acacccugag    10560
cuucgugugu ccuuggugug ccucccagca gacccugcaa gacaucgucc ugcaucugga    10620
gccccagaac gaaauucccg uggaccugcu gggccaucag cagcucuccg acuccgagga    10680
ggaaaacgac gagaucgauu gaugaggcgc gcccacccag cggccgcaua cagcagcaau    10740
uggcaagcug cuuacauaga acucgcggcg auuggcaugc cgccuaaaa uuuuuauuuu     10800 auuuuucuuu ucuuuuccga aucggauuuu guuuuaaua uuucaaaaaa aaaaaaaaaa     10860
aaaaaaaaaa aaaaaaaaaa aaagaagag cguuuaaaca cgugauaucu ggccucaugg     10920
gccuuccuuu cacugcccgc uuuccagucg ggaaaccugu cgugccagcu gcauuaacau    10980
ggucauagcu guuccuugc guauggggcg cucuccgcuu cccgcucac ugacucgcug      11040 cgcucggucg uucggguaaa gccuggggug ccuaaugagc aaaaggccag caaaaggcca    11100
ggaaccguaa aaaggccgcg uugcuggcgu uuuuccauag gcuccgcccc ccugacgagc    11160
aucacaaaaa ucgacgcuca agucagaggu ggcgaaaccc gacaggacua uaaagauacc    11220
aggcguuucc cccuggaagc ucccucgugc gcucuccugu uccgacccug ccgcuuaccg    11280
gauaccuguc cgccuuucuc ccuucgggaa gcguggcgcu uucucauagc ucacgcugua    11340
gguaucucag uucgguguag gucguucgcu ccaagcuggg cuguugugcac gaacccccg    11400 uucagcccga ccgcugcgcc uuauccggua acuaucgucu ugaguccaac ccgguaagac    11460
acgacuuauc gccacuggca gcagccacug guaacaggau uagcagagcg agguauguag    11520
gcggugcuac agaguucuug aaguggugc cuaacuacgg cuacacuaga gaacaguauu    11580
uugguaucug cgcucugcug aagccaguua ccuucggaaa aagaguugguu agcucuugau    11640 ccggcaaaca aaccaccgcu gguagcggug guuuuuugu uugcaagcag cagauuacgc    11700
gcagaaaaaa aggaucucaa gaagauccuu ugaucuuuuc uacggggucu gacgcucagu    11760
ggaacgaaaa cucacguuaa gggauuuugg ucaugaauac acggugccug acugcguuag    11820 caauuaacu gugauaaacu accgcauuaa agcuuaucga ugauaagcug ucaaacauga    11880
gaauucuuag aaaaacucau cgagcaucaa augaaacugc aauuuauuca uaucaggauu    11940
aucaauacca uauuuugaa aaagccguuu cuguaaugaa ggagaaaacu caccgaggca    12000
guuccauagg auggcaagau ccugguaucg gucugcgauu ccgacucguc caacaucaau    12060
acaaccuauu aauuucccu cgucaaaaau aagguuauca agugagaaau caccaugagu    12120
gacgacugaa uccggugaga auggcaaaag cuuaugcauu ucuuuccaga cuuguucaac    12180
aggccagcca uuacgcucgu caucaaaauc acucgcauca accaaaccgu uauucauucg    12240
ugauugcgcc ugagcgagac gaaauacgcg aucgcuguua aaaggacaau acaaacagg    12300 aaucgaaugc aaccggcgca ggaacacugc cagcgcauca acaauauuuu caccugaauc    12360
aggauauucu ucuaauaccu ggaaugcugu uuucccgggg aucgcaguggg ugaguaacca   12420 ugcaucauca ggagucggga uaaaaugcuu gauggucgga agaggcauaa auuccgucag    12480
ccaguuuagu cugaccaucu caucuguaac aucauuggca acgcuaccuu ugccauguuu    12540
```

| | |
|---|---|
| cagaaacaac ucuggcgcau cgggcuuccc auacaaucga uagauugucg caccugauug | 12600 |
| cccgacauua ucgcgagccc auuuauaccc auauaaauca gcauccaugu uggaauuuaa | 12660 |
| ucgcggccuc gagcaagacg uuucccguug aauauggcuc auaacacccc uuguauuacu | 12720 |
| guuuauguaa gcagacaguu uuauuguuca ugagcggaua cauauuugaa uguauuaga | 12780 |
| aaaauaaaca aauaggggu ccgcgcacau uccccgaaaa agugccaccu aaauuguaag | 12840 |
| cguuaauauu uuguuaaaau ucgcguuaaa uuuuuguuaa aucagcucau uuuuaacca | 12900 |
| auaggccgaa aucggcaaaa ucccuuauaa aucaaaagaa uagaccgaga uaggguugag | 12960 |
| uggccgcuac agggcgcucc cauucgccau ucaggcugcg caacuguugg gaagggcguu | 13020 |
| ucggugcggg ccucuucgcu auuacgccag cuggcgaaag ggggauguagc ugcaaggcga | 13080 |
| uuaaguuggg uaacgccagg guuucccag ucacacgcgu aauacgacuc acuauag | 13137 |

<210> SEQ ID NO 12
<211> LENGTH: 15582
<212> TYPE: DNA
<213> ORGANISM: Artificial
<220> FEATURE:
<223> OTHER INFORMATION: synthetic polynucleotide

<400> SEQUENCE: 12

| | |
|---|---|
| ataggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg acaagaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc gacaagtctc tatcaccaag | 540 |
| ccaataaggg agttagagtc gcctactgga taggctttga caccaccct tttatgttta | 600 |
| agaacttggc tggagcatat ccatcatact ctaccaactg ggccgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |
| tcgttaaaag aatagctatc agtccaggcc tgtatgggaa gccttcaggc tatgctgcta | 960 |
| cgatgcaccg cgagggattc ttgtgctgca aagtgacaga cacattgaac ggggagaggg | 1020 |
| tctctttcc cgtgtgcacg tatgtgccag ctacattgtg tgaccaaatg actggcatac | 1080 |
| tggcaacaga tgtcagtgcg gacgacgcgc aaaaactgct ggttgggctc aaccagcgta | 1140 |
| tagtcgtcaa cggtcgcacc cagagaaaca ccaataccat gaaaaattac cttttgcccg | 1200 |
| tagtggccca ggcatttgct aggtgggcaa aggaatataa ggaagatcaa gaagatgaaa | 1260 |
| ggccactagg actacgagat agacagttag tcatggggtg ttgttgggct tttagaaggc | 1320 |
| acaagataac atctatttat aagcgcccgg atacccaaac catcatcaaa gtgaacagcg | 1380 |
| atttccactc attcgtgctg cccaggatag gcagtaacac attggagatc gggctgagaa | 1440 |

```
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg tttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt gggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc gggaaaagt tgtccgtccc aggcaaaatg gttgactggt    3600
tgtcagaccg gcctgaggct accttcagag ctcggctgga tttaggcatc ccaggtgatg    3660
tgcccaaata tgcataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
```

```
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag     4080 gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga atgggaaat gactctcaag gaagcagtgg     4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccg tcacgcactc      5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag gcatttaca acaaaaatca gtaaggcaaa      5760
cggtgctatc cgaagtggtg ttggagagga ccgaattgga gatttcgtat gccccgcgcc    5820
tcgaccaaga aaagaagaa ttactacgca agaaattaca gttaaatccc acacctgcta     5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
```

```
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatggctaag gccgccatgc tcgctaagtt taaggaactg tacggcgtct cctttccga   7620 gctcgtgaga ccttttcaagt ccaacaagtc cacctgctgt gactggtgca ttgctgcctt   7680
cggcctgaca ccctccatcg ccgactccat caagacactg ctgcaacagt actgcctgta   7740
tctgcacatc cagagcctgg cttgcagctg gggaatggtg gtgctgctgc tcgtcaggta   7800
caagtgcggc aagaacaggg aaaccattga gaagctgctg agcaagctgc tgtgcgtcag   7860
ccctatgtgc atgatgattg agccccctaa gctcaggagc acagctgccg ctctctattg   7920
gtacaaaacc ggaatctcca acatcagcga ggtgtacggc gacacccctg agtggattca   7980
aaggcaaaca gtgctccagc atagcttcaa cgattgcacc ttcgagctga gccaaatggt   8040
gcaatgggcc tacgataacg acatcgtgga tgatagcgag attgcttaca aatatgccca   8100
gctggccgac acaaacagca acgcctccgc tttcctgaag tccaacagcc aagccaaaat   8160
cgtgaaggac tgcgctacca tgtgtaggca ctacaaaaga gccgagaaga agcaaatgag   8220
catgagccag tggatcaaat atagatgcga cagggtcgac gatggaggag attggaagca   8280
gatcgtcatg tttctcagat accagggcgt ggaatttatg agcttctga ccgccctgaa   8340 gagatttctc cagggcatcc ctaaaaagaa ctgtattctg ctgtatggcg ctgccaacac   8400
cgacaaaagc ctgttcggaa tgagcctcat gaagtttctg caggggcagcg tgatctgttt   8460 cgtgaacagc aagagccatt tctggctcca gcccctcgct gacgccaaga tcggaatgct   8520
ggacgacgct accgtcccct tgctggaacta catcgatgat aatctcagaa acgctctgga   8580
```

```
tggcaacctg gtgagcatgg acgtcaagca cagacccctg gtccaactga aatgtccccc      8640
tctcctcatc acaagcaaca ttaacgccgg caccgatagc aggtggccct atctccataa      8700
cagactggtg gtgtttacct tccccaacga atttcccttc gacgaaaacg gcaatcctgt      8760
gtacgagctc aacgacaaaa actggaagtc cttcttcagc agaacatggt ccagactgag      8820
cctcggagga ggaggaggaa aacaaggagc catgctcgcc gtcttcaagg acacctacgg      8880
cctcagcttt accgacctcg tcagaaactt taaatccgat aaaaccacct gcacagattg      8940
ggtgaccgcc attttcggag tgaatcccac cattgccgaa ggcttcaaga cactgatcca      9000
acctttcatc ctgtacgccc acattcagtg tctcgactgt aagtggggcg tgctgattct      9060
ggccctgctg agatacaaat gcggcaagtc cagactcaca gtggccaagg gcctctccac      9120
actgctgcat gtccccgaga cctgcatgct gattcaacct cccaaactca ggagcagcgt      9180
ggctgctctg tactggtata ggacaggcat ttccaacatt tccgaggtca tgggagacac      9240
acctgaatgg attcaaagac tgaccatcat ccagcacggc atcgatgact ccaacttcga      9300
cctgagcgaa atggtccagt gggctttcga caacgagctg accgacgagt ccgacatggc      9360
cttcgagtac gctctcctcg ctgactccaa ctccaatgct gctgcttttc tcaagtccaa      9420
ctgccaggct aagtacctga agactgcgc caccatgtgc aagcattaca ggcgtgctca      9480
aaaaaggcag atgaatatgt cccaatggat tagatttagg tgctccaaga tcgatgaggg      9540
aggcgactgg agacccattg tgcagttcct caggtaccag cagatcgagt ttatcacatt      9600
tctgggagct ctgaagtcct tcctgaaggg caccccccaag aaaaactgtc tggtgttctg      9660
cggccctgct aatacagata aaagctactt cggcatgtcc ttcatccact ttatccaggg      9720
cgctgtgatc agcttcgtga atagcacatc ccacttttgg ctggaacccc tcacagacac      9780
aaaggtggcc atgctggatg acgctacaac aacctgttgg acctatttcg ataccatcat      9840
gaggaacgct ctcgacggca ccctattag cattgataga aaacacaaac ctctgatcca      9900
gctgaagtgc cctcccatcc tcctcacaac caacattcac cccgccaagg acaatagatg      9960
gccttacctc gagagcagga tcaccgtctt tgagtttcct aacgccttcc cctttgacaa     10020
gaacggcaac cccgtgtatg aaatcaatga taaaaattgg aaatgtttct cgagaggac      10080
atggagcaga ctcgatctcg gaggcggcgg cggagatcct caggaaaggc ctaggaaact     10140
ccccccagctg tgcaccgagc tgcagaccac cattcacgac attatcctgg agtgcgtcta     10200
ctgcaagcaa cagctgctca aagggaggt ctatgatttt gccagaaggg atctgtgcat     10260
tgtgtacaga gacggcaatc cttatgccgt ctgcgataag tgcctgaaat tctatagcaa     10320
aatctccgaa tacagacact actgctacag cctgtatgga accaccctcg agcagcagta     10380
caataaaccc ctgtgcgatc tgctcatcag gaggatcaac tgtcaaaagc ccctgtgtcc     10440
cgaggaaaag cagagacacc tggataagaa acagaggttc cacaatatca ggggcagatg     10500
gaccggcaga tgcatgtcct gttgtaggtc cagcggcgga ggaggaggag accctaccag     10560
aaggccctat aagctgcctg acctctgcac agaactcaat accagcctgc aggatatcga     10620
gatcacatgt gtctattgca agaccgtgct ggaactgacc gaagtgttcg agtttgctag     10680
gaaagacctc ttcgtcgtgt acagggacag catcccccat gccgcctgcc acaagtgtat     10740
tgacttctac tccaggatta gggagctcag gcactactcc gactccgtct atggcgacac     10800
cctcgagaag ctcacaaaca ccggcctcta taatctcctc atcaggaggc tgagatgcca     10860
aaagcccctc aaccctgctg agaaactgag gcacctgaat gagaagagaa gatttcataa     10920
```

```
cattgccgga cactacagag gacagtgtca cagctgttgc aacagggctg gcggaggagg   10980
aggcgacacc gaagagaaac ccagaaccct ccacgacctg tgtcaggctc tcgagacaac   11040
catccataac atcgagctcc agtgtgtgga atgcaagaaa cccctgcaga ggtccgaggt   11100
gtatgatttc gccagagccg atctgacagt ggtctatagg gagggaaacc cttttggcat   11160
ctgcaaactg tgtctcaggt ttctctccaa gatcagcgag tatagacatt ataactacag   11220
cgtgtacggc aacaccctgg agcaaaccgt gaaaaagccc ctgaacgaga tcctcattag   11280
gaggatcatt tgtcagaggc ccctctgtcc ccaggagaag aagagacatg tggacctgaa   11340
taaaagattc cataacatca gcggcagatg ggccggcaga tgtgccgctt gctggagatc   11400
cagaggagga ggaggcggcg atcccaagca aagaccctac aagctgcctg atctgtgcac   11460
agagctgaac acaagcctcc aagatgtctc catcgcctgt gtctactgta aggccacact   11520
ggaaaggaca gaggtgtacc agtttgccag gaaggatctc tgcatcgtct acagggattg   11580
catcgcttac gccgcttgtc acaaatgtat cgatttttat tccagaatca gggaactgag   11640
atactatagc aactccgtct acggcgaaac cctcgagaaa attacaaaca cagaactcta   11700
caacctgctg attaggaggc tgagatgtca aaagcctctc aaccccgccg agaaaagaag   11760
gcacctcaaa gacaagagga gattccactc catcgctggc cagtacagag gccagtgtaa   11820
cacatgttgc gatcaggccg gaggaggagg cggcgaccct gccacaagac ccaggaccct   11880
ccacgagctc tgcgaggtgc tggagagtc cgtgcacgag attaggctcc agtgcgtgca   11940
gtgcaagaag gaactccaaa ggagagaagt gtataaattc ctgaggaccg acctcaggat   12000
tgtctatagg gacaacaacc cctacggagt gtgcattatg tgcctgaggt tcctcagcaa   12060
gatttccgaa tacaggcatt atcagtacag cctctacggc aaaaccctcg aggagagggt   12120
caaaaaaccc ctctccgaaa tcaccatcag aaggatcatc tgtcagacac ctctctgccc   12180
tgaggaaaag gaaaggcacg tgaacgctaa caagaggttc cataatatca tgggcaggtg   12240
gaccggaaga tgcagcgagt gctggagacc tagaggcggc ggcggaggcg atgctgaaga   12300
gaagcctagg accctgcacg atctgtgtca gccctggaa accagcgtcc acgaaatcga   12360
actgaaatgt gtcgagtgca aaagaccct gcagaggagc gaagtctacg attttgtgag   12420
agccgacctg agaattgtct acagagacgg aaaccccttc gccgtctgca aggtctgcct   12480
caggctgctc tccaaaatca gcgaatatag gcattacaat tactccctct acggcgacac   12540
actggagcaa acactcaaga agtgcctcaa cgagatcctg atcagaagaa tcatctgcca   12600
gaggcctctc tgcccccaag agaagaagag gcacgtggac ctgaacaaaa ggtttcacaa   12660
catcagcggc aggtggaccg gcagatgcgc cgtgtgttgg agacctagag gcggaggcgg   12720
aggaaatccc gctgagaggc ccagaaaact gcacgaactg tccagcgccc tggagattcc   12780
ttacgacgaa ctgaggctca actgcgtgta ttgcaaggga caactcaccg agaccgaagt   12840
gctggacttc gccaggaccg atctcaccat tgtctataga gacgacaccc ctcacggcgt   12900
gtgcaccaaa tgcctcaggt tctactccaa ggtcagcgag tttaggtggt acagatactc   12960
cgtgtacggc accaccctcg aaaagctgac caacaaggga atttgcgacc tcctgattag   13020
aaggattaca tgccagagac ccctgtgccc tgaggagaaa caaaggcacc tggacaagaa   13080
gaagagattc cacaacatcg gcggcagatg gacaggcaga tgcatcgcct gctggaggag   13140
gccttgatga ggcgcgccca cccagcggcc gcatacagca gcaattggca agctgcttac   13200
atagaactcg cggcgattgg catgccgcct taaaattttt atttttattt tcttttcttt   13260
tccgaatcgg attttgtttt taatatttca aaaaaaaaaa aaaaaaaaaa aaaaaaaaaa   13320
```

```
aaaaaaaaag aagagcgttt aaacacgtga tatctggcct catgggcctt cctttcactg    13380
cccgctttcc agtcgggaaa cctgtcgtgc cagctgcatt aacatggtca tagctgtttc    13440
cttgcgtatt gggcgctctc cgcttcctcg ctcactgact cgctgcgctc ggtcgttcgg    13500
gtaaagcctg gggtgcctaa tgagcaaaag gccagcaaaa ggccaggaac cgtaaaaagg    13560
ccgcgttgct ggcgtttttc cataggctcc gcccccctga cgagcatcac aaaaatcgac    13620
gctcaagtca gaggtggcga aacccgacag gactataaag ataccaggcg tttccccctg    13680
gaagctccct cgtgcgctct cctgttccga ccctgccgct taccggatac ctgtccgcct    13740
ttctcccttc gggaagcgtg gcgctttctc atagctcacg ctgtaggtat ctcagttcgg    13800
tgtaggtcgt tcgctccaag ctgggctgtg tgcacgaacc ccccgttcag cccgaccgct    13860
gcgccttatc cggtaactat cgtcttgagt ccaacccggt aagacacgac ttatcgccac    13920
tggcagcagc cactggtaac aggattagca gagcgaggta tgtaggcggt gctacagagt    13980
tcttgaagtg gtggcctaac tacggctaca ctagaagaac agtatttggt atctgcgctc    14040
tgctgaagcc agttaccttc ggaaaaagag ttggtagctc ttgatccggc aaacaaacca    14100
ccgctggtag cggtggtttt tttgtttgca agcagcagat tacgcgcaga aaaaaggat    14160 ctcaagaaga tcctttgatc ttttctacgg ggtctgacgc tcagtggaac gaaaactcac    14220
gttaagggat tttggtcatg aatacacggt gcctgactgc gttagcaatt taactgtgat    14280
aaactaccgc attaaagctt atcgatgata agctgtcaaa catgagaatt cttagaaaaa    14340
ctcatcgagc atcaaatgaa actgcaattt attcatatca ggattatcaa taccatattt    14400
ttgaaaaagc cgtttctgta atgaaggaga aaactcaccg aggcagttcc ataggatggc    14460
aagatcctgg tatcggtctg cgattccgac tcgtccaaca tcaatacaac ctattaattt    14520
cccctcgtca aaaataaggt tatcaagtga gaaatcacca tgagtgacga ctgaatccgg    14580
tgagaatggc aaaagcttat gcatttcttt ccagacttgt tcaacaggcc agccattacg    14640
ctcgtcatca aaatcactcg catcaaccaa accgttattc attcgtgatt gcgcctgagc    14700
gagacgaaat acgcgatcgc tgttaaaagg acaattacaa acaggaatcg aatgcaaccg    14760
gcgcaggaac actgccagcg catcaacaat attttcacct gaatcaggat attcttctaa    14820
tacctggaat gctgttttcc cggggatcgc agtggtgagt aaccatgcat catcaggagt    14880
acggataaaa tgcttgatgg tcggaagagg cataaattcc gtcagccagt ttagtctgac    14940
catctcatct gtaacatcat tggcaacgct acctttgcca tgtttcagaa acaactctgg    15000
cgcatcgggc ttcccataca atcgatagat tgtcgcacct gattgcccga cattatcgcg    15060
agcccattta tacccatata aatcagcatc catgttggaa tttaatcgcg gcctcgagca    15120
agacgtttcc cgttgaatat ggctcataac accccttgta ttactgttta tgtaagcaga    15180
cagttttatt gttcatgagc ggatacatat ttgaatgtat ttagaaaaat aaacaaatag    15240
gggttccgcg cacatttccc cgaaaagtgc cacctaaatt gtaagcgtta atattttgtt    15300
aaaattcgcg ttaaattttt gttaaatcag ctcatttttt aaccaatagg ccgaaatcgg    15360
caaaatccct tataaatcaa agaatagacc gagataggg ttgagtggcc gctcagggc     15420 gctcccattc gccattcagg ctgcgcaact gttgggaagg gcgttcggt gcgggcctct    15480 tcgctattac gccagctggc gaaaggggga tgtgctgcaa ggcgattaag ttgggtaacg    15540
ccagggtttt cccagtcaca cgcgtaatac gactcactat ag                      15582
```

<210> SEQ ID NO 13

<211> LENGTH: 15582
<212> TYPE: RNA
<213> ORGANISM: Artificial
<220> FEATURE:
<223> OTHER INFORMATION: synthetic polynucleotide

<400> SEQUENCE: 13

| | | | | | |
|---|---|---|---|---|---|
| auaggcggcg | caugagagaa | gcccagacca | auuaccuacc | caaaauggag | aaaguucacg | 60 |
| uugacaucga | ggaagacagc | ccauuccuca | gagcuuugca | gcggagcuuc | ccgcaguuug | 120 |
| agguagaagc | caagcagguc | acugauaaug | accaugcuaa | ugccagagcg | uuuucgcauc | 180 |
| uggcuucaaa | acugaucgaa | acggaggugg | acccauccga | cacgauccuu | gacauuggaa | 240 |
| gugcgcccgc | ccgcagaaug | uauucuaagc | acaaguauca | uuguaucugu | ccgaugagau | 300 |
| gugcggaaga | uccggacaga | uuguauaagu | augcaacuaa | gcugaagaaa | aacuguaagg | 360 |
| aaauaacuga | uaaggaauug | gacaagaaaa | ugaaggagcu | cgccgccguc | augagcgacc | 420 |
| cugaccugga | aacugagacu | augugccucc | acgacgacga | gucgucgcgc | uacgaagggc | 480 |
| aagucgcugu | uuaccaggau | guauacgcgg | uugacggacc | gacaagucuc | uaucaccaag | 540 |
| ccaauaaggg | aguuagaguc | gccuacugga | uaggcuuuga | caccaccccu | uuuauguuua | 600 |
| agaacuuggc | uggagcauau | ccaucauacu | cuaccaacug | ggccgacgaa | accguguuaa | 660 |
| cggcucguaa | cauaggccua | ugcagcucug | acguuaugga | gcggucacgu | agagggaugu | 720 |
| ccauucuuag | aaagaaguau | uugaaaccau | ccaacaaugu | cuauucucu | guggcucga | 780 |
| ccaucuacca | cgagaagagg | gacuuacuga | ggagcuggca | ccugccgucu | guauuucacu | 840 |
| uacguggcaa | gcaaaauuac | acaugucggu | gugagacuau | aguuaguugc | gacggguacg | 900 |
| ucguuaaaag | aauagcuauc | aguccaggcc | uguaugggaa | gccuucaggc | uaugcugcua | 960 |
| cgaugcaccg | cgagggauuc | uugugcugca | aagugacaga | cacauugaac | ggggagaggg | 1020 |
| ucucuuuucc | cgugugcacg | uaugugccag | cuacauugug | ugaccaaaug | acuggcauac | 1080 |
| uggcaacaga | ugucagugcg | gacgacgcgc | aaaaacugcu | gguugggcuc | aaccagcgua | 1140 |
| uagucgucaa | cggucgcacc | cagagaaaca | ccaauaccau | gaaaaauuac | cuuuugcccg | 1200 |
| uaguggccca | ggcauuugcu | aggugggcaa | aggaauauaa | ggaagaucaa | gaagaugaaa | 1260 |
| ggccacuagg | acuacgagau | agacaguuag | ucaugggggug | uguugggcu | uuuagaaggc | 1320 |
| acaagauaac | aucuauuuau | aagcgcccgg | auacccaaac | caucaucaaa | gugaacagcg | 1380 |
| auuuccacuc | auucgugcug | cccaggauag | gcaguaacac | auuggagauc | gggcugagaa | 1440 |
| caagaaucag | gaaaauguua | gaggagcaca | aggagccguc | accucucauu | accgccgagg | 1500 |
| acguacaaga | agcuaagugc | gcagccgaug | aggcuaagga | ggugcgugaa | gccgaggagu | 1560 |
| ugcgcgcagc | ucuaccaccu | uuggcagcug | auguugagga | gcccacucug | gaagccgaug | 1620 |
| ucgacuugau | guuacaagag | gcuggggccg | gcucagugga | gacaccucgu | ggcuugauaa | 1680 |
| agguuaccag | cuacgauggc | gaggacaaga | ucggcucuua | cgcugugcuu | ucuccgcagg | 1740 |
| cuguacucaa | gagugaaaaa | uuacuuugca | uccacccucu | cgcugaacaa | gucauaguga | 1800 |
| uaacacacuc | uggccgaaaa | gggcguuaug | ccguggaacc | auaccauggu | aaaguagugg | 1860 |
| ugccagaggg | acaugcaaua | cccguccagg | acuuucaagc | ucugagugaa | agugccacca | 1920 |
| uuguguacaa | cgaacgugag | uucguaaaca | gguaccugca | ccauauugcc | acacauggag | 1980 |
| gagcgcugaa | cacugaugaa | gaauauuaca | aaacugucaa | gcccagcgag | cacgacggcg | 2040 |
| aauaccugua | cgacaucgac | aggaaacagu | gcgucaagaa | agaacuaguc | acugggcuag | 2100 |
| ggcucacagg | cgagcugguu | gauccucccu | uccugaauu | cgccuacgag | agucgagaa | 2160 |

```
cacgaccagc cgcuccuuac caaguaccaa ccauaggggu guauggcgug ccaggaucag    2220
gcaagucugg caucauuaaa agcgcaguca ccaaaaaaga ucuaguggug agcgccaaga    2280
aagaaaacug ugcagaaauu auaagggacg ucaagaaaau gaaagggcug gacgucaaug    2340
ccagaacugu ggacucagug ucuugaaug gaugcaaaca ccccguagag acccuguaua    2400
uugacgaagc uuuugcuugu caugcaggua cucucagagc gcucauagcc auuauaagac    2460
cuaaaaaggc agugcucugc ggggaucccca aacagugcgg uuuuuuuaac augaugugcc    2520
ugaaagugca uuuuaaccac gagauuugca cacaagucuu ccacaaaagc aucucucgcc    2580
guugcacuaa aucgugacu ucggucgucu caaccuuguu uuacgacaaa aaaugagaa    2640 cgacgaaucc gaaagagacu aagauuguga uugacacuac cggcaguacc aaaccuaagc    2700
aggacgaucu cauucucacu uguuucagag ggugggugaa gcaguugcaa auagauuaca    2760
aaggcaacga aauaaugacg gcagcugccu ucaagggcu gacccguaaa ggugugaug    2820 ccguucggua caaggugaau gaaaauccuc uguacgcacc caccucagaa caugugaacg    2880
uccuacugac ccgcacggag gaccgcaucg uguggaaaac acuagccggc gacccauga    2940 uaaaaacacu gacugccaag uacccuggga auucacugc cacgauagag gaguggcaag    3000
cagagcauga ugccaucaug aggcacaucu uggagagacc ggacccuacc gacgucuucc    3060
agaauaaggc aaacgugugu uggggccaagg cuuuagugcc ggugcugaag accgcuggca    3120
uagacaugac cacugaacaa uggaacacug uggauuauuu ugaaacggac aaagcucacu    3180
cagcagagau aguauugaac caacuaugcg ugaguucu uggacucgau cuggacuccg    3240 gucuauuuuuc ugcacccacu guuccguauau ccauuaggaa uaaucacugg gauaacuccc    3300
cgucgccuaa cauguacggg cugaauaaag aaguggccg ucagcucucu cgcagguacc    3360
cacaacugcc ucgggcaguu gccacuggaa gagucuauga caugaacacu gguacacugc    3420
gcaauuauga uccgcgcaua aaccuaguac cuguaaacag aagacugcc caugcuuuag    3480 uccuccacca uaaugaacac ccacagagug acuuucuuc auucgucagc aaauugaagg    3540
gcagaacugu ccugguguc ggggaaagu ugucgucccc aggcaaaaug guugacuggu    3600
ugucagaccg gccugaggcu accuucagag cucggcugga uuuaggcauc caggugaug    3660 ugcccaaaua ugacauaaua uuuuguuaaug ugaggacccc auauaaauac caucacuauc    3720
agcaguguga agaccaugcc auuaagcuua gcaugugac caagaaagcu ugucugcauc    3780
ugaaucccgg cggaaccugu gucagcauag guuaugguua cgcugacagg gccagcgaaa    3840
gcaucauugg ugcuauagcg cggcaguuca aguuuccccg gguaugcaaa ccgaaauccu    3900
cacuugaaga gacggaaguu cuguuuguau ucauggggua cgaucgcaag gcccguacgc    3960
acaauccuua caagcuuuca ucaaccuuga ccaacauuua uacagguucc agacuccacg    4020
aagccggaug ugcacccuca uaucauguggg ugcgagggga uauugccacg gccaccgaag    4080
gagugauuau aaaugcugcu aacacagcaaag gacaaccugg cggagggug ucggagcgcg    4140 uguauaagaa auucccggaa agcuucgauu uacagccgau cgaaguagga aaagcgcgac    4200 uggcaaagg ugcagcuaaa cauaucauuc augccguagg accaaacuuc aacaaaguuu    4260
cggagguuga aggugacaaa caguuggcag aggcuuauga guccaucgcu aagauuguca    4320
acgauaacaa uuacaaguca guagcgauuc cacguuguc caccggcauc uuuuccggga    4380
acaaagaucg acuaacccaa ucauugaacc auuugcugac agcuuuagac accacugaug    4440
cagauguagc cauauacugc agggacaaga auggaaau gacucucaag gaagcagugg    4500
```

| | |
|---|---|
| cuaggagaga agcaguggag gagauaugca uauccgacga cucuucagug acagaaccug | 4560 |
| augcagagcu ggugagggug cauccgaaga guucuuuggc uggaaggaag ggcuacagca | 4620 |
| caagcgaugg caaaacuuuc ucauauuugg aagggaccaa guuucaccag gcggccaagg | 4680 |
| auauagcaga aauuaaugcc augggcccg uugcaacgga ggccaaugag cagguaugca | 4740 |
| uguauauccu cggagaaagc augagcagua uuaggucgaa augccccguc gaagagucgg | 4800 |
| aagccuccac accaccuagc acgcugccuu gcuugugcau ccaugccaug acuccagaaa | 4860 |
| gaguacagcg ccuaaaagcc ucacguccag aacaaauuac ugugugcuca uccuuuccau | 4920 |
| ugccgaagua uagaaucacu ggugugcaga agauccaaug cucccagccu auauuguucu | 4980 |
| caccgaaagu gccugcguau auucauccaa ggaaguaucu cguggaaaca ccaccgguag | 5040 |
| acgagacucc ggagccaucg gcagagaacc aauccacaga ggggacaccu gaacaaccac | 5100 |
| cacuuauaac cgaggaugag accaggacua gaacgccuga gccgaucauc aucgaagagg | 5160 |
| aagaagagga uagcauaagu uugcugucag auggcccgac ccaccaggug cugcaagucg | 5220 |
| aggcagacau ucacgggccg cccucuguau cuagcucauc cuggccauu ccucaugcau | 5280 |
| ccgacuuuga uguggacagu uuauccauac uugacacccu ggaggagcu agcgugacca | 5340 |
| gcggggcaac gucagccgag acuaacucuu acuucgcaaa gaguauggag uuucggcgc | 5400 |
| gaccggugcc ugcgccucga acaguauuca ggaacccucc acaucccgcu ccgcgcacaa | 5460 |
| gaacaccguc acuugcaccc agcagggccu gcucgagaac cagccuaguu uccacccgc | 5520 |
| caggcgugaa uagggugauc acuagagagg agcucgaggc gcuuacccg ucacgcacuc | 5580 |
| cuagcagguc ggucucgaga accagccugg ucuccaaccc gccaggcgua aauagggguga | 5640 |
| uuacaagaga ggaguuugag gcguucguag cacaacaaca augacggu gaugcgggug | 5700 |
| cauacaucuu uuccuccgac accgucaag ggcauuuaca acaaaaauca guaaggcaaa | 5760 |
| cggugcuauc cgaaguggug uuggagagga ccgaauugga gauucguau gccccgcgcc | 5820 |
| ucgaccaaga aaaagaagaa uuacacgca agaaauuaca guuaaauccc acaccugcua | 5880 |
| acagaagcag auaccagucc aggaaggugg agaacaugaa agccauaaca gcuagacgua | 5940 |
| uucugcaagg ccuagggcau uauuugaagg cagaaggaaa aguggagugc uaccgaacc | 6000 |
| ugcauccugu uccuuuguau ucaucuagug ugaaccgugc cuuuucaagc cccaaggucg | 6060 |
| caguggaagc cguaacgcc augguugaaag agaacuuucc gacuguggcu ucuuacugua | 6120 |
| uuauuccaga guacgaugcc uauuuggaca ugguugacgg agcuucaugc ugcuuagaca | 6180 |
| cugccaguuu uugcccugca aagcugcgca gcuuuccaaa gaaacacucc uauuuggaac | 6240 |
| ccacaauacg aucggcagug ccuucagcga uccagaacac gcuccagaac guccuggcag | 6300 |
| cugccacaaa aagaaauugc aaugucacgc aaaugagaga auugcccgua uuggauucgg | 6360 |
| cggccuuuaa uguggaaugc uucaagaaau augcguguaa uaaugaauau uggggaaacgu | 6420 |
| uuaaagaaaa ccccaucagg cuuacugaag aaaacguggu aaauuacauu accaaauuaa | 6480 |
| aaggaccaaa agcugcugcu cuuuuugcga agacacauaa uuugaauaug uugcaggaca | 6540 |
| uaccaaugga cagguuugua auggacuuaa agagagacgu gaaagugacu ccaggaacaa | 6600 |
| aacauacuga agaacggccc aagguacagg ugauccaggc ugccgauccg cuagcaacag | 6660 |
| cguaucugug cggaauccac cgagagcugg uuaggagauu aaaugcgguc cugcuuccga | 6720 |
| acauucauac acuguuugau augcggcug aagacuuuga cgcuauuaua gccgagcacu | 6780 |
| uccagccugg ggauugucuu cggaaacug acaucgcguc guuugauaaa aguaggacg | 6840 |
| acgccauggc ucugaccgcg uuaaugauuc uggaagacuu aggugugggac gcagagcugu | 6900 |

```
ugacgcugau ugaggcggcu uucggcgaaa uuucaucaau acauuugccc acuaaaacua     6960
aauuuaaauu cggagccaug augaaaucug gaauguuccu cacacuguuu gugaacacag     7020
ucauuaacau uguaaucgca agcagagugu ugagagaacg gcuaaccgga ucaccaugug     7080
cagcauucau uggagaugac aauaucguga aaggagucaa aucggacaaa uuaauggcag     7140
acaggugcgc caccuggvuug aauauggaag ucaagauuau agaugcugug gugggcgaga     7200
aagcgccuua uuucguggga ggguuuauuu ugugugacuc cgugaccggc acagcgugcc     7260
guguggcaga cccccuaaaa aggcuguuua agcuuggcaa accucuggca gcagacgaug     7320
aacaugauga ugacaggaga agggcauugc augaagaguc aacacgcugg aaccgagugg     7380
guauucuuuc agagcugugc aaggcaguag aaucaaggua ugaaaccgua ggaacuucca     7440
ucauaguuau ggccaugacu acucuagcua gcaguguuaa aucauucagc uaccugagag     7500
gggccccuau aacucucuac ggcuaaccug aauggacuac gacauagucu aguccgccaa     7560
gauggcuaag gccgccaugc ucgcuaaguu uaaggaacug uacggcgucu ccuuuuccga     7620
gcucgugaga ccuuucaagu ccaacaaguc caccugcugu gacuggugca uugcugccuu     7680
cggccugaca ccuccaucg ccgacuccau caagacacug cugcaacagu acugccugua     7740
ucugcacauc cagagccugg cuugcagcug gggaauggug gugcugcugc cgucaggua      7800 caagugcggc aagaacaggg aaaccauuga gaagcugcgc agcaagcugc ugugcgucag     7860
cccuaugugc augaugauug agcccccuaa gcucaggagc acagcugccg cucucuauug     7920
guacaaaacc ggaaucucca acaucagcga ggucuacggc gacacccug agugggauuca     7980 aaggcaaaca gugcuccagc auagcuucaa cgauugcacc uucgagcuga gccaaaugg      8040 gcaaugggcc uacgauaacg acaucgugga ugauagcgag auugcuuaca aauaugccca     8100
gcuggccgac acaaacagca acgccuccgc uuuccugaag uccaacagcc aagccaaaau     8160
cgugaaggac ugcgcuacca uguguaggca cuacaaaaga gccgagaaga agcaaaugag     8220
caugagccag uggaucaaau auagaugcga cagggucgac gauggaggag auuggaagca     8280
gaucgucaug uuucucagau accagggcgu ggaauuuaug agcuuucuga ccgcccugaa     8340
gagauuucuc cagggcaucc cuaaaaagaa cuguauucug cuguauggcg cugccaacac     8400
cgacaaaagc cuguucggaa ugagccucau gaaguuucug cagggcagcg ugaucuguuu     8460
cgugaacagc aagagccauu ucuggcucca gccccucgcu gacgcaaaga ucggaaugcu     8520
ggacgacgcu accguccccu ugcuggaacua caucgaugau aaucucagaa acgcucugga     8580 uggcaaaccug gugagcaugg acgucaagca cagaccccug guccaacuga auguccccc     8640 ucuccucauc acaagcaaca uuaacgccgg caccgauagc agguggcccu aucuccauaa     8700
cagacuggug guguuuaccu uccccaacga auuucccuuc gacgaaaacg gcaaccugu      8760 guacgagcuc aacgacaaaa acuggaaguc cuucuucagc agaacauggu ccagacugag     8820
ccucggagga ggaggaggaa acaaggagc caugcucgcc gucuucaagg acaccuacgg     8880
ccucagcuuu accgaccucg ucagaaacuu uaaauccgau aaaaccaccu gcacagauug     8940
ggugaccgcc auuucggag ugaauccac cauugccgaa ggcuucaaga cacugaucca     9000
accuuucauc cuguacgccc acauucagug ucucgacgu aagugggcg ugcugauucu     9060 ggcccugcug agauacaaau gcggcaaguc cagacucaca guggccaagg ccucuccac     9120 acugcugcau gucccgaga ccugcaugcu gauucaaccu cccaaacuca ggagcagcgu     9180
ggcugcucug uacugguaua ggacaggcau uuccaacauu uccgagguca ugggagacac     9240
```

```
accugaaugg auucaaagac ugaccaucau ccagcacggc aucgaugacu ccaacuucga    9300
ccugagcgaa augguccagu gggcuuucga caacgagcug accgacgagu ccgacauggc    9360
cuucgaguac gcucuccucg cugacuccaa cuccaaugcu gcugcuuuuc ucaaguccaa    9420
cugccaggcu aaguaccuga aagacugcgc caccaugugc aagcauuaca ggcgugcuca    9480
aaaaaggcag augaauaugu cccaauggau uagauuuagg ugcuccaaga ucgaugaggg    9540
aggcgacugg agaccccauug ugcaguuccu cagguaccag cagaucgagu uuaucacauu    9600
ucugggagcu cugaagaguccu uccugaaggg caccccaag aaaaacuguc ggugguucug    9660
cggcccugcu aauacagaua aaagcuacuu cggcaugucc uucauccacu uuaccaggg    9720 cgcugugauc agcuucguga auagcacauc ccacuuuugg cuggaacccc ucacagacac    9780
aaagguggcc augcuggaug acgcuacaac aaccguuugg accauuucg auaccuacau    9840 gaggaacgcu cucgacggca acccuauuag cauugauaga aaacacaaac cucugaucca    9900
gcugaagugc ccucccaucc uccucacaac caacauucac cccgccaagg acaauagaug    9960
gccuuaccuc gagagcagga ucaccgucuu ugaguuuccu aacgccuucc ccuuugacaa    10020
gaacggcaac cccguguaug aaaucaauga uaaaaauugg aaauguuucu ucgagaggac    10080
auggagcaga cucgaucucg gaggcggcgg cggagauccu caggaaaggc cuaggaaacu    10140
cccccagcug ugcaccgagc ugcagaccac cauuacgac auuauccugg agugcgucua    10200
cugcaagcaa cagcugcuca aaggggaggu cuaugauuuu gccagaaggg aucgugcau    10260 uguguacaga gacggcaauc cuuaugccgu cugcgauaag ugccugaaau ucuauagcaa    10320
aaucuccgaa uacagacacu acugcuacag ccuguaugga accacccccg agcagcagua    10380
caauaaaccc cugugcgauc ugcucaucag gaggaucaac ugucaaaagc ccugugucc    10440 cgaggaaaag cagagacacc uggauaagaa acagagguuc cacaauauca ggggcagaug    10500
gaccggcaga ugcaugccuu guuguagguc cagcggcgga ggaggaggag acccuaccag    10560
aaggcccuau aagcgccug accucugcac agaacucaau accagccugc aggauaucga    10620
gaucacaugu gucuauugca agaccgugcu ggaacugacc gaaguguucg aguuugcuag    10680
gaaagaccuc uucgcgcgugu acagggacag caucccccau gccgccugcc acaaguguau    10740
ugacuucuac uccaggauua gggagcucag gcacuacucc gacuccgucu auggcgacac    10800
ccucgagaag cucacaaaca ccggccucua uaaucccuc aucaggaggc ugagaugcca    10860
aaagcccucc aacccugcug agaaacugag gcaccugaau gagaagagaa gauuucauaa    10920
cauugccgga cacuacagag gacaguguca cagcuguuugc aacagggcug gcggagggag    10980
aggcgacacc gaagagaaac ccagaacccu ccacgaccug gucaggcuc ucgagacaac    11040 cauccauaac aucgagcucc aguugugga augcaagaaa ccccugcaga ggyuccgaggu    11100 guaugauuuc gccagagccg aucgacagu ggucuauagg gagggaaacc cuuuuggcau    11160
cugcaaacug ugucucaggu uucucuccaa gaucagcgag uauagacauu auaacuacag    11220
cguguacggc aacacccugg agcaaaccgu gaaaaagccc cugaacgaga ucccucauuag    11280 gaggaucauu ugucagaggc cccucugucc ccaggagaag aagagacaug uggaccugaa    11340
uaaaagauuc cauaacauca gcggcagaug ggccggcaga ugugccgcuu gcuggagauc    11400
cagaggagga ggaggcggcg aucccaagca aagacccuac aagcugccug aucugugcac    11460
agagcugaac acaagccucc aagaugucuc caucgccugu gucuacugua aggccacacu    11520
ggaaaggaca gagguguacc aguuugccag gaaggaucuc ugcaucgucu acagggaauug    11580 caucgcuuac gccgcuuguc acaaauguau cgauuuuuau uccagaauca gggaacugag    11640
```

```
auacuauagc aacuccgucu acggcgaaac ccucgagaaa auuacaaaca cagaacucua   11700
caaccugcug auuaggaggc ugagauguca aagccucuc aaccccgccg agaaaagaag    11760
gcaccucaaa gacaagagga gauuccacuc caucgcuggc caguacagag gccaguguaa   11820
cacauguugc gaucaggccg gaggaggagg cggcgacccu gccacaagac ccaggacccu   11880
ccacgagcuc ugcgaggugc uggaggaguc cgugcacgag auuaggcucc agugcgugca   11940
gugcaagaag gaacuccaaa ggagagaagu guauaaauuc cugaggaccg accucaggau   12000
ugucuauagg gacaacaacc ccuacggagu gugcauuaug ugccugaggu ccucagcaa    12060 gauuccgaa uacaggcauu aucaguacag ccucuacggc aaaacccucg aggagagggu    12120 caaaaaccc cucuccgaaa ucaccaucag aaggaucauc ugucagacac cucucugccc    12180
ugaggaaaag gaaaggcacg ugaacgcuaa caagagguuc cauaauauca ugggcaggug   12240
gaccggaaga ugcagcgagu gcuggagacc uagaggcggc ggcggaggcg augcugaaga   12300
gaagccuagg acccugcacg aucugugca agcccuggaa accagcgucc acgaaaucga   12360
acugaaaugu gucgagugca aaaagacccu gcagaggagc gaagucuacg auuuugugag   12420
agccgaccug agaauugucu acagagacgg aaacccuuc gccgucugca aggucugccu    12480
caggcugcuc uccaaaauca gcgaauauag gcauuacaau uacucccucu acggcgacac   12540
acuggagcaa acacucaaga agugccucaa cgagauccug aucagaagaa ucaucgcca    12600 gaggccucuc ugcccccaag agaagaagag gcacguggau cugaacaaaa gguuucacaa   12660
caucagcggc agguggaccg gcagaugcgc cgugcguugg agaccuagag gcggaggcgg   12720
aggaaauccc gcugagaggc ccagaaaacu gcacgaacug ccagcgccc uggagauucc    12780 uuacgacgaa cugaggcuca acugcgugua uugcaaggga caacucaccg agaccgaagu   12840
gcuggacuuc gccaggaccg aucucaccau ugucuauaga gacgacaccc cucacggcgu   12900
gugcaccaaa ugccucaggu ucuacuccaa ggucagcgag uuuaggguggu acagauacuc   12960 cguguacggc accccccucg aaaagcugac caacaaggga auuugcgacc uccugauuag   13020
aaggauuaca ugccagagac cccugugccc ugaggagaaa caaaggcacc uggacaagaa   13080
gaagagauuc cacaacaucg gcggcagaug gacaggcaga ugcaucgccu gcuggaggag   13140
gccuugauga ggcgcgccca cccagcggcc gcauacagca gcaauuggca agcugcuuac   13200
auagaacucg cggcgauugg caugccgccu uaaaauuuuu auuuuauuuu ucuuuucuuu   13260
uccgaaucgg auuuuguuuu uaauauuuca aaaaaaaaa aaaaaaaaa aaaaaaaaa     13320 aaaaaaaaag aagagcguuu aaacacguga uaucuggccu cauggggccu uccuuucacug   13380 cccgcuuucc agucgggaaa ccugucgugc cagcugcauu aacaugguca uagcuguuuc   13440
cuugcguauu gggcgcucuc cgcuuccucg cucacugacu cgcugcgcuc ggucguucgg   13500
guaaagccug gggugccuaa ugagcaaaag gccagcaaaa ggccaggaac cguaaaaagg   13560
ccgcguugcu ggcguuuuuc cauaggcucc gcccccuga cgagcaucac aaaaaucgac    13620
gcucaaguca gagguggcga aacccgacag gacuauaaag auaccaggcg uuuccccug    13680 gaagcucccu cgugcgcucu ccuguuccga cccugccgcu uaccggauac cugcucgccu   13740
uucucccuuc gggaagcgug cgcuuucuc auagcucacg cuguagguau ucaguucgg    13800 uguaggucgu ucgcuccaag cugggcugug ugcacgaacc ccccguucag cccgaccgcu   13860
gcgccuuauc cgguaacuau cgucuugagu ccaacccggu aagacacgac uuaucgccac   13920
uggcagcagc cacugguaac aggauuagca gagcgaggua uguaggcggu gcuacagagu   13980
```

-continued

```
ucuugaagug guggccuaac uacggcuaca cuagaagaac aguauuuggu aucugcgcuc    14040
ugcugaagcc aguuaccuuc ggaaaaagag uugguagcuc uugauccggc aaacaaacca    14100
ccgcuggnag cgguggnuuuu uuuguuugca agcagcagau uacgcgcaga aaaaaaggau   14160
cucaagaaga uccuuugauc uuuucuacgg ggucugacgc ucaguggaac gaaaacucac    14220
guuaagggau uuggucaug aauacacggu gccugacugc guuagcaauu uaacugugau     14280
aaacuaccgc auuaaagcuu aucgaugaua agcugucaaa caugagaauu cuuagaaaaa    14340
cucaucgagc aucaaaugaa acugcaauuu auucauauca ggauuaucaa uaccauauuu    14400
uugaaaaagc cguuucugua augaaggaga aaacucaccg aggcaguucc auaggauggc    14460
aagauccugg uaucggucug cgauuccgac ucguccaaca ucaauacaac cuauuaauuu    14520
ccccucguca aaauaaggu uaucaaguga gaaaucacca ugagugacga cugaauccgg     14580
ugagaauggc aaaagcuuau gcauuucuuu ccagacuugu ucaacaggcc agccauuacg    14640
cucgucauca aaaucacucg caucaaccaa accguuauuc auucgugauu gcgccugagc    14700
gagacgaaau acgcgaucgc uguuaaaagg acaauuacaa acaggaaucg aaugcaaccg    14760
gcgcaggaac acugccagcg caucaacaau auuuucaccu gaaucaggau auucuucuaa    14820
uaccuggaau gcuguuuucc cggggaucgc aguggugagu aaccaugcau caucaggagu    14880
acggauaaaa ugcuugaugg ucggaagagg cauaaauucc gucagccagu uuagucugac    14940
caucucaucu guaacaucau uggcaacgcu accuuugcca uguuucagaa caacucugg    15000 cgcaucgggc uucccauaca aucgauagau ugucgcaccu gauugcccga cauuaucgcg    15060
agcccauuua uacccauaua aaucagcauc caugungaa uuuaaucgcg gccucgagca     15120
agacguuucc cguugaauau ggcucauaac accccuugua uuacuguuua guaagcaga    15180 caguuuauu guucaugagc ggauacauau uugaauguau uuagaaaau aaacaaauag      15240 ggguuccgcg cacauuuccc cgaaaagugc caccuaaauu guaagcguua auauuugu     15300 aaaauucgcg uuaaauuuuu guuaaaucag cucauuuuuu aaccaauagg ccgaaucgg     15360 caaaaucccu uauaaaucaa aagaauagac cgagauaggg uugaguggcc gcuacagggc    15420
gcucccauuc gccauucagg cugcgcaacu guugggaagg gcguuucggu gcgggccucu    15480
ucgcuauuac gccagcuggc gaagggggga ugugcugcaa ggcgauuaag uuggguaacg    15540
ccaggguuuu cccagucaca cgcguaauac gacucacuau ag                       15582
```

<210> SEQ ID NO 14
<211> LENGTH: 649
<212> TYPE: PRT
<213> ORGANISM: human papilloma virus

<400> SEQUENCE: 14

```
Met Ala Asp Pro Ala Gly Thr Asn Gly Glu Glu Gly Thr Gly Cys Asn
1               5                   10                  15

Gly Trp Phe Tyr Val Glu Ala Val Val Glu Lys Lys Thr Gly Asp Ala
            20                  25                  30

Ile Ser Asp Asp Glu Asn Glu Asn Asp Ser Asp Thr Gly Glu Asp Leu
        35                  40                  45

Val Asp Phe Ile Val Asn Asp Asn Asp Tyr Leu Thr Gln Ala Glu Thr
    50                  55                  60

Glu Thr Ala His Ala Leu Phe Thr Ala Gln Glu Ala Lys Gln His Arg
65                  70                  75                  80

Asp Ala Val Gln Val Leu Lys Arg Lys Tyr Leu Val Ser Pro Leu Ser
                85                  90                  95
```

-continued

```
Asp Ile Ser Gly Cys Val Asp Asn Asn Ile Ser Pro Arg Leu Lys Ala
                100                 105                 110
Ile Cys Ile Glu Lys Gln Ser Arg Ala Ala Lys Arg Arg Leu Phe Glu
            115                 120                 125
Ser Glu Asp Ser Gly Tyr Gly Asn Thr Glu Val Glu Thr Gln Gln Met
130                 135                 140
Leu Gln Val Glu Gly Arg His Glu Thr Glu Thr Pro Cys Ser Gln Tyr
145                 150                 155                 160
Ser Gly Gly Ser Gly Gly Cys Ser Gln Tyr Ser Gly Ser Gly
                165                 170                 175
Gly Glu Gly Val Ser Glu Arg His Thr Ile Cys Gln Thr Pro Leu Thr
                180                 185                 190
Asn Ile Leu Asn Val Leu Lys Thr Ser Asn Ala Lys Ala Ala Met Leu
                195                 200                 205
Ala Lys Phe Lys Glu Leu Tyr Gly Val Ser Phe Ser Glu Leu Val Arg
                210                 215                 220
Pro Phe Lys Ser Asn Lys Ser Thr Cys Cys Asp Trp Cys Ile Ala Ala
225                 230                 235                 240
Phe Gly Leu Thr Pro Ser Ile Ala Asp Ser Ile Lys Thr Leu Leu Gln
                245                 250                 255
Gln Tyr Cys Leu Tyr Leu His Ile Gln Ser Leu Ala Cys Ser Trp Gly
                260                 265                 270
Met Val Val Leu Leu Leu Val Arg Tyr Lys Cys Gly Lys Asn Arg Glu
                275                 280                 285
Thr Ile Glu Lys Leu Leu Ser Lys Leu Leu Cys Val Ser Pro Met Cys
                290                 295                 300
Met Met Ile Glu Pro Pro Lys Leu Arg Ser Thr Ala Ala Ala Leu Tyr
305                 310                 315                 320
Trp Tyr Lys Thr Gly Ile Ser Asn Ile Ser Glu Val Tyr Gly Asp Thr
                325                 330                 335
Pro Glu Trp Ile Gln Arg Gln Thr Val Leu Gln His Ser Phe Asn Asp
                340                 345                 350
Cys Thr Phe Glu Leu Ser Gln Met Val Gln Trp Ala Tyr Asp Asn Asp
                355                 360                 365
Ile Val Asp Asp Ser Glu Ile Ala Tyr Lys Tyr Ala Gln Leu Ala Asp
                370                 375                 380
Thr Asn Ser Asn Ala Ser Ala Phe Leu Lys Ser Asn Ser Gln Ala Lys
385                 390                 395                 400
Ile Val Lys Asp Cys Ala Thr Met Cys Arg His Tyr Lys Arg Ala Glu
                405                 410                 415
Lys Lys Gln Met Ser Met Ser Gln Trp Ile Lys Tyr Arg Cys Asp Arg
                420                 425                 430
Val Asp Asp Gly Gly Asp Trp Lys Gln Ile Val Met Phe Leu Arg Tyr
                435                 440                 445
Gln Gly Val Glu Phe Met Ser Phe Leu Thr Ala Leu Lys Arg Phe Leu
                450                 455                 460
Gln Gly Ile Pro Lys Lys Asn Cys Ile Leu Leu Tyr Gly Ala Ala Asn
465                 470                 475                 480
Thr Gly Lys Ser Leu Phe Gly Met Ser Leu Met Lys Phe Leu Gln Gly
                485                 490                 495
Ser Val Ile Cys Phe Val Asn Ser Lys Ser His Phe Trp Leu Gln Pro
                500                 505                 510
```

```
Leu Ala Asp Ala Lys Ile Gly Met Leu Asp Asp Ala Thr Val Pro Cys
            515                 520                 525

Trp Asn Tyr Ile Asp Asp Asn Leu Arg Asn Ala Leu Asp Gly Asn Leu
    530                 535                 540

Val Ser Met Asp Val Lys His Arg Pro Leu Val Gln Leu Lys Cys Pro
545                 550                 555                 560

Pro Leu Leu Ile Thr Ser Asn Ile Asn Ala Gly Thr Asp Ser Arg Trp
                565                 570                 575

Pro Tyr Leu His Asn Arg Leu Val Val Phe Thr Phe Pro Asn Glu Phe
            580                 585                 590

Pro Phe Asp Glu Asn Gly Asn Pro Val Tyr Glu Leu Asn Asp Lys Asn
        595                 600                 605

Trp Lys Ser Phe Phe Ser Arg Thr Trp Ser Arg Leu Ser Leu His Glu
    610                 615                 620

Asp Glu Asp Lys Glu Asn Asp Gly Asp Ser Leu Pro Thr Phe Lys Cys
625                 630                 635                 640

Val Ser Gly Gln Asn Thr Asn Thr Leu
                645

<210> SEQ ID NO 15
<211> LENGTH: 365
<212> TYPE: PRT
<213> ORGANISM: human papilloma virus

<400> SEQUENCE: 15

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240
```

```
Pro Arg Ser Glu Pro Asp Thr Gly Asn Pro Cys His Thr Thr Lys Leu
            245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
            275                 280                 285

Val His Leu Lys Gly Asp Ala Asn Thr Leu Lys Cys Leu Arg Tyr Arg
            290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
            325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
            355                 360                 365

<210> SEQ ID NO 16
<211> LENGTH: 158
<212> TYPE: PRT
<213> ORGANISM: human papilloma virus

<400> SEQUENCE: 16

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
        50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
        130                 135                 140

Ser Cys Cys Arg Ser Ser Arg Thr Arg Arg Glu Thr Gln Leu
145                 150                 155

<210> SEQ ID NO 17
<211> LENGTH: 98
<212> TYPE: PRT
<213> ORGANISM: human papilloma virus

<400> SEQUENCE: 17

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
            35                  40                  45
```

```
Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 18
<211> LENGTH: 420
<212> TYPE: PRT
<213> ORGANISM: artificial
<220> FEATURE:
<223> OTHER INFORMATION: synthetic polypeptide

<400> SEQUENCE: 18

Ala Lys Ala Ala Met Leu Ala Lys Phe Lys Glu Leu Tyr Gly Val Ser
 1               5                  10                  15

Phe Ser Glu Leu Val Arg Pro Phe Lys Ser Asn Lys Ser Thr Cys Cys
                 20                  25                  30

Asp Trp Cys Ile Ala Ala Phe Gly Leu Thr Pro Ser Ile Ala Asp Ser
             35                  40                  45

Ile Lys Thr Leu Leu Gln Gln Tyr Cys Leu Tyr Leu His Ile Gln Ser
 50                  55                  60

Leu Ala Cys Ser Trp Gly Met Val Val Leu Leu Val Arg Tyr Lys
 65                  70                  75                  80

Cys Gly Lys Asn Arg Glu Thr Ile Glu Lys Leu Leu Ser Lys Leu Leu
                 85                  90                  95

Cys Val Ser Pro Met Cys Met Met Ile Glu Pro Pro Lys Leu Arg Ser
                100                 105                 110

Thr Ala Ala Leu Tyr Trp Tyr Lys Thr Gly Ile Ser Asn Ile Ser
                115                 120                 125

Glu Val Tyr Gly Asp Thr Pro Glu Trp Ile Gln Arg Gln Thr Val Leu
                130                 135                 140

Gln His Ser Phe Asn Asp Cys Thr Phe Glu Leu Ser Gln Met Val Gln
145                 150                 155                 160

Trp Ala Tyr Asp Asn Asp Ile Val Asp Ser Glu Ile Ala Tyr Lys
                165                 170                 175

Tyr Ala Gln Leu Ala Asp Thr Asn Ser Asn Ala Ser Ala Phe Leu Lys
                180                 185                 190

Ser Asn Ser Gln Ala Lys Ile Val Lys Asp Cys Ala Thr Met Cys Arg
                195                 200                 205

His Tyr Lys Arg Ala Glu Lys Lys Gln Met Ser Met Ser Gln Trp Ile
                210                 215                 220

Lys Tyr Arg Cys Asp Arg Val Asp Asp Gly Gly Asp Trp Lys Gln Ile
225                 230                 235                 240

Val Met Phe Leu Arg Tyr Gln Gly Val Glu Phe Met Ser Phe Leu Thr
                245                 250                 255

Ala Leu Lys Arg Phe Leu Gln Gly Ile Pro Lys Lys Asn Cys Ile Leu
                260                 265                 270

Leu Tyr Gly Ala Ala Asn Thr Gly Lys Ser Leu Phe Gly Met Ser Leu
                275                 280                 285

Met Lys Phe Leu Gln Gly Ser Val Ile Cys Phe Val Asn Ser Lys Ser
                290                 295                 300
```

```
His Phe Trp Leu Gln Pro Leu Ala Asp Ala Lys Ile Gly Met Leu Asp
305                 310                 315                 320

Asp Ala Thr Val Pro Cys Trp Asn Tyr Ile Asp Asp Asn Leu Arg Asn
                325                 330                 335

Ala Leu Asp Gly Asn Leu Val Ser Met Asp Val Lys His Arg Pro Leu
            340                 345                 350

Val Gln Leu Lys Cys Pro Pro Leu Leu Ile Thr Ser Asn Ile Asn Ala
        355                 360                 365

Gly Thr Asp Ser Arg Trp Pro Tyr Leu His Asn Arg Leu Val Val Phe
    370                 375                 380

Thr Phe Pro Asn Glu Phe Pro Phe Asp Glu Asn Gly Asn Pro Val Tyr
385                 390                 395                 400

Glu Leu Asn Asp Lys Asn Trp Lys Ser Phe Phe Ser Arg Thr Trp Ser
                405                 410                 415

Arg Leu Ser Leu
            420

<210> SEQ ID NO 19
<211> LENGTH: 420
<212> TYPE: PRT
<213> ORGANISM: artificial
<220> FEATURE:
<223> OTHER INFORMATION: synthetic polypeptide

<400> SEQUENCE: 19

Lys Gln Gly Ala Met Leu Ala Val Phe Lys Asp Thr Tyr Gly Leu Ser
1               5                   10                  15

Phe Thr Asp Leu Val Arg Asn Phe Lys Ser Asp Lys Thr Thr Cys Thr
                20                  25                  30

Asp Trp Val Thr Ala Ile Phe Gly Val Asn Pro Thr Ile Ala Glu Gly
            35                  40                  45

Phe Lys Thr Leu Ile Gln Pro Phe Ile Leu Tyr Ala His Ile Gln Cys
    50                  55                  60

Leu Asp Cys Lys Trp Gly Val Leu Ile Leu Ala Leu Leu Arg Tyr Lys
65                  70                  75                  80

Cys Gly Lys Ser Arg Leu Thr Val Ala Lys Gly Leu Ser Thr Leu Leu
                85                  90                  95

His Val Pro Glu Thr Cys Met Leu Ile Gln Pro Pro Lys Leu Arg Ser
            100                 105                 110

Ser Val Ala Ala Leu Tyr Trp Tyr Arg Thr Gly Ile Ser Asn Ile Ser
    115                 120                 125

Glu Val Met Gly Asp Thr Pro Glu Trp Ile Gln Arg Leu Thr Ile Ile
130                 135                 140

Gln His Gly Ile Asp Asp Ser Asn Phe Asp Leu Ser Glu Met Val Gln
145                 150                 155                 160

Trp Ala Phe Asp Asn Glu Leu Thr Asp Glu Ser Asp Met Ala Phe Glu
                165                 170                 175

Tyr Ala Leu Leu Ala Asp Ser Asn Ser Asn Ala Ala Phe Leu Lys
            180                 185                 190

Ser Asn Cys Gln Ala Lys Tyr Leu Lys Asp Cys Ala Thr Met Cys Lys
    195                 200                 205

His Tyr Arg Arg Ala Gln Lys Arg Gln Met Asn Met Ser Gln Trp Ile
210                 215                 220

Arg Phe Arg Cys Ser Lys Ile Asp Glu Gly Gly Asp Trp Arg Pro Ile
225                 230                 235                 240
```

-continued

```
Val Gln Phe Leu Arg Tyr Gln Gln Ile Glu Phe Ile Thr Phe Leu Gly
                245                 250                 255

Ala Leu Lys Ser Phe Leu Lys Gly Thr Pro Lys Lys Asn Cys Leu Val
            260                 265                 270

Phe Cys Gly Pro Ala Asn Thr Gly Lys Ser Tyr Phe Gly Met Ser Phe
        275                 280                 285

Ile His Phe Ile Gln Gly Ala Val Ile Ser Phe Val Asn Ser Thr Ser
    290                 295                 300

His Phe Trp Leu Glu Pro Leu Thr Asp Thr Lys Val Ala Met Leu Asp
305                 310                 315                 320

Asp Ala Thr Thr Thr Cys Trp Thr Tyr Phe Asp Thr Tyr Met Arg Asn
                325                 330                 335

Ala Leu Asp Gly Asn Pro Ile Ser Ile Asp Arg Lys His Lys Pro Leu
            340                 345                 350

Ile Gln Leu Lys Cys Pro Pro Ile Leu Leu Thr Thr Asn Ile His Pro
        355                 360                 365

Ala Lys Asp Asn Arg Trp Pro Tyr Leu Glu Ser Arg Ile Thr Val Phe
    370                 375                 380

Glu Phe Pro Asn Ala Phe Pro Phe Asp Lys Asn Gly Asn Pro Val Tyr
385                 390                 395                 400

Glu Ile Asn Asp Lys Asn Trp Lys Cys Phe Phe Glu Arg Thr Trp Ser
                405                 410                 415

Arg Leu Asp Leu
            420

<210> SEQ ID NO 20
<211> LENGTH: 288
<212> TYPE: PRT
<213> ORGANISM: artificial
<220> FEATURE:
<223> OTHER INFORMATION: synthetic polypeptide

<400> SEQUENCE: 20

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
                20                  25                  30

Trp Lys His Met Arg Leu Glu Cys Ala Ile Tyr Tyr Lys Ala Arg Glu
            35                  40                  45

Met Gly Phe Lys His Ile Asn His Gln Val Val Pro Thr Leu Ala Val
        50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175
```

```
Lys Tyr Ser Lys Asn Lys Val Trp Glu Val His Ala Gly Gly Gln Val
            180                 185                 190

Ile Leu Cys Pro Thr Ser Val Phe Ser Gly Gly Thr Gly Gly Ser Thr
        195                 200                 205

Thr Pro Ile Val His Leu Lys Gly Asp Ala Asn Thr Leu Lys Cys Leu
    210                 215                 220

Arg Tyr Arg Phe Lys Lys His Cys Thr Leu Tyr Thr Ala Val Ser Ser
225                 230                 235                 240

Thr Trp His Trp Thr Gly His Asn Val Lys His Lys Ser Ala Ile Val
                245                 250                 255

Thr Leu Thr Tyr Asp Ser Glu Trp Gln Arg Asp Gln Phe Leu Ser Gln
            260                 265                 270

Val Lys Ile Pro Lys Thr Ile Thr Val Ser Thr Gly Phe Met Ser Ile
        275                 280                 285

<210> SEQ ID NO 21
<211> LENGTH: 292
<212> TYPE: PRT
<213> ORGANISM: artificial
<220> FEATURE:
<223> OTHER INFORMATION: synthetic polypeptide

<400> SEQUENCE: 21

Met Gln Thr Pro Lys Glu Thr Leu Ser Glu Arg Leu Ser Cys Val Gln
1               5                   10                  15

Asp Lys Ile Ile Asp His Tyr Glu Asn Asp Ser Lys Asp Ile Asp Ser
            20                  25                  30

Gln Ile Gln Tyr Trp Gln Leu Ile Arg Trp Glu Asn Ala Ile Phe Phe
        35                  40                  45

Ala Ala Arg Glu His Gly Ile Gln Thr Leu Asn His Gln Val Val Pro
    50                  55                  60

Ala Tyr Asn Ile Ser Lys Ser Lys Ala His Lys Ala Ile Glu Leu Gln
65                  70                  75                  80

Met Ala Leu Gln Gly Leu Ala Gln Ser Ala Tyr Lys Thr Glu Asp Trp
                85                  90                  95

Thr Leu Gln Asp Thr Cys Glu Glu Leu Trp Asn Thr Glu Pro Thr His
            100                 105                 110

Cys Phe Lys Lys Gly Gly Gln Thr Val Gln Val Tyr Phe Asp Gly Asn
        115                 120                 125

Lys Asp Asn Cys Met Thr Tyr Val Ala Trp Asp Ser Val Tyr Tyr Met
130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Gly Gly
        195                 200                 205

Thr Gly Gly Ser Thr Thr Pro Ile Ile His Leu Lys Gly Asp Arg Asn
    210                 215                 220

Ser Leu Lys Cys Leu Arg Tyr Arg Leu Arg Lys His Ser Asp His Tyr
225                 230                 235                 240

Arg Asp Ile Ser Ser Thr Trp His Trp Thr Gly Ala Gly Asn Glu Lys
                245                 250                 255
```

```
Thr Gly Ile Leu Thr Val Thr Tyr His Ser Glu Thr Gln Arg Thr Lys
            260                 265                 270

Phe Leu Asn Thr Val Ala Ile Pro Asp Ser Val Gln Ile Leu Val Gly
            275                 280                 285

Tyr Met Thr Met
        290

<210> SEQ ID NO 22
<211> LENGTH: 288
<212> TYPE: PRT
<213> ORGANISM: artificial
<220> FEATURE:
<223> OTHER INFORMATION: synthetic polypeptide

<400> SEQUENCE: 22

Met Glu Thr Leu Ser Gln Arg Leu Asn Val Cys Gln Asp Lys Ile Leu
1               5                   10                  15

Glu His Tyr Glu Asn Asp Ser Lys Arg Leu Cys Asp His Ile Asp Tyr
            20                  25                  30

Trp Lys His Ile Arg Leu Glu Cys Val Leu Met Tyr Lys Ala Arg Glu
        35                  40                  45

Met Gly Ile His Ser Ile Asn His Gln Val Val Pro Ala Leu Ser Val
    50                  55                  60

Ser Lys Ala Lys Ala Leu Gln Ala Ile Glu Leu Gln Met Met Leu Glu
65                  70                  75                  80

Thr Leu Asn Asn Thr Glu Tyr Lys Asn Glu Asp Trp Thr Met Gln Gln
                85                  90                  95

Thr Ser Leu Glu Leu Tyr Leu Thr Ala Pro Thr Gly Cys Leu Lys Lys
            100                 105                 110

His Gly Tyr Thr Val Glu Val Gln Phe Asp Gly Asp Val His Asn Thr
        115                 120                 125

Met His Tyr Thr Asn Trp Lys Phe Ile Tyr Leu Cys Ile Asp Gly Gln
    130                 135                 140

Cys Thr Val Val Glu Gly Gln Val Asn Cys Lys Gly Ile Tyr Tyr Val
145                 150                 155                 160

His Glu Gly His Ile Thr Tyr Phe Val Asn Phe Thr Glu Glu Ala Lys
                165                 170                 175

Lys Tyr Gly Thr Gly Lys Lys Trp Glu Val His Ala Gly Gly Gln Val
            180                 185                 190

Ile Val Phe Pro Glu Ser Val Phe Ser Gly Thr Gly Gly Ser Thr
        195                 200                 205

Thr Pro Ile Ile His Leu Lys Gly Asp Ala Asn Ile Leu Lys Cys Leu
    210                 215                 220

Arg Tyr Arg Leu Ser Lys Tyr Lys Gln Leu Tyr Glu Gln Val Ser Ser
225                 230                 235                 240

Thr Trp His Trp Thr Cys Thr Asp Gly Lys His Lys Asn Ala Ile Val
                245                 250                 255

Thr Leu Thr Tyr Ile Ser Thr Ser Gln Arg Asp Asp Phe Leu Asn Thr
            260                 265                 270

Val Lys Ile Pro Asn Thr Val Ser Val Ser Thr Gly Tyr Met Thr Ile
        275                 280                 285

<210> SEQ ID NO 23
<211> LENGTH: 288
<212> TYPE: PRT
<213> ORGANISM: artificial
<220> FEATURE:
```

<223> OTHER INFORMATION: synthetic polypeptide

<400> SEQUENCE: 23

```
Met Glu Glu Ile Ser Ala Arg Leu Asn Ala Val Gln Glu Lys Ile Leu
1               5                   10                  15

Asp Leu Tyr Glu Ala Asp Lys Thr Asp Leu Pro Ser Gln Ile Glu His
            20                  25                  30

Trp Lys Leu Ile Arg Met Glu Cys Ala Leu Leu Tyr Thr Ala Lys Gln
        35                  40                  45

Met Gly Phe Ser His Leu Cys His Gln Val Val Pro Ser Leu Leu Ala
    50                  55                  60

Ser Lys Thr Lys Ala Phe Gln Val Ile Glu Leu Gln Met Ala Leu Glu
65                  70                  75                  80

Thr Leu Ser Lys Ser Gln Tyr Ser Thr Ser Gln Trp Thr Leu Gln Gln
                85                  90                  95

Thr Ser Leu Glu Val Trp Leu Cys Glu Pro Pro Lys Cys Phe Lys Lys
            100                 105                 110

Gln Gly Glu Thr Val Thr Val Gln Tyr Asp Asn Asp Lys Lys Asn Thr
        115                 120                 125

Met Asp Tyr Thr Asn Trp Gly Glu Ile Tyr Ile Glu Glu Asp Thr
    130                 135                 140

Cys Thr Met Val Thr Gly Lys Val Asp Tyr Ile Gly Met Tyr Tyr Ile
145                 150                 155                 160

His Asn Cys Glu Lys Val Tyr Phe Lys Tyr Phe Lys Glu Asp Ala Ala
                165                 170                 175

Lys Tyr Ser Lys Thr Gln Met Trp Glu Val His Val Gly Gly Gln Val
            180                 185                 190

Ile Val Cys Pro Thr Ser Ile Ser Ser Gly Thr Gly Ser Val
        195                 200                 205

Ala Pro Ile Val His Leu Lys Gly Glu Ser Asn Ser Leu Lys Cys Leu
    210                 215                 220

Arg Tyr Arg Leu Lys Pro Tyr Lys Glu Leu Tyr Ser Ser Met Ser Ser
225                 230                 235                 240

Thr Trp His Trp Thr Ser Asp Asn Lys Asn Ser Lys Asn Gly Ile Val
                245                 250                 255

Thr Val Thr Phe Val Thr Glu Gln Gln Gln Gln Met Phe Leu Gly Thr
            260                 265                 270

Val Lys Ile Pro Pro Thr Val Gln Ile Ser Thr Gly Phe Met Thr Leu
        275                 280                 285
```

<210> SEQ ID NO 24
<211> LENGTH: 293
<212> TYPE: PRT
<213> ORGANISM: artificial
<220> FEATURE:
<223> OTHER INFORMATION: synthetic polypeptide

<400> SEQUENCE: 24

```
Met Lys Met Gln Thr Pro Lys Glu Ser Leu Ser Glu Arg Leu Ser Ala
1               5                   10                  15

Leu Gln Asp Lys Ile Leu Asp His Tyr Glu Asn Asp Ser Lys Asp Ile
            20                  25                  30

Asn Ser Gln Ile Ser Tyr Trp Gln Leu Ile Arg Leu Glu Asn Ala Ile
        35                  40                  45

Leu Phe Thr Ala Arg Glu His Gly Ile Thr Lys Leu Asn His Gln Val
    50                  55                  60
```

Val Pro Pro Ile Asn Ile Ser Lys Ser Lys Ala His Lys Ala Ile Glu
65                  70                  75                  80

Leu Gln Met Ala Leu Lys Gly Leu Ala Gln Ser Lys Tyr Asn Asn Glu
            85                  90                  95

Glu Trp Thr Leu Gln Asp Thr Cys Glu Glu Leu Trp Asn Thr Glu Pro
            100                 105                 110

Ser Gln Cys Phe Lys Lys Gly Lys Thr Val His Val Tyr Phe Asp
            115                 120                 125

Gly Asn Lys Asp Asn Cys Met Asn Tyr Val Val Trp Asp Ser Ile Tyr
130                 135                 140

Tyr Ile Thr Glu Thr Gly Ile Trp Asp Lys Thr Ala Ala Cys Val Ser
145                 150                 155                 160

Tyr Trp Gly Val Tyr Tyr Ile Lys Asp Gly Asp Thr Thr Tyr Tyr Val
                165                 170                 175

Gln Phe Lys Ser Glu Cys Glu Lys Tyr Gly Asn Ser Asn Thr Trp Glu
            180                 185                 190

Val Gln Tyr Gly Gly Asn Val Ile Asp Cys Asn Asp Ser Met Cys Ser
        195                 200                 205

Gly Gly Thr Gly Ser Thr Thr Pro Ile Ile His Leu Lys Gly Asp
210                 215                 220

Lys Asn Ser Leu Lys Cys Leu Arg Tyr Arg Leu Arg Lys Tyr Ala Asp
225                 230                 235                 240

His Tyr Ser Glu Ile Ser Ser Thr Trp His Trp Thr Gly Cys Asn Lys
                245                 250                 255

Asn Thr Gly Ile Leu Thr Val Thr Tyr Asn Ser Glu Val Gln Arg Asn
            260                 265                 270

Thr Phe Leu Asp Val Val Thr Ile Pro Asn Ser Val Gln Ile Ser Val
            275                 280                 285

Gly Tyr Met Thr Ile
        290

<210> SEQ ID NO 25
<211> LENGTH: 289
<212> TYPE: PRT
<213> ORGANISM: artificial
<220> FEATURE:
<223> OTHER INFORMATION: synthetic polypeptide

<400> SEQUENCE: 25

Met Glu Ser Ile Pro Ala Arg Leu Asn Ala Val Gln Glu Lys Ile Leu
1               5                   10                  15

Asp Leu Tyr Glu Ala Asp Ser Asn Asp Leu Asn Ala Gln Ile Glu His
            20                  25                  30

Trp Lys Leu Thr Arg Met Glu Cys Val Leu Phe Tyr Lys Ala Lys Glu
            35                  40                  45

Leu Gly Ile Thr His Ile Gly His Gln Val Val Pro Pro Met Ala Val
        50                  55                  60

Ser Lys Ala Lys Ala Cys Gln Ala Ile Glu Leu Gln Leu Ala Leu Glu
65                  70                  75                  80

Ala Leu Asn Lys Thr Gln Tyr Ser Thr Asp Gly Trp Thr Leu Gln Gln
            85                  90                  95

Thr Ser Leu Glu Met Trp Arg Ala Glu Pro Gln Lys Tyr Phe Lys Lys
            100                 105                 110

His Gly Tyr Thr Ile Thr Val Gln Tyr Asp Asn Asp Lys Asn Asn Thr
            115                 120                 125

```
Met Asp Tyr Thr Asn Trp Lys Glu Ile Tyr Leu Leu Gly Glu Cys Glu
        130                 135                 140

Cys Thr Ile Val Glu Gly Gln Val Asp Tyr Tyr Gly Leu Tyr Tyr Trp
145                 150                 155                 160

Cys Asp Gly Glu Lys Ile Tyr Phe Val Lys Phe Ser Asn Asp Ala Lys
                165                 170                 175

Gln Tyr Cys Val Thr Gly Val Trp Glu Val His Val Gly Gly Gln Val
            180                 185                 190

Ile Val Cys Pro Ala Ser Val Ser Ser Gly Thr Gly Gly Ser Thr
        195                 200                 205

Ala Pro Ile Ile His Leu Lys Gly Asp Pro Asn Ser Leu Lys Cys Leu
        210                 215                 220

Arg Tyr Arg Val Lys Thr His Lys Ser Leu Tyr Val Gln Ile Ser Ser
225                 230                 235                 240

Thr Trp His Trp Thr Ser Asn Glu Cys Thr Asn Asn Lys Leu Gly Ile
                245                 250                 255

Val Thr Ile Thr Tyr Ser Asp Glu Thr Gln Arg Gln Phe Leu Lys
            260                 265                 270

Thr Val Lys Ile Pro Asn Thr Val Gln Val Ile Gln Gly Val Met Ser
            275                 280                 285

Leu

<210> SEQ ID NO 26
<211> LENGTH: 288
<212> TYPE: PRT
<213> ORGANISM: artificial
<220> FEATURE:
<223> OTHER INFORMATION: synthetic polypeptide

<400> SEQUENCE: 26

Met Glu Glu Ile Ser Ala Arg Leu Ser Ala Val Gln Asp Lys Ile Leu
1               5                   10                  15

Asp Ile Tyr Glu Ala Asp Lys Asn Asp Leu Thr Ser Gln Ile Glu His
            20                  25                  30

Trp Lys Leu Ile Arg Met Glu Cys Ala Ile Met Tyr Thr Ala Arg Gln
        35                  40                  45

Met Gly Ile Ser His Leu Cys His Gln Val Val Pro Ser Leu Val Ala
    50                  55                  60

Ser Lys Thr Lys Ala Phe Gln Val Ile Glu Leu Gln Met Ala Leu Glu
65                  70                  75                  80

Thr Leu Asn Ala Ser Pro Tyr Lys Thr Asp Glu Trp Thr Leu Gln Gln
                85                  90                  95

Thr Ser Leu Glu Val Trp Leu Ser Glu Pro Gln Lys Cys Phe Lys Lys
            100                 105                 110

Lys Gly Ile Thr Val Thr Val Gln Tyr Asp Asn Asp Lys Ala Asn Thr
        115                 120                 125

Met Asp Tyr Thr Asn Trp Ser Glu Ile Tyr Ile Glu Glu Thr Thr
    130                 135                 140

Cys Thr Leu Val Ala Gly Glu Val Asp Tyr Val Gly Leu Tyr Tyr Ile
145                 150                 155                 160

His Gly Asn Glu Lys Thr Tyr Phe Lys Tyr Phe Lys Glu Asp Ala Lys
                165                 170                 175

Lys Tyr Ser Lys Thr Gln Leu Trp Glu Val His Val Gly Ser Arg Val
            180                 185                 190
```

```
Ile Val Cys Pro Thr Ser Ile Pro Ser Gly Gly Thr Gly Ser Val
            195                 200                 205

Ser Pro Ile Val His Leu Lys Gly Asp Pro Asn Ser Leu Lys Cys Leu
210                 215                 220

Arg Tyr Arg Leu Lys Pro Phe Lys Asp Leu Tyr Cys Asn Met Ser Ser
225                 230                 235                 240

Thr Trp His Trp Thr Ser Asp Asp Lys Gly Asp Lys Val Gly Ile Val
            245                 250                 255

Thr Val Thr Tyr Thr Thr Glu Thr Gln Arg Gln Leu Phe Leu Asn Thr
            260                 265                 270

Val Lys Ile Pro Pro Thr Val Gln Ile Ser Thr Gly Val Met Ser Leu
            275                 280                 285
```

<210> SEQ ID NO 27
<211> LENGTH: 140
<212> TYPE: PRT
<213> ORGANISM: artificial
<220> FEATURE:
<223> OTHER INFORMATION: synthetic polypeptide

<400> SEQUENCE: 27

```
Asp Pro Gln Glu Arg Pro Arg Lys Leu Pro Gln Leu Cys Thr Glu Leu
1               5                   10                  15

Gln Thr Thr Ile His Asp Ile Ile Leu Glu Cys Val Tyr Cys Lys Gln
            20                  25                  30

Gln Leu Leu Arg Arg Glu Val Tyr Asp Phe Ala Phe Arg Asp Leu Cys
        35                  40                  45

Ile Val Tyr Arg Asp Gly Asn Pro Tyr Ala Val Cys Asp Lys Cys Leu
    50                  55                  60

Lys Phe Tyr Ser Lys Ile Ser Glu Tyr Arg His Tyr Cys Tyr Ser Leu
65                  70                  75                  80

Tyr Gly Thr Thr Leu Glu Gln Gln Tyr Asn Lys Pro Leu Cys Asp Leu
                85                  90                  95

Leu Ile Arg Cys Ile Asn Cys Gln Lys Pro Leu Cys Pro Glu Glu Lys
            100                 105                 110

Gln Arg His Leu Asp Lys Lys Gln Arg Phe His Asn Ile Arg Gly Arg
        115                 120                 125

Trp Thr Gly Arg Cys Met Ser Cys Cys Arg Ser Ser
    130                 135                 140
```

<210> SEQ ID NO 28
<211> LENGTH: 140
<212> TYPE: PRT
<213> ORGANISM: artificial
<220> FEATURE:
<223> OTHER INFORMATION: synthetic polypeptide

<400> SEQUENCE: 28

```
Asp Pro Thr Arg Arg Pro Tyr Lys Leu Pro Asp Leu Cys Thr Glu Leu
1               5                   10                  15

Asn Thr Ser Leu Gln Asp Ile Glu Ile Thr Cys Val Tyr Cys Lys Thr
            20                  25                  30

Val Leu Glu Leu Thr Glu Val Phe Glu Phe Ala Phe Lys Asp Leu Phe
        35                  40                  45

Val Val Tyr Arg Asp Ser Ile Pro His Ala Ala Cys His Lys Cys Ile
    50                  55                  60

Asp Phe Tyr Ser Arg Ile Arg Glu Leu Arg His Tyr Ser Asp Ser Val
65                  70                  75                  80
```

```
Tyr Gly Asp Thr Leu Glu Lys Leu Thr Asn Thr Gly Leu Tyr Asn Leu
                85                  90                  95

Leu Ile Arg Cys Leu Arg Cys Gln Lys Pro Leu Asn Pro Ala Glu Lys
            100                 105                 110

Leu Arg His Leu Asn Glu Lys Arg Arg Phe His Asn Ile Ala Gly His
        115                 120                 125

Tyr Arg Gly Gln Cys His Ser Cys Cys Asn Arg Ala
    130                 135                 140

<210> SEQ ID NO 29
<211> LENGTH: 140
<212> TYPE: PRT
<213> ORGANISM: artificial
<220> FEATURE:
<223> OTHER INFORMATION: synthetic polypeptide

<400> SEQUENCE: 29

Asn Pro Ala Glu Arg Pro Arg Lys Leu His Glu Leu Ser Ser Ala Leu
1               5                   10                  15

Glu Ile Pro Tyr Asp Glu Leu Arg Leu Asn Cys Val Tyr Cys Lys Gly
                20                  25                  30

Gln Leu Thr Glu Thr Glu Val Leu Asp Phe Ala Phe Thr Asp Leu Thr
            35                  40                  45

Ile Val Tyr Arg Asp Asp Thr Pro His Gly Val Cys Thr Lys Cys Leu
    50                  55                  60

Arg Phe Tyr Ser Lys Val Ser Glu Phe Arg Trp Tyr Arg Tyr Ser Val
65                  70                  75                  80

Tyr Gly Thr Thr Leu Glu Lys Leu Thr Asn Lys Gly Ile Cys Asp Leu
                85                  90                  95

Leu Ile Arg Cys Ile Thr Cys Gln Arg Pro Leu Cys Pro Glu Glu Lys
            100                 105                 110

Gln Arg His Leu Asp Lys Lys Arg Phe His Asn Ile Gly Gly Arg
        115                 120                 125

Trp Thr Gly Arg Cys Ile Ala Cys Trp Arg Arg Pro
    130                 135                 140

<210> SEQ ID NO 30
<211> LENGTH: 140
<212> TYPE: PRT
<213> ORGANISM: artificial
<220> FEATURE:
<223> OTHER INFORMATION: synthetic polypeptide

<400> SEQUENCE: 30

Asp Thr Glu Glu Lys Pro Arg Thr Leu His Asp Leu Cys Gln Ala Leu
1               5                   10                  15

Glu Thr Thr Ile His Asn Ile Glu Leu Gln Cys Val Glu Cys Lys Lys
                20                  25                  30

Pro Leu Gln Arg Ser Glu Val Tyr Asp Phe Ala Phe Ala Asp Leu Thr
            35                  40                  45

Val Val Tyr Arg Glu Gly Asn Pro Phe Gly Ile Cys Lys Leu Cys Leu
    50                  55                  60

Arg Phe Leu Ser Lys Ile Ser Glu Tyr Arg His Tyr Asn Tyr Ser Val
65                  70                  75                  80

Tyr Gly Asn Thr Leu Glu Gln Thr Val Lys Lys Pro Leu Asn Glu Ile
                85                  90                  95

Leu Ile Arg Cys Ile Ile Cys Gln Arg Pro Leu Cys Pro Gln Glu Lys
```

```
                100               105                 110
Lys Arg His Val Asp Leu Asn Lys Arg Phe His Asn Ile Ser Gly Arg
            115                 120                 125

Trp Ala Gly Arg Cys Ala Ala Cys Trp Arg Ser Arg
            130                 135                 140

<210> SEQ ID NO 31
<211> LENGTH: 140
<212> TYPE: PRT
<213> ORGANISM: artificial
<220> FEATURE:
<223> OTHER INFORMATION: synthetic polypeptide

<400> SEQUENCE: 31

Asp Pro Lys Gln Arg Pro Tyr Lys Leu Pro Asp Leu Cys Thr Glu Leu
1               5                   10                  15

Asn Thr Ser Leu Gln Asp Val Ser Ile Ala Cys Val Tyr Cys Lys Ala
            20                  25                  30

Thr Leu Glu Arg Thr Glu Val Tyr Gln Phe Ala Phe Lys Asp Leu Cys
        35                  40                  45

Ile Val Tyr Arg Asp Cys Ile Ala Tyr Ala Ala Cys His Lys Cys Ile
50                  55                  60

Asp Phe Tyr Ser Arg Ile Arg Glu Leu Arg Tyr Tyr Ser Asn Ser Val
65                  70                  75                  80

Tyr Gly Glu Thr Leu Glu Lys Ile Thr Asn Thr Glu Leu Tyr Asn Leu
            85                  90                  95

Leu Ile Arg Cys Leu Arg Cys Gln Lys Pro Leu Asn Pro Ala Glu Lys
            100                 105                 110

Arg Arg His Leu Lys Asp Lys Arg Arg Phe His Ser Ile Ala Gly Gln
            115                 120                 125

Tyr Arg Gly Gln Cys Asn Thr Cys Cys Asp Gln Ala
            130                 135                 140

<210> SEQ ID NO 32
<211> LENGTH: 140
<212> TYPE: PRT
<213> ORGANISM: artificial
<220> FEATURE:
<223> OTHER INFORMATION: synthetic polypeptide

<400> SEQUENCE: 32

Asp Pro Ala Thr Arg Pro Arg Thr Leu His Glu Leu Cys Glu Val Leu
1               5                   10                  15

Glu Glu Ser Val His Glu Ile Arg Leu Gln Cys Val Gln Cys Lys Lys
            20                  25                  30

Glu Leu Gln Arg Arg Glu Val Tyr Lys Phe Leu Phe Thr Asp Leu Arg
        35                  40                  45

Ile Val Tyr Arg Asp Asn Asn Pro Tyr Gly Val Cys Ile Met Cys Leu
50                  55                  60

Arg Phe Leu Ser Lys Ile Ser Glu Tyr Arg His Tyr Gln Tyr Ser Leu
65                  70                  75                  80

Tyr Gly Lys Thr Leu Glu Glu Arg Val Lys Lys Pro Leu Ser Glu Ile
            85                  90                  95

Thr Ile Arg Cys Ile Ile Cys Gln Thr Pro Leu Cys Pro Glu Glu Lys
            100                 105                 110

Glu Arg His Val Asn Ala Asn Lys Arg Phe His Asn Ile Met Gly Arg
            115                 120                 125
```

-continued

```
Trp Thr Gly Arg Cys Ser Glu Cys Trp Arg Pro Arg
    130                 135                 140

<210> SEQ ID NO 33
<211> LENGTH: 140
<212> TYPE: PRT
<213> ORGANISM: artificial
<220> FEATURE:
<223> OTHER INFORMATION: synthetic polypeptide

<400> SEQUENCE: 33

Asp Ala Glu Glu Lys Pro Arg Thr Leu His Asp Leu Cys Gln Ala Leu
1               5                   10                  15

Glu Thr Ser Val His Glu Ile Glu Leu Lys Cys Val Glu Cys Lys Lys
            20                  25                  30

Thr Leu Gln Arg Ser Glu Val Tyr Asp Phe Val Phe Ala Asp Leu Arg
        35                  40                  45

Ile Val Tyr Arg Asp Gly Asn Pro Phe Ala Val Cys Lys Val Cys Leu
    50                  55                  60

Arg Leu Leu Ser Lys Ile Ser Glu Tyr Arg His Tyr Asn Tyr Ser Leu
65                  70                  75                  80

Tyr Gly Asp Thr Leu Glu Gln Thr Leu Lys Lys Cys Leu Asn Glu Ile
                85                  90                  95

Leu Ile Arg Cys Ile Ile Cys Gln Arg Pro Leu Cys Pro Gln Glu Lys
            100                 105                 110

Lys Arg His Val Asp Leu Asn Lys Arg Phe His Asn Ile Ser Gly Arg
        115                 120                 125

Trp Thr Gly Arg Cys Ala Val Cys Trp Arg Pro Arg
    130                 135                 140

<210> SEQ ID NO 34
<211> LENGTH: 72
<212> TYPE: PRT
<213> ORGANISM: artificial
<220> FEATURE:
<223> OTHER INFORMATION: synthetic polypeptide

<400> SEQUENCE: 34

Arg Ala His Tyr Asn Ile Val Thr Phe Cys Cys Lys Cys Asp Ser Thr
1               5                   10                  15

Leu Arg Leu Cys Val Gln Ser Thr His Val Asp Ile Arg Thr Leu Glu
            20                  25                  30

Asp Leu Leu Met Gly Thr Leu Gly Ile Val Cys Pro Ile Cys Ser Gln
        35                  40                  45

Lys Pro Thr Leu His Glu Tyr Met Leu Asp Leu Gln Pro Glu Thr Thr
    50                  55                  60

Asp Leu Tyr Gly Tyr Gln Gln Leu
65                  70

<210> SEQ ID NO 35
<211> LENGTH: 84
<212> TYPE: PRT
<213> ORGANISM: artificial
<220> FEATURE:
<223> OTHER INFORMATION: synthetic polypeptide

<400> SEQUENCE: 35

Arg His Thr Met Leu Cys Met Cys Cys Lys Cys Glu Ala Arg Ile Lys
1               5                   10                  15

Leu Val Val Glu Ser Ser Ala Asp Asp Leu Arg Ala Phe Gln Gln Leu
```

```
                20              25              30
Phe Leu Asn Thr Leu Ser Phe Val Cys Pro Trp Cys Ala Ser Gln Gln
            35              40              45

Thr Leu Gln Asp Ile Val Leu His Leu Glu Pro Gln Asn Glu Ile Pro
        50              55              60

Val Asp Leu Leu Gly His Gln Gln Leu Ser Asp Ser Glu Glu Glu Asn
65              70              75              80

Asp Glu Ile Asp

<210> SEQ ID NO 36
<211> LENGTH: 24
<212> TYPE: PRT
<213> ORGANISM: artificial
<220> FEATURE:
<223> OTHER INFORMATION: linker

<400> SEQUENCE: 36

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 37
<211> LENGTH: 5
<212> TYPE: PRT
<213> ORGANISM: artificial
<220> FEATURE:
<223> OTHER INFORMATION: linker

<400> SEQUENCE: 37

Gly Gly Gly Gly Gly
1               5

<210> SEQ ID NO 38
<211> LENGTH: 6
<212> TYPE: PRT
<213> ORGANISM: artificial
<220> FEATURE:
<223> OTHER INFORMATION: linker

<400> SEQUENCE: 38

Gly Gly Thr Gly Gly Ser
1               5
```

VIRAL ANTIGENS

CROSS-REFERENCE TO RELATED APPLICATIONS

This application is filed pursuant to 35 U.S.C. § 371 as a United States National Phase Application of International Application No. PCT/EP2018/076009 filed 25 Sep. 2018 which claims priority from EP 17193469.8 filed 27 Sep. 2017.

FIELD OF THE INVENTION

The present invention relates to immunogenic RNA constructs and compositions useful in the treatment of persistent HPV infection and low-grade HPV lesions, particularly infections and lesions of human anogenital epithelial tissue, such as cervical epithelia.

BACKGROUND

Human Papillomavirus (HPV) is a small DNA virus that infects mucosal and/or cutaneous skin and causes multiple disease conditions, including common warts, anogenital warts (condyloma acuminate), and neoplastic conditions of the epithelium (cervical neoplasia, cervical cancer, and other anogenital cancers). Human Papillomavirus (HPV) is a non-enveloped deoxyribonucleic acid (DNA) virus, with a circular genome of double-stranded DNA encoding six early proteins (E1, E2, E4, E5, E6 and E7) and two late proteins (L1 and L2). HPV E1 and E2 proteins are required for replication of the virus. HPV E4 and E5 function in viral assembly and cellular proliferation. HPV E6 induces DNA synthesis and interacts with various cellular proteins and the tumor suppressor, p53. HPV E7 induces cell proliferation and interacts with cell cycle regulators and tumor suppressors, such as pRB. Both E6 and E7 are considered oncogenic due to their capacity to interfere with tumor suppressors and promote malignant transformation. Late proteins L1 and L2 provide viral structural proteins.

The "early" proteins have regulatory functions, affecting HPV genome replication and transcription, as well as immune modulation and structural modification of infected cells. The E1 protein is required for initiation of viral DNA replication, and is needed for replication and amplification of the viral episome in the nucleus of the infected cell.

The HPV E1 protein includes an N-terminal regulatory region required for optimal replication in vivo but not in vitro, a DNA Binding Domain, and a C-terminal enzymatic domain (which comprises a minimal oligomerization domain sufficient for self-assembly into hexamers, ATPase activity region capable of unwinding DNA duplexes, and a brace region for assembly and stabilization of the E1 hexamer).

Regulatory HPV E2 protein plays an accessory role in initiation of DNA replication by activating or repressing transcription. The E2 protein contains a transactivation domain (TAD) important for transcriptional activation/repression and replication; a flexible linker, and a DNA binding dimerization domain (DBD) that affects transcriptional activation/repression and replication.

HPV E6 protein plays a role in the induction and maintenance of cellular transformation, and acts by stimulating the destruction of host cell regulatory proteins. E6 associates with host cell E6-AP ubiquitin-protein ligase (E6AP) and inactivates tumor suppressors such as TP53 by targeting them to the 26S proteasome for degradation. A PDZ ligand on the C-terminal of the E6 protein interacts with cellular PDZ-containing proteins, which can alter differentiation of cells.

HPV establish productive infections within the stratified epithelia of the skin, and the mucosal epithelium of the anogenital tract and the oral cavity. HPVs can infect basal cells (the proliferating component of stratified epithelia). After basal cell division, daughter cells typically migrate into the suprabasal compartment and undergo terminal differentiation; HPV infection disturbs or prevents the differentiation of the epithelial cells, but continues to support DNA synthesis and cell proliferation. The circular viral DNA genome, normally harbored in the infected cell as a nuclear plasmid, may become integrated into the host genome, leading to up-regulation of the oncogenes HPV E6 and E7, and a growth advantage over other cells. Studies suggest that HPV E6 and E7 proteins are responsible for the malignant phenotype of cervical carcinoma cells.

Both E6 and E7 proteins are typically expressed in HPV-carrying anogenital malignant tumors. The progression of low-grade HPV cervical lesions to invasive cancer is associated with the integration of the HPV genome into the host chromosomes, the loss or disruption of E2 expression, and upregulation of E6 and E7 oncogene expression.

A majority of HPV infections of the cervical epithelium are subclinal and self-resolving within a two-year period. However, persistent infection with high risk HPV types may cause lesions and progress to invasive cancer. Large-scale epidemiological studies have identified infection with high-risk HPV types as the major risk factor for cervical cancer, which is reported to be one of the most common cancers in women worldwide. The risk that an HPV infection will progress to clinical disease varies with the type of HPV. HPV types have been divided into those known to be associated with high-grade cervical intraepithelial neoplasia and cancer, and those not known to be associated with high-grade lesions or cancer.

There are over 40 types of HPV known to infect the anogenital tract of humans and about 15 high-risk HPV genotypes are causally associated with human cervical cancers.

Various systems exist for the classification of cervical dysplasia caused by HPV infection, e.g., the Bethesda System (Solomon (1990)) and the Cervical Intraepithelial Neoplasia (CIN) scale (Richart (1990)). Low-grade precursors of cervical cancer are known as CIN grade 1 (CIN scale) or low-grade squamous intraepithelial lesions (LSIL) (Bethesda system); these may progress to high-grade precursors (CIN grades 2 and 3/high-grade squamous intraepithelial lesions (HSIL)). Additionally, there is evidence that CIN3 can develop directly from infection by certain high-risk HPV types, without a stage of CIN1 or 2 (see, e.g., Winer et al., 2005). The 'grade' of CIN is based on the percentage of cells that are abnormal (dysplastic).

Studies suggest that many HPV infections become undetectable within 1-2 years. However, the duration of infection appears to be longer for high-risk HPV types compared to low-risk types. A study of longer-term infection with a median follow-up of 5.1 years (Schiffman et al., 2005) showed a longer persistence of HPV 16 compared with other HPV types.

In cervical HPV infections, the relative frequency of different HPV types varies among the stages of cervical lesion. HPV16 has been found to be twice as prevalent in HSIL than in LSIL, for example. Other HPV types are found more often in LSIL (see WHO/IC summary report, 2010 showing eg. 6.1% prevalence of HPV 66 in LSIL, and 0.4% in Cervical Cancer (CC)). See also IARC Monograph, vol. 90, pp. 193-194, Table 26.

Thus, among the HPV types known to infect human anogenital epithelial tissue, some are associated with a higher risk for progression to cervical cancer, compared to other HPV types. High risk HPV types (hrHPV) include: 16, 18, 31, 33, 35, 39, 45, 51, 52, 56, 58, 59, 68, 73, 82. In invasive cancers caused by HPV, high-risk HPV genomes are frequently integrated into the host genome. Integration of HPV can also be found in high-grade lesions (e.g., grade 2/3 CIN). IARC monograph, p. 441.

The HPV L1 Open Reading Frame (ORF) is used to distinguish among, and identify new, HPV types, as it is the most conserved region in the HPV genome. A new type is recognized if the complete genome has been cloned and the DNA sequence of the L1 ORF differs by more than 10% from the closest known type. Differences in homology of between 2% and 10% define a subtype and those of less than 2% define a variant. (IARC Monograph Vol. 90, page 52).

Prophylactic vaccines are designed to prevent infection, and prophylactic HPV vaccines have been developed (see, e.g., FUTURE II Study Group, 2007; Garland et al., 2007). GARDISIL™ 9 (Merck & Co) contains antigenic "late" proteins from nine HPV types (6, 11, 16, 18, 31, 33, 45, 52 and 58). CERVARIX™ (GlaxoSmithKline), contains antigenic "late" proteins from HPV 16 and 18. Both GARDISIL and CERVARIX provide virus-like particles (VLPs) of the HPV major capsid L1 protein. As stated in the current GARDISIL™ prescribing information for the United States, the efficacy of the vaccine is believed to be mediated by humoral responses induced by vaccination. Animal studies further support that the efficacy of HPV L1 VLP vaccines is largely mediated by the development of a humoral immune response.

A cross-protective effect of prophylactic HPV vaccines has been reported. Wheeler et al. (2012) evaluated the cross-protective efficacy of CERVARIX™ (HPV-16/18 AS04-adjuvanted vaccine) against HPV types other than HPV16 and HPV18. See also Malagon et al. (2012).

A therapeutic HPV vaccine is one designed for the treatment of HPV infection or related disease, and thus acts to eradicate infected cells, significantly reduce the number of infected cells, decrease the duration of infection, or slow or prevent the progression of low-grade lesions (e.g., CIN1 or LSIL). Once HPV infection has been established, it is considered unlikely that antibodies play a role in eradicating infected cells. Cytotoxic T lymphocytes (CTL) are believed to be the primary effectors of eradication (see, e.g., IARC monograph volume 90, p. 174).

VLPs can also induce T-cell responses. Vaccination of subjects with HPV 16 VLPs was shown to induce both CD4+ and CD8+ T-cell responses (Pinto et al., 2003; Oh, Y. K. et al., 2004). Herrin et al. report that both CERVARIX™ (HPV16/18) and GARDISIL™ (HPV6/11/16/18) are associated with CD4 T cell responses (Einstein et al., (2011); Herrin et al., (2014)). Chimeric VLPs that contain a linked segment of HPV E7 have been shown to induce specific HLA T cells in humans after in-vitro vaccination (Kaufmann et al., 2001).

Various live vector-based, peptide/protein-based, nucleic acid-based and whole cell-based therapeutic HPV vaccines targeting HPV E6 and E7 oncoproteins have been assessed (for review, see Lin et al., 2010; Hung et al., 2008).

Recombinant vaccinia viruses, which are able to carry large inserts and do not persist in the host, have been studied for use as vaccine vectors. However, individuals may have pre-existing immunity to vaccinia virus which reduces the response to the administered vector. A recombinant vaccinia virus expressing the E6 and E7 genes of HPV 16 and 18 was created (Kaufmann et al., 2002). After a single vaccination, four patients developed cytotoxic T cells and eight developed serological responses to the HPV proteins. A recombinant vaccinia virus encoding modified E6 and E7 from HPV 16 and 18 has been tested in patients with vulvar intraepithelial neoplasia (VIN) (Baldwin et al., 2003; Davidson et al., 2003). Davidson et al. (2003) vaccinated 18 women with HPV 16-positive high-grade VIN with a single dose, which resulted in a reduction in the size of the lesion by at least 50% in eight patients. A second vaccination formulation, HPV 16 L2E6E7 fusion protein, has been tested in 10 patients with high-grade VIN. All but one demonstrated HPV 16-specific proliferative T-cell and/or serological responses following vaccination. However, no direct correlation between immunological and clinical responses was seen (Davidson et al., 2004).

Clinical trials of other viral delivery systems, including recombinant adenoviruses (Tobery et al., 2003), adeno-associated virus (Liu et al., 2000), RNA-based poliovirus (van Kuppeveld et al., 2002) and alphavirus (Velders et al., 2001) vaccines, constructed to express E7 or poly-epitope proteins, have been proposed or initiated.

Currently there is no effective treatment for persistent cervical HPV infection, LSIL or CIN1. Health care providers may choose to 'wait and watch' HPV infections, causing stress and anxiety in the patient due to the risk of progression to cervical cancer. Accordingly, there is a need for therapeutic treatments directed at persistent cervical HPV infection, or low-grade HPV lesions, particularly when caused by known high risk HPV types.

SUMMARY OF THE INVENTION

In a first aspect, the present invention provides one or more RNA construct(s) comprising nucleic acid sequences encoding:
- at least two antigenic Human Papillomavirus (HPV) polypeptides from a first HPV early protein, where said antigenic HPV polypeptides are from at least two different high-risk HPV types, and share at least 70% amino acid sequence identity with at least one additional high-risk HPV type, and
- at least two antigenic HPV polypeptides from a second HPV early protein, where said antigenic HPV polypeptides are from at least two different high-risk HPV types, and share at least 70% amino acid sequence identity with at least one additional high-risk HPV type.

In one aspect, the invention provides self-replicating RNA molecules comprising the RNA construct(s) as described herein.

In another aspect, the invention provides DNA molecules encoding the RNA construct(s) or the self-replicating RNA molecule as described herein.

In another aspect, the invention provides vectors comprising the RNA construct(s), the self-replicating RNA molecule or the DNA molecules as described herein.

In another aspect, the invention provides an immunogenic composition comprising the RNA construct(s), the self-replicating RNA molecule, the DNA molecule or the vector according to the invention and a pharmaceutically acceptable carrier.

In another aspect, there is provided the RNA construct(s), the self-replicating RNA molecule, the DNA molecule, the vector or the immunogenic composition according to the invention, for use in therapy.

In another aspect, there is provided the RNA construct(s), the self-replicating RNA molecule, the DNA molecule, the vector or the immunogenic composition according to the invention, for use in the treatment of an HPV-related condition of the human anogenital tract, selected from infection by HPV such as a high-risk HPV type, and, lesions of the cervical epithelium, such as Cervical Intraepithelial Neoplasia grade 1 (CIN1) and low-grade squamous intraepithelial lesions (LSIL).

In another aspect, there are provided two or more RNA constructs according to the invention, where the two or more RNA constructs encode at least one antigenic polypeptide from (a) different HPV early proteins, or (b) different HPV types, for use in a method of inducing an immune response in a mammalian subject, wherein the two or more RNA constructs are co-administered.

In another aspect, there is provided the use of one or more RNA construct(s) or immunogenic composition according to the invention in the manufacture of a medicament for treating an HPV-related condition of the human anogenital tract, selected from infection by a high-risk HPV type, CIN, and LSIL.

In another aspect, there is provided a method of inducing an immune response in a mammalian subject comprising administering to the subject one or more RNA construct(s) or immunogenic composition according to the invention.

In another aspect, there is provided a method of treating infection of the human anogenital epithelium by a high-risk HPV type, comprising co-administering to a subject in need of treatment, RNA constructs expressing:
(a) an antigenic polypeptide from each of E1, E2 and E6 from HPV16,
(b) an antigenic polypeptide from each of E1, E2, and E6 from HPV18, and
(c) an antigenic polypeptide sequence from the E2 or E6 protein from no more than six additional HPV types, said additional HPV types selected from the group consisting of HPV31, 33, 45, 52, 58, 56, 51, 39, 35, 59, 68, 73, and 82;

In another aspect, the invention provides a method of manufacturing an immunogenic composition comprising the steps of combining (i) one or more RNA construct(s), self-replicating RNA molecule(s), DNA molecule or vector(s) according to the invention with (ii) a non-viral delivery material, such as a submicron cationic oil-in-water emulsion; a liposome; or a biodegradable polymeric microparticle delivery system, preferably CNEs or LNPs; wherein the one or more RNA construct(s), self-replicating RNA molecule(s), DNA molecule or vector(s) according to the invention are (A) in physical contact with said non-viral delivery material or (B) packaged in a first container and said non-viral delivery material packaged in a second container.

Figure 1:
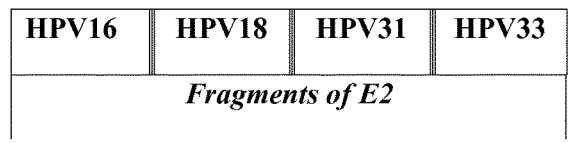
FIG. 1—Diagrams of nucleotide insert constructs (A) insert no 1: Gly_E2$^4$, (B) insert no 2: Gly_E2$^3$E7$^2$ and (C) insert no 3: Gly_E1E6$^7$. Double lines indicate the position of the 5xGly. (Fragments of HPV proteins are not drawn to scale). "Gly" indicates the presence of either the 5xGly linker.
Figure 1:
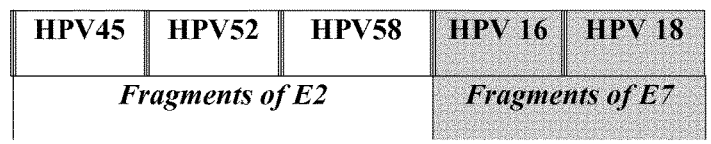
Figure 1:
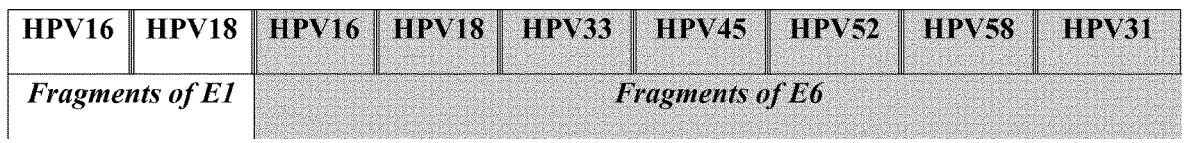

& E7 antigens 15 days after primo immunization with different LNP-formulated SAM-HPV constructs. Naïve inbred CB6F1 mice (n=6/gr) were intramuscularly immunized on day 0 with 1 µg of LNP-formulated SAM-HPV construct 1 or 2 or 3. Negative control mice (n=3/gr) were treated with NaCl 150 mM solution. At day 15 post first immunization (15PI), mice in each group were culled for T cells analysis. Percentage of HPV-specific and cross-reactive CD4+ T cells secreting IFN-γ and/or IL-2 and/or TNF-α were measured in the systemic compartment. Intracellular staining was performed on splenocytes stimulated ex-vivo during 6 hours with pools of 15mer peptides covering the amino acid sequences of the HPV E1 (A), E2 (B), E6 (C) & E7 (D) antigens from 5 high risk HPV types (HPV16/18/33/35/45). The value used as the cut-off to identify specific CD4+ T cell responses in vaccine-immunized mice correspond to the $95^{th}$ percentile of CD8+ T cell responses obtained in the saline group when combining all HPV antigens. These cut off values were obtained by computing the anti log of $95^{th}$ quantile of the normal distribution that is assumed for the log frequencies, i.e. the mean of log frequencies+1.64×their standard deviation. Plots represent CD4+ T cell responses in the systemic compartment for each individual mouse. The median of the CD4+ T cell responses towards each HPV antigen is showed by the dotted line.

Figure 7:
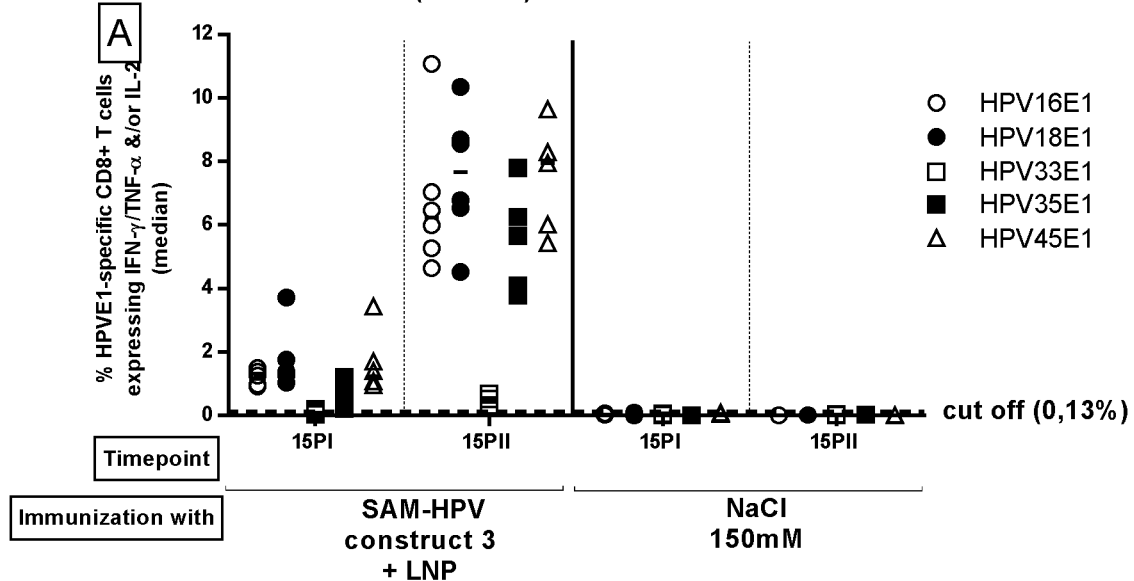
Figure 7:
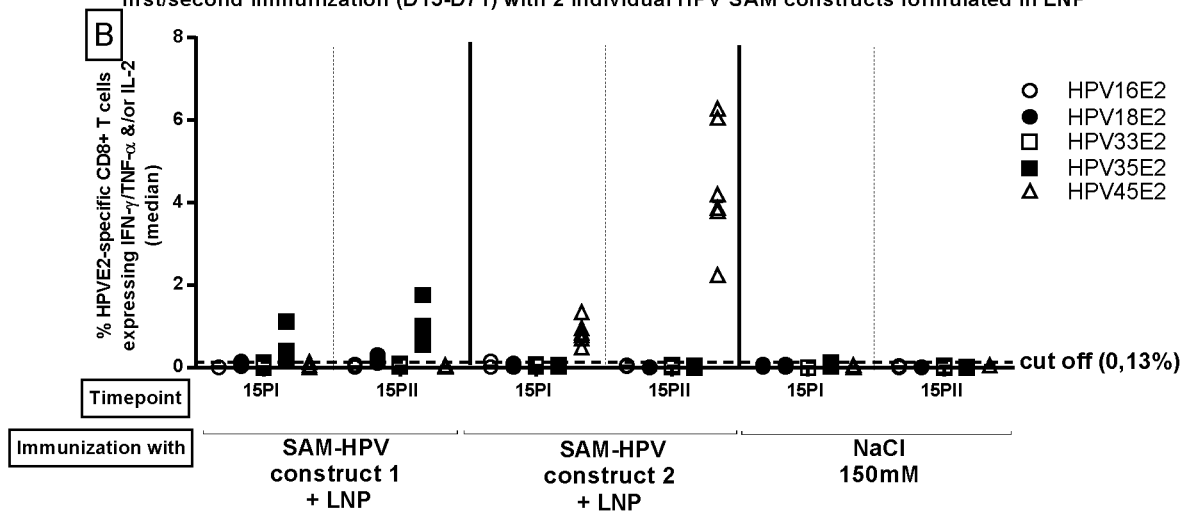
Figure 7:
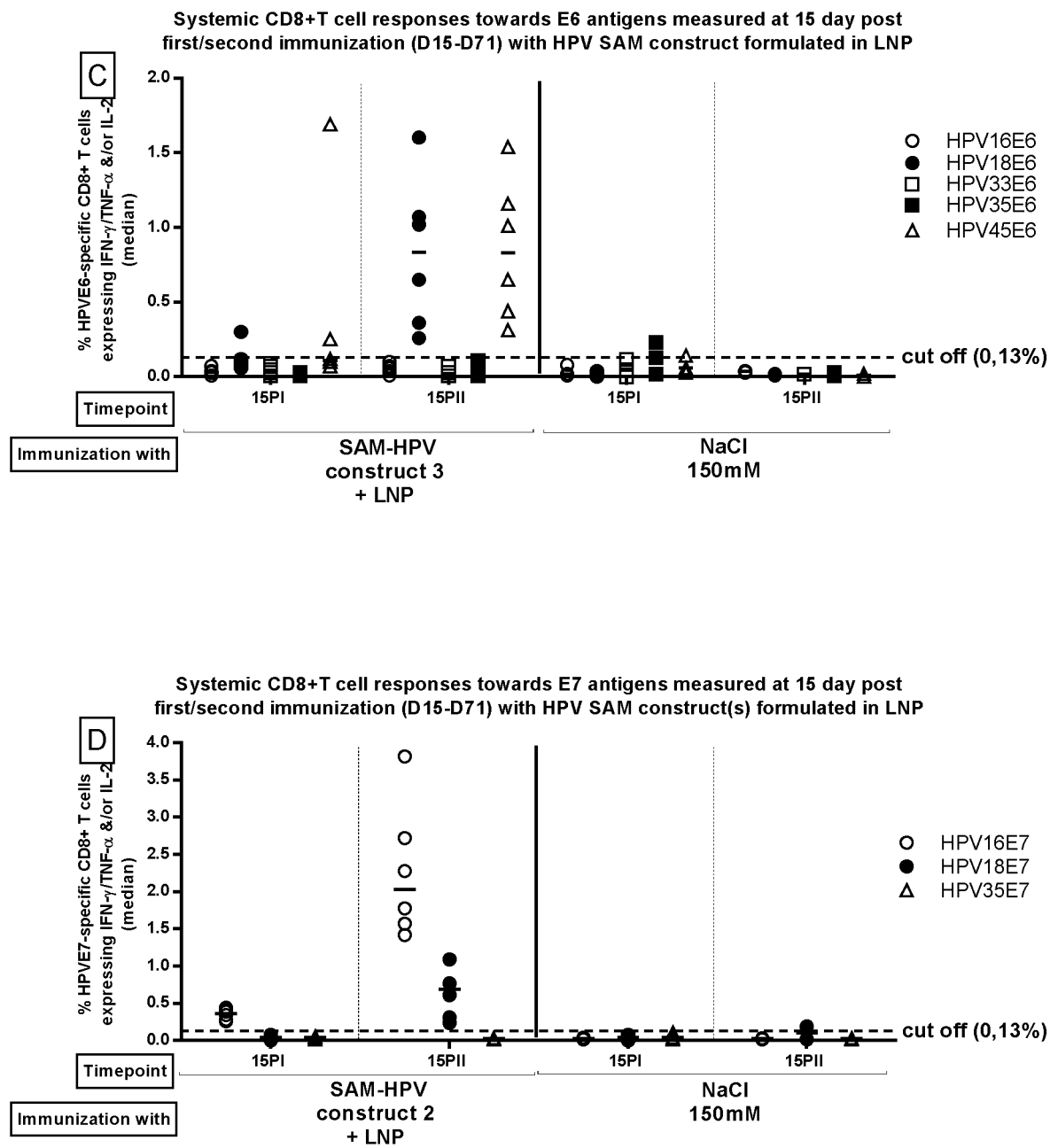

FIG. 7—Comparative systemic evaluation of HPV-specific and cross-reactive CD8+ T cell responses elicited towards E1, E2, E6 & E7 antigens 15 days after first or second immunization with different LNP-formulated SAM-HPV constructs. Naïve inbred CB6F1 mice (n=6/gr) were intramuscularly immunized on days 0 & 56 with 1 µg of LNP-formulated SAM-HPV construct 1 or 2 or 3. Negative control mice (n=3/gr) were treated with NaCl 150 mM solution. At day 15 post first and second immunization (15PI-15PII), mice in each group were culled for spleen collection and percentage of HPV-specific and cross-reactive CD8+ T cells secreting IFN-γ and/or IL-2 and/or TNF-α were measured in the systemic compartment. Intracellular staining was performed on splenocytes stimulated ex-vivo during 6 hours with pools of 15mer peptides covering the amino acid sequences of the HPV E1 (A), E2 (B), E6 (C) & E7 (D) antigens from 5 high risk HPV types (HPV16/18/33/35/45). The value used as the cut-off to identify specific CD8+ T cell responses in vaccine-immunized mice correspond to the $95^{th}$ percentile of CD8+ T cell responses obtained in the saline group when combining all HPV antigens. These cut off values were obtained by computing the anti log of $95^{th}$ quantile of the normal distribution that is assumed for the log frequencies, i.e. the mean of log frequencies+1.64×their standard deviation. Plots represent CD8+ T cell responses in the systemic compartment for each individual mouse. The median of the CD8+ T cell responses towards each HPV antigen is showed by the dotted line.

Figure 8:
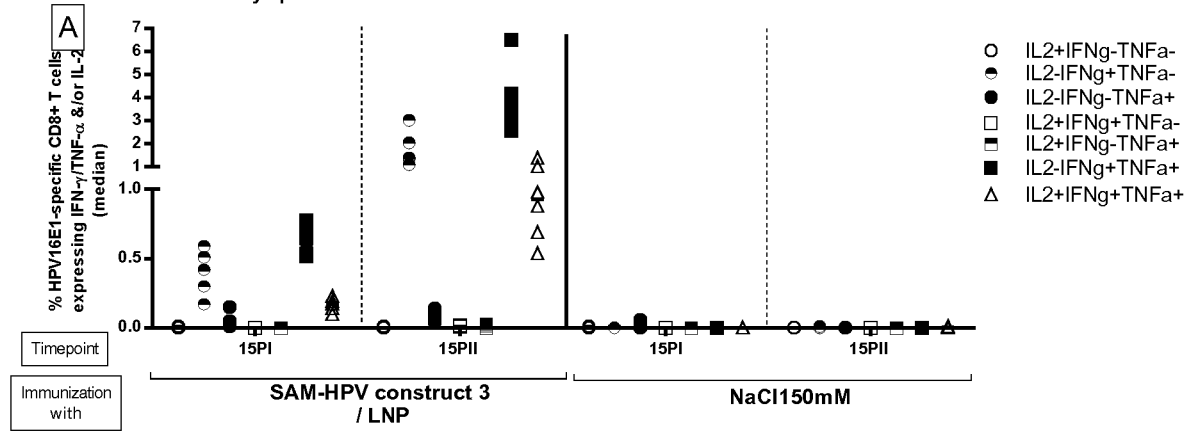
Figure 8:
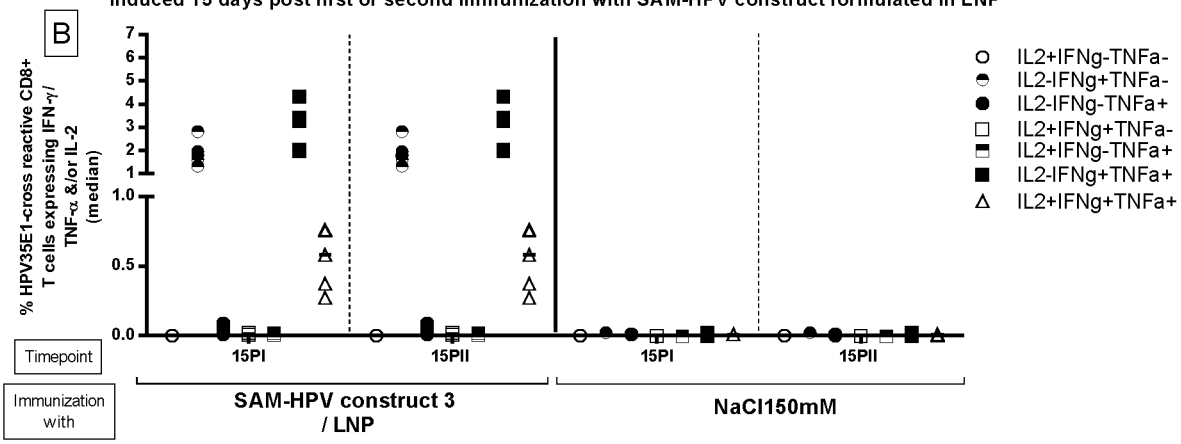

FIG. 8—Comparative systemic evaluation of the polyfunctional profile of HPV16E1-specific & HPV35E1 cross-reactive CD8+ T cell response after first and second immunization with LNP-formulated SAM-HPV construct. Naïve inbred CB6F1 mice (n=6/gr) were intramuscularly immunized on days 0 & 56 with 1 µg of LNP-formulated SAM-HPV construct 3. Negative control mice (n=3/gr) were treated with NaCl 150 mM solution. At days 15 post first and second immunization (15PI-15PII), mice in each group were culled for T cells analysis. Splenocytes were stimulated ex-vivo during 6 hours with a pool of 15mer peptides covering the amino acid sequence of E1 antigens from HPV16 or HPV35 types. The polyfunctional profile of HPV16E1-specific (A) and HPV35E1 cross-reactive (B) CD8+ T cells were evaluated by measuring IFN-γ, IL-2 and TNF-α cytokine production. Each plot represents data from individual mice.

Figure 9:
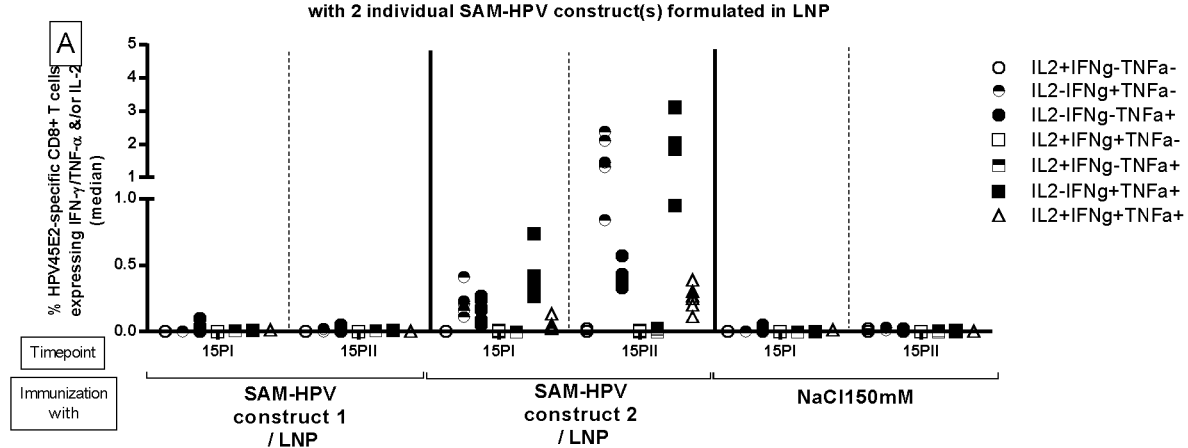
Figure 9:
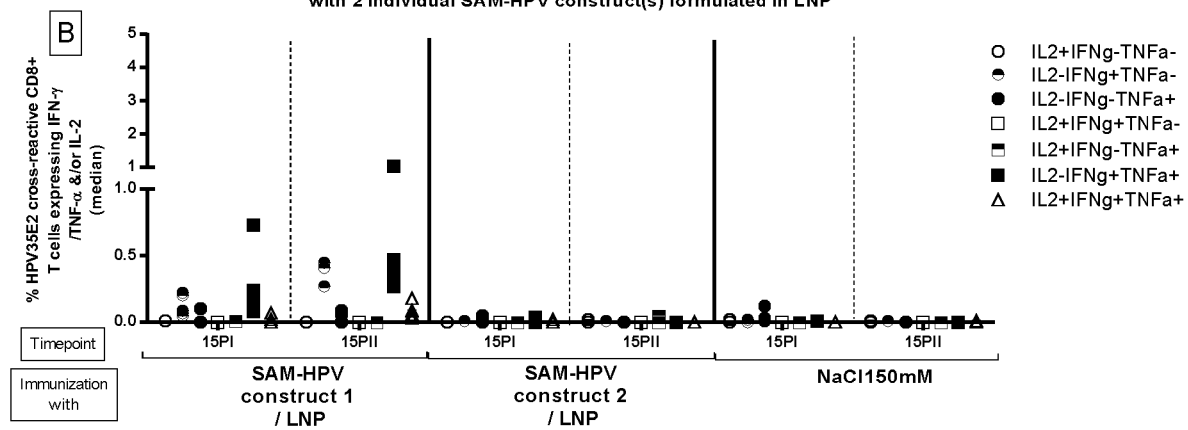

FIG. 9—Comparative systemic evaluation of the polyfunctional profile of HPV45E2-specific & HPV35E2 cross-reactive CD8+ T cell response after first and second immunization with LNP-formulated SAM-HPV constructs. Naïve inbred CB6F1 mice (n=6/gr) were intramuscularly immunized on days 0 & 56 with 1 µg of LNP-formulated SAM-HPV construct 1 or 2. Negative control mice (n=3/gr) were treated with NaCl 150 mM solution. At days 15 post first and second immunization (15PI-15PII), mice in each group were culled for T cells analysis. Splenocytes were stimulated ex-vivo during 6 hours with a pool of 15mer peptides covering the amino acid sequence of E2 antigens from HPV45 or HPV35 types. The polyfunctional profile of HPV45E2-specific (A) and HPV35E2 cross-reactive (B) CD8+ T cells were evaluated by measuring IFN-γ, IL-2 and TNF-α cytokine production. Each plot represents data from individual mice.

Figure 10:
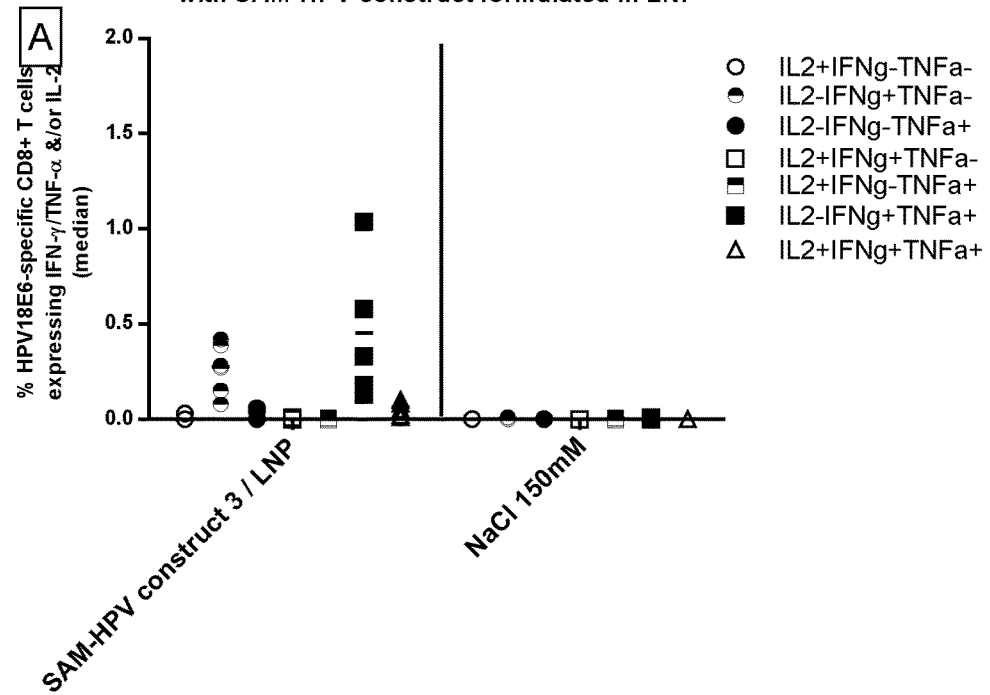
Figure 10:
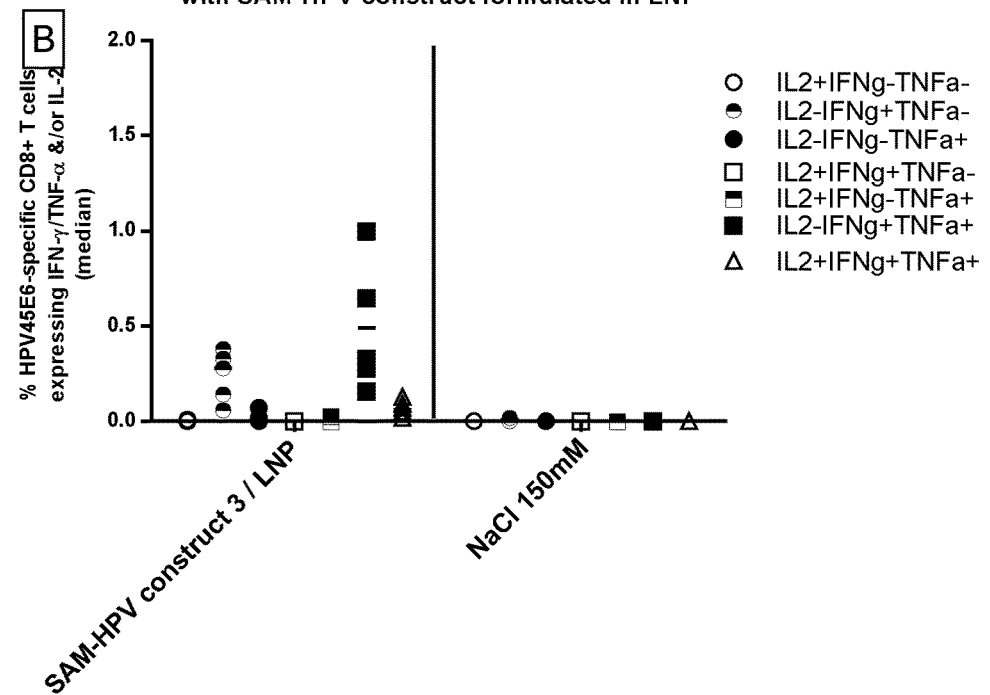

FIG. 10—Systemic evaluation of the polyfunctional profile of HPV18/45E6-specific CD8+ T cell response 15 days post second immunization with LNP-formulated SAM-HPV construct. Naïve inbred CB6F1 mice (n=6/gr) were intramuscularly immunized on days 0 & 56 with 1 µg of LNP-formulated SAM-HPV construct 3. Negative control mice (n=3/gr) were treated with NaCl 150 mM solution. At days 15 post second immunization (15PII), mice in each group were culled for T cells analysis. Splenocytes were stimulated ex-vivo during 6 hours with a pool of 15mer peptides covering the amino acid sequence of E6 antigens from HPV18 or HPV45 types. The polyfunctional profile of HPV18E6-specific (A) and HPV45E6-specific (B) CD8+ T cells were evaluated by measuring IFN-γ, IL-2 and TNF-α cytokine production. Each plot represents data from individual mice.

Figure 11:
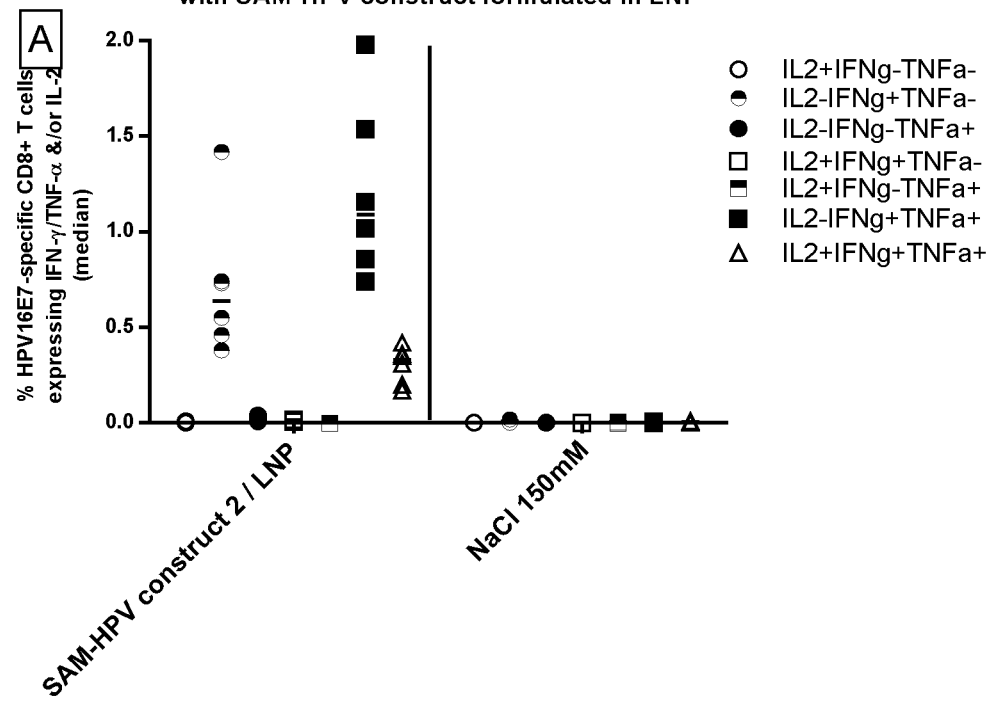
Figure 11:
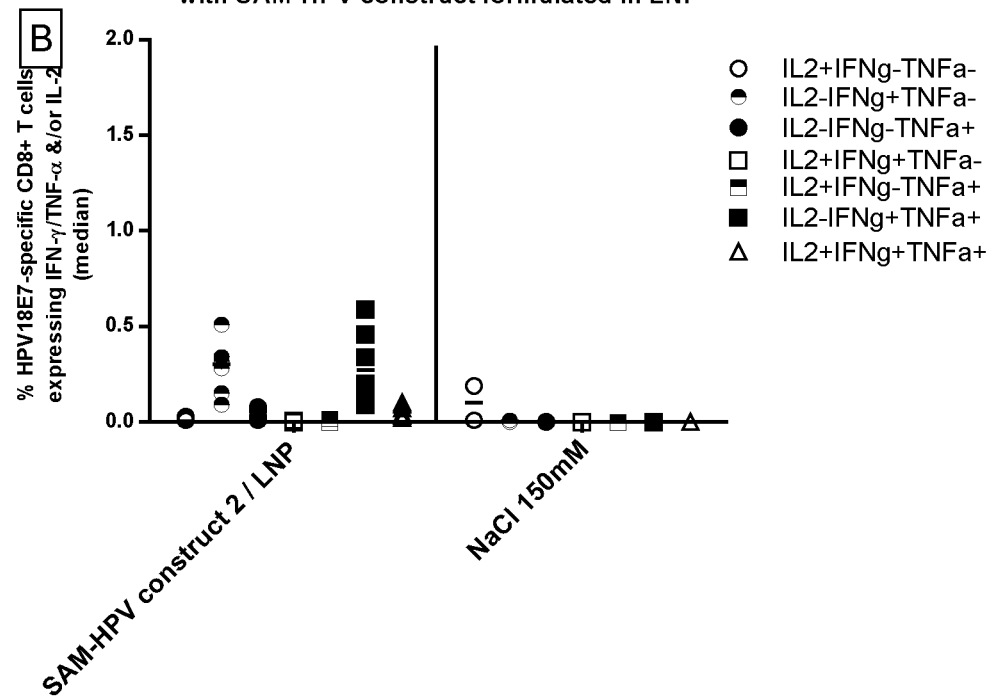

FIG. 11—Systemic evaluation of the polyfunctional profile of HPV16/18E7-specific CD8+ T cell response 15 days post second immunization (D71) with LNP-formulated SAM-HPV construct. Naïve inbred CB6F1 mice (n=6/gr) were intramuscularly immunized on days 0 & 56 with 1 µg of LNP-formulated SAM-HPV construct 2. Negative control mice (n=3/gr) were treated with NaCl 150 mM solution. At days 15 post second immunization (15PII), mice in each group were culled for spleen collection and T cells analysis. Splenocytes were stimulated ex-vivo during 6 hours with a pool of 15mer peptides covering the amino acid sequence of E7 antigens from HPV16 or HPV18 types. The polyfunctional profile of HPV16E7-specific (A) and HPV18E7-specific (B) CD8+ T cells were evaluated by measuring IFN-γ, IL-2 and TNF-α cytokine production. Each plot represents data from individual mice.

Figure 12:
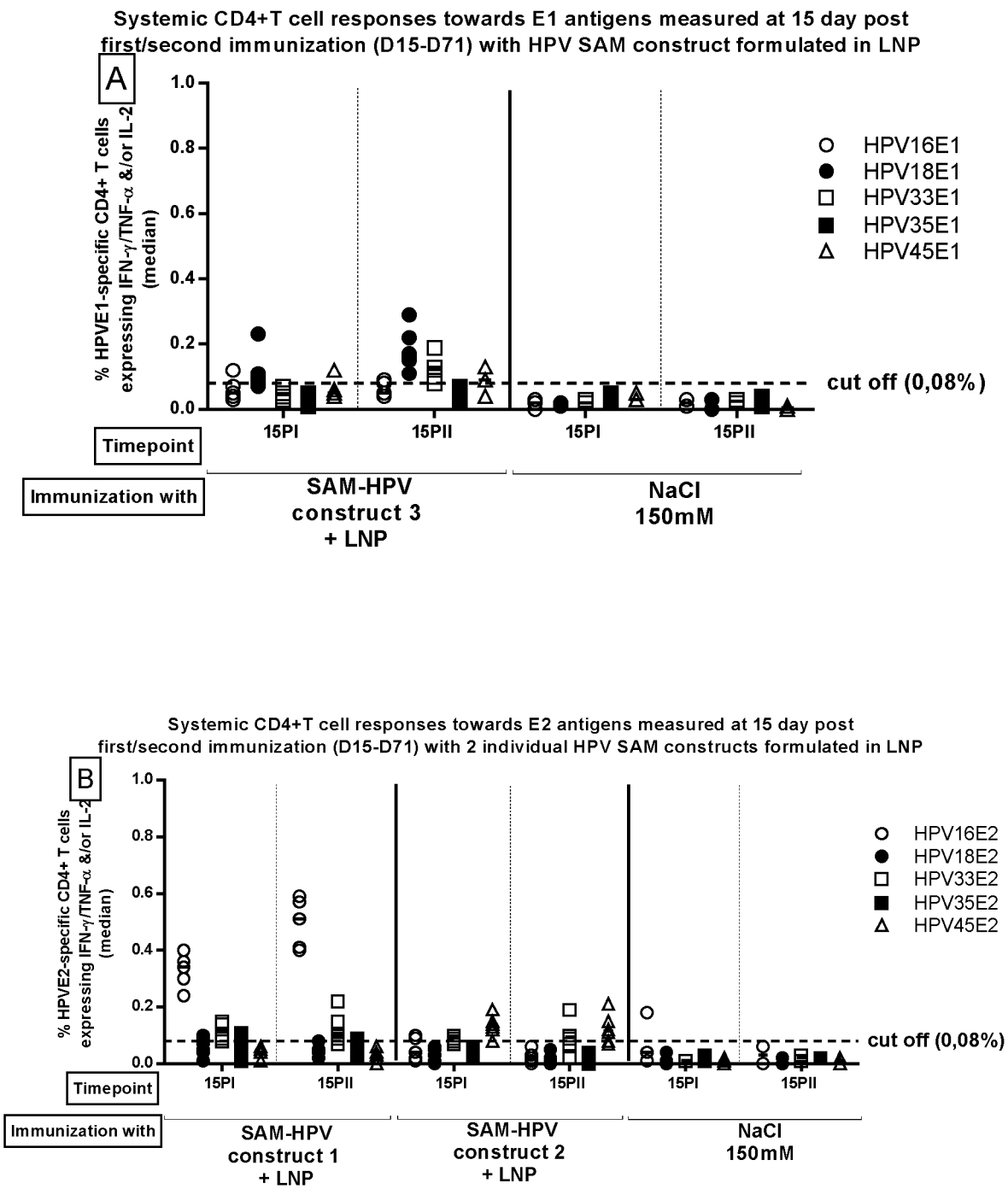
Figure 12:
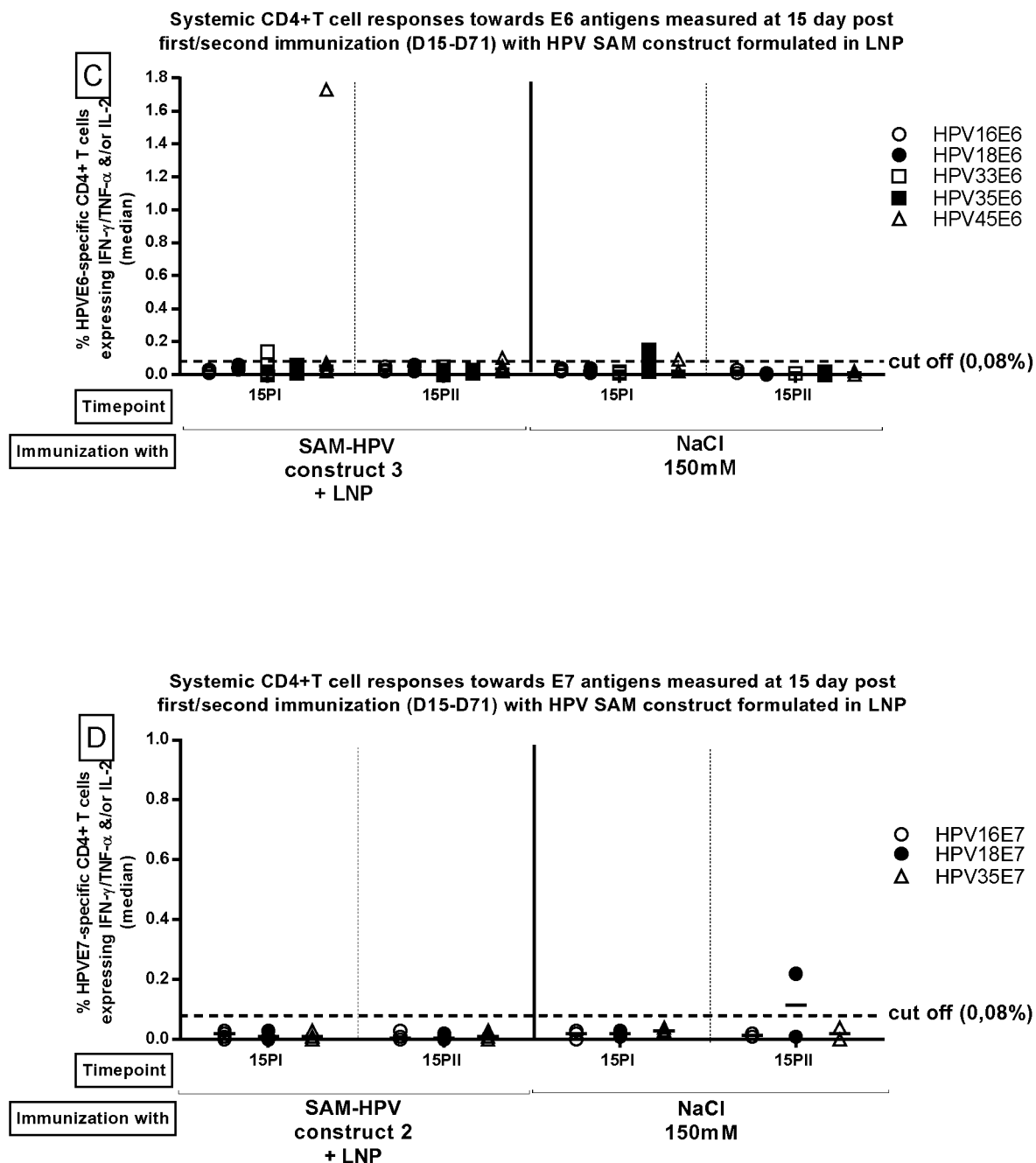

FIG. 12—Comparative systemic evaluation of HPV-specific and cross-reactive CD4+ T cell responses elicited towards E1, E2, E6 & E7 antigens 15 days after first or second immunization with different LNP-formulated SAM-HPV constructs. Naïve inbred CB6F1 mice (n=6/gr) were intramuscularly immunized on days 0 & 56 with 1 µg of LNP-formulated SAM-HPV construct 1 or 2 or 3. Negative control mice (n=3/gr) were treated with NaCl 150 mM solution. At day 15 post first and second immunization (15PI-15PII), mice in each group were culled for spleen collection and T cells analysis. Percentage of HPV-specific and cross-reactive CD4+ T cells secreting IFN-γ and/or IL-2 and/or TNF-α were measured in the systemic compartment. Intracellular staining was performed on splenocytes stimulated ex-vivo during 6 hours with pools of 15mer peptides covering the amino acid sequences of the HPV E1 (A), E2 (B), E6 (C) & E7 (D) antigens from 5 high risk HPV types (HPV16/18/33/35/45). The value used as the cut-off to identify specific CD4+ T cell responses in vaccine-immunized mice correspond to the 95$^{th}$ percentile of CD4+ T cell responses obtained in the saline group when combining all HPV antigens. These cut off values were obtained by computing the anti log of 95$^{th}$ quantile of the normal distribution that is assumed for the log frequencies, i.e. the mean of log frequencies+1.64×their standard deviation. Plots represent CD4+ T cell responses in the systemic compartment for each individual mice. The median of the CD4+ T cell responses towards each HPV antigen is showed by the dotted line.

DESCRIPTION OF THE SEQUENCES

SEQ ID NO:1—Sequence for empty SAM construct.
SEQ ID NO:2—E2_SAM insert polypeptide sequence
SEQ ID NO:3—E2_SAM insert polynucleotide sequence
SEQ ID NO:4—E2E7_SAM insert polypeptide sequence
SEQ ID NO:5—E2E7_SAM insert polynucleotide sequence
SEQ ID NO:6—E1E6_SAM insert polypeptide sequence
SEQ ID NO:7—E1E6_SAM insert polynucleotide sequence
SEQ ID NO:8—SAM E2 construct DNA sequence
SEQ ID NO:9—SAM E2 construct RNA sequence
SEQ ID NO:10—SAM E2E7 construct DNA sequence
SEQ ID NO:11—SAM E2E7 construct RNA sequence
SEQ ID NO:12—SAM E1E6 construct DNA sequence
SEQ ID NO:13—SAM E1E6 construct DNA sequence
SEQ ID NO:14—HPV16-E1 full length sequence
SEQ ID NO:15—HPV16-E2 full length sequence
SEQ ID NO:16—HPV16-E6 full length sequence
SEQ ID NO:17—HPV16-E7 Full length sequence
SEQ ID NO:18—HPV16 E1 aa 203-622
SEQ ID NO:19—HPV18 E1 aa 210-629
SEQ ID NO:20—HPV16 E2: AA1-201+GGTGGS linker+aa285-365
SEQ ID NO:21—HPV 18 E2: AA1-206+GGTGGS linker+aa286-365
SEQ ID NO:22—HPV 31 E2: AA1-201+GGTGGS linker+aa292-372
SEQ ID NO:23—HPV 33 E2: AA1-201+GGTGGS linker+aa273-353
SEQ ID NO:24—HPV45 E2: AA1-208+GGTGGS linker+aa290-368
SEQ ID NO:25—HPV52 E2: AA1-201+GGTGGS linker+aa287-368
SEQ ID NO:26—HPV58 E2: AA1-201+GGTGGS linker+aa278-358
SEQ ID NO:27—HPV 16 E6: aa11-150
SEQ ID NO:28—HPV 18 E6: aa6-145
SEQ ID NO:29—HPV 31 E6: aa4-143
SEQ ID NO:30—HPV 33 E6: aa4-143
SEQ ID NO:31—HPV 45 E6: aa6-145
SEQ ID NO:32—HPV 52 E6: aa4-143
SEQ ID NO:33—HPV 58 E6: aa4-143
SEQ ID NO:34—HPV 16 E7: aa49-98+aa7-28, C24G and E26Q substitutions
SEQ ID NO:35—HPV 18 E7: aa58-105+aa7-42, C27G and E29Q substitutions SEQ ID NO:36. 2A sequence (amino acid)
SEQ ID NO:37. 5× Gly Linker
SEQ ID NO:38. linker

DETAILED DESCRIPTION

The present invention provides RNA constructs capable of encoding HPV peptides useful in inducing a therapeutic immune response to persistent HPV infection, such as HPV infection of the cervical epithelium. The RNA constructs are designed to encode antigenic HPV peptides capable of inducing a cross-reactive immune response in a subject against more than one high-risk HPV type. SAM constructs encoding the antigenic HPV peptides are also provided.

RNA Constructs

In a first aspect, the present invention provides one or more RNA construct(s) comprising nucleic acid sequences encoding:

at least two antigenic Human Papillomavirus (HPV) polypeptides from a first HPV early protein, where said antigenic HPV polypeptides are from at least two different high-risk HPV types, and share at least 70% amino acid sequence identity with at least one additional high-risk HPV type, and at least two antigenic HPV polypeptides from a second HPV early protein, where said antigenic HPV polypeptides are from at least two different high-risk HPV types, and share at least 70% amino acid sequence identity with at least one additional high-risk HPV type.

Preferably, each antigenic HPV polypeptide includes at least one T cell epitope.

In one embodiment, the nucleic acid sequences encode separate antigenic HPV polypeptides. In a preferred embodiment, the nucleic acid sequences encode antigenic HPV polypeptides that are linked by a peptide linker.

In a preferred embodiment, the RNA construct(s) do not comprise any nucleic acid sequence encoding an antigenic polypeptide from an HPV Late 1 (L1) protein or an HPV Late 2 (L2) protein.

In one embodiment, the nucleic acid sequences encoding antigenic HPV polypeptides from the first and second HPV early protein are located on the same RNA construct. In an alternative embodiment, the nucleic acid sequences encoding antigenic HPV polypeptides from the first and second HPV early protein are located on two or more RNA constructs.

Preferably, the RNA construct(s) according to the invention comprise antigenic polypeptide sequences selected from HPV types HPV16, HPV18, HPV31, HPV33, HPV35, HPV39, HPV45, HPV51, HPV52, HPV56, HPV58, HPV59, HPV68, HPV73 and HPV82, preferably antigenic polypeptide sequences selected from HPV types HPV16, HPV18, HPV31, HPV33, HPV45, HPV52 and HPV58, more preferably antigenic polypeptide sequences selected from HPV types HPV16 and HPV18.

In one embodiment, the first HPV early protein is Early 1 (E1), and the second HPV early protein is selected from Early 2 (E2), Early 6 (E6), and Early 7 (E7). In another embodiment, the first HPV early protein is E2, and the second HPV early protein is selected from E1, E6 and E7. In another embodiment, the first HPV early protein is E6, and the second HPV early protein is selected from E1, E2 and E7. In another embodiment, the first HPV early protein is E7, and the second HPV early protein is selected from E1, E2 and E6.

Preferably, the first HPV early protein is Early 1 (E1). Preferably still, the antigenic HPV polypeptides from E1 include antigenic polypeptides from HPV16 E1 and HPV18 E1. Suitably, the antigenic HPV polypeptides from E1 do not include antigenic polypeptides from other HPV types. In a preferred embodiment, the second HPV early protein is Early 2 (E2), and the antigenic HPV polypeptides from E2 include antigenic polypeptides from HPV16 E2 and HPV18 E2, and preferably also from HPV31 E2, HPV33 E2, HPV45 E2, HPV52 E2 and/or HPV58 E2.

Suitably, the RNA construct(s) encode:
E1 antigenic polypeptides having an amino acid sequence corresponding to amino acids 203-622 of HPV 16 E1 (SEQ ID NO:14), and optionally comprising a Glycine to Aspartic acid substitution at position 482 (G482D) of SEQ ID NO:14, and/or
E1 antigenic polypeptides having an amino acid sequence corresponding to amino acids 210-629 of HPV 18 E1, and optionally comprising a Glycine to Aspartic acid substitution at position 489 (G489D) of full length HPV18 E1.

In a preferred embodiment, the RNA construct(s) according to the invention further comprise a nucleic acid sequence encoding at least two antigenic HPV polypeptides from a third HPV early protein, where said antigenic HPV polypeptides are from at least two different high-risk HPV types, and share at least 70% amino acid sequence identity with at least one additional high-risk HPV type. Preferably, each antigenic HPV polypeptide includes at least one T cell epitope. Suitably, the first HPV early protein is E1, the second HPV early protein is E2 and the third HPV early protein is E6. In a preferred embodiment, the nucleic acid sequences encode antigenic polypeptides from HPV16 E1, HPV18 E1, HPV16 E2, HPV18 E2, HPV16 E6 and HPV18 E6, and preferably also from HPV31 E2, HPV33 E2, HPV45 E2, HPV52 E2, HPV58 E2, HPV31 E6, HPV33 E6, HPV45 E6, HPV52 E6 and/or HPV58 E6. In one embodiment, the nucleic acid sequences encode antigenic polypeptides from HPV16 E1, HPV18 E1, HPV16 E2, HPV18 E2, HPV16 E6, HPV18 E6, HPV31 E2, HPV33 E2, HPV45 E2, HPV52 E2, HPV58 E2, HPV31 E6, HPV33 E6, HPV45 E6, HPV52 E6, HPV52 E6 and HPV58 E6.

Suitably, the RNA construct(s) according to the invention further comprise a nucleic acid sequence encoding at least two antigenic HPV polypeptides from a fourth HPV early protein, where said antigenic HPV polypeptides are from at least two different high-risk HPV types, and share at least 70% amino acid sequence identity with at least one additional high-risk HPV type. Preferably, each antigenic HPV polypeptide includes at least one T cell epitope. Preferably, the first HPV early protein is E1, the second HPV early protein is E2, the third HPV early protein is E6 and the fourth HPV early protein is E7. In a preferred embodiment, the nucleic acid sequences encode antigenic polypeptides from HPV16 E1, HPV18 E1, HPV16 E2, HPV18 E2, HPV16 E6, HPV18 E6, HPV16 E7 and HPV18 E7, and preferably also from HPV31 E2, HPV33 E2, HPV45 E2, HPV52 E2, HPV58 E2, HPV31 E6, HPV33 E6, HPV45 E6, HPV52 E6 and/or HPV58 E6. In one embodiment, the nucleic acid sequences also encode antigenic polypeptides from HPV16 E1, HPV18 E1, HPV16 E2, HPV18 E2, HPV16 E6, HPV18 E6, HPV16 E7, HPV18 E7, HPV31 E2, HPV33 E2, HPV45 E2, HPV52 E2, HPV58 E2, HPV31 E6, HPV33 E6, HPV45 E6, HPV52 E6, HPV52 E6 and HPV58 E6.

According to one embodiment of the RNA construct(s) according to the invention, the nucleic acid sequences encode one or more polypeptides that are at least 90%, 92%, 95%, 97%, 98%, 99% or 100% identical to a sequence selected from the group of SEQ ID NO:18 to SEQ ID NO:35.

In one embodiment, the RNA construct(s) encode an E1 antigenic polypeptides having an amino acid sequence which is at least 90%, 92%, 95%, 97%, 98%, 99% or 100% identical to SEQ ID NO:18, and/or an E1 antigenic polypeptides having an amino acid sequence which is at least 90%, 92%, 95%, 97%, 98%, 99% or 100% identical to SEQ ID NO:19. Preferably, the RNA construct(s) encode an E1 antigenic polypeptides having an amino acid sequence which is at least 90%, 92%, 95%, 97%, 98%, 99% or 100% identical to SEQ ID NO:18, and an E1 antigenic polypeptides having an amino acid sequence which is at least 90%, 92%, 95%, 97%, 98%, 99% or 100% identical to SEQ ID NO:19.

In one embodiment, the RNA construct(s) encode an E2 antigenic polypeptides having an amino acid sequence which is at least 90%, 92%, 95%, 97%, 98%, 99% or 100% identical to SEQ ID NO:20, and/or an E2 antigenic polypeptides having an amino acid sequence which is at least 90%, 92%, 95%, 97%, 98%, 99% or 100% identical to SEQ ID NO:21. Preferably, the RNA construct(s) encode an E2 antigenic polypeptides having an amino acid sequence which is at least 90%, 92%, 95%, 97%, 98%, 99% or 100% identical to SEQ ID NO:20, and an E2 antigenic polypeptides having an amino acid sequence which is at least 90%, 92%, 95%, 97%, 98%, 99% or 100% identical to SEQ ID NO:21. Preferably still, the RNA construct(s) further encode an E2 antigenic polypeptides having an amino acid sequence which is at least 90%, 92%, 95%, 97%, 98%, 99% or 100% identical to a sequence selected from SEQ ID NO:22, 23, 24, 25 and 26. In a preferred embodiment, the RNA construct(s) encode seven E2 antigenic polypeptides having an amino acid sequence which are at least 90%, 92%, 95%, 97%, 98%, 99% or 100% identical to SEQ ID NO:20, 21, 22, 23, 24, 25 and 26 respectively.

In one embodiment, the RNA construct(s) encode an E6 antigenic polypeptides having an amino acid sequence which is at least 90%, 92%, 95%, 97%, 98%, 99% or 100% identical to SEQ ID NO:27, and/or an E6 antigenic polypeptides having an amino acid sequence which is at least 90%, 92%, 95%, 97%, 98%, 99% or 100% identical to SEQ ID NO:28. Preferably, the RNA construct(s) encode an E6 antigenic polypeptides having an amino acid sequence which is at least 90%, 92%, 95%, 97%, 98%, 99% or 100% identical to SEQ ID NO:27, and an E6 antigenic polypeptides having an amino acid sequence which is at least 90%, 92%, 95%, 97%, 98%, 99% or 100% identical to SEQ ID NO:28. Preferably still, the RNA construct(s) further encode an E6 antigenic polypeptides having an amino acid sequence which is at least 90%, 92%, 95%, 97%, 98%, 99% or 100% identical to a sequence selected from SEQ ID NO:29, 30, 31, 32 and 33. In a preferred embodiment, the RNA construct(s) encode seven E6 antigenic polypeptides having an amino acid sequence which are at least 90%, 92%, 95%, 97%, 98%, 99% or 100% identical to SEQ ID NO:27, 28, 29, 30, 31, 32 and 33 respectively.

In one embodiment, the RNA construct(s) encode an E7 antigenic polypeptides having an amino acid sequence which is at least 90%, 92%, 95%, 97%, 98%, 99% or 100% identical to SEQ ID NO:34, and/or an E7 antigenic polypeptides having an amino acid sequence which is at least 90%, 92%, 95%, 97%, 98%, 99% or 100% identical to SEQ ID NO:35. Preferably, the RNA construct(s) encode an E7 antigenic polypeptides having an amino acid sequence which is at least 90%, 92%, 95%, 97%, 98%, 99% or 100% identical to SEQ ID NO:34, and an E7 antigenic polypeptides having an amino acid sequence which is at least 90%, 92%, 95%, 97%, 98%, 99% or 100% identical to SEQ ID NO:35.

In a preferred embodiment, the RNA construct(s) encode:
two E1 antigenic polypeptides having an amino acid sequence which are at least 90%, 92%, 95%, 97%, 98%, 99% or 100% identical to SEQ ID NO:18 and 19 respectively;
two E2 antigenic polypeptides having an amino acid sequence which are at least 90%, 92%, 95%, 97%, 98%, 99% or 100% identical to SEQ ID NO:20 and 21 respectively;
two E6 antigenic polypeptides having an amino acid sequence which are at least 90%, 92%, 95%, 97%, 98%, 99% or 100% identical to SEQ ID NO:27 and 28 respectively; and
two E7 antigenic polypeptides having an amino acid sequence which are at least 90%, 92%, 95%, 97%, 98%, 99% or 100% identical to SEQ ID NO:3427 and 35 respectively.

Suitably, the RNA construct(s) encode:
two E1 antigenic polypeptides having an amino acid sequence which are at least 90%, 92%, 95%, 97%, 98%, 99% or 100% identical to SEQ ID NO:18 and 19 respectively;
seven E2 antigenic polypeptides having an amino acid sequence which are at least 90%, 92%, 95%, 97%, 98%, 99% or 100% identical to SEQ ID NO:27, 28, 29, 30, 31, 32 and 33 respectively;
seven E6 antigenic polypeptides having an amino acid sequence which are at least 90%, 92%, 95%, 97%, 98%, 99% or 100% identical to SEQ ID NO:27, 28, 29, 30, 31, 32 and 33 respectively; and
two E7 antigenic polypeptides having an amino acid sequence which are at least 90%, 92%, 95%, 97%, 98%, 99% or 100% identical to SEQ ID NO:3427 and 35 respectively.

In one embodiment, the RNA construct(s) comprise:
an RNA construct comprising a nucleic acid sequence encoding a polypeptide that is at least 90%, 92%, 95%, 97%, 98%, 99% or 100% identical to SEQ ID NO:2,
an RNA construct comprising a nucleic acid sequence encoding a polypeptide that is at least 90%, 92%, 95%, 97%, 98%, 99% or 100% identical to SEQ ID NO:4, and/or
an RNA construct comprising a nucleic acid sequence encoding a polypeptide that is at least 90%, 92%, 95%, 97%, 98%, 99% or 100% identical to SEQ ID NO:6.

Suitably, the RNA construct(s) comprise:
an RNA construct comprising a nucleic acid sequence encoding a polypeptide corresponding to SEQ ID NO:2,
an RNA construct comprising a nucleic acid sequence encoding a polypeptide corresponding to SEQ ID NO:4, and/or
an RNA construct comprising a nucleic acid sequence encoding a polypeptide corresponding to SEQ ID NO:6.

In one embodiment, the RNA construct(s) comprise an RNA construct comprising a nucleic acid sequence encoding a polypeptide that is at least 90%, 92%, 95%, 97%, 98%, 99% or 100% identical to SEQ ID NO:2, and an RNA construct comprising a nucleic acid sequence encoding a polypeptide that is at least 90%, 92%, 95%, 97%, 98%, 99% or 100% identical to SEQ ID NO:4. Suitably, the RNA construct(s) comprise an RNA construct comprising a nucleic acid sequence encoding a polypeptide corresponding to SEQ ID NO:2, and an RNA construct comprising a nucleic acid sequence encoding a polypeptide corresponding to SEQ ID NO:4.

In one embodiment, the RNA construct(s) comprise an RNA construct comprising a nucleic acid sequence encoding a polypeptide that is at least 90%, 92%, 95%, 97%, 98%, 99% or 100% identical to SEQ ID NO:2, and an RNA construct comprising a nucleic acid sequence encoding a polypeptide that is at least 90%, 92%, 95%, 97%, 98%, 99% or 100% identical to SEQ ID NO:6. Suitably, the RNA construct(s) comprise an RNA construct comprising a nucleic acid sequence encoding a polypeptide corresponding to SEQ ID NO:2, and an RNA construct comprising a nucleic acid sequence encoding a polypeptide corresponding to SEQ ID NO:6.

In one embodiment, the RNA construct(s) comprise an RNA construct comprising a nucleic acid sequence encoding a polypeptide that is at least 90%, 92%, 95%, 97%, 98%, 99% or 100% identical to SEQ ID NO:4, and an RNA construct comprising a nucleic acid sequence encoding a polypeptide that is at least 90%, 92%, 95%, 97%, 98%, 99% or 100% identical to SEQ ID NO:6. Suitably, the RNA construct(s) comprise an RNA construct comprising a nucleic acid sequence encoding a polypeptide corresponding to SEQ ID NO:4, and an RNA construct comprising a nucleic acid sequence encoding a polypeptide corresponding to SEQ ID NO:6.

In one embodiment, the RNA construct(s) comprise an RNA construct comprising a nucleic acid sequence encoding a polypeptide that is at least 90%, 92%, 95%, 97%, 98%, 99% or 100% identical to SEQ ID NO:2, an RNA construct comprising a nucleic acid sequence encoding a polypeptide that is at least 90%, 92%, 95%, 97%, 98%, 99% or 100% identical to SEQ ID NO:4, and an RNA construct comprising a nucleic acid sequence encoding a polypeptide that is at least 90%, 92%, 95%, 97%, 98%, 99% or 100% identical to SEQ ID NO:6. Suitably, the RNA construct(s) comprise an RNA construct comprising a nucleic acid sequence encoding a polypeptide corresponding to SEQ ID NO:2, an RNA construct comprising a nucleic acid sequence encoding a polypeptide corresponding to SEQ ID NO:4, and an RNA construct comprising a nucleic acid sequence encoding a polypeptide corresponding to SEQ ID NO:6.

In one embodiment, the RNA construct(s) comprise:
an RNA construct comprising a nucleic acid sequence that is at least 90%, 92%, 95%, 97%, 98%, 99% or 100% identical to SEQ ID NO:3,
an RNA construct comprising a nucleic acid sequence that is at least 90%, 92%, 95%, 97%, 98%, 99% or 100% identical to SEQ ID NO:5, and/or
an RNA construct comprising a nucleic acid sequence that is at least 90%, 92%, 95%, 97%, 98%, 99% or 100% identical to SEQ ID NO:7.

Suitably, the RNA construct(s) comprise:
an RNA construct comprising a nucleic acid sequence corresponding to SEQ ID NO:3,
an RNA construct comprising a nucleic acid sequence corresponding to SEQ ID NO:5, and:or
an RNA construct comprising a nucleic acid sequence corresponding to SEQ ID NO:7.

In one embodiment, the RNA construct(s) comprise an RNA construct comprising a nucleic acid sequence that is at least 90%, 92%, 95%, 97%, 98%, 99% or 100% identical to SEQ ID NO:3, and an RNA construct comprising a nucleic acid sequence that is at least 90%, 92%, 95%, 97%, 98%, 99% or 100% identical to SEQ ID NO:5. Suitably, the RNA construct(s) comprise an RNA construct comprising a nucleic acid sequence corresponding to SEQ ID NO:3, and an RNA construct comprising a nucleic acid sequence corresponding to SEQ ID NO:5.

In one embodiment, the RNA construct(s) comprise an RNA construct comprising a nucleic acid sequence that is at least 90%, 92%, 95%, 97%, 98%, 99% or 100% identical to SEQ ID NO:3, and an RNA construct comprising a nucleic acid sequence that is at least 90%, 92%, 95%, 97%, 98%, 99% or 100% identical to SEQ ID NO:7. Suitably, the RNA construct(s) comprise an RNA construct comprising a nucleic acid sequence corresponding to SEQ ID NO:3, and an RNA construct comprising a nucleic acid sequence corresponding to SEQ ID NO:7.

In one embodiment, the RNA construct(s) comprise an RNA construct comprising a nucleic acid sequence that is at least 90%, 92%, 95%, 97%, 98%, 99% or 100% identical to SEQ ID NO:5, and an RNA construct comprising a nucleic acid sequence that is at least 90%, 92%, 95%, 97%, 98%, 99% or 100% identical to SEQ ID NO:7. Suitably, the RNA construct(s) comprise an RNA construct comprising a nucleic acid sequence corresponding to SEQ ID NO:5, and an RNA construct comprising a nucleic acid sequence corresponding to SEQ ID NO:7.

In one embodiment, the RNA construct(s) comprise an RNA construct comprising a nucleic acid sequence that is at least 90%, 92%, 95%, 97%, 98%, 99% or 100% identical to SEQ ID NO:3, an RNA construct comprising a nucleic acid sequence that is at least 90%, 92%, 95%, 97%, 98%, 99% or 100% identical to SEQ ID NO:5, and an RNA construct comprising a nucleic acid sequence that is at least 90%, 92%, 95%, 97%, 98%, 99% or 100% identical to SEQ ID NO:7. Suitably, the RNA construct(s) comprise an RNA construct comprising a nucleic acid sequence corresponding to SEQ ID NO:3, an RNA construct comprising a nucleic acid sequence corresponding to SEQ ID NO:5, and an RNA construct comprising a nucleic acid sequence corresponding to SEQ ID NO:7.

In one embodiment of the RNA construct(s) according to the invention, the nucleic acid sequence does not encode any antigenic polypeptide having at least 70% identity to an HPV Early protein from a non-high risk HPV type.

In one embodiment, the sequence of the RNA construct(s) is codon optimized.

In one aspect, the invention provides self-replicating RNA molecules comprising the RNA construct(s) as described herein.

In one aspect, the invention provides DNA molecules encoding the RNA construct(s) or the self-replicating RNA molecule as described herein.

In one aspect, the invention provides vectors comprising the RNA construct(s), the self-replicating RNA molecule or the DNA molecules as described herein.

Immunogenic Compositions

In one aspect, the invention provides an immunogenic composition comprising the RNA construct(s), the self-replicating RNA molecule, the DNA molecule or the vector according to the invention and a pharmaceutically acceptable carrier.

In one embodiment, the immunogenic composition comprises two or three RNA construct(s) according to the invention.

In one embodiment, the immunogenic composition further comprises a non-viral delivery material, such as a submicron cationic oil-in-water emulsion; a liposome; or a biodegradable polymeric microparticle delivery system, preferably CNEs or LNPs.

In one embodiment, the immunogenic composition further comprises an adjuvant. Suitable adjuvants for use in the present invention include metal salts, saponins, cytokines, monophosphoryl lipid A, 3-de-O-acylated monophosphoryl lipid A (3D-MPL), Toll-like receptor (TLR) agonists, and immunostimulatory oligonucleotides containing unmethylated CpG dinucleotides.

In one embodiment, the immunogenic composition further comprises at least one isolated antigenic HPV polypeptide from HPV E1, E2, E6 or E7, from a high-risk HPV type.

In one embodiment, the immunogenic composition does not comprise any antigenic polypeptides from Late (L) HPV proteins.

Use in Therapy and Methods of Treatment

In another aspect, there is provided the RNA construct(s), the self-replicating RNA molecule, the DNA molecule, the vector or the immunogenic composition according to the invention, for use in therapy.

In another aspect, there is provided the RNA construct(s), the self-replicating RNA molecule, the DNA molecule, the vector or the immunogenic composition according to the invention, for use in the treatment of an HPV-related condition of the human anogenital tract, selected from infection by HPV such as a high-risk HPV type, and, lesions of the cervical epithelium, such as Cervical Intraepithelial Neoplasia grade 1 (CIN1) and low-grade squamous intraepithelial lesions (LSIL).

In another aspect, there are provided two or more RNA constructs according to the invention, where the two or more RNA constructs encode at least one antigenic polypeptide from (a) different HPV early proteins, or (b) different HPV types, for use in a method of inducing an immune response in a mammalian subject, wherein the two or more RNA constructs are co-administered.

Suitably, the two or more RNA constructs together encode antigenic polypeptides from the E2 protein and E6 protein from each of HPV16, 18, 31, 33, 45, 52 and 58, and antigenic polypeptides from the E1 protein and the E7 protein from each of HPV16 and 18.

In a preferred embodiment, the method of inducing an immune response is a method of treatment of HPV-related disease of the human anogenital tract selected from infection by HPV such as a high-risk HPV type, and, lesions of the cervical epithelium, such as Cervical Intraepithelial Neoplasia grade 1 (CIN1) and low-grade squamous intraepithelial lesions (LSIL).

Suitably, the method comprises subsequent administration of further RNA construct(s) according to the invention.

Suitably, the method further comprises co-administration with the two or more RNA constructs, of one or more isolated antigenic polypeptide(s) from at least one HPV early protein from a high-risk HPV type, optionally with an adjuvant.

Suitably, the method further comprises subsequent administration of one or more isolated antigenic polypeptide(s) from at least one HPV early protein from a high-risk HPV type, and an adjuvant.

In another aspect, there is provided the use of one or more RNA construct(s), self-replicating RNA molecule(s), DNA molecule(s), vector(s) or immunogenic composition according to the invention in the manufacture of a medicament for treating an HPV-related condition of the human anogenital tract, selected from infection by a high-risk HPV type, CIN, and LSIL.

In another aspect, there is provided a method of inducing an immune response in a mammalian subject comprising administering to the subject one or more RNA construct(s), self-replicating RNA molecule(s), DNA molecule(s), vector(s) or immunogenic composition according to the invention.

In another aspect, there is provided a method of treating infection of the human anogenital epithelium by a high-risk HPV type, comprising co-administering to a subject in need of treatment, RNA constructs expressing:

(a) an antigenic polypeptide from each of E1, E2 and E6 from HPV16, (b) an antigenic polypeptide from each of E1, E2, and E6 from HPV18, and (c) an antigenic polypeptide sequence from the E2 or E6 protein from no more than six additional HPV types, said additional HPV types selected from the group consisting of HPV31, 33, 45, 52, 58, 56, 51, 39, 35, 59, 68, 73, and 82;

where said antigenic polypeptides include at least one sequence having at least 70% sequence identity to an Early protein from each of HPV31, 33, 45, 52, 58, 56, 51, 39, 35, 59, 68, 73, and 82; and wherein administration induces specific cell-mediated immunity against HPV16 and HPV18, and cross-reactive cell-mediated immunity against at least one of the additional HPV types that was not selected in step (c).

Preferably, the RNA construct(s) express antigenic polypeptides from both the E2 and E6 protein from said no more than six additional HPV types. Suitably, the RNA construct(s) express antigenic polypeptides from both the E2 and E6 proteins of HPV31, 33, 45, 52 and 58, wherein administration induces cross-reactive cell-mediated immunity against HPV35.

Suitably, the antigenic polypeptides are co-administered using one or more self-replicating RNA (or "SAM") constructs. In one embodiment, the infection of the human anogenital epithelium by a high-risk HPV type has resulted in lesions of the cervical epithelium, such as lesions identified as CIN1 or LSIL. In one embodiment, no antigenic polypeptides from HPV Late proteins are co-administered.

In another aspect, the invention provides a method of manufacturing an immunogenic composition comprising the steps of combining (i) one or more RNA construct(s), self-replicating RNA molecule(s), DNA molecule or vector(s) according to the invention with (ii) a non-viral delivery material, such as a submicron cationic oil-in-water emulsion; a liposome; or a biodegradable polymeric microparticle delivery system; wherein the one or more RNA construct(s), self-replicating RNA molecule(s), DNA molecule or vector(s) according to the invention (A) in physical contact with said non-viral delivery material or (B) packaged in a first container and said non-viral delivery material packaged in a second container.

RNA Constructs

RNA constructs according to the invention can take various forms (e.g. single-stranded, double-stranded, vectors etc.). RNA constructs may be circular or branched, but will preferably be linear.

The RNA constructs used herein are preferably provided in purified or substantially purified form i.e. substantially free from other nucleic acids (e.g. free from naturally-occurring nucleic acids), particularly from other viral or host cell nucleic acids, generally being at least about 50% pure (by weight), and usually at least about 90% pure.

RNA constructs may be prepared in many ways e.g. by chemical synthesis in whole or in part, by digesting longer nucleic acids using nucleases (e.g. restriction enzymes), by joining shorter nucleic acids or nucleotides (e.g. using ligases or polymerases), from genomic or cDNA libraries, etc.

The term "nucleic acid" in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. The RNA constructs of the present disclosure may or may not have a 5' cap.

The RNA constructs herein comprise an RNA sequence which encodes the antigenic HPV polypeptides as described herein. Typically, the RNA constructs of the invention will be in recombinant form, i. e. a form which does not occur in nature. For example, the nucleic acid may comprise one or more heterologous RNA sequences (e.g. a sequence encoding another antigen and/or a control sequence such as an internal ribosome entry site) in addition to the sequence encoding at least one HPV antigen or the HPV transgene. The RNA construct may be part of a vector i. e. part of a nucleic acid construct designed for transduction/transfection of one or more cell types. Vectors may be, for example, "expression vectors" which are designed for expression of a nucleotide sequence in a host cell, or "viral vectors" which are designed to result in the production of a recombinant virus or virus-like particle. In another embodiment, the RNA construct may be a messenger RNA.

Alternatively, or in addition, the sequence or chemical structure of the RNA constructs may be modified compared to a naturally-occurring sequence which encodes the antigenic HPV polypeptides. The sequence of the RNA constructs may be modified, e.g. to increase the efficacy of expression or replication of the RNA construct, or to provide additional stability or resistance to degradation.

The RNA construct encoding the antigenic HPV polypeptides described above may be codon optimized. By "codon optimized" is intended modification with respect to codon usage that may increase translation efficacy and/or half-life of the nucleic acid. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increases translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g. cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. The preparation of nucleotides and modified nucleotides and nucleosides are well-known in the art, see the following references: U.S. Pat. Nos. 4,373, 071, 4,458,066, 4,500,707, 4,668,777, 4,973,679, 5,047,524, 5,132,418, 5,153,319, 5,262,530, 5,700,642. Many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-0-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-0-ribosyladenosine (phosphate)); I (inosine); mil (1-methylinosine); m'1m (1,2'-0-dimethylinosine); m3C (3-methylcytidine); Cm (2T-0-methylcytidine); s2C (2-thiocytidine); ac4C (N4-acetylcytidine); £5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-0-methylguanosine); m22G (N2,N2-dimethylguanosine); m2Gm (N2,2'-0-dimethylguanosine); m22Gm (N2,N2,2'-0-trimethylguanosine); Gr(p) (2'-0-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-0-dimethyluridine); s4U (4-thiouridine); m5 s2U (5-methyl-2-thiouridine); s2Um (2-thio-2'-0-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (5-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyluridine); ncm5Um (5-carbamoylmethyl-2'-0-methyluridine); cmnm5U (5-carboxymethylaminomethyluridine); cnmm5Um (5-carboxymethy 1 aminomethyl-2-L-Omethyluridine); cmnm5s2U (5-carboxymethylaminomethyl-2-thiouridine); m62A (N6,N6-dimethyladenosine); Tm (2'-0-methylinosine); m4C (N4-methylcytidine); m4Cm (N4,2-0-dimethylcytidine); hm5C (5-hydroxymethylcytidine); m3U (3-methyluridine); cm5U (5-carboxymethyluridine); m6Am (N6,T-0-dimethyladenosine); m62Am (N6,N6,0-2-trimethyladenosine); m2'7G (N2,7-dimethylguanosine); m2'2'7G (N2,N2,7-trimethylguanosine); m3Um (3,2T-0-dimethyluridine); m5D (5-methyldihydrouridine); £5Cm (5-formyl-2'-0-methylcytidine); m1Gm (1,2'-0-dimethylguanosine); m'Am (1,2-O-dimethyl adenosine) irinomethyluridine); tm5s2U (S-taurinomethyl-2-thiouridine)); iniG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(Ci-Ce)-alkyluracil, 5-methyluracil, 5-(C2-C6)-alkenyluracil, 5-(C2-Ce)-alkynyluracil, 5-(hydroxymethyl)uracil, 5-chlorouracil, 5-fluorouracil, 5-bromouracil, 5-hydroxycytosine, 5-(Ci-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-0-methyl-U. Many of these modified nucleobases and their corresponding ribonucleosides are available from commercial suppliers.

Terms

As used herein, a "high-risk" HPV type (hrHPV type) is one where cervical infection with that type is known to be associated with high-grade cervical intraepithelial neoplasia or cancer. As used herein, hrHPV types are 16, 18, 31, 33, 35, 39, 45, 51, 52, 56, 58, 59, 68, 73, and 82, which have been identified in the scientific literature as high-risk. "Low-risk" HPV types are those where cervical infection with that type has not been associated with high-grade cervical intraepithelial neoplasia or cancer.

As used herein, the term "antigen" refers to a molecule containing one or more epitopes (e.g., linear, conformational or both) capable of stimulating a mammalian host's immune system to make a humoral and/or cellular antigen-specific immunological response (i.e. an immune response which specifically recognizes a naturally occurring polypeptide, e.g., a viral or bacterial protein). An "epitope" is that portion of an antigen that determines its immunological specificity. T- and B-cell epitopes can be identified empirically (e.g. using PEPSCAN or similar methods).

As used herein, an "HPV antigenic peptide" refers to a fragment of a naturally-occurring HPV protein of at least 10, 15, 20, 30, 40, 50, 60, 100, 200, 300 or more amino acids, or a peptide having an amino acid sequence of at least 85%, 90%, 95%, 97%, 98%, 99%, or 99.5% sequence identity to a naturally-occurring HPV protein (or to a fragment of a naturally-occurring HPV protein of at least about 10, 15, 20, 30, 40, 50, 60 or more amino acids). Thus an HPV antigenic peptide may be a fragment of a naturally occurring HPV protein, of at least 10 amino acids, and may comprise one or more amino acid substitutions, deletions or additions. "HPV antigenic peptides" are antigens as defined herein. Examples of full-length HPV16 E1, E2, E6 and E7 proteins are provided herein as SEQ ID NOs: 14, 15, 16 and 17, respectively. The amino acid sequences of Early proteins for additional HPV types are publicly available, e.g., via the GenBank™ genetic sequence database, National Center for Biotechnology Information (available at www(dot)ncbi.nlm.nih.gov/genbank/(see also Nucleic Acids Research, January 2013: 41(D1):D36-42)).

As used herein, the term "fragment" as applied to a protein or peptide refers to a subsequence of a larger protein or peptide. A "fragment" of a protein or peptide is at least about 10 amino acids in length (amino acids naturally occurring as consecutive amino acids; e.g., as for a single linear epitope); for example at least about 15, 20, 30, 40, 50, 60, 100, 200, 300 or more amino acids in length (and any integer value in between). Antigenic HPV polypeptides may comprise two or more fragments of an HPV protein linked together.

As used herein, a peptide "fusion construct" or a "fusion protein" refers to a polypeptide comprising amino acid sequences (full-length sequence or fragments) from at least two distinct proteins. Thus a fusion construct may contain two, three, or more sequences of the same protein from at least two HPV types (e.g., fragments of E6 protein from HPV 31 and HPV33), or sequences of different proteins from a single HPV type (e.g., fragments or full-length sequences of E1 and E7 proteins from HPV16). The sequences are typically covalently linked via a peptide bond, either directly or via an amino acid linker. The term may also refer to a protein comprising at least two sequences from distinct polypeptides that are linked non-covalently. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. The sequences in a peptide fusion construct may also contain amino acid substitutions, deletions or additions.

A peptide linker sequence may be employed to separate the polypeptide components of a fusion protein. Separation is by a distance sufficient to ensure that each polypeptide folds into functional secondary and tertiary structures. Such a peptide linker sequence is incorporated into the fusion protein using standard techniques known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46 (1985); Murphy et al., Proc. Natl. Acad. Sci. USA 83:8258-8262 (1986); U.S. Pat. Nos. 4,935,233 and 4,751,180. The linker sequence may generally be from 1 to about 50 amino acids in length for example 1, 5, 10, 15, 20, 25, 30, 35 or 40 amino acids in length. Linker sequences are not required when the first and second polypeptides have non-essential N-terminal amino acid regions that can be used to separate the functional domains and prevent steric interference.

An HPV E protein (e.g., E1, E2, E6, or E7) may vary in amino acid sequence between different HPV strains. For this reason the term 'equivalent amino acids,' or 'corresponding amino acids' refers to amino acids in a first sequence which correspond to those of an identified reference strain. A region of equivalent amino acids may be determined by aligning the amino acid sequences of the proteins from the different strains, using an alignment program such as BLAST® (available at blast.ncbi.nlm.nih.gov, last accessed 12 Sep. 2016).

As used herein, the terms "treat" and "treatment," as well as words stemming therefrom, are not meant to imply a "cure" of the condition being treated in all individuals, or 100% effective treatment in any given population. Rather, there are varying degrees of treatment which one of ordinary skill in the art recognizes as having beneficial therapeutic effect(s). In this respect, the inventive methods can provide any level of treatment of HPV-associated disease in a subject in need of such treatment, and may comprise elimination of an HPV infection, reduction in the severity or duration of one or more conditions or symptoms of HPV-associated disease, a delay in the progression of low-grade clinical disease (e.g., CIN1 or LSIL), or a reduction in the percentage of abnormal (dysplatic) cervical epithelial cells. The methods of the invention may simultaneously treat persistent cervical infection and low-grade HPV-related lesions, as infected cells may exist outside of identifiable lesions.

As used herein, "therapeutic immunization" or "therapeutic vaccination" refers to administration of the immunogenic compositions of the invention to a subject, preferably a human subject, who is known to be infected with HPV at the time of administration, to treat the HPV infection or HPV-related disease.

The terms polypeptide, peptide and protein are used interchangeably herein.

In one aspect, polynucleotides or polypeptides described herein are suitably isolated. An "isolated" polynucleotide or polypeptide is one that is removed from its original environment. An isolated antigenic HPV polypeptide is one that is removed from the HPV environment. An isolated antigenic HPV polypeptide 'from' a particular HPV protein is a polypeptide whose sequence aligns with a wild-type HPV sequence, optionally containing one, two, or more amino acid substitutions, deletions or insertions, such that the sequence of the isolated antigenic HPV polypeptide is at least 90%, 92%, 95%, 97%, 98%, 99% or 100% identical to the corresponding amino acids in the wild-type sequence. A polypeptide 'from' an HPV protein (or HPV type) does not mean the polypeptide has been removed from an intact protein (or HPV type), the polypeptide may be provided synthetically or recombinantly.

A naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

In one aspect, the polynucleotides described herein are suitably recombinant. Recombinant means that the polynucleotide is the product of at least one of cloning, restriction or ligation steps, or other procedures that result in a polynucleotide that is distinct from a polynucleotide found in nature. A recombinant vector is a vector comprising a recombinant polynucleotide. A 'recombinant virus' includes progeny of the original recombinant virus. A 'RNA vector' includes replicates of the original RNA vector. A 'recombinant polynucleotide' includes replicates of the original recombinant polynucleotide.

As used herein, a polynucleotide introduced by genetic engineering techniques into a plasmid or vector derived from a different species (or different genus, subfamily or family) is a heterologous polynucleotide. A promoter removed from its native coding sequence and operatively linked to a coding sequence with which it is not naturally found linked is a heterologous promoter. A specific recombination site that has been cloned into a genome of a virus or viral vector, wherein the genome of the virus does not naturally contain it, is a heterologous recombination site. A heterologous nucleic acid sequence also includes a sequence naturally found in a viral genome, but located at a non-native position within the viral vector.

Typically, "heterologous" means derived from a genotypically distinct entity from that of the rest of the entity to which it is being compared. With regard to viral vectors, a heterologous nucleic acid sequence refers to any nucleic acid sequence that is not isolated from, derived from, or based upon a naturally occurring nucleic acid sequence of the viral vector. "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

A "functional derivative" of a polypeptide suitably refers to a modified version of a polypeptide, e.g. wherein one or more amino acids of the polypeptide may be deleted, inserted, modified and/or substituted.

"Variant" as used herein, is a peptide sequence that differs in sequence from a reference peptide sequence, but retains essential properties of the reference molecule. Changes in the sequence of peptide variants are limited or conservative, so that the sequences of the reference peptide and the variant are closely similar overall and, in many regions, identical. A variant and reference peptide can differ in amino acid sequence by one or more substitutions, additions, deletions in any combination. A variant of a peptide can be naturally occurring such as an allelic variant, or can be a variant that is not known to occur naturally. Non-naturally occurring variants of nucleic acids and peptides may be made by mutagenesis techniques or by direct synthesis.

A "vector" is a replicon, such as plasmids, phagemids, cosmids, baculoviruses, bacmids, bacterial artificial chromosomes (BACs), yeast artificial chromosomes (YACs), as well as other bacterial, yeast and viral vectors, to which another nucleic acid segment may be operably inserted so as to bring about the replication or expression of the inserted segment. "Expression vector" refers to a vector comprising expression control sequences operatively linked to a nucleotide sequence to be expressed. An expression vector comprises sufficient cis-acting elements for expression; other elements for expression can be supplied by the host cell or in an in vitro expression system. Expression vectors include cosmids, plasmids, and viruses (e.g., lentiviruses, retroviruses, adenoviruses, and adeno-associated viruses) that incorporate or encode the RNA construct(s).

"Encoding" refers to the inherent property of specific sequences of nucleotides in a polynucleotide, to act as a template for synthesis of other polymers and macromolecules in biological processes, e.g., synthesis of peptides or proteins. Both the coding strand of a double-stranded nucleotide molecule (the sequence of which is usually provided in sequence listings), and the non-coding strand (used as the template for transcription of a gene or cDNA), can be referred to as encoding the peptide or protein. Unless otherwise specified, as used herein a "nucleotide sequence encoding an amino acid sequence" includes all nucleotide sequences that are degenerate versions of each other and that encode the same amino acid sequence.

The term "expression" or "expressing" as used herein is defined as the transcription and/or translation of a particular nucleotide sequence driven by its operably linked promoter.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example and is synonymous with the term "for example."

Amino acid sequences provided herein are designated by either single-letter or three-letter nomenclature, as is known in the art (see, e.g., Eur. J. Biochem. 138:9-37(1984)).

"Fusion protein" and "chimeric protein" are used interchangeably herein, and refer to a recombinant polypeptide sequence that comprises contiguous sequences from two separate proteins, i.e., two proteins encoded by different genes.

To facilitate review of the various embodiments of this disclosure, the preceeding explanations of terms are provided. Additional terms and explanations are provided in the context of this disclosure.

Sequence Comparison

For the purposes of comparing two closely-related polynucleotide or polypeptide sequences, the "sequence identity" or "% identity" between a first sequence and a second sequence may be calculated using an alignment program, such as BLAST® (available at blast.ncbi.nlm.nih.gov, last accessed 12 Sep. 2016) using standard settings. The percentage identity is the number of identical residues divided by the length of the alignment, multiplied by 100. An alternative definition of identity is the number of identical residues divided by the number of aligned residues, multiplied by 100. Alternative methods include using a gapped method in which gaps in the alignment, for example deletions in one sequence relative to the other sequence, are considered.

Sequences that preserve the functionality of the polynucleotide or a polypeptide encoded thereby are likely to be more closely identical. Polypeptide or polynucleotide sequences are said to be identical to other polypeptide or polynucleotide sequences, if they share 100% sequence identity over their entire length.

A "difference" between two sequences refers to an insertion, deletion or substitution, e.g., of a single amino acid residue in a position of one sequence, compared to the other sequence.

For the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

Suitably substitutions in the sequences of the present invention may be conservative substitutions. A conservative substitution comprises the substitution of an amino acid with another amino acid having a physic-chemical property similar to the amino acid that is substituted (see, for example, Stryer et al, *Biochemistry*, 5th Edition 2002, pages 44-49). Preferably, the conservative substitution is a substitution selected from the group consisting of: (i) a substitution of a basic amino acid with another, different basic amino acid; (ii) a substitution of an acidic amino acid with another, different acidic amino acid; (iii) a substitution of an aromatic amino acid with another, different aromatic amino acid; (iv) a substitution of a non-polar, aliphatic amino acid with another, different non-polar, aliphatic amino acid; and (v) a substitution of a polar, uncharged amino acid with another, different polar, uncharged amino acid. A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

Transgenes

The present inventors disclose compositions comprising RNA construct(s) which encode antigenic HPV polypeptides as described herein. Such compositions may be a nucleic acid-based vaccine. The part of the RNA construct encoding the antigenic HPV polypeptides is also referred to as transgene and further defined herein.

The "transgene" is a nucleic acid sequence, heterologous to the vector sequences flanking the transgene, which encodes protein(s) or peptide(s) of interest (i.e. "transgene product"), including, e.g. a protein having a therapeutic effect when delivered to a subject in need of treatment. The transgene nucleic acid coding sequence is operatively linked to regulatory components in a manner which permits transgenetranslation, and/or expression in a host cell. HPV transgenes as disclosed herein may be used for induction of an immune response in order to treat HPV-related disease (a therapeutic vaccine), such as low-grade HPV lesions, in particular infections and lesions of human anogenital tissue such as cervical epithelia. As used herein, induction of an immune response refers to the ability of a protein to induce a T cell and/or a humoral immune response to the protein.

The transgene sequences of the present invention are designed to encode multiple antigenic HPV polypeptide sequences (or to encode one or polypeptides comprising multiple linked antigenic HPV peptide sequences). The antigenic HPV peptide(s) comprise fragment(s) of HPV Early proteins from fewer than all of the hrHPV types (as defined herein), where the antigenic HPV peptides are selected or designed to include sequences that are conserved across multiple high-risk HPV types, and to include CD8 and/or CD4 T-cell epitopes. Such sequences increase the ability of the transgene to induce cross-reactive or immune response to multiple hrHPV types when administered to a mammalian subject such as a human, including inducing immune responses to 'additional' hrHPV types (i.e., those hrHPV types that are not represented in the transgene).

Cross-reactivity to additional hrHPV types is obtained by: analyzing the sequence of an HPV early protein from a first hrHPV type and selecting regions (e.g., fragments) of that protein with high levels of identity and/or similarity across multiple hrHPV types (see eg. Table 1 herein). This process may be repeated for additional early proteins from the first hrHPV type, and repeated for HPV early proteins from a second, third, fourth, fifth, sixth, seventh and/or eighth hrHPV type (selected' HPV types). The vaccine RNA constructs of the present invention are designed to provide a group of antigenic polypeptides that include polypeptides having at least about 60% sequence similarity, at least about 70% sequence identity, at least about 75% sequence identity, at least about 80% or higher sequence identity to corresponding early proteins from additional (non-selected) hrHPV types.

The amino acid sequences of full-length HPV16 E1, E2, E6 and E7 proteins are provided herein as SEQ ID NOs: 14, 15, 16 and 17, respectively. The amino acid sequences of Early proteins for additional HPV types are publicly available, e.g., via the GenBank™ genetic sequence database, National Center for Biotechnology Information (available at www(dot)ncbi.nlm.nih.gov/genbank/(see also Nucleic Acids Research, January 2013: 41(D1):D36-42)).

Stated another way, the method of the present invention comprises administration of one or more RNA construct(s) (eg. co-administration of two or more RNA constructs) expressing antigenic polypeptides from two or more HPV Early proteins, from fewer than all fifteen hrHPV types (i.e., from a selected subset of the fifteen hrHPV types identified herein), such that the expressed polypeptides include polypeptides having at least about 70% identity with the corresponding region of the Early proteins of at least one additional (i.e., non-selected) hrHPV type. The RNA construct(s) used in the present invention may further express antigenic polypeptides from a third and optionally a fourth HPV Early protein of the selected hrHPV types, to provide polypeptides having at least about 70% identity with the corresponding region of the third and optionally fourth Early protein of at least one additional (non-selected) hrHPV type. In a preferred embodiment, the one or more RNA construct(s) express antigenic polypeptides from HPV E1, E2 and E6 from fewer than all fifteen hrHPV types such that the expressed polypeptides include polypeptides having at least about 70% identity with the corresponding region of HPV E1, E2 and E6 of at least one additional (i.e., non-selected) hrHPV type. More preferably, the RNA construct(s) express antigenic polypeptides from HPV E7 from fewer than all fifteen hrHPV types such that the expressed polypeptides include polypeptides having at least about 70% identity with the corresponding region of HPV E7 of at least one additional (i.e., non-selected) hrHPV type.

In one embodiment, the method of the present invention comprises administration of one or more RNA construct(s) (eg. co-administration of two, three or more RNA constructs) that express (a) antigenic polypeptides from each of E1, E2 and E6 of HPV16 and HPV18, and (b) additional antigenic polypeptides from E1, E2 and/or E6 from an additional one, two, three, four, five or six hrHPV types; such that for each of the fifteen hrHPV types identified herein, at least one antigenic polypeptide is administered that has at least 70% sequence identity to at least one of the hrHPV E1, E2 or E6 proteins.

In one embodiment, the method of the present invention comprises administration of one or more RNA construct(s) (eg. co-administration of two, three or more RNA constructs) that express (a) antigenic polypeptides from each of E1, E2, E6 and E7 of HPV16 and HPV18, and (b) additional antigenic polypeptides from E1, E2, E6 and/or E7 from an additional one, two, three, four, five or six hrHPV types; such that for each of the fifteen hrHPV types identified herein, at least one antigenic polypeptide is administered that has at least 70% sequence identity to at least one of the hrHPV E1, E2, E6 or E7 proteins.

In a further embodiment, the method of the present invention comprises administration of one or more RNA construct(s) (eg. co-administration of two, three or more RNA constructs) that express (a) antigenic polypeptides from each of E1, E2 and E6 of HPV16 and HPV18, and (b) additional antigenic polypeptides from E1, E2 and/or E6 from HPV31, 33, 45, 52 and 58; such that antigenic polypeptides having at least about 70% similarity to at least two of the E1, E2 and E6 early proteins from each of HPV16, 18, 31, 33, 45, 52 and 58 are administered. In one embodiment, no E1 antigenic polypeptides from HPV31, 33, 45, 52 and 58 are administered.

In a further embodiment, the method of the present invention comprises administration of one or more RNA construct(s) (eg. co-administration of two, three or more RNA constructs) that express (a) antigenic polypeptides from each of E1, E2, E6 and E7 of HPV16 and HPV18, and (b) additional antigenic polypeptides from E1, E2, E6 and/or E7 from HPV31, 33, 45, 52 and 58; such that antigenic polypeptides having at least about 70% similarity to at least two of the E1, E2, E6 and E7 early proteins from each of HPV16, 18, 31, 33, 45, 52 and 58 are administered. In one embodiment, no E7 antigenic polypeptides from HPV31, 33, 45, 52 and 58 are administered. In one embodiment, no E1 antigenic polypeptides from HPV31, 33, 45, 52 and 58 and no E7 antigenic polypeptides from HPV31, 33, 45, 52 and 58 are administered.

An antigenic HPV polypeptide from a specific Early protein, from a specific HPV type, as utilized in the present invention, may include two non-contiguous amino acid sequences from that Early protein, linked either directly or via a short (e.g., ten or fewer amino acids) peptide linker. Additionally, an antigenic HPV polypeptide may contain one, two, three, or more amino acid substitutions (compared to the wild-type sequence), e.g., to eliminate or alter the activity of the expressed polypeptides. In one embodiment, an antigenic HPV polypeptide contains a single amino acid substitution. In another embodiment, an antigenic HPV polypeptide contains two amino acid substitutions.

Antigenic HPV polypeptides utilized in the present methods are preferably selected to contain at least one CD8 or CD4 T-cell epitope. Epitopes may be those identified theoretically or empirically.

In one aspect of the present invention, the transgene of the RNA construct(s) encodes at least one antigenic peptide from the E2 and E6 proteins of at least two high-risk HPV types. In one embodiment, the transgene encodes at least one antigenic peptide from each of HPV16 E2 and E6, and at least one antigenic peptide from each of HPV18 E2 and E6.

In a further embodiment, the transgene additionally encodes at least one antigenic HPV peptide from E1 and/or E7 of HPV16 and/or HPV18. In a further embodiment, the transgene additionally encodes at least one antigenic peptide from the E2 and E6 proteins of an additional hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from the E2 and E6 proteins of at least two high-risk HPV types. In one embodiment, the transgene encodes at least one antigenic peptide from each of HPV16 E2 and E6 proteins, and at least one antigenic peptide from each of HPV18 E2 and E6 proteins; in a further embodiment, the transgene additionally encodes at least one antigenic HPV peptide from the E2 protein and/or at least one antigenic HPV peptide from the E6 protein, of another hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from the E1 and E7 proteins of at least two high-risk HPV types. In one embodiment, the transgene encodes at least one antigenic peptide from each of HPV16 E1 and E7 proteins, and at least one antigenic peptide from each of HPV18 E1 and E7 proteins; in a further embodiment, the transgene additionally encodes at least one antigenic HPV peptide from the E1 protein, and/or at least one antigenic HPV peptide from the E7 protein, of another hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from the E1 and E2 proteins of at least two high-risk HPV types. In one embodiment, the transgene encodes at least one antigenic peptide from each of HPV16 E1 and E2 proteins, and at least one antigenic peptide from each of HPV18 E1 and E2 proteins; in a further embodiment, the transgene additionally encodes at least one antigenic HPV peptide from the E1 protein, and/or at least one antigenic HPV peptide from the E2 protein, of another hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from the E1 and E6 proteins of at least two high-risk HPV types. In one embodiment, the transgene encodes at least one antigenic peptide from each of HPV16 E1 and E6 proteins, and at least one antigenic peptide from each of HPV18 E1 and E6 proteins; in a further embodiment, the transgene additionally encodes at least one antigenic HPV peptide from the E1 protein, and/or at least one antigenic HPV peptide from the E6 protein, of another hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from the E2 and E7 proteins of at least two high-risk HPV types. In one embodiment, the transgene encodes at least one antigenic peptide from each of HPV16 E2 and E7 proteins, and at least one antigenic peptide from each of HPV18 E2 and E7 proteins; in a further embodiment, the transgene additionally encodes at least one antigenic HPV peptide from the E2 protein, and/or at least one antigenic HPV peptide from the E7 protein, of another hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from the E6 and E7 proteins of at least two high-risk HPV types. In one embodiment, the transgene encodes at least one antigenic peptide from each of HPV16 E6 and E7 proteins, and at least one antigenic peptide from each of HPV18 E6 and E7 proteins; in a further embodiment, the transgene additionally encodes at least one antigenic HPV peptide from the E6 protein, and/or at least one antigenic HPV peptide from the E7 protein, of another hrHPV type (e.g., HPV31, 33, 35, 39, 45, 51, 52, 56, 58, 59, 68, 73, or 82).

In another aspect of the present invention, the transgene of the RNA construct(s) encodes at least one antigenic peptide from each of E1, E2 and E6 proteins of at least two high-risk HPV types. In one embodiment, the transgene encodes at least one antigenic peptide from HPV16 E1, E2 and E6 proteins, and at least one antigenic peptide from each of HPV18 E1, E2 and E6 proteins. In a further embodiment, the transgene additionally encodes at least one antigenic HPV peptide from the E1, E2 or E6 proteins of another hrHPV type (e.g., HPV31, 33, 35, 39, 45, 51, 52, 56, 58, 59, 68, 73, or 82).

In another aspect of the present invention, the transgene of the RNA construct(s)encodes at least one antigenic peptide from any three of the E1, E2, E6 and E7 proteins of at least two high-risk HPV types. In one embodiment, the transgene encodes at least one antigenic peptide from any three of HPV16 E1, E2, E6 and E7 proteins, and at least one antigenic peptide from each of HPV18 E1, E2, E6 and E7 proteins; in a further embodiment, the transgene additionally encodes at least one antigenic HPV peptide from the E1, E2, E6 or E7 proteins of another hrHPV type (e.g., HPV31, 33, 35, 39, 45, 51, 52, 56, 58, 59, 68, 73, or 82).

In one embodiment the transgene of the RNA construct(s) encodes E1 antigenic peptide(s) comprising or consisting of one or more sequences selected from amino acids 14-90, aa203-622, aa211-622 (amino acid numbering corresponds to HPV16 E1, SEQ ID NO:14). The E1 fragment may comprise a Glycine to Aspartic acid substitution at amino acid residue 482 (G482D; numbering corresponds to SEQ ID NO:14). Where two E1 polypeptide sequences are used that are non-contiguous in the naturally occurring protein ('non-contiguous fragments'), they may be joined directly, joined via a peptide or non-peptide linker, or the transgene may be constructed so that the E1 fragments are expressed as separate peptides.

In one embodiment the transgene of the RNA construct(s) encodes E2 antigenic peptide(s) comprising or consisting of one or more sequences selected from amino acids 1-138, aa1-201, aa150-210, aa260-365, and aa285-365 (amino acid numbering corresponds to HPV16 E2, SEQ ID NO:15). Where the transgene encodes an E2 antigenic peptide comprising the TAD, and an E2 antigenic peptide comprising the DBD, a peptide or non-peptide linker may be placed between the TAD and DBD peptides (e.g., a peptide linker consisting of GGTGGS, SEQ ID NO:38). The E2 antigenic peptide may contain a Lysine to Alanine substitution at amino acid residue 111 (K111A, numbering corresponds to HPV16E2, SEQ ID NO:15). Where non-contiguous E2 fragments are used, they may be joined directly, joined via a peptide or non-peptide linker, or the transgene may be constructed so that the E2 fragments are expressed as separate peptides.

In one embodiment the transgene of the RNA construct(s) encodes E6 antigenic peptide(s) comprising or consisting of a sequence selected from amino acids 8-147 and aa11-150 (numbering corresponds to HPV16 E6, SEQ ID NO:16). The E6 antigenic peptide may contain a phenylalanine to arginine substitution at amino acid residue 54 (F54R) and/or a cysteine to arginine substitution at amino acid residue 110 (C110R); numbering corresponds to to HPV16 E6, SEQ ID NO:16.

In one embodiment the transgene of the RNA construct(s) encodes E7 antigenic peptide(s) comprising or consisting of one or more sequences selected from amino acids 49-98 and aa7-28 (amino acid numbering corresponds to HPV16 E7, SEQ ID NO:17). When the transgene contains a fragment comprising aa49-98 and a fragment comprising aa7-28 of E7, fragment aa49-98 may be placed N-terminal to aa7-28. The E7 antigenic peptide may contain a cysteine to glycine substitution at amino acid residue 24 (C24G), and/or a glutamic acid to glutamine substitution at residue 26 (E26Q); numbering corresponds to HPV16 E7, SEQ ID NO:17.

In one embodiment, the transgene comprises nucleotide sequence(s) encoding one or more HPV E1 sequences that are at least 90%, 92%, 95%, 97%, 98%, 99% or 100% identical to a sequence selected from SEQ ID NO:18 and SEQ ID NO:19. In one embodiment the transgene comprises nucleotide sequence(s) encoding one or more HPV E2 sequences that are at least 90%, 92%, 95%, 97%, 98%, 99% or 100% identical to a sequence selected from SEQ ID NO:20, SEQ ID NO:21, SEQ ID NO:22, SEQ ID NO:23, SEQ ID NO:24, SEQ ID NO:25 and SEQ ID NO:26. In one embodiment the transgene comprises nucleotide sequence(s) encoding one or more HPV E6 sequences that are at least 90%, 92%, 95%, 97%, 98%, 99% or 100% identical to a sequence selected from SEQ ID NO:27, SEQ ID NO:28 SEQ ID NO:29, SEQ ID NO:30, SEQ ID NO:31, SEQ ID NO:32 and SEQ ID NO:33. In one embodiment the transgene comprises nucleotide sequence(s) encoding one or more HPV E7 sequences that are at least 90%, 92%, 95%, 97%, 98%, 99% or 100% identical to a sequence selected from SEQ ID NO:34 and SEQ ID NO:35.

Any of the encoded HPV antigenic fragments may additionally comprise an initial methionine residue where required.

In the transgene constructs of the present invention, the nucleic acid sequences coding for HPV antigenic peptides may be separated by a peptide or non-peptide linker, or a sequence such as a ribosomal skipping sequence that interrupts translation of the transgene and results in expression of multiple peptides.

In one embodiment of the present invention, the transgene comprises or consists of a nucleotide sequence encoding an amino acid sequence that is at least 90%, 92%, 95%, 97%, 98%, 99% or 100% identical to a sequence selected from SEQ ID NO:2, SEQ ID NO:4 and SEQ ID NO:6.

In one embodiment of the present invention, the transgene comprises or consists of a nucleotide sequence that is at least 90%, 92%, 95%, 97%, 98%, 99% or 100% identical to a sequence selected from SEQ ID NO:3, SEQ ID NO:5 and SEQ ID NO:7.

In one embodiment of the present invention, the transgene does not comprise a nucleotide sequence encoding an antigenic fragment of an HPV Late protein. In another embodiment, the transgene does not comprise a nucleotide sequence encoding an antigenic fragment of an Early protein from a non-high risk HPV type.

Accordingly, in one embodiment, a transgene comprising nucleic acid sequences encoding HPV E1, E2, E6 and/or E7 antigenic peptides, from multiple hrHPV types, is incorporated into one or more RNA construct(s), such as one or more self-replicating RNA (or 'SAM') construct(s).

The sequences of the invention may be produced by any suitable means, including recombinant production, chemical synthesis, or other synthetic means. Suitable production techniques are well known to those of skill in the art. Alternatively, peptides can also be synthesized by well known solid phase peptide synthesis methods.

Self-Replicating RNA (or "SAM")

In certain embodiments, the RNA-based vaccine comprises a self-replicating RNA molecule. The self-replicating RNA molecule may be an alphavirus-derived RNA replicon.

Self-replicating RNA (or "SAM") molecules are well known in the art and can be produced by using replication elements derived from, e.g., alphaviruses, and substituting the structural viral proteins with a nucleotide sequence encoding a protein of interest. A self-replicating RNA molecule is typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded polypeptide (i.e. comprising HPV antigens), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are +-stranded RNAs which lead to translation of a replicase (or replicase-transcriptase) after delivery to a cell. The replicase is translated as a polyprotein which auto-cleaves to provide a replication complex which creates genomic-strand copies of the +-strand delivered RNA. These --strand transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons, see the following reference: WO2005/113782.

In certain embodiments, the self-replicating RNA molecule described herein encodes (i) a RNA-dependent RNA polymerase which can transcribe RNA from the self-replicating RNA molecule and (ii) a HPV antigen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, in certain embodiments, the self-replicating RNA molecules do not encode alphavirus structural proteins. Thus, the self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the present disclosure and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an antigen. In some embodiments the RNA may have additional (e.g. downstream) open reading frames e.g. to encode further antigens or to encode accessory polypeptides.

In certain embodiments, the self-replicating RNA molecule disclosed herein has a 5' cap (e.g. a 7-methylguanosine). This cap can enhance in vivo translation of the RNA. In some embodiments the 5' sequence of the self-replicating RNA molecule must be selected to ensure compatibility with the encoded replicase.

A self-replicating RNA molecule may have a 3' poly-A tail. It may also include a poly-A polymerase recognition sequence (e.g. AAUAAA) near its 3' end.

Self-replicating RNA molecules can have various lengths but they are typically 5000-25000 nucleotides long. Self-replicating RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-replicating RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the self-replicating RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

A self-replicating RNA can include (in addition to any 5' cap structure) one or more nucleotides having a modified nucleobase. A RNA used with the invention ideally includes only phosphodiester linkages between nucleosides, but in some embodiments it can contain phosphoramidate, phosphorothioate, and/or methylphosphonate linkages.

The self-replicating RNA molecule may encode a single heterologous polypeptide antigen or two or more heterologous antigens linked together in a way that each of the sequences retains its identity (e.g. HPV antigens) when expressed as an amino acid sequence. The heterologous polypeptides generated from the self-replicating RNA may then be produced as a fusion polypeptide or engineered in such a manner to result in separate polypeptide or peptide sequences.

The self-replicating RNA molecules described herein may be engineered to express multiple nucleotide sequences or transgenes, from two or more open reading frames, thereby allowing co-expression of proteins, such as one, two or more HPV antigens (e.g. one, two, three, four or five HPV antigen) together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes HPV antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode one or more HPV antigenic polypeptides can also be tested for ability to induce humoral immune responses, as evidenced, for example, by induction of B cell production of antibodies specific for an HPV antigen of interest. These assays can be conducted using, for example, peripheral B lymphocytes from immunized individuals. Such assay methods are known to those of skill in the art. Other assays that can be used to characterize the self-replicating RNA molecules can involve detecting expression of the encoded HPV antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

In some embodiments, the self-replicating RNA molecules comprise a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:9, SEQ ID NO:11 or SEQ ID NO:13. In some embodiments, the self-replicating RNA molecule comprises a fragment of a full-length sequence selected from the group consisting of SEQ ID NO:9, SEQ ID NO:11 or SEQ ID NO:13 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence.

In some embodiments, a DNA sequence encoding a self-replicating RNA molecule is provided, such as a DNA sequence encoding a self-replicating RNA molecule comprises a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:8, SEQ ID NO:10 or SEQ ID NO:12. In some embodiments, the DNA sequence encoding a self-replicating RNA molecule comprises a fragment of a full-length sequence selected from the group consisting of SEQ ID NO:8, SEQ ID NO:10 or SEQ ID NO:12 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence.

The nucleic acid-based composition comprising the RNA-based constructs may comprise a viral or a non-viral delivery system. The delivery system (also referred to herein as a delivery vehicle) may have adjuvant effects which enhance the immunogenicity of the encoded HPV antigen. For example, the nucleic acid molecule may be encapsulated in liposomes, non-toxic biodegradable polymeric microparticles or viral replicon particles (VRPs), or complexed with particles of a cationic oil-in-water emulsion. In some embodiments, the nucleic acid-based vaccine comprises a cationic nano-emulsion (CNE) delivery system or a lipid nanoparticle (LNP) delivery system. In some embodiments, the nucleic acid-based vaccine comprises a non-viral delivery system, i.e., the nucleic acid-based vaccine is substantially free of viral capsid. Alternatively, the nucleic acid-based vaccine may comprise viral replicon particles. In other embodiments, the nucleic acid-based vaccine may comprise a naked nucleic acid, such as naked RNA (e.g. mRNA), but delivery via CNEs or LNPs is preferred.

In certain embodiments, the nucleic acid-based vaccine comprises a cationic nano-emulsion (CNE) delivery system. CNE delivery systems and methods for their preparation are described in the following reference: WO2012/006380. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in the following references: WO2012/006380; WO2013/006834; and WO2013/006837 (the contents of each of which are incorporated herein in their entirety).

Thus, in a nucleic acid-based vaccine of the invention, an RNA molecule encoding a HPV antigenic polypeptides may be complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio) propane (DOTAP). In some preferred embodiments, the delivery system is a non viral delivery system, such as CNE, and the nucleic acid-based vaccine comprises a self-replicating RNA (mRNA). This may be particularly effective in eliciting humoral and cellular immune responses. Advantages also include the absence of a limiting anti-vector immune response and a lack of risk of genomic integration.

LNP delivery systems and non-toxic biodegradable polymeric microparticles, and methods for their preparation are described in the following references: WO2012/006376 (LNP and microparticle delivery systems); Geall et al. (2012) PNAS USA. September 4; 109(36): 14604-9 (LNP delivery system); and WO2012/006359 (microparticle delivery systems). LNPs are non-virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example; DSPC (zwitterionic, saturated), DlinDMA (cationic, unsaturated), and/or DMG (anionic, saturated). Preferred LNPs for use with the invention include an amphiphilic lipid which can form liposomes, optionally in combination with at least one cationic lipid (such as DOTAP, DSDMA, DODMA, DLinDMA, DLenDMA, etc.). A mixture of DSPC, DlinDMA, PEG-DMG and cholesterol is particularly effective. Other useful LNPs are described in the following references: WO2012/006376; WO2012/030901; WO2012/031046; WO2012/031043; WO2012/006378; WO2011/076807; WO2013/033563; WO2013/006825; WO2014/136086; WO2015/095340; WO2015/095346; WO2016/037053. In some embodiments, the LNPs are RV01 liposomes, see the following references: WO2012/006376 and Geall et al. (2012) PNAS USA. September 4; 109(36): 14604-9.

Pharmaceutical Compositions; Immunogenic Compositions

The disclosure provides compositions comprising one or more RNA constructs encoding antigenic HPV polypeptides as described herein. The composition may be a pharmaceutical composition, e.g., an immunogenic composition or a vaccine composition. Accordingly, the composition may also comprise a pharmaceutically acceptable carrier.

A "pharmaceutically acceptable carrier" includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

Pharmaceutical compositions may include the constructs, nucleic acid sequences, and/or polypeptide sequences described elsewhere herein in plain water (e.g. "w.f.i.") or in a buffer e.g. a phosphate buffer, a Tris buffer, a borate buffer, a succinate buffer, a histidine buffer, or a citrate buffer. Buffer salts will typically be included in the 5-20 mM range. Pharmaceutical compositions may have a pH between 5.0 and 9.5 e.g. between 6.0 and 8.0. Compositions may include sodium salts (e.g. sodium chloride) to give tonicity. A concentration of 10±2 mg/mL NaCl is typical, e.g. about 9 mg/mL. Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 µM e.g. 0.1 mM. A citrate salt, such as sodium citrate, can also act as a chelator, while advantageously also providing buffering activity. Pharmaceutical compositions may have an osmolality of between 200 mOsm/kg and 400 mOsm/kg, e.g. between 240-360 mOsm/kg, or between 290-310 mOsm/kg. Pharmaceutical compositions may include one or more preservatives, such as thiomersal or 2-phenoxyethanol. Mercury-free compositions are preferred, and preservative-free vaccines can be prepared. Pharmaceutical compositions may be aseptic or sterile. Pharmaceutical compositions may be non-pyrogenic e.g. containing <1 EU (endotoxin unit, a standard measure) per dose, and preferably <0.1 EU per dose. Pharmaceutical compositions may be gluten free. Pharmaceutical compositions may be prepared in unit dose form. In some embodiments a unit dose may have a volume of between 0.1-1.0 mL e.g. about 0.5 mL.

In some embodiments, the compositions disclosed herein are immunogenic composition that, when administered to a subject, induce a humoral and/or cellular antigen-specific immune response (i.e. an immune response which specifically recognizes a naturally occurring HPV polypeptide). For example, an immunogenic composition may induce a memory T and/or B cell population relative to an untreated subject following HPV infection, particularly in those embodiments where the composition comprises a nucleic acid comprising a sequence which encodes HPV antigen or comprises HPV antigen. In some embodiments, the subject is a vertebrate, such as a mammal e.g. a human or a veterinary mammal.

The compositions of the invention can be formulated as vaccine compositions. The vaccine will comprise an immunologically effective amount of antigen. By "an immunologically effective amount" is intended that the administration of that amount to a subject, either in a single dose or as part of a series, is effective for inducing a measurable immune response against HPV in the subject. This amount varies depending upon the health and physical condition of the individual to be treated, age, the taxonomic group of individual to be treated (e.g. human, non-human primate, etc.), the capacity of the individual's immune system to synthesize antibodies, the degree of protection desired, the formulation of the composition or vaccine, the treating doctor's assessment of the medical situation, the severity of the disease, the potency of the compound administered, the mode of administration, and other relevant factors. It is expected that the amount will fall in a relatively broad range that can be determined through routine trials. Vaccines as disclosed herein may either be prophylactic (i.e. to prevent infection) or therapeutic (i.e. to treat infection), but will typically be therapeutic. In some embodiments, the vaccine compositions disclosed herein may induce an effective immune response against an HPV infection, i.e., a response sufficient for treatment or prevention of HPV infection, such as recurrent HPV. Further uses of immunogenic compositions or vaccines comprising the nucleic acid constructs as described herein are provided herein below.

A composition of the present disclosure may also comprise, or be administered in conjunction with, one or more adjuvants (e.g. vaccine adjuvants), in particular where the composition comprises an immunologically effective amount of a nucleic acid encoding a HPV antigen. By adjuvant is intended that is capable of increasing an immune response against an antigen compared to administration of said antigen alone. In some aspects, adjuvant compositions as disclosed herein further comprise one or more immunostimulants, for example, a saponin such as QS21.

Adjuvants which may be used in compositions of the invention include, but are not limited to: (A) Mineral-containing compositions, for example aluminum and calcium salts, such as aluminum phosphates. (B) Oil emulsions, for example squalene-in-water emulsions, such as MF59 or AS03. Complete Freund's adjuvant (CFA) and incomplete Freund's adjuvant (IF A) may also be used. (C) Saponin formulations. (D) Virosomes and virus-like particles (VLPs). (E) Bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof (F) Human immunomodulators, for example cytokines, such as interleukins, interferons, macrophage colony stimulating factor, and tumor necrosis factor. (G) Bioadhesives and mucoadhesives, such as esterified hyaluronic acid microspheres, cross-linked derivatives of poly(acrylic acid), polyvinyl alcohol, polyvinyl pyrollidone, polysaccharides and carboxymethylcellulose. (H) Microparticles, for example particles of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB). (I) Liposomes. (J) Polyoxyethylene ether and polyoxyethylene ester formulations. (K) Polyphosphazene (PCPP). (L) Muramyl peptides. (M) Imidazoquinolone compounds, for example Imiquamod and its homologues.

Combinations of one or more of the adjuvants identified above may also be used with the invention.

Therapeutic RNA Vaccine Constructs

Because of the diversity of HPV types that can establish infection and result in LSIL/CIN1 in humans, the RNA based vaccine constructs of the present invention are designed express antigenic Early HPV proteins and/or peptides that induce or boost CD8+ T cells that are reactive to multiple HPV types. Suitably, the antigenic HPV polypeptides also induce a CD4+ T-cell response. The antigenic proteins are selected to induce an immune reaction to specific HPV types; the targeted HPV types are selected based on HPV protein expression patterns and the prevalence of HPV types in human infection, LSIL and CIN1. Accordingly, the vaccine constructs of the present invention are useful in treating a range of HPV-related disease, including persistent HPV infection, LSIL and/or CIN1.

Thus, the present invention provides RNA construct(s), such as SAM construct(s), comprising a transgene capable of expressing immunogenic peptide(s) derived from HPV proteins. Suitable transgenes are described herein.

In one embodiment, the recombinant RNA constructs of the present invention are designed for use in a therapeutic vaccination program as described herein (see Methods of Use) to treat e.g., HPV infection, LSIL, and/or CIN1, in a human subject in need of treatment thereof. In one embodiment, the RNA construct(s) comprise a transgene expressing antigenic peptide fragments from hrHPV early proteins, selected from certain high-risk HPV types, where the peptides are selected or designed to provide cross-reactivity to additional high-risk HPV types.

In one embodiment the recombinant RNA construct(s) of the present invention comprise a transgene encoding antigenic peptide(s) of HPV E1, E2, E6 and/or E7 polypeptides from hrHPV types. In another embodiment of the present invention, the nucleotide sequence is capable of expressing HPV E2 and E6 antigenic peptides from hrHPV types; in another embodiment the nucleotide sequence is capable of expressing E1 and E7 antigenic peptides from hrHPV types. In another embodiment the nucleotide sequence is capable of expressing antigenic peptides from any two, three or four of HPV E1, E2, E6, and E7 proteins, where the proteins are from hrHPV types.

More specifically, in one embodiment the present invention provides RNA construct(s) wherein a first RNA construct expresses antigenic peptides from E1 of hrHPV types 16 and 18 and antigenic peptides from E6 proteins of hrHPV types 16, 18, 31, 33, 45, 52 and 58;

a second RNA construct expresses antigenic peptides from E2 of hrHPV types 16, 18, 31 and 33; and a third RNA construct expresses antigenic peptides from E7 of hrHPV types 16 and 18 and antigenic peptides from E2 proteins of hrHPV types 45, 52 and 58.

The transgene may further comprises a peptide or non-peptide linker located between adjacent HPV sequences, or a sequence that induces separate translation of the adjacent HPV sequences (such as the 2A ribosomal skipping sequence described herein).

Methods of Use

The RNA constructs of the present invention are useful as therapeutic vaccines, to treat persistent HPV infection or subclinical HPV infection of the human anogenital epithelium, such as cervical epithelium, or HPV-related conditions such as CIN1 or LSIL, in a subject in need of such treatment. Suitable subjects include humans.

In treating human subjects, a self-replicating RNA molecule provides an efficient delivery vehicle that can deliver a selected transgene to a selected host cell in vivo. In one embodiment, the nucleic acid-based constructs and the cells are mixed ex vivo; the transfected cells are cultured using conventional methodologies; and the transduced cells are re-introduced into the patient. These techniques are suited to transgene delivery for therapeutic purposes and for immunization.

The RNA constructs comprising HPV transgenes may be administered in immunogenic compositions. An immunogenic composition as described herein is a composition comprising one or more RNA constructs capable of inducing an immune response, for example a humoral (e.g., antibody) and/or cell-mediated (e.g., a cytotoxic T cell) response(s), against a transgene product delivered by the RNA construct(s) following delivery to a mammal, suitably a human. RNA constructs comprising transgenes encoding selected hrHPV antigenic peptide(s), as described herein, are therefore suitable for use in a therapeutic vaccine to treat HPV infection or HPV-related disease.

Accordingly, in one embodiment the present invention provides RNA constructs, such as SAM constructs, for use in the treatment HPV infection or HPV-related disease, including HPV-related lesions staged or diagnosed as CIN1 or LSIL.

In further embodiments, the present invention provides the use of one or more RNA construct(s) according to the present invention in the manufacture of a medicament for the generation of an immune response against HPV. Thus, the present invention provides the use of one or more RNA construct(s) comprising an expression cassette comprising a transgene encoding immunogenic peptides derived from hrHPV, as described herein, in the manufacture of a medicament for the treatment of HPV infection or associated disease.

In one embodiment the present invention provides a method of treating infection or disease caused by HPV, comprising the administration of an effective amount of one or more RNA construct(s) comprising an expression cassette comprising a transgene encoding immunogenic peptides derived from hrHPV, as described herein. In one embodiment the present invention provides a method of generating or enhancing an immune response directed against HPV, comprising the administration of one or more RNA construct(s) according to the present invention. Particularly, the method of generating or enhancing an immune response comprises the administration of an effective amount of one or more SAM construct(s) comprising a transgene encoding at least two antigenic HPV polypeptides from a first HPV early protein, such as E1, where the antigenic HPV polypeptides are from different high-risk HPV types (e.g., an antigenic polypeptide from HPV16 E1 and an antigenic polypeptide from HPV18 E1), and where the antigenic polypeptides share at least 70% amino acid sequence identity with an additional high-risk HPV type (where the transgene does not encode antigenic polypeptides from that additional high-risk HPV type). The transgene typically further encodes at least two antigenic HPV polypeptides from a second HPV early protein, such as E2 or E6, where the antigenic HPV polypeptides are from different high-risk HPV types (e.g., an antigenic polypeptide from HPV16 E2 or HPV16 E6 and an antigenic polypeptide from HPV18 E2 or HPV18 E6), and where the antigenic polypeptides share at least 70% amino acid sequence identity with an additional high-risk HPV type (e.g., HPV35), though the transgene does not encode antigenic polypeptides from that additional high-risk HPV type. Additionally, the antigenic polypeptides may be selected to include at least one T cell epitope.

Such vaccines or other immunogenic compositions may be formulated in a suitable delivery vehicle. Generally, doses for the immunogenic compositions are in the range defined below under 'Delivery Methods and Dosage'. The levels of immunity (humoral and/or cell based) to the selected peptide(s) can be monitored to determine the need, if any, for subsequent (booster) immunizations. Following an assessment of antibody titers in the serum, optional booster immunizations may be administered.

The RNA construct(s) are administered in an immunogenic amount, that is, an amount of RNA construct(s) that is effective in a route of administration to transfect the desired target cells and provide sufficient levels of expression of the selected polynucleotide sequences to induce an effective immune response. As used herein, an effective immune response is one resulting in a therapeutic effect.

The RNA constructs described herein are expected to be efficacious at inducing cytolytic T cells directed to the HPV antigenic protein(s) expressed by the construct.

It will be apparent to one skilled in the art that the use of certain sequences in the transgene, between the HPV sequences, will result in the addition of amino acids to the HPV antigenic sequence. Use of the '2A' sequence as described herein between (in 5' to 3' direction) a nucleotide sequence encoding a first HPV peptide and a nucleotide sequence encoding a second HPV peptide results in the addition of amino acids 1-23 of SEQ ID NO:36 to the first expressed HPV peptide, and addition of a Proline residue to the second expressed HPV peptide.

Administration Regimens

It will be readily understood that the RNA constructs of the invention are suited for use in regimens involving repeated delivery of HPV immunogenic peptide(s) over time for therapeutic purposes. The regimens may involve multiple delivery of the same transgene(s) or a delivery over time of different transgenes. These regimens may deliver the same or different therapeutic immunogenic HPV peptide(s). These regimens are not limited to delivery of RNA constructs but can utilize other types of nucleic acid vectors such as adenoviral vectors, eg. non-human primate adenoviral sequences or human adenoviral sequences, in combination with the RNA constructs.

"Simultaneous" administration refers to administration in a time period such that the simultaneously administered components contribute to the same ongoing immune response, e.g., the components are administered at the same time (e.g., co-formulated into a unitary dose, or admixed just prior to administration to the subject) or delivered in separate formulations in a limited time frame (e.g., a single day, hour, or fraction of an hour). Simultaneous administration is also referred to as co-administration. In some embodiments, co-administration may involve administration of one or more RNA construct(s) and administration of a protein component, which may be an adjuvanted protein composition.

A prime-boost regimen may be used in the methods of the present invention. Prime-boost refers to eliciting two separate immune responses in the same individual: (i) an initial priming of the immune system followed by (ii) a secondary or boosting of the immune system weeks or months after the primary immune response has been established.

Delivery Methods and Dosage

The compositions disclosed herein are for use in a method for inducing a cross-reactive immune response against hrHPVs of at least three different hrHPV types in a mammalian subject, the method comprising administering to a subject in need of treatment an immunologically effective amount of the compositions as provided herein.

In some embodiments, a composition comprising the RNA construct(s) of the invention is administered to a subject by intramuscular injection, intravaginal injection, intravenous injection, intraperitoneal injection, subcutaneous injection, epicutaneous administration, intradermal administration, nasal administration or oral administration.

Because RNA constructs may be limited in the size of the transgene that they can effectively carry and express, in one embodiment the therapeutic method of the present invention comprises the administration of two or more RNA constructs carrying different transgenes, in order to achieve sufficient expression of multiple HPV antigenic peptides in the subject. Alternatively, the different transgenes may express antigenic peptides from the same HPV Early proteins, but from different hrHPV types.

In one embodiment, the therapeutic method of the present invention comprises the administration of three SAM constructs, wherein:
  a first SAM construct may express antigenic peptides from E1 of hrHPV types 16 and 18 and antigenic peptides from E6 proteins of hrHPV types 16, 18, 31, 33, 45, 52 and 58;
  a second SAM construct may express antigenic peptides from E2 of hrHPV types 16, 18, 31 and 33; and
  a third SAM construct may express antigenic peptides from E7 of hrHPV types 16 and 18 and antigenic peptides from E2 proteins of hrHPV types 45, 52 and 58.

If the therapeutic regimen involves co-administration of more than one RNA construct, the RNA constructs may be co-formulated in a single unit dose. Where RNA constructs are formulated in different compositions, they may be administered co-locationally at or near the same site. For example, the components can be administered to a subject (e.g. via an administration route selected from intramuscular, transdermal, intradermal, sub-cutaneous) to the same side or extremity ("co-lateral" administration) or to opposite sides or extremities ("contra-lateral" administration).

Dosages of the RNA construct will depend primarily on factors such as the route of administration, the condition being treated, the age, weight and health of the patient, and may thus vary among patients. Generally a human dose will be in a volume of between 0.1 ml and 2 ml. Thus the composition described herein can be formulated in a volume of, for example, about 0.1, 0.15, 0.2, 0.5, 1.0, 1.5 or 2.0 ml human dose per individual or combined immunogenic components.

One of skill in the art may adjust these doses, depending on the route of administration and the subject being treated.

The therapeutic immune response against the protein encoded by the selected transgene can be monitored to determine the need, if any, for boosters. Following an assessment of the immune response (e.g., of CD4+/CD8+ T cell response, antibody titers, in the serum, or both), optional booster immunizations may be administered.

The present invention will now be further described by means of the following non-limiting examples.

EXAMPLES

Example 1—Antigen Design to target 7 hrHPV types

Investigations were carried out to identify HPV antigens capable of eliciting an immunogenic response to at least seven of fifteen high risk HPV types, and to prepare constructs capable of expressing the antigens. The amino acid sequences of E1, E2, E6 and E7 proteins from fifteen hrHPV types were compared, and regions of high similarity that contained CD4/CD8 epitopes were identified. Antigenic regions were selected to target seven hrHPV types: 16, 18, 31, 33, 45, 52, and 58.

Table 1 and Table 2 illustrate that, for each of the proteins studied, combinations of conserved sequences from certain HPV types provided a minimum 70% identity or 70% similarity to other HPV types (for that protein). In Tables 1 and 2, for each protein (E1, E2, E6 or E7), crossed squares indicate the HPV type from which a sequence was selected; the percent identity or similarity to other HPV types that is provided by the selected sequences is indicated in the other squares of the column (blank squares indicate less than 70% similarity or identity; n/d indicates not done).

TABLE 1

| Identity Threshold 70% | | | | |
| --- | --- | --- | --- | --- |
|  | E1 | E2 | E6 | E7 |
| HPV16 | X | X | X | X |
| HPV18 | X | X | X | X |
| HPV31 | 79% | X | X | 72% |
| HPV33 | X | X | X |  |
| HPV45 | 89% | X | X | 78% |
| HPV52 | 79% | X | X |  |
| HPV58 | 90% | X | X |  |
| HPV56 |  |  |  |  |
| HPV51 |  |  |  |  |
| HPV39 | 80% |  |  |  |
| HPV35 | 78% | 73% | 72% | 72% |
| HPV59 | 81% |  |  |  |
| HPV68 |  |  |  |  |
| HPV73 |  |  |  |  |
| HPV82 |  |  |  |  |

TABLE 2

| Similarity Threshold 70% | | | | |
| --- | --- | --- | --- | --- |
| E1 | E2 | E6 | E7 |
| X | X | X | X |
| X | X | X | X |
| 90% | X | X | n/d |
| X | X | X | n/d |
| 95% | X | X | n/d |
| 92% | X | X | n/d |
| 96% | X | X | n/d |
| 81% |  | 73% | n/d |
| 80% |  | 74% | n/d |
| 89% | 74% | 78% | n/d |
| 90% | 81% | 81% | n/d |
| 93% | 76% | 76% | n/d |
| 90% | 74% | 79% | n/d |
| 83% | 71% | 74% | n/d |
| 79% |  | 72% | n/d |

Regions of HPV E1, E2, E6 and E7 were identified for inclusion:

E1=aa203-622: The E1 constructs from HPV 16 and 18 contained aa203-622, (numbering corresponds to full length HPV 16 E1 (SEQ ID NO:14)). See SEQ ID NO:18 (HPV16 E1 construct), SEQ ID NO:19 (HPV18 E1 construct).

E2=aa1-201+GGTGGS+aa285-365: The E2 constructs from HPV 16, 18, 31, 33, 45, 52 and 58 contained a TAD segment (amino acids corresponding to aa1-201 of full-length HPV16 E2 (SEQ ID NO:15)), a GGTGGS linker, and a DBD domain segment (amino acids corresponding to aa285-365 of full-length HPV16 E2 (SEQ ID NO:15). See SEQ ID NO:20 (HPV16 E2 construct), SEQ ID NO: 21 (HPV18 E2 construct), SEQ ID NO:22 (HPV31 E2 construct), SEQ ID NO:23 (HPV33 E2 construct), SEQ ID NO:24 (HPV45 E2 construct), SEQ ID NO:25 (HPV52 E2 construct), and SEQ ID NO:26 (HPV58 E2 construct).

E6=aa11-150: The E6 constructs from HPV 16, 18, 31, 33, 45, 52 and 58 contained amino acids 11-150 (numbering based on HPV16 E6 full length, SEQ ID NO:16). See SEQ ID NO:27 (HPV16 E6 construct), SEQ ID NO:28 (HPV18 E6 construct), SEQ ID NO:29 (HPV31 E6 construct), SEQ ID NO:30 (HPV33 E6 construct), SEQ ID NO:31 (HPV45 E6 construct), SEQ ID NO:32 (HPV52 E6 construct), and SEQ ID NO:33 (HPV58 E6 construct).

E7=aa49-98 and aa7-28, with fragment aa49-98 placed N-terminal to aa7-28, and with C24G and E26Q substitutions: The E7 construct comprises aa49-98 and aa7-28, with fragment aa49-98 placed N-terminal to aa7-28. (Numbering corresponds to HPV 16 E7 (SEQ ID NO:17)). See SEQ ID NO: 34 (HPV16 E7 construct) and SEQ ID NO:35 (HPV18 E7 construct).

Nucleotide insert constructs Gly_E2$^4$, Gly_E2$^3$E7$^2$ and Gly_E1$^2$E6$^7$, as shown in Table 3, were generated. "Gly" indicates that a nucleotide sequence encoding a 5xGly linker (SEQ ID NO:37) was placed between adjacent HPV-encoding sequences in the construct. These constructs are shown schematically in FIG. 1, where the triple vertical lines indicate the presence the 5xGly linker.

The following mutations were introduced into these inserts to eliminate the native activity of the wild-type E1, E2, E6 and E7 proteins (mutation positions are with respect to the native sequences of HPV16 E1, E2, E6 and E7. Mutations were introduced at corresponding positions for other serotypes):

E1=203-622+mut G482D;
E2=1-201+GGTGGS+285-365+mut K111A;
E6=11-150+mut C110R and mut F54R;

E7 HPV16=49-98+7-28+mutations C24G and E26Q/E7 HPV18=58-105+7-42+mutations C27G and E29Q.E1=203-622+mut G482D.

TABLE 3A

E2 and E2E7 inserts

Figure 2:
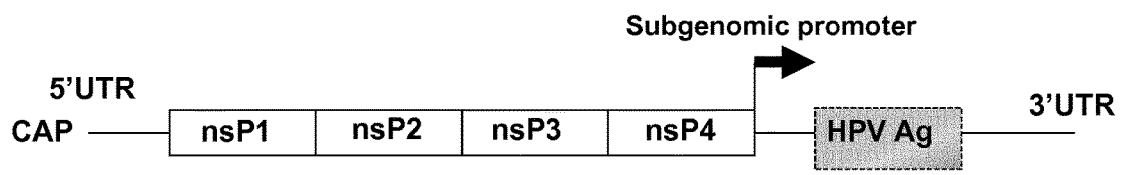
FIG. 2—SAM-HPV constructs. The SAM background consists of VEE TC-83 replicon encoding the viral non-structural proteins 1-4 (nsP1-4), followed by the subgenomic promoter, and a transgene encoding antigenic HPV polypeptides. The empty construct is shown in SEQ ID NO: 1.

| Insert Identifier[1] | E2 | E7 |
|---|---|---|
| Gly_E2[4] SEQ ID NO: 2 FIG. 2° | HPV16 (SEQ ID NO: 20) HPV18 (SEQ ID NO: 21) HPV31 (SEQ ID NO: 22) HPV33 (SEQ ID NO: 23) | |
| Gly_E2[3]E7[2] SEQ ID NO: 4 FIG. 2B | HPV45 (SEQ ID NO: 24) HPV52 (SEQ ID NO: 25) HPV58 (SEQ ID NO: 26) | HPV16 (SEQ ID NO: 34) HPV18 (SEQ ID NO: 35) |

[1]superscript numbers in construct identifiers indicate the number of HPV types; "Gly" indicates a 5xGly linker was placed between HPV antigenic peptides in the construct.

TABLE 3B

E1E6 inserts

| Insert Identifier[1] | E1 | E6 |
|---|---|---|
| Gly_E1[2]E6[7] SEQ ID NO: 6 FIG. 2C | HPV16 (SEQ ID NO: 18) HPV18 (SEQ ID NO: 19) | HPV16 (SEQ ID NO: 27) HPV18 (SEQ ID NO: 28) HPV33 (SEQ ID NO: 30) HPV45 (SEQ ID NO: 31) HPV52 (SEQ ID NO: 32) HPV58 (SEQ ID NO: 33) HPV31 (SEQ ID NO: 29) |

[1]superscript numbers in construct identifiers indicate the number of HPV types; "Gly" indicates a 5xGly linker was placed between HPV antigenic peptides in the construct.

Example 2—Design of SAM Constructs Encoding Antigenic HPV Polypeptides

The SAM platform is based on synthetic, self-amplifying mRNA derived from the alphavirus genome, expressing antigens of interest. The SAM constructs were evaluated for robust antigen productions and antigenicity and further tested for their immunogenicity and efficacy using in vivo models.

The design of the HPV-SAM constructs of FIG. 2 includes cloning the sequence encoding the antigenic HPV peptides, under the subgenomic promoter in the SAM construct. Modifications to the SAM HPV constructs were made including codon optimisation of the coding sequence for the antigen.

The SAM construct VEE TC-83 as described in WO2005/113782 was used as the background construct for cloning. This background construct has the nucleic acid sequence of SEQ ID NO: 1.

Gly_E2[4], Gly_E2[3]E7[2] and Gly_E1[2]E6[7] were then cloned into SAM constructs 1, 2 and 3 (one construct for each insert) after nucleotide 7561 of SEQ ID NO:1. Point mutations were included to inhibit protein activity.

SAM constructs having the sequence of SEQ ID NO: 9, SEQ ID NO: 11 and SEQ ID NO:13 were designed and obtained.

The design of each SAM insert was as follow:
SAM-HPV construct no 1: Gly_E2[4] (SEQ ID No 2)
HPV16E2 (1-201+GGTGGS+285-365 aa+mut K111A)/HPV18E2 (1-206+GGTGGS+286-365 aa mut K115A)/HPV31E2 (1-201+GGTGGS+292-372 mut K111A)/HPV33E2 (1-201+GGTGGS+273-353 mut K111A).

SAM-HPV construct no 2: Gly_E2[3]E7[2] (SEQ ID No 4)
HPV45E2 (1-208+GGTGGS+290-368aa+mut K117A)/HPV52E2 (1-201+GGTGGS+287-368 aa+mut K111A)/HPV58E2 (1-201+GGTGGS+278-358+mut K111A).
HPV16E7 (49-98+7-28 aa+mut C24G and E26Q)/HPV18E7 (58-105+7-42 aa+mut C27G and E29Q).

SAM-HPV construct no 3: Gly_E1[2]E6[7] (SEQ ID No 6)
HPV16E1 (203-622 aa+mut G482D)/HPV18E1 (210-629 aa+mut G489D).
HPV16E6 (11-150 aa+mut F54R and C110R)/
HPV18E6 (6-145 aa+mut F49R and C105R)/
HPV33E6 (4-143 aa+mut F47R and C103R)/
HPV45E6 (6-145 aa+mut F49R and C105R)/
HPV52E6 (4-143 aa+mut F47R and C103R)/
HPV58E6 (4-143 aa+mut F47R and C103R)/
HPV31E6 (4-143 aa+mut F47R and C103R).

Example 3—Characterization of the T Cell Immune Responses Induced by Immunization with SAM-HPV Constructs in CB6F1 Mice Materials and Methods
Animal Model CB6F1 mice (hybrid of C57Bl/6 and Balb/C mice) have been shown to generate potent CD4+/CD8+ T cell and humoral immune responses following vaccination with various types of immunogens, including adjuvanted proteins and viral vectors.

Cellular Immune Response—Intracellular Cytokine Staining (ICS)

The frequencies of HPV-specific CD4+ & CD8+ T-cells producing IL-2, IFN-γ and/or TNF-α were evaluated by intracellular cytokines staining (ICS) in splenocytes collected 15 days post 1$^{st}$ & 2$^{nd}$ immunization.

Isolation of splenocytes—Spleens were collected from individual mice 15 days after 1" or 2$^{nd}$ immunization and placed in RPMI 1640 medium supplemented with RPMI additives (Glutamine, Penicillin/streptomycin, Sodium Pyruvate, non-essential amino-acids & 2-mercaptoethanol). Cell suspensions were prepared from each spleen using a tissue grinder. The splenic cell suspensions were filtered (cell stainer 100 μM) and then the filter was rinsed with 40 mL of cold PBS-EDTA 2 mM. After centrifugation (335 g, 10 min at 4° C.), cells were resuspended in 5 mL of cold PBS-EDTA 2 mM, cell suspensions were filtered (cell stainer 100 μM) again and then the filter was rinsed with 40 mL of cold PBS-EDTA 2 mM. A second washing step was performed as previously describe and the cells were finally resuspended in 2 ml of cold RPMI/additives supplemented with 5% FCS.

Cell suspensions were then diluted 20×(10 μL) in PBS buffer (190 μL) for cell counting (using MACSQuant Analyzer). After counting, cells were centrifuged (335 g, 10 min at RT) and resuspended at 10$^7$ cells/ml in cold RPMI/additives supplemented with 5% FCS.

Cell preparation & ex-vivo peptide pool stimulation—Fresh splenocytes were seeded in round bottom 96-well plates at approximately 1 million cells per well. Splenocytes were then stimulated for 6 hours (37° C., 5% CO$_2$) with anti-CD28 (clone 37.51) and anti-CD49d (clone 9C10 (MFR4.B)) at 1 μg/ml, with or without 100 μL of:
 a pool of 15mer peptides overlapping by 11aa covering the whole amino acids sequence of HPV16/18E1/E2/E6/E7 & HPV35E7 proteins (working concentration: 1 μg/mL per peptide).

a pool of 15mer peptides overlapping by 11 aa covering the antigen-designed protein sequence of HPV33/35/45E1/E2/E6 proteins (working concentration: 1 µg/mL per peptide).

PMA—ionomycin solution at working concentrations of 0.25 µg/mL and 2,5 µg/mL respectively (as positive control of the assay).

After 2 hours of ex vivo stimulation, Brefeldin A diluted 1/200 in RPMI/additives supplemented with 5% FCS was added for 4 additional hours to inhibit cytokine secretion. Plates were then transferred at 4° C. overnight.

Intracellular Cytokine Staining (ICS)—After overnight incubation at 4° C., cells were transferred to V-bottom 96-well plates, centrifuged (2000 rpm, 3 min at 4° C.) and washed in 250 µL PBS 1% FCS. After a second centrifugation (2000 rpm, 3 min at 4° C.) cells were resuspended, to block unspecific antibody binding, in 50 µL of Flow buffer (cold PBS+1% FCS) containing anti-CD16/32 antibodies (clone 2.4G2) diluted 1/50 for 10 min at 4° C. Then, 50 µL Flow Buffer containing mouse anti-CD4-V450 antibody (clone RM4-5, diluted at 1/100) and anti-CD8-PerCp-Cy5.5 antibody (clone 53-6.7, diluted at 1/50) and Live/Dead™ Fixable Yellow dead cell stain (1/500) was added for 30 min in obscurity at 4° C. After incubation, 100 µL of Flow buffer was added into each well and cells were then centrifuged (2000 rpm for 3 min at 4° C.). A second washing step was performed with 200, of Flow buffer and after centrifugation, cells were fixed and permeabilized by adding 200 µL of Cytofix-Cytoperm solution for 20 min at 4° C. in obscurity. After plates centrifugation (2000 rpm for 3 min at 4° C.), cells were washed with 200 µL of Perm/Wash buffer, centrifuged (2000 rpm for 3 min at 4° C.) and resuspended in 50 µL of Perm/Wash buffer containing mouse anti-IL2-FITC (clone JES6-5H4, diluted 1/400), anti-IFN-γ-APC (clone XMG1.2, diluted 1/200) and anti-TNFα-PE (clone MP6-XT22, diluted 1/700) antibodies, for 1 hours at 4° C. in obscurity. Cells were then finally washed twice with 200 µl of Perm/Wash buffer, centrifuged (2000 rpm for 3 min at 4° C.) and resuspended in 220 µl PBS.

Cell acquisition and analysis—Stained cells were analyzed by flow cytometry using a LSRII flow cytometer and the FlowJo software. Live cells were identified with the Live/Dead staining and then lymphocytes were isolated based on FSC/SSC gating. The acquisition was performed on ~20,000 CD4+ T-cell events and ~5000 CD8+ T-cell events. The percentages of IFN-$\gamma^{+/-}$, IL-$2^{+/-}$ and TNF-$\alpha^{+/-}$ producing cells were calculated on CD4+ T and CD8+ T cell populations.

Results

Mice displayed mainly polyfunctional HPV-specific CD8+ T cell responses in the systemic compartment after primo immunization with LNP-formulated SAM-HPV constructs.

Naive CB6F1 inbred mice were intramuscularly (i.m.) immunized at day 0 with 1 µg of LNP-formulated SAM-HPV construct 1 or 2 or 3 (n=12/group). An additional group of mice was immunized with a saline solution (NaCl 150 mM; n=6) and used as negative control group. Fifteen days after primo-immunization, 6 mice in each SAM-HPV immunized group & 3 mice in the NaCl group were culled for T cell analysis. Splenocytes were harvested and stimulated ex-vivo for six hours with pools of 15mer peptides covering the amino acid sequences of 4 different HPV antigens (E1, E2, E6 and E7) from different genotypes (HPV16/18/33/35/45) to assess HPV-specific and cross-reactive T cell responses. The frequencies of HPV-specific and cross-reactive T cells secreting IFN-γ, IL-2 or TNF-α were measured by intracellular staining. The cut-off value for identifying specific and cross reactive CD4+/CD8+ T cell responses in vaccine-immunized mice corresponds to the $95^{th}$ percentile (p95) of the T cell responses obtained in the saline group.

Figure 3:
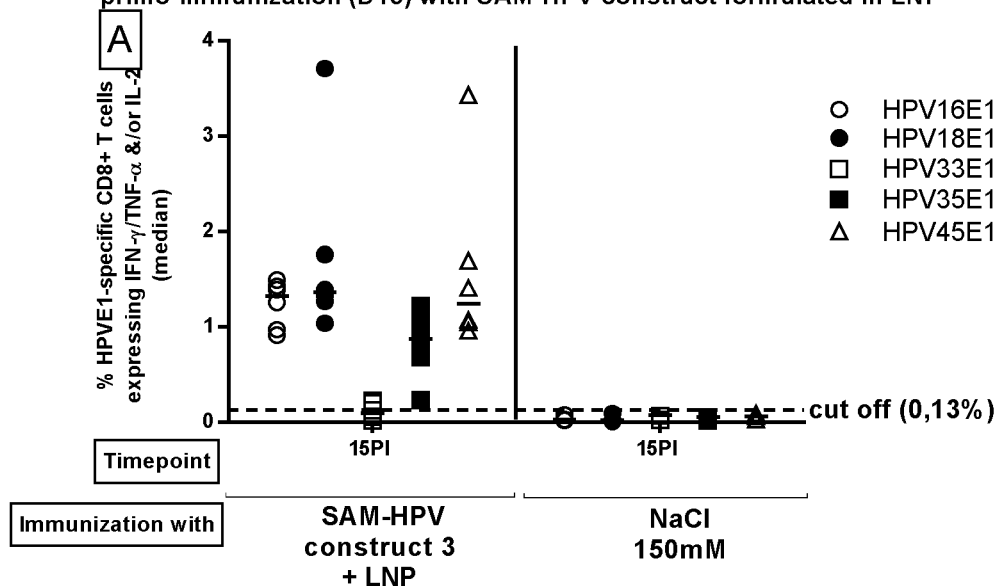
FIG. 3—Systemic evaluation of HPV-specific and cross-reactive CD8+ T cell responses elicited towards E1, E2, E6 & E7 antigens 15 days after primo immunization with different LNP-formulated SAM-HPV constructs. Naïve inbred CB6F1 mice (n=6/gr) were intramuscularly immunized on day 0 with 1 µg of LNP-formulated SAM-HPV construct 1 or 2 or 3. Negative control mice (n=3/gr) were treated with NaCl 150 mM solution. At day 15 post first immunization (15PI), mice in each group were culled for T cell analysis. Percentage of HPV-specific and cross-reactive CD8+ T cells secreting IFN-γ and/or IL-2 and/or TNF-α were measured in the systemic compartment. Intracellular staining was performed on splenocytes stimulated ex-vivo during 6 hours with pools of 15mer peptides covering the amino acid sequences of the HPV E1 (A), E2 (B), E6 (C) & E7 (D) antigens from 5 high risk HPV types (HPV16/18/33/35/45). The value used as the cut-off to identify specific CD8+ T cell responses in vaccine-immunized mice correspond to the 95$^{th}$ percentile of CD8+ T cell responses obtained in the saline group when combining all HPV antigens. These cut off values were obtained by computing the anti log of 95$^{th}$ quantile of the normal distribution that is assumed for the log frequencies, i.e. the mean of log frequencies+1.64×their standard deviation. Plots represent CD8+ T cell responses in the systemic compartment for each individual mouse. The median of the CD8+ T cell responses towards each HPV antigen is showed by the dotted line.
Figure 3:
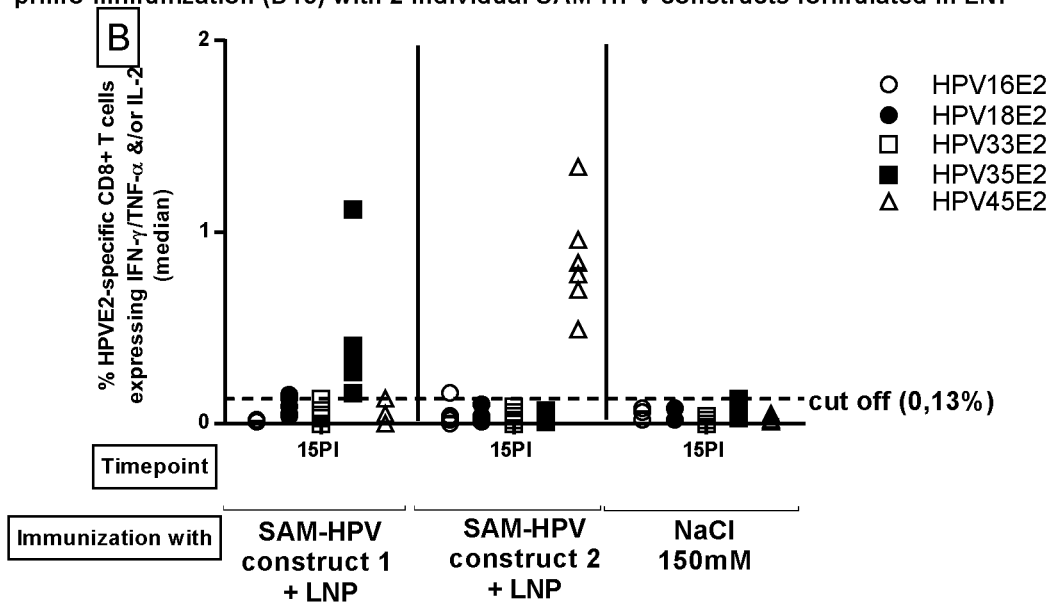
Figure 3:
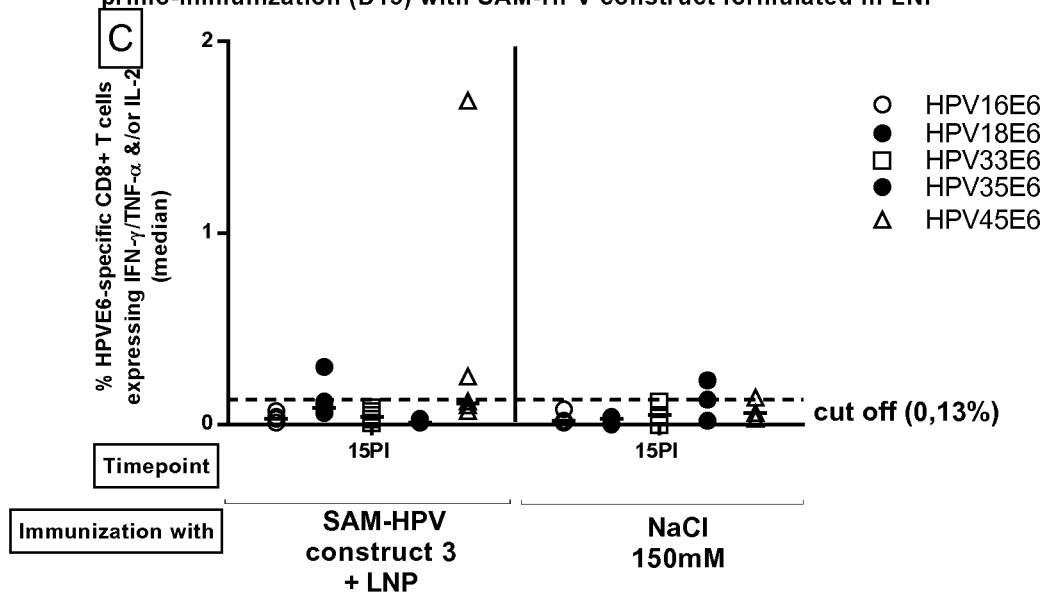
Figure 3:
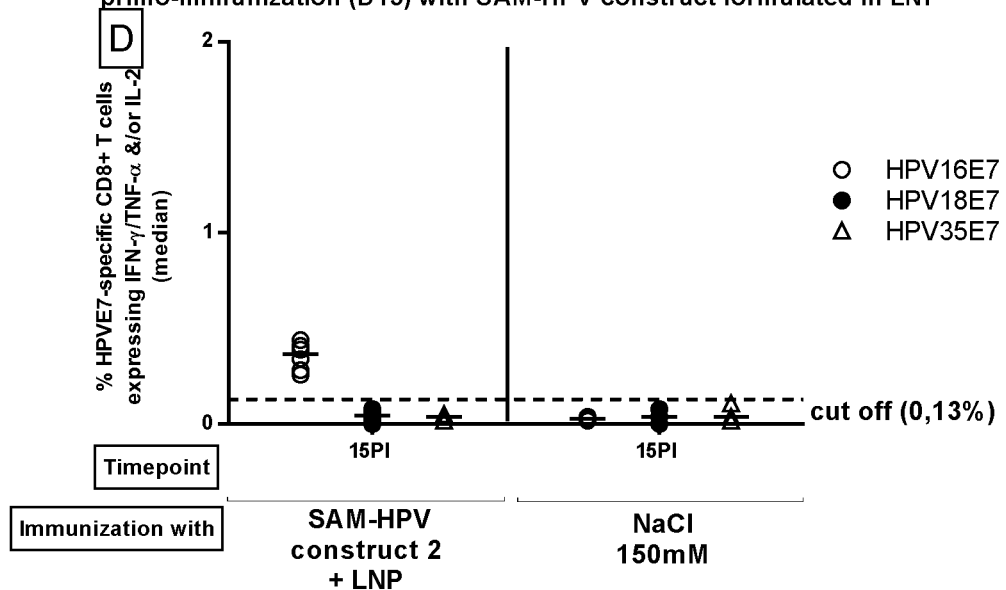
Figure 4:
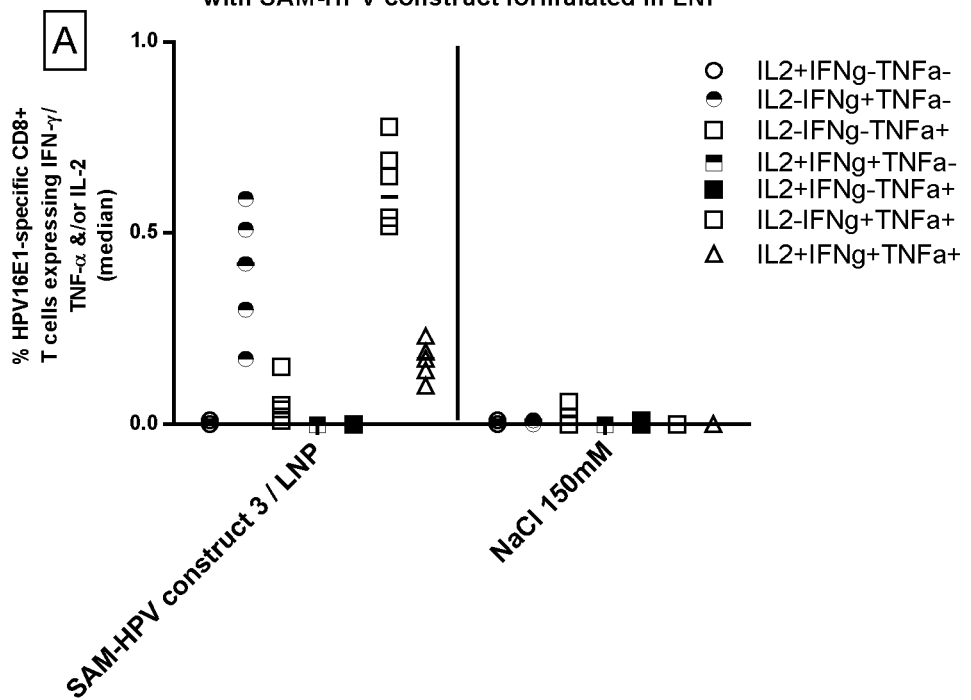
FIG. 4—Systemic evaluation of the polyfunctional profile of HPV16E1-specific & HPV35 cross-reactive CD8+ T cell response after primo immunization with LNP-formulated SAM-HPV construct. Naïve inbred CB6F1 mice (n=6/gr) were intramuscularly immunized on day 0 with 1 µg of LNP-formulated SAM-HPV construct 3. Negative control mice (n=3/gr) were treated with NaCl 150 mM solution. At day 15 post first immunization (15PI), mice in each group were culled for T cells analysis. Splenocytes were stimulated ex-vivo during 6 hours with a pool of 15mer peptides covering the amino acid sequence of E1 antigens from HPV16 or HPV35 types. The polyfunctional profile of HPV16E1-specific (A) and HPV35E1 cross-reactive (B) CD8+ T cells were evaluated by measuring IFN-γ, IL-2 and TNF-α cytokine production. Each plot represents data from individual mice. The median is represented by the dotted line.
Figure 4:
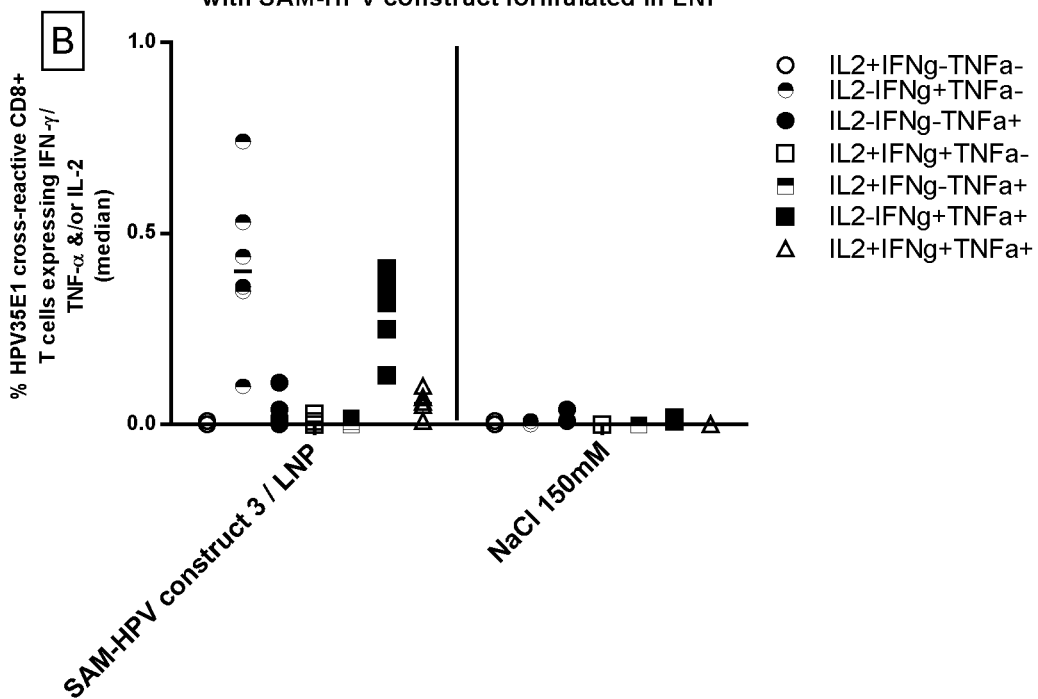

Compared to p95 of saline group, mice immunized with LNP-formulated SAM-HPV construct no 3 (construct containing E1 & E6 antigens), developed consistent HPV16/18 E1-specific & HPV35/45 cross-reactive CD8+ T cell responses at similar intensity in the systemic compartment 15 days after one immunization (15PI) (FIG. 3A). A few mice developed low cross-reactive CD8+ T cell response towards E1 antigen from HPV33 genotype compared to control group (FIG. 3A). The poly-functional profiles of HPV E1-specific and cross-reactive CD8+ T cells were evaluated by measuring IFN-γ, IL-2 and TNF-α cytokine production. FIGS. 4A & 4B show that the mice displayed polyfunctional HPV-specific and cross-reactive CD8+ T cell responses after immunization with LNP-formulated SAM-HPV construct 3, suggesting that effective T cell immune response towards E1 antigens from several HPV genotypes was induced. Since the polyfunctionality profile of the HPVE1-specific CD8+ T cell response was similar between all HPV genotypes tested, only HPV16E1-specific & HPV35E1 cross-reactive CD8+ T cell responses are illustrated as example (FIG. 4A & FIG. 4B). As shown in this figure, the most dominant HPVE1-specific and cross-reactive CD8+ T cell response to LNP-formulated SAM-HPV was to secrete IFN-γ and TNF-α but not IL-2, and to secrete IFN-γ but not TNF-α or IL-2. Cytokine responses to the HPVE1 antigen also included a small cohort of CD8+ T cells that secreted IFN-γ, TNF-α and IL-2. Regarding E6 antigen, only limited number of mice immunized with construct 3 developed HPV16/45-specific CD8+ T cell responses to E6 antigens after one dose of LNP-formulated SAM-HPV (15PI).

Figure 5:
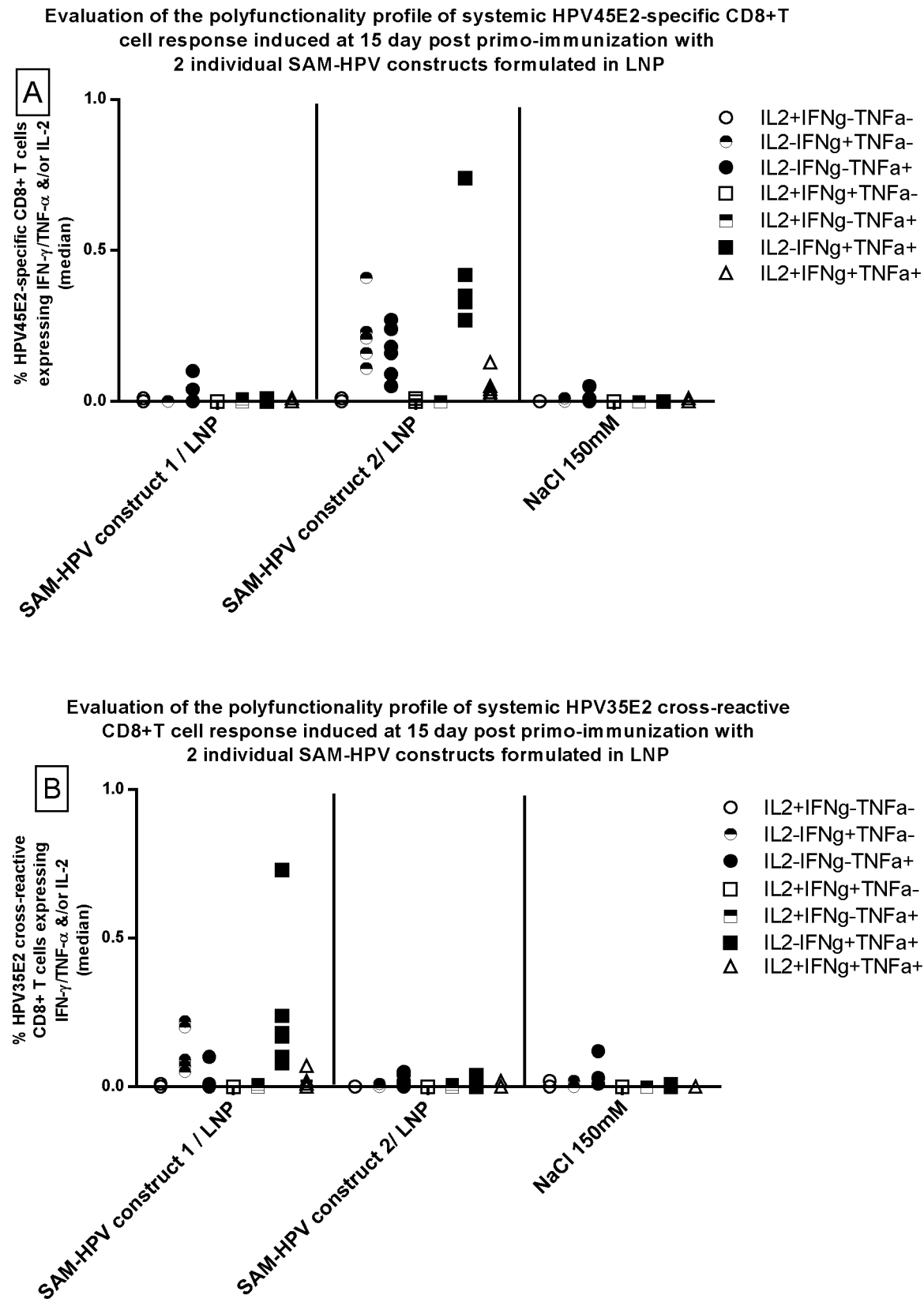
FIG. 5—Systemic evaluation of the polyfunctional profile of HPV45E2-specific & HPV35 cross-reactive CD8+ T cell response after primo immunization with LNP-formulated SAM-HPV constructs. Naïve inbred CB6F1 mice (n=6/gr) were intramuscularly immunized on day 0 with 1 µg of LNP-formulated SAM-HPV construct 1 or 2. Negative control mice (n=3/gr) were treated with NaCl 150 mM solution. At day 15 post first immunization (15PI), mice in each group were culled for T cells analysis. Splenocytes were stimulated ex-vivo during 6 hours with a pool of 15mer peptides covering the amino acid sequence of E2 antigens from HPV35 or HPV45 types. The polyfunctional profile of HPV45E2-specific (A) and HPV35E2 cross-reactive (B) CD4+ T cells were evaluated by measuring IFN-γ, IL-2 and TNF-α cytokine production. Each plot represents data from individual mice. The median is represented by the dotted line.

Combined data generated with LNP-formulated SAM-HPV construct 1 & 2 (construct 1 containing only E2 antigens and constructs 2 E2 & E7 antigens) shows that HPV45-specific and HPV35-cross reactive CD8+ T cell responses towards E2 antigen were induced in the systemic compartment 15 days after 1 immunization dose (15PI) (FIG. 3B). FIGS. 5A & 5B show that the mice displayed polyfunctional HPV-specific and cross-reactive CD8+ T cell responses after immunization with LNP-formulated SAM-HPV construct 1 & 2, suggesting that effective T cell immune response towards E2 antigens from two different HPV genotypes was induced (FIG. 5A & FIG. 5B). Contrary to other antigens, cytokine responses to the HPV42 E2 antigen also included a cohort of CD8+ T cells that secreted TNF-α but not IFN-γ and IL-2 (FIG. 5A).

Figure 6:
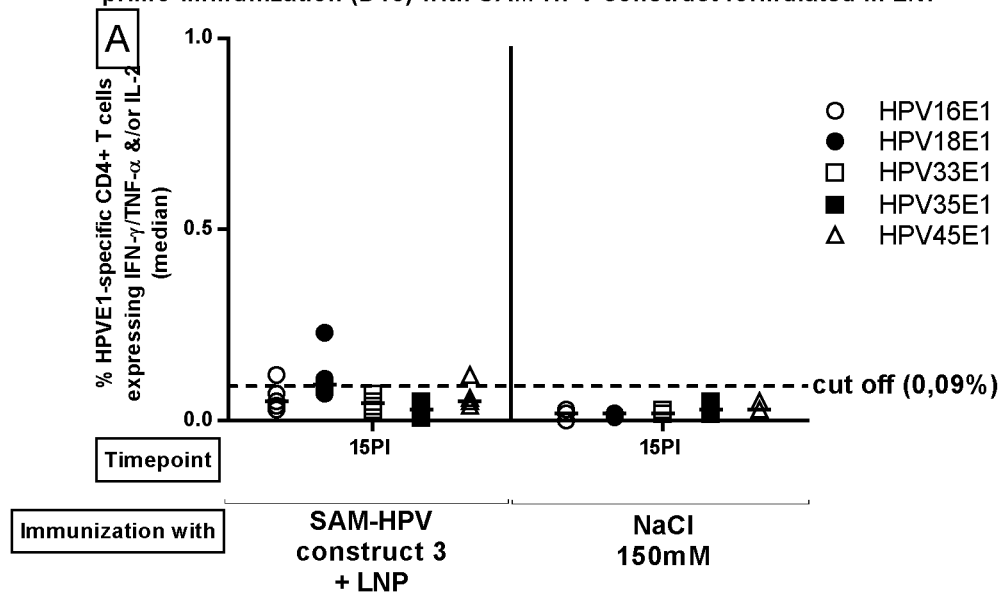
FIG. 6—Systemic evaluation of HPV-specific and cross-reactive CD4+ T cell responses elicited towards E1, E2, E6
Figure 6:
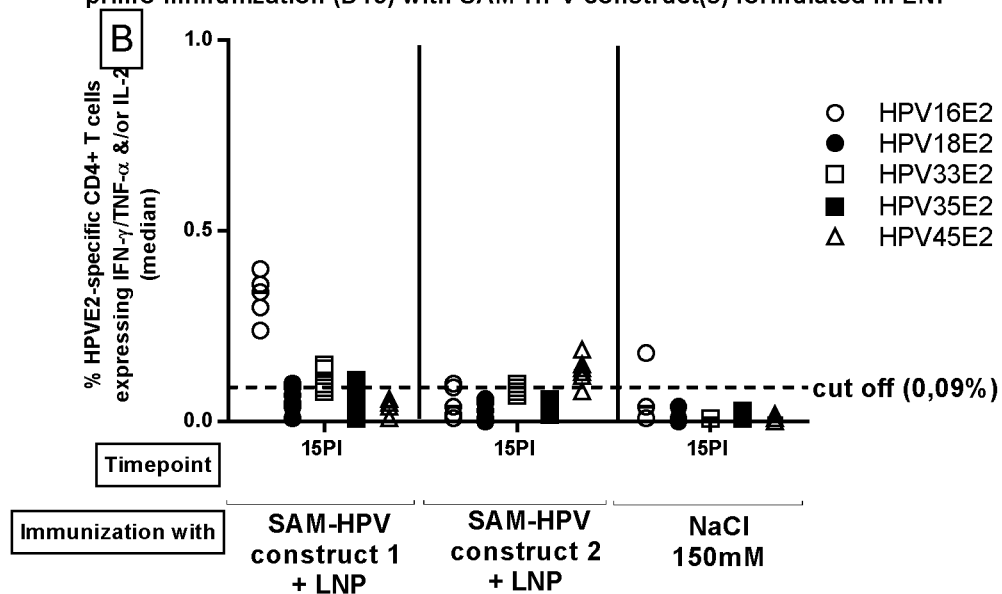
Figure 6:
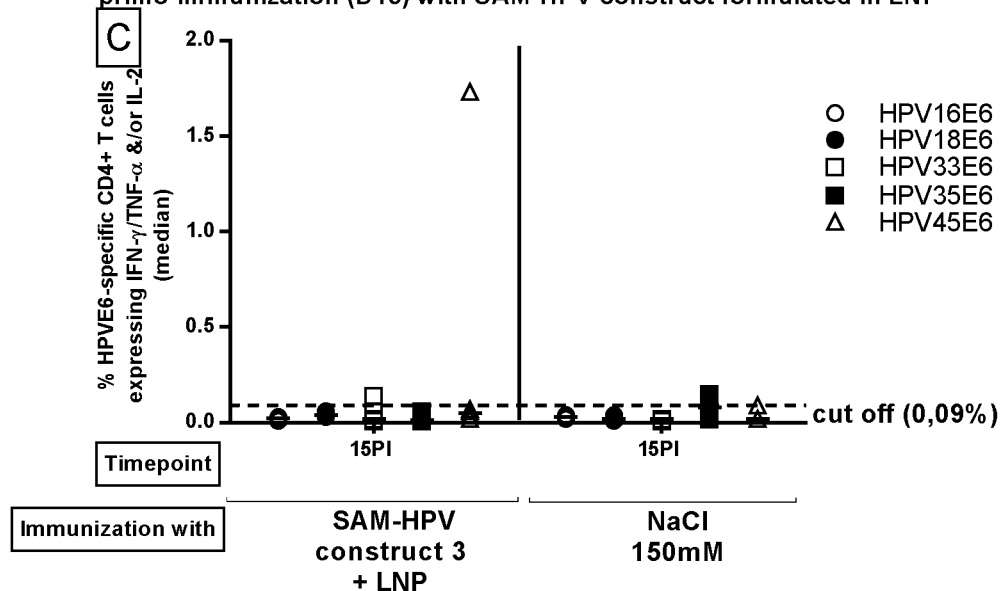
Figure 6:
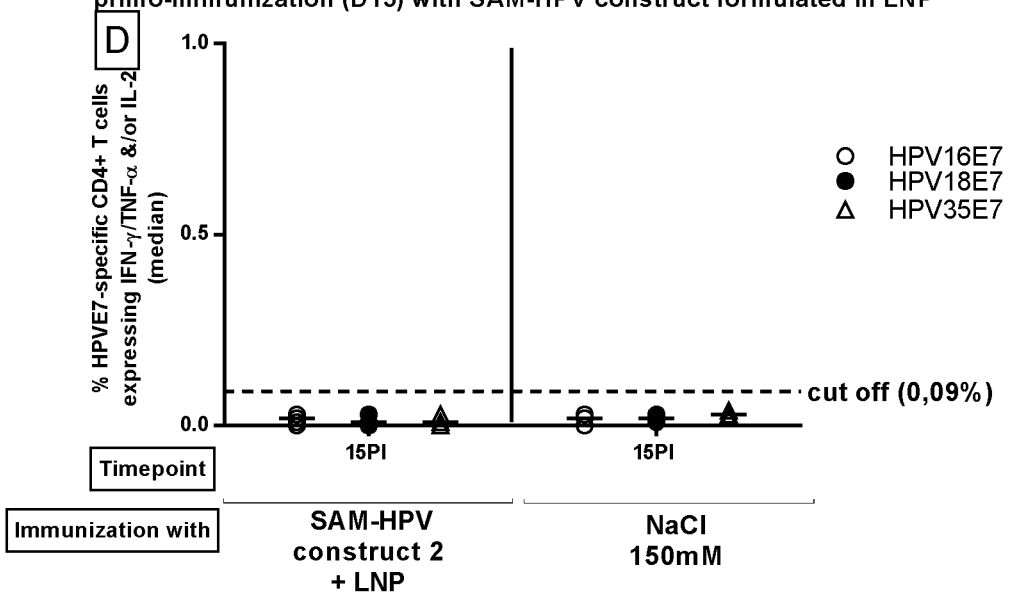

Finally, mice immunized with LNP-formulated construct 2 displayed also HPV16-specific CD8+ T cell response towards E7 antigen 15 days after one immunization (FIG. 3D). Regarding HPV-specific and cross-reactive CD4+ T cell responses, only mice immunized with construct 1 displayed consistent HPV16-specific CD4+ T cell response against E2 antigen 15 days after one immunization (15PI) (FIG. 6B). By looking at data generated with construct 1 et 2, inconsistent HPV45-specific and HPV33 cross-reactive CD4+ T cell responses were also observed towards E2 antigen (FIG. 6B).

A Second Homologous Immunization is Able to Boost Pre-Existing Poly-Functional HPV-Specific T Cell Responses Induced by LNP-Formulated SAM-HPV Naive CB6F1 inbred mice were intramuscularly (i.m.) immunized at days 0 & 56 with 1 µg of LNP-formulated SAM-HPV construct 1 or 2 or 3 (homologous prime/boost).

An additional group of mice was immunized with a saline solution (NaCl 150 mM) and used as negative control group. Fifteen days after $2^{nd}$ immunization (15PII), the last 6 mice from each LNP-formulated SAM-HPV immunized group & the last 3 mice from the NaCl group were culled for T cell analysis. Splenocytes were harvested and stimulated ex-vivo for six hours with pools of 15mer peptides covering the amino acid sequences of 4 different HPV antigens (E1, E2, E6 and E7) from different genotypes (HPV16/18/33/35/45) to assess HPV-specific and cross-reactive T cell responses. The frequencies of HPV-specific and cross-reactive T cells secreting IFN-γ, IL-2 or TNF-α were measured by intracellular staining. The cut-off value for identifying specific and cross reactive CD4+/CD8+ T cell responses in vaccine-immunized mice corresponds to the p95 of the T cell responses obtained in the saline group. Due to technical issues during the acquisition of Raw data by flow cytometry, 3 different samples (1 from mice immunized with construct 1 and 3 and 1 mice from the saline control group) collected 15 days post second immunization were excluded for the final analysis.

At day 15 following the booster immunization (15PII) with LNP-formulated SAM-HPV construct 3 (containing E1 & E6 antigens), the intensity of the HPV16/18-specific and HPV35/45 cross-reactive CD8+ T cell responses to E1 antigen was increased (about 5×) compared to the responses in the group immunized once (15PI) (FIG. 7A). Interestingly, the intensity of HPV18/45-specific CD8+ T cell responses towards E6 antigen was also increased (about 5×) 15 days post second immunization with LNP-formulated SAM-HPV construct 3 compared to 15PI (FIG. 7C). FIGS. 8A & 8B and 10A & 10B show that the mice displayed similar polyfunctional HPV-specific and cross-reactive CD8+ T cell responses towards E1 & E6 after one or two immunizations with LNP-formulated SAM-HPV construct 3. As after one immunization, the most dominant HPV-specific and cross-reactive CD8+ T cell response to LNP-formulated SAM-HPV construct 3 was to secrete IFN-γ and TNF-α but not IL-2, and to secrete IFN-γ but not TNF-α or IL-2. Cytokine responses to the HPVE1/E6 antigens also included a cohort of CD8+ T cells that secreted IFN-γ, TNF-α and IL-2 (FIGS. 8A & 8B and 10A & 10B). Since the polyfunctionality profile of the HPV E1-specific CD8+ T cell response was similar between all HPV types tested, only HPV16 E1-specific & HPV 35E1 cross-reactive CD8+ T cell responses were illustrated as example (FIGS. 8A & 8B). As detected after one immunization, the most dominant HPV-specific and cross-reactive CD8+ T cell response to LNP-formulated SAM-HPV constructs 1 & 2 was to secrete IFN-γ and TNF-α but not IL-2, and to secrete IFN-γ but not TNF-α or IL-2 and then IFN-γ, TNF-α and IL-2 (FIGS. 9A & 9B, FIGS. 11A & 11B). Cytokine responses to the HPV42 E2 antigen also included a cohort of CD8+ T cells that secreted TNF-α but not IFN-γ and IL-2 (FIG. 9A).

Regarding HPV-specific and cross-reactive CD4+ T cell responses, only mice immunized with construct 1 & 3 displayed higher intensity for some CD4+ T cell responses detected after second immunization compared to the level of response after one immunization. Indeed, intensity of HPV16-specific and HPV33 cross-reactive CD4+ T cell responses to E1 antigen was increased 15 days after the second immunization (15PII) (FIG. 12A). In addition, level of HPV16-specific CD4+ T cell response against E2 antigen was also increased after the second immunization (FIG. 12B).

Finally, these results suggest that LNP-formulated SAM-HPV is immunogenic in mice and able to boost pre-existing polyfunctional T cell responses in mice.

REFERENCES

Baldwin et al., Clin Cancer Research 9(14) (November 2003)
Davidson et al., Cancer research 63(18):6032-41 (2003)
Davidson et al., Vaccine 22(21): 2722-2729 (2004)
Einstein et al., Comparison of the immunogenicity of the human papillomavirus (HPV)-16/18 vaccine and the HPV-6/11/16/18 vaccine for oncogenic non-vaccine types HPV-31 and HPV-45 in healthy women aged 18-45 years. Hum Vaccin. 7(12):1359-73 (2011).
Future II Study Group. "Prophylactic efficacy of a quadrivalent human papillomavirus (HPV) vaccine in women with virological evidence of HPV infection." Journal of Infectious Diseases 196(10): 1438-1446 (2007)
Garland et al., New England Journal of Medicine 356(19): 1928-1943 (2007)
Herrin et al., Hum Vaccin Immunother 10:3446-54 (2014)
Hung et al., Therapeutic human papillomavirus vaccines: 8(4):421-39 (2008).
IARC Monograph, vol. 90, pp. 193-194, Table 26. Available at monographs (dot) iarc (dot) fr/ENG/Monographs/vol90/mono90 (dot) pdf (accessed 15 Aug. 2016)
Kaufmann et al., Int. J. Cancer 15; 92(2):285-93 (2001)
Kaufmann et al., Clinical Cancer Research 8(12):3676-3685 (2002)
Khan Selina et al., *Development of a replication-deficient adenoviral vector based vaccine candidate for the interception of HPV16- and HPV18-induced infections and disease*. International journal of Cancer, 2017.
Lin et al. J Formos Med Assoc.; 109(1):4-24 (2010)
Liu et al., Journal of virology 74(19): 9083-9089 (2000)
Oh, Y. K. et al., Virology, 328(2): 266-273 (2004)
Pinto et al., Journal of Infectious Diseases, 188(2):327-338 (2003)
Ragonnaud Emeline et al., *Therapeutic Vaccine Against Primate Papillomavirus Infections of the Cervix*, J Immunother 2017; 40:51-61.
Ragonnaud E. et al., *Breadth of T Cell Responses After Immunization with Adenovirus Vectors Encoding Ancestral Antigens or Polyvalent Papillomavirus Antigens*, Scandinavian Journal of Immunology, 2017, 85, 182-190.
Richart R M. Obstet Gynecol; 75:131-3 (1990)
Schiffman et al., Virology, 337(1): 76-84 (2005)
Solomon. The 1988 Bethesda System for reporting cervical/vaginal cytologic diagnoses. Human Pathology (7):704-8 (1990).
Tobery et al., Vaccine, 21(13):1539-1547 (2003)
van Kuppeveld et al., FEMS Immunology & Medical Microbiology, 34(3): 201-208. (2002)
Velders et al., Cancer research, 61(21):7861-7867 (2001)
Wheeler et al., 4-year end-of-study analysis of the randomised, double-blind PATRICIA trial. Lancet Oncology, 13:100-110 (2012)
WHO/IC summary report, 2010, available at www.hpvcentre.net
Winer et al., Journal of Infectious Diseases, 191(5):731-738 (2005)

The invention claimed is:

1. One or more RNA construct(s) comprising nucleic acid sequences encoding:
   (a) two antigenic Human Papillomavirus (HPV) polypeptides from a first HPV early protein, wherein said first HPV early protein is Early 1 (E1) and said two antigenic HPV polypeptides
      (i) are from E1 of two different HPV types selected from high-risk HPV types HPV16, HPV18, HPV31, HPV33, HPV35, HPV39, HPV45, HPV51, HPV52, HPV56, HPV58, HPV59, HPV68, HPV73 and HPV82, and
      (ii) share at least 70% amino acid sequence identity with corresponding region of E1 of one additional high-risk HPV type, and
   (b) two antigenic HPV polypeptides from a second HPV early protein, wherein said second HPV early protein is Early 2 (E2) and wherein said two antigenic HPV polypeptides
      (i) are from E2 of two different high-risk HPV types selected from HPV types HPV16, HPV18, HPV31, HPV33, HPV35, HPV39, HPV45, HPV51, HPV52, HPV56, HPV58, HPV59, HPV68, HPV73 and HPV82, and
      (ii) share at least 70% amino acid sequence identity with corresponding region of E2 of one additional high-risk HPV type.

2. The RNA construct(s) according to claim 1, wherein the nucleic acid sequences expressing antigenic HPV polypeptides from the first HPV early protein and the second HPV early protein are located on the same RNA construct.

3. The RNA construct(s) according to claim 1, wherein the nucleic acid sequences expressing antigenic HPV polypeptides from the first HPV early protein and second HPV early protein are located on two or more RNA constructs.

4. The RNA construct(s) according to claim 1, comprising antigenic polypeptide sequences selected from HPV types HPV16, HPV18, HPV31, HPV33, HPV45, HPV52, and HPV58.

5. The RNA construct(s) according to claim 1, comprising antigenic polypeptide sequences selected from HPV types HPV16 and HPV18.

6. The RNA construct(s) according to claim 1, wherein said two antigenic HPV polypeptides from a first HPV early protein are Early 1 (E1) proteins from HPV16 and HPV18, and wherein said two antigenic HPV polypeptides from a second HPV early protein are Early 2 (E2) proteins selected from HPV16 and HPV18.

7. The RNA construct(s) according to claim 6, further comprising E2 antigenic polypeptides from HPV31 E2, HPV33 E2, HPV45 E2, HPV52 E2 and/or HPV58 E2.

8. The RNA construct(s) according to claim 1, further comprising a nucleic acid sequence encoding two antigenic HPV polypeptides from a third HPV early protein, wherein said two antigenic HPV polypeptides are selected from two different high-risk HPV types selected from HPV types HPV16, HPV18, HPV31, HPV33, HPV35, HPV39, HPV45, HPV51, HPV52, HPV56, HPV58, HPV59, HPV68, HPV73 and HPV82, and share at least 70% amino acid sequence identity with corresponding early protein region of one additional high-risk HPV type.

9. The RNA construct(s) according to claim 8, comprising nucleic acid sequences encoding antigenic polypeptides from HPV16 E1, HPV18 E1, HPV16 E2, HPV18 E2, HPV16 E6 and HPV18 E6.

10. The RNA construct(s) according to claim 8, further comprising a nucleic acid sequence encoding two antigenic HPV polypeptides from a fourth HPV early protein, wherein said two antigenic HPV polypeptides are from two different high-risk HPV types selected from HPV types HPV16, HPV18, HPV31, HPV33, HPV35, HPV39, HPV45, HPV51, HPV52, HPV56, HPV58, HPV59, HPV68, HPV73 and HPV82, and share at least 70% amino acid sequence identity with corresponding early protein region of one additional high-risk HPV type, and wherein said first HPV early protein is E1, said second HPV early protein is E2, said third HPV early protein is E6 and said fourth HPV early protein is E7.

11. The RNA construct(s) according to claim 10, comprising nucleic acid sequences encoding antigenic polypeptides from HPV16 E1, HPV18 E1, HPV16 E2, HPV18 E2, HPV16 E6, HPV18 E6, HPV16 E7 and HPV18 E7.

12. The RNA construct(s) according to claim 1, wherein the nucleic acid sequence encodes a polypeptide that is at least 90%, 92%, 95%, 97%, 98%, 99% or 100% identical to a sequence selected from the group consisting of SEQ ID NO: 2, SEQ ID NO:4, and SEQ ID NO:6.

13. A self-replicating RNA molecule comprising an RNA construct selected from the RNA constructs of claim 1.

14. A DNA molecule encoding an RNA molecule selected from (a) an RNA construct of claim 1 or (b) a self-replicating RNA molecule comprising an RNA construct selected from the RNA constructs of claim 1.

15. A vector comprising a nucleotide selected from (a) the RNA construct(s) of claim 1, (b) a self-replicating RNA molecule comprising an RNA construct selected from the RNA constructs of claim 1, (c) a DNA molecule encoding an RNA construct of claim 1, or (d) a DNA molecule encoding a self-replicating RNA molecule comprising an RNA construct selected from the RNA constructs of claim 1.

16. An immunogenic composition comprising a pharmaceutically acceptable carrier and a nucleotide selected from (a) the RNA construct(s) of claim 1, (b) a self-replicating RNA molecule comprising an RNA construct selected from the RNA constructs of claim 1, (c) a DNA molecule encoding an RNA construct of claim 1, or (d) a DNA molecule encoding a self-replicating RNA molecule comprising an RNA construct selected from the RNA constructs of claim 1.

17. The immunogenic composition according to claim 16, wherein the immunogenic composition further comprises a non-viral delivery material.

18. An immunogenic composition comprising a pharmaceutically acceptable carrier and a vector according to claim 14.

19. The immunogenic composition according to claim 18, wherein the composition further comprises a non-viral delivery material.

* * * * *